(12) United States Patent
Miura et al.

(10) Patent No.: US 7,871,788 B2
(45) Date of Patent: Jan. 18, 2011

(54) METHOD OF JUDGING GRADE OF MALIGNANCY OF CARCINOMA CELL USING ATBF-1

(75) Inventors: Yutaka Miura, Nagoya (JP); Makoto Kawaguchi, Imizu (JP); Hirotaka Iwase, Nagoya (JP); Minoru Hamazaki, Shizuoka (JP); Jung Cha-Gyun, Nagoya (JP); Hitoo Nishino, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 480 days.

(21) Appl. No.: 11/658,784

(22) PCT Filed: Jul. 29, 2005

(86) PCT No.: PCT/JP2005/013911

§ 371 (c)(1),
(2), (4) Date: Jan. 30, 2007

(87) PCT Pub. No.: WO2006/011587

PCT Pub. Date: Feb. 2, 2006

(65) Prior Publication Data

US 2009/0004647 A1   Jan. 1, 2009

(30) Foreign Application Priority Data

Jul. 30, 2004   (JP) .............................. 2004-224280
Mar. 18, 2005   (JP) .............................. 2005-079435

(51) Int. Cl.
*G01N 33/574* (2006.01)
*G01N 33/53* (2006.01)

(52) U.S. Cl. ....................................... 435/7.23; 435/7.1

(58) Field of Classification Search .................. None
See application file for complete search history.

(56) References Cited

FOREIGN PATENT DOCUMENTS

WO    WO-01/72332    10/2001
WO    WO-2006/093138    9/2006

OTHER PUBLICATIONS

Kataoka et al (Oncogene, 2001, 20:869-873).*
Tockman et al (Cancer Res., 1992, 52:2711s-2718s).*
Kataoka et al (Oncogene, 2001, 20:869-873, IDS).*
National Cancer Institute, Tumor Grade: Questions and Answers (printed Jan. 8, 2010; p. 1-3).*
Miura, Y., et al.; "Cloning and Characterization of an ATBF1 Isoform That Expresses in a Neuronal Differentiation-dependent Manner;" *The Journal of Biological Chemistry*; vol. 270, No. 45, pp. 26840-26848. (1995).
Kataoka, H., et al.; "Alpha-fetoprotein producing gastric cancer lacks transcription factor ATBF1;" *Oncogene*; vol. 20; pp. 869-873. (2001).
Ishii, Y. et al.; "ATBF1-A Protein, but Not ATBF1-B, Is Preferentially Expressed in Developing Rat Brain;" *The Journal of Comparative Neurology*; vol. 465, pp. 57-71. (2003).
Kataoka, H., et al.; "ING1 Represses Transcription by Direct DNA Binding and through Effects on p53;" *Cancer Research*; vol. 63, pp. 5785-5792. (2003).
Noguchi, J., et al.; "A Long Survival Case of Brain Metastases from AFP Producing Gastric Cancer;" *Japanese Society of Gastroenterological Surgery*; vol. 36, No. 12, pp. 1659-1664. (2003).
Miura, Y., et al.; "Susceptibility to Killer T Cells of Gastric Cancer Cells Enhanced by Mitomycin-C Involves Induction of ATBF1 and Activation of p21 (Waf1/Cip1) Promoter;" *Microbiol. Immunol.*; vol. 48, No. 2, pp. 137-145. (2004).
Iida, M., et al.; "Alteration of the AT motif binding factor-1 expression in α-fetoprotein producing gastric cancer: Is it an event for differentiation and proliferation of the tumors?;" *Oncology Reports*; vol. 11, pp. 3-7 (2004).
Kašpar, Petr; et al.; "Myb-interacting Protein, ATBF1, Represses Transcriptional Activity of Myb Oncoprotein;" *The Journal of Biological Chemistry*; vol. 274, No. 20, pp. 14422-14428. (1999).
Sun, X., et al.; "Frequent somatic mutations of the transcription factor ATBF1 in human prostate cancer;" *Nature Genetics*; vol. 37, No. 4, pp. 407-412. (2005).
Zhang et al., "ATBF1-A Messenger RNA Expression Is Correlated with Better Prognosis in Breast Cancer," Clinical Cancer Research (2005), 11:193-198.
European Search Report for related application EP05767060.6, dated Jan. 19, 2010.

* cited by examiner

*Primary Examiner*—Laura B Goddard
(74) *Attorney, Agent, or Firm*—Edwards Angell Palmer & Dodge LLP

(57) ABSTRACT

Means for easily determining the grade of malignancy of cancer cells. The amount of ATBF1 in the whole cell structure of test cancer cells separated from a living organism is detected, and on the basis of detection results, the grade of malignancy of test cancer cells is judged. Alternatively, the amount of ATBF1 in the nuclei of test cancer cells separated from a living organism is detected, and on the basis of detection results, the grade of malignancy of test cancer cells is judged. Still alternatively, the amount of ATBF1 in the cytoplasms of test cancer cells separated from a living organism is detected, and on the basis of detection results, the grade of malignancy of test cancer cells is judged. In a preferred from, at least one of (1) the amount of intranuclear presence and/or intracytoplasmic presence a region corresponding to exon 10 of an ATBF1 gene, (2) the amount of intranuclear presence and/or intracytoplasmic presence a region corresponding to exon 11 of an ATBF1 gene, and (3) the amount of intranuclear presence and/or intracytoplasmic presence a region corresponding to exon 3 of an ATBF1 gene is detected as the amount of ATBF1.

5 Claims, 53 Drawing Sheets a potential nuclear localization signal (NLS) in ATBF1
consensus sequence    "KR------K"

ATBF1  277   KRKPILMCFLC-K           (SEQ ID NO.17)
ATBF1  2987  KRVVQVWFQNARAKEKKSK     (SEQ ID NO.18)

b potential nuclear exporting signal (NES) in ATBF1
consensus sequence    "L-L-L---L"

ATBF1  1267  LQL-HLTHL               (SEQ ID NO.19)
ATBF1  2471  LPQLVSLPSL              (SEQ ID NO.20)
ATBF1  2504  LSHL-PLKPL              (SEQ ID NO.21)
                                     (SEQ ID NO.22)

Fig. 3

Autoclave treatment
 staining observed mainly in the nucleus        staining observed mainly in the cytoplasm
| | non-infiltrating cancer | infiltrating cancer |
|---|---|---|
| DAKO TRS | ● | ● |
| DAKO TRS High pH | ● | ● |
| citrate buffer | ● | ● |
| NaOH-added citrate buffer | ● | ● |
| TE(Tris-EDTA) buffer | ● | ● |
| Tris-HCl buffer | ● | ● |
| Tris/EDTA/Tween20 | ● | ● |
| EDTA solution | ● | ● |
| Urea solution | — | — |
Fig.9 microwave oven treatment

● staining observed mainly in the nucleus   ○ staining observed mainly in the cytoplasm

|  | non-infiltrating cancer | infiltrating cancer |
|---|---|---|
| DAKO TRS | ○ | ○ |
| DAKO TRS High pH | ○ | ● |
| citrate buffer | ○ | ○ |
| NaOH-added citrate buffer | ○ | ○ |
| TE(Tris-EDTA) buffer | ○ | ○ |
| Tris-HCl buffer | ○ | ○ |
| Tris/EDTA/Tween20 | ○ | ○ |
| EDTA solution | ● | ○ |
| Urea solution | ● | ● |

Fig.10 pressure cooker treatment

● staining observed mainly in the nucleus      ○ staining observed mainly in the cytoplasm

| | non-infiltrating cancer | infiltrating cancer |
|---|---|---|
| DAKO TRS | ● | ○ |
| DAKO TRS High pH | ● | ● |
| citrate buffer | ● | ○ |
| NaOH-added citrate buffer | ● | ○ |
| TE(Tris-EDTA) buffer | ● | ○ |
| Tris-HCl buffer | ● | ○ |
| Tris/EDTA/Tween20 | ● | ○ |
| EDTA solution | ● | ● |
| Urea solution | ● | ○ |

Fig.11

● NT440, human ATBF1-A, N-terminal specific polyclonal antibody

● NT440-1: human ATBF1-A, 4 CDSPVVSGKDNG 15 (SEQ ID NO.6)
        (mouse 4 CDSPVVSGKDNG 15) (SEQ ID NO.23)

● NT440-2: human ATBF1-A 429 CKSSEGKDSGAAEGEKQE 445 (SEQ ID NO.7)
        (mouse 429 CKSSEGKDSGAAEGDKQE 445) (SEQ ID NO.24)

● NT440-3: human ATBF1-A 500 CPSELDEELEDRPHEEPG 516 (SEQ ID NO.8)
        (mouse 497 CPNDLEEELEDSPSEESG 513) (SEQ ID NO.25)

● 1-12, ATBF1-A-(phosphorylated 148 serine) specific monoclonal antibody human ATBF1-A, 143 CIVESLS$^{148}$QLTQGGG 155 (SEQ ID NO.9)
    (mouse 143 CIVESLS    QLTQSGA 155) (SEQ ID NO.26)

● D1-120, polyclonal antibody common to ATBF1-A and B mouseATBF1, 2114 LQTLPAQLPPQLGPVEPLPADLAQLYQHQLNPTLLQQQNKR (HD1) 2154 (SEQ ID NO.27)
    (the same as human sequence 2107-2147)

● AT6, polyclonal antibody common to ATBF1-A and B (including entire Zn finger #22 and part of Zn finger #23)

humanATBF1, 3405 PGAPSPDKDPAKESPKPEEQKNTPREVSPLLPKLPEEPEA
        ESKSADSLYDPFIVPKVQYKLVCRKCQAGFSDEEAARSHL
        KSLCFFGQSVVNLQEMVLHVPTGGGGGGSGGGGGGG
        GGGGGGSYHCLACESALCGEEALSQHLE 3549 (SEQ ID NO.10)

Fig.31

```
gene            1..282783

ORIGIN
    1 ccgcgcgtcc ctgtgcgtcc ccgggtccct gcgggcgggc gggcgcggtc gccgccgagc   Exon 2
   61 aacccggcct gcgcccggca cgactgtaga tgtcaggctt tgcccgggga gccgagcggc
  121 agcggggctg tgagtttcaa attaaccttc cgctttgttg ctgtgtaatg tggatccccg
  181 aaggccccccc gccccgcccg ccccccttcc ccgggcggtg cgcgctgcaa actgcgagtt
  241 ggcttcatt  tacataaagc gattccgggc gggcggcggc agaggaggag gcggcggcgg
  301 cgggcaggcc ggggacccgg acgccagcgc cgcgccccgt ggtgaatcc  ccgccgcgtc
  361 ccggggacct ccctccgggg acgggccgac cgccagccct gccgccacca tgagctcccc
  421 tccccctgtct ccggggcccc tgctcctgac cagagccacc tccgagtcct ggggccagcg
  481 ggaggtgggg agcatgccgc ctgggtgtgg tgagctcggg gctcgggtgc cactggaatt
  541 tcccgttgtt gcgcatggcg cgcgcgcccc cggacctgca agtgccgcct ccctccggag
  601 gtgcgcggag gcttggtgtg ccaggtgagt gcagcctccc tccgggtccg cgcagccggc 88141 tccctcctcc cccttgcct  ctgcccttca ggtccgagcc tccgtactgg gtgcaatgaa  Exon 3
88201 agctccacgc aggccttacc atggaaggct gtgactcgcc cgtcgtctcg gggaaggaca
88261 atgggtgcgg tatccctcag caccagcaat ggactgaact caacagcacc cacctccctg
88321 acaaacccag tagcatggag cagtccacag gcgagagcca cgggcccttg acagcctga
88381 gggccccctt caatgagcgc ctcgcgagca gcaccgccgc ggccgggccc ccctccgagc
88441 ccgccagcaa ggaggtcacc tgcaacgaat gttcggcctc cttttgccagc ctccagacct
88501 acatggagca ccactgcccc agcgcgcgcc ccccgccacc cctgagagag gagagcgcca
88561 gcgacaccgg tgaggagggg gacgaggaga gtgacgtgga gaacctgccc ggggagatcg
88621 tctaccagcc ggacggctcc gcgtacattg tggagagcct gagccagctg acccagggcg
88681 ggggcgcctg tgggagtggc agtggcagtg ggcctctccc ctcgcttttc ctgaactctc
88741 tccctggcgc ggggggcaag caagggggacc cttcgtgtgc tgcacccgtg tacccgcaga
88801 tcatcaacac tttccacata gcctcatcct tcgggaaatg gtttgaggcc cagaccagg
88861 cttttccgaa tacctcagcc ctggcggggc tcagccccgt cctgcacagc ttccgcgtgt
88921 ttgacgtgcg acacaaaagc aacaaggatt acctgacaca cgacggttct gccaaaagct
88981 cctgcgtatc caaagatgtt cccaacaatg tggaccgtc  caaattcgat ggctttgtgc
89041 tctatggcaa gaggaagccc atcctgatgt gtttcttgtg caaactctcc tttgggtacg
89101 tccgttcgtt tgtgacccac gcggtgcatg accatcgaat gacctgagc  gaagacgagc
89161 ggaaaattct tagcaataag aacatctccg ctatcatcca agggatcggc aaagacaagg
89221 aaccccttgt aagttttctg gaaccaaaaa acaaaaactt tcaacaccct ttagtttcca
89281 cagctaacct cataggcccc ggacacagtt tttatggtaa atttagtggc attcgaatgg
89341 aaggggagga agctctccca gcgggctccg ccgctggccc cgagcagccc caggctggtc
89401 tcttgactcc cagcaccctg ttgaaccttg gcgggctcca cagctcggta ctgaagaccc
89461 ccattacctc agtcccccctg gggcctctgg cttccagtcc taccaaatcc tcagaggca
89521 aggactctgg ggcggcagaa ggagagaagc aggaagtggg cgacgggcat tgcttctctg
89581 agaaggtaga gccagccgaa gaggaggcgg aggaggaaga ggaggaggaa gaggcggagg
89641 aggaggagga agaagaggag gaggaagaag aggaggagga agacgaggt  tgcaaagac
89701 tctttccaag cgagttggat gaggaactgg aggacaggcc ccatgagcag cctggggccg
89761 cagcaggtag tagcagcaaa aaggaccttg ctctctcaaa ccaaagcatt tctaactccc
89821 ctttaatgcc taacgtgctc cagaccctgt cgaggggcac agcttctact agttctaatt
89881 ctgcttcttc ctttgttgtc tttgatggtg cgaacaggag gaatcgttta agctttaaca
89941 gtgagggcgt caggtgccaat gtgccagagg gcggcaggag gctggacttc gctgacgaaa
90001 gtgccaataa agacaatgcc acagcaccag aaccaaatga agcacagag  ggtgacgatg
90061 ggggcttcgt tccccatcac cagcacgctg gctccctctg cgagcttggg gttggggagt
90121 gcccctcggg gagtggcgtg gagtgcccca aatgcgacac ggtcctgcgc tcctcccgct
90181 cgctggggcg ccacatgacc atgatgcatt ctcgtaactc gtgtaagaca ctcaagtgcc
90241 ccaagtgcaa ctggcactat aagtaccagc agaccctgga ggcacacatg aaggagaagc
90301 acccggagcc ggggggctcc tgtgtctact gcaaaagcgg gcagccccac cccggctgg
90361 cacgaggcga gagctacacg tgtggttaca agccttccg  ctgcgagctg tgtaactact
90421 ccacaactac caaaggcaac ctcagtattc atatgcagca tgacaagcat ctcaacaaca
90481 tgcagaacct gcagaatgga gggggagggagc aggtcttcag ccacactgcc ggggcggcg
90541 cggcggcggt ggctgcgcg  cgcgcggcag ccaatatcag tagctcctgc ggggccccct
90601 cgccgaccaa accaaaaacc aaacccacct ggcggtgcga ggtgtgtgat tatgagacca
90661 acgtggccag gaacctccgc attcacatga ccagtgagaa gcacatgcat aacatgatgt
90721 tactgcaaca gaacatgacc cagatccaac acaaccgcca cctgggcctc ggcagcctgc
90781 cctcacccgc cgaggccgag ctctaccaat actacctggc ccagaacatg aacctgccca
90841 acctgaagat ggacagtgct gcctcggacg cccagttcat gatgagcgga ttccagctgg
90901 atcccgccgg gccatggcc  gccatgacgc ctgctctagg tgaggatgac tacgtgtttg
```

Fig.50

```
 97381 tccttctctc cttccctgca gtgggcggtg agatccccct agacatgcgg ctcgggggcg Exon 4
 97441 ggcagctggt gtcagaggag ctgatgaacc tgggcgagag cttcatccag accaacgacc
 97501 cgtcgctgaa gctcttccag tgcgccgtct gcaacaagtt cacgacggac aacctggaca
 97561 tgctgggcct gcacatgaac gtggagcgca gcctgtcgga gcacgagtgg aaggcggtga
 97621 tgggggactc ataccagtgc aagctctgcc gctacaacac ccagctcaag tccaacttcc
 97681 agctgcactg caagacagac aagcacgtgc agaagtacca gctggtggcc cacatcaagg
 97741 agggcggcaa ggccaacgag tggaggctca agtgtgtggc catcggcaac cccgtgcacc
 97801 tcaagtgcaa cgcctgtgac tactcacacc acagcctgga gaagctgcgg ctgcacacgg
 97861 tcaactccag gcacgaggcc agcctgaagt tgtacaaggt aaggcccagc tccttatcgc 158401 cttttgttac ttgcagcacc tgcagcagca tcagagtggt gtagaaggtg agagctgcta Exon 5
158461 ctaccactgc gttctgtgca actactccac caaggccaag ctcaacctca tccagcatgt
158521 gcgctccatg aagcaccagc gaagcgagag cctgcgaaag ctgcagcggc tgcagaaggg
158581 ccttccagag gaggacgagg acctggggca gatcttcacc atccgcaggt gcccctccac
158641 ggacccaggt gagtggtctc acaggcatgg gaggcccagg ttgggcctgg gtgttcacct 239941 tttattttta acccttgaca tgtttttctt ctgtttcaga agaacccatt gaagatgttg Exon 6
240001 aaggacccag tgaaacagct gctgatccag aggagcttgc taaggaccaa gagggcggag 257761 ggtctggctg ctgtattgca tcttctactt tctcttttag catcctccag ccaagcagag Exon 7
257821 aaggagctga cagattctcc tgcaacctcc aaacgcatct ccttcccagg tagctcagag
257881 tctcccctct cttcgaagcg accaaaaaca gctgaggaga tcaaaccgga gcaggtgagg 258061 gatgtaccag tgtccctact gcaagtacag taatgccgat gtcaaccggc tccgggtgca Exon 8
258121 tgccatgacg cagcactcgg tgcaacccat gcttcgctgc ccctgtgcc aggacatgct
258181 caacaacaag atccacctcc agctgcacct cacccactc cacacgtgg cacctgactg
258241 cgtggagaag ctcattatga cggtaaggca gccaggagca gcaccctgtg gtctttctcc 269701 gctcctcagg tgaccacccc tgagatggtg atgccaagca gcatgttcct cccagcagct Exon 9
269761 gttccagatc gagatgggaa ttccaatttg gaagaggcag gaaaccagcc tggtcagtat 271021 gattctgtgt tcatgaggcc tgactaggta gaccgctctg ggtgccatcc ttgaaacaaa
271081 gccttcttta tctttgggtt tgatttttt ttttttttta acagaaacct cagaggatct Exon 10
271141 gggaaagaac atcttgccat ccgcaagcac agagcaaagc gcagatttga aaccatcccc
271201 tgctgaccca ggctctgtga gagaagactc aggcttcatc tgctggaaga aggggtgcaa
271261 ccaggttttc aaaacttctg ctgcccttca gacgcattt aatgaagtgc atgccaagag
271321 gcctcagctg ccggtgtcag atcgccatgt gtacaagtac ccctgtaatc agtgtagcct
271381 ggccttcaag accattgaaa agttgcagct ccattctcag taccatgtga tcagagctgc
271441 caccatgtgc tgtctttgtc agcgcagttt ccgaactttc caggtctga agaagcacct
271501 tgagacaagc cacctggagc tgagtgaggc tgacatccaa cagctttatg gtggcctgct
271561 ggccaatggg gacctcctgg caatgggaga cccactctg gcagaggacc ataccataat
271621 tgttgaggaa gacaaggagg aggagga cttgcaagat aaacaggcc caacgggcag
271681 tgactctggg tcagtacaag aagactcggg ctcagagcca aagagagctc tgcctttcag
271741 aaaaggtccc aattttacta tggaaaagtt cctagaccct tctcgccctt acaagtgtac
271801 cgtctgcaag gaatctttca ctcaaaagaa tatcctgcta gtacactaca attctgtctc
271861 ccacctgcat aagttaaaga gagcccttca agaatcagca accggtcagc cagaacccac
271921 cagcagccca gacaacaaac ctttttaagtg taacacttgt aatgtggcct acagccagag
271981 ttccactctg gagatccata tgaggtctgt gttacatcaa accaaggccc gggcagccaa
272041 gctggaggct gcaagtggca gcagcaatgg gactggcaac agcagcagta tttccttgag
272101 ctcctccacg ccaagtcctg tgagcaccag tggcagtaac accttacca cctccaatcc
272161 aagcagtgct ggcattgctc caagctctaa cttactaagc caagtgccca ctgagagtgt
272221 agggatgcca ccctggggga atcctattgg tgccaacatt gcttcccctt cagagcccaa
272281 agaggcaat cggaagaaac tggcagatat gattgcatcc acgcagcagc aacaacagca
272341 gcagcaacag caacaacaac aacaacaaca acaacaacaa gcacaaacgc tggcccaggc
272401 ccaggctcaa gttcaagctc acctgcagca ggagctgcag caacaggctg ccctgatcca
272461 gtctgcactg tttaacccca ccctcctttcc tcacttcccc atgacaagtg agaccctgct
272521 gcaactacag cagcagcagc acctcctctc tcctttctac atcccagtg ctgagttcca
272581 gcttaaccc gaggtgagct tgccagtgac cagtgggca ctgacactga ctgggacagg
272641 cccaggcctg ctggaagatc tgaaggctca ggttcaggtc ccacagcaga gccatcagca
272701 gatcttgccc cagcagcagc agaaccaact ctctatagcc cagagtcact ctgccctcct
272761 tcagccaagc cagcaccccg aaaagaagaa caaattggtc atcaaagaaa aggaaaaaga
272821 aagccagaga gagagggaca gcgccgaggg gggagagggc aacaccggtc gaaggaaac
```

Fig.51

```
272881 actgccagat gccttgaacg ccaaagagaa gaaagagttg gcaccagcgg gtggttctga
272941 gccttccatg ctccctccac gcattgcttc agatgccaga gggaacgcca ccaaggccct
273001 gctggagaac tttggctttg agttggtcat ccagtataat gagaacaagc agaaggtgca
273061 gaaaaagaat gggaagactg accagggaga gaacctggaa aagctcgagt gtgactcctg
273121 cggcaagttg ttttccaaca tcttgatttt aaagagtcat caagagcacg ttcatcagaa
273181 ttactttcct ttcaaacacc tcgagaggtt tgccaaacag tacagagacc actacgataa
273241 actgtaccca ctgaggcccc agacccaga gccaccacca cctcccctc caccccctcc
273301 accccccactt ccggcagccc cgcctcagcc ggcgtccaca ccagccatcc ccgcatcagc
273361 cccaccatc acctcaccta caattgcacc ggcccagcca tcagtgccgc tcacccagct
273421 ctccatgccg atggagctcc ccatcttctc gccgctgatc atgcagacga tgccgctgca
273481 gaccttgccg gctcagctac cccgcagct gggacctgtg gagcctctgc ctgcgcacct
273541 ggcccaactc taccagcatc agctcaatcc aaccctgctc cagcagcaga caagaggcc
273601 tcgcaccagg atcacagatg atcagctccg agtcttgcgc caatattttg acattaacaa
273661 ctcccccagt gaagagcaaa taaaagagat ggcagacaag tccgggttgc cccagaaagt
273721 gatcaagcac tggttcagca acactctctt caaagagagg cagcgtaaca aggactcccc
273781 ttacaacttc agtaatcctc ctatcaccag cctggaggag ctcaagattg actcccggcc
273841 cccttcgccg gaacctccaa agcaggagta ctggggaagc aagaggtctt caagaacaag
273901 gtttacggac taccagctca gggtcttaca ggacttcttc gatgccaatg cttacccaaa
273961 ggatgatgaa tttgagcaac tctctaattt actgaacctt ccaaccccag tgatagtggt
274021 gtggtttcag aatgcccgac agaaggccag gaagaattat gagaatcagg gagagggcaa
274081 agatggagag cggcgtgacc ttacaaatga tagatacatt cgaacaacca acttgaacta
274141 ccagtgcaaa aaatgtagcc tggtgtttca gcgcatcttt gatctcatca agcaccagaa
274201 gaagctgtgt tacaaggatg aggatgagga ggggcaggac gacagccaaa atgaggattc
274261 catggatgcc atggaaatcc tgacgcctac cagctcatcc tgcagtaccc cgatgccctc
274321 acaggcttac agcgccccag caccatcagc caataataca gcttcctccg ctttcttgca
274381 gcttacagcg gaggctgacg aactggccac cttcaattca aaaacagagg caggcgatga
274441 gaaaccaaag ctggcggaag ctcccagtgt acagccaaac caaacccaag aaaagcaagg
274501 acaaccaaag ccagagctcc agcagcaaga gcagcccgag cagaagacca cactcccca
274561 gcagaagctc cccagctggg tgtccctgcc ttcgttgcca cagcctcctc cacaagcgcc
274621 cctccacag tgcccttac cccagtcgag ccccagtcct tccagctct cccacctgcc
274681 cctcaagccc ctccacacat caactcctca acagctcgca aacctacctc ctcagctaat
274741 cccctaccag tgtgaccact gtaagttggc atttccgtca tttgagcact ggcagcagca
274801 tcagcagctc cacttcctca gcgcgcagaa ccagttcatc caccccccagt ttttggacag
274861 gtccctggat atgcctttca tgctctttga tcccagtaac ccactcctgg ccagccagct
274921 gctctctggg gccataccctc agattccagc aagctcagcc acttctcctt caactccaac
274981 ctccacaatg aacactctca gaggaagct ggaggaaaag gccagtgcaa gccctggcga
275041 aaacgacagt gggacaggag gagaagacc tcagagagac aagcgtttga gaacaaccat
275101 cacaccggaa caactagaaa ttctctacca gaagtatcta ctggattcca atccgactcg
275161 aaagatgttg gatcacattg cacacgaggt gggcttgaag aaacgtgtgg tacaagtctg
275221 gtttcagaac ccccgagctc gggaaaggaa aggacagttc cgggctgtag gcccagcgca
275281 ggcccacagg agatgcccctt tttgcagagc gctcttcaaa gccaagactg ctcttgaggc
275341 tcatatccgg tcccgtcact ggcatgaagc caagagagct ggctacaacc taactctgtc
275401 tgcgatgctc ttagactgtg atgggggact ccagatgaaa ggagatattt ttgacggaac
275461 tagcttttcc cacctacccc caagcagtag tgatggtcag ggtgtccccc tctcacctgt
275521 gagtaaaacc atggaattct cacccagaac tcttctaagc ccttcctcca ttaaggtgga
275581 agggattgaa gactttgaaa gccctccat gtcctcagtt aatctaaact ttgaccaaac
275641 taagctggac aacgatgact gttcctctgt caacacagca atcacagata ccacaactgg
275701 agacgagggc aacgcagata cgacagtgc aacgggaata gcaactgaaa ccaaatcctc
275761 ttctgcacc aacgaaggct tgaccaaagc ggccatgatg gcaatgtctg agtatgaaga
275821 tcggttgtca tctggtctga tcagcccgc cccgagcttt tatagcaagg aatatgacaa
275881 tgaaggtaca gtggactaca gtgaaacctc aagccttgca gatccctcct cccgagtcc
275941 tggtgcgagt ggatctgcag gcaaatctgg tgacagcgga gatcggcctg ggcagaaacg
276001 ttttcgcact caaatgacca atctgcagct gaaggtcctc aagtcatgct ttaatcacta
276061 caggacaccc actatgctag aatgtgaggt cctgggcaat gacattgcac tgcaaagag
276121 agtcgttcag gtctggttcc agaatgcccg ggcaaaagaa aagaagtcca agttaagcat
276181 ggcaagcat tttggtataa accaaacgag ttatgaggga cccaaaacag agtgcacttt
276241 gtgtggcatc aagtacagcg ctcggctgtc tgtacgtgac catatctttt cccaacagca
276301 tatctccaaa gttaaagaca ccattggaag ccagctggac aaggagaaag aatactttga
276361 cccagccacc gtacgtcact tgatggctca acaagagttg gaccggatta aaaaggccaa
276421 cgaggtcctt ggactggcag ctcagcagca agggatgttt gacaacaccc ctcttcaggc
276481 cctttaaacctt cctacagcat atccagcgct ccagggcatt cctcctgtgt tgctcccggg
276541 cctcaacagc ccctccttcc caggctttac tccatccaac acaggtgggt tctgctctag
```

Fig.52

```
280981 ttcctttcag ctttaacgtc tcctaagccg aacttgatgg gtctgcccag cacaactgtt  Exon 11
281041 ccttcccctg gcctccccac ttctggatta ccaaataaac cgtcctcagc gtcgctgagc
281101 tccccaaccc cagcacaagc cacgatggcg atgggccctc agcaaccccc ccagcagcag
281161 cagcagcagc agcaaccaca ggtgcagcag cctccccgc cgccagcagc ccagccgcca
281221 cccacaccac agctcccact gcaacagcag cagcaacgca aggacaaaga cagtgagaaa
281281 gtaaaggaga aggaaaaggc acacaaaggg aaaggggaac cctgcctgt ccccaagaag
281341 gagaaaggag aggcccccac ggcaactgca gccacgatct cagccccgct gccaccatg
281401 gagtatgcgg tagaccctgc acagctgcag gccctgcagg ccgcgttgac ttcggacccc
281461 acagcattgc tcacaagcca gttccttcct tactttgtac caggctttc tccttattat
281521 gctccccaga tccctggcgc cctgcagagc gggtacctgc agcctatgta tggcatggaa
281581 ggcctgttcc cctacagccc tgcactgtcg caggccctga tggggctgtc cccaggctcc
281641 ctactgcagc agtaccagca ataccagcag agtctgcagg aggcaattca gcagcagcag
281701 cagcggcaac tacagcagca gcagcagcaa aaagtgcagc agcagcagcc caaagcaagc
281761 caaacccag tcccccccgg ggctccttcc ccagacaaag accctgccaa agaatccccc
281821 aaaccagaag aacagaaaaa cacccccg gaggtgtccc cctcctgcc gaaactccct
281881 gaagagccag aagcagaaag caaaagtgcg gactccctct acgacccctt cattgttcca
281941 aaggtgcagt acaagttggt ctgccgcaag tgccaggcgg gcttcagcga cgaggaggca
282001 gcgaggagcc acctgaagtc cctctgcttc ttcggccagt ctgtggtgaa cctgcaagag
282061 atggtgcttc acgtccccac cggcggcggc ggcggtggca gtgcggcgg cggcggcggt
282121 ggcggcggcg gcggcggcgg cggctcgtac cactgcctgg cgtgcgagag cgcgctctgt
282181 ggggaggaag ctctgagtca acatctcgag tcggccttgc acaaacacag aacaatcacg
282241 agagcagcaa gaaacgccaa agagcaccc agtttattac ctcactctgc ctgcttcccc
282301 gatcctagca ccgcatctac ctcgcagtct gccgctcact caaacgacag cccccctccc
282361 ccgtcggccg ccgccccctc ctccgcttcc cccacgcct ccaggaagtc ttggccgcaa
282421 gtggtctccc gggcttcggc agcgaagccc ccttcttttc ctcctctctc ctcatcttca
282481 acgttacct caagttcatg cagcacctca ggggttcagc cctcgatgcc aacagacgac
282541 tattcggagg agtctgacac ggatctcagc caaaagtccg acggaccggc gagcccggtg
282601 gagggtccca agacccag ctgcccaag gacagtggtc tgaccagtgt aggaacggac
282661 accttcagat tgtaagcttt gaagatgaac aatacaaaca aatgaattta aatacaaaaa
282721 ttaataacaa accaatttca aaaatagac aactgcaatt ccaaagcttc taaccaaaaa
282781 aca
```

Fig.53

METHOD OF JUDGING GRADE OF MALIGNANCY OF CARCINOMA CELL USING ATBF-1

TECHNICAL FIELD

The present invention relates to a means for determining a grade of malignancy of a cancer cell. More particularly, the present invention relates to a method of determining a grade of malignancy of a cancer cell, as well as a reagent and a kit used in the method.

BACKGROUND ART

A cancer referring to malignant tumors in general presents various pathologic conditions depending upon tissues in which it is formed, genetic factors, environmental factors, and the like, of patients. In treatment of cancers, in general, a therapy that is thought to have the highest efficacy is preferentially selected from chemotherapy, radiation treatment, surgical operation, or the like. In determination of a treatment policy of a cancer, it is extremely important to understand a grade of malignancy of a cancer cell precisely. The grade of malignancy is generally determined by the proliferation potency of cancer cells and the efficacy of chemotherapy or radiation treatment. In cancers having a low grade of malignancy, the proliferation potency is low, and the cancer can be easily removed by surgical excision, or the chemotherapy or radiation treatment is effective, so that the prognosis is good. In cancers having a high grade of malignancy, the proliferation potency is high, and the surgical excision is difficult, or the chemotherapy or radiation treatment is ineffective, so that the prognosis is poor. Cancers having a particularly high grade of malignancy require rapid and exact surgical excision. In such cancers, exact auxiliary treatment (radiation treatment or chemotherapy) is essential. Misjudgement of a grade of malignancy makes it impossible to obtain expected therapeutic effect and causes progression of pathologic conditions, occurrence of serious adverse effect, or recurrence. Actually, in many cases, since there is no effective means for determining a feature of cancer, in particular, a grade of malignancy of cancer, treatment is carried out under wrong treatment policy and effective therapeutic effect cannot be obtained, resulting in the termination of death.

To date, the grade of malignancy of cancers have been tried to be judged (discriminated) by using a maker for pathologic conditions or tumors, employing histopathological examination, and the like. However, a definite judgment method that can be commonly employed in almost all malignant tumors has never been established. Furthermore, in conventional judgment, since two pathologic conditions that have been judged to have the same level of grade of malignancy may have utterly different prognoses, they are desired to be discriminated.

Note here that reports relating to the present invention are listed below.

[non-patent document 1] Miura et al. Cloning and characterization of an ATBF1 isoform that expresses in a neuronal differentiation-dependent manner. J. Biol. Chem. (1995) 270: 26840-26848

[non-patent document 2] Kataoka et al. Alpha-fetoprotein producing gastric cancer lacks transcription factor ATBF1. Oncogene (2001) 20: 869-873

[non-patent document 3] Ishii et al. ATBF1-A protein, but not ATBF1-B, is preferentially expressed in developing rat brain. J. Comparative Neurology (2003) 465: 57-71

[non-patent document 4] Kataoka et al., ING1 represses transcription by direct DNA binding and through effects on p53. Cancer Res. (2003) 15:5785-92.

[non-patent document 5] Noguchi et al., One example of long term survival from AFP production gastric cancer with brain metastasis. Journal of Digestive Surgery, Japan, (2003) 36 (12):1659-1664

[non-patent document 6] Miura et al. Susceptibility to killer T cells of gastric cancer cells enhanced by mitomycin-C induction of ATBF1 and activation of p21 (Waf1-/Cip1) promoter. Microbiol. Immunol (2004) 48: 137-145

[non-patent document 7] Iida et al. Alteration of the AT motif binding factor-1 expression in alpha-fetoprotein producing gastric cancer: is it an event for differentiation and proliferation of the tumors? Oncology Report (2004) 11: 3-7

[non-patent document 8] Kaspar et al. Myb-interacting protein, ATBF1, represses transcriptional activity of Myb oncoprotein. J. Biol. Chem. (1999) 274: 14422-1442

[non-patent document 9] Sun X et al., Frequent somatic mutations of the transcription factor ATBF1 in human prostate cancer. Nat Genet. (2005) Mar. 6; [Epub ahead of print]

DISCLOSURE OF INVENTION

Problems to be Solved by the Invention

As mentioned above, in determining a treatment policy, it is extremely important to precisely determine a grade of malignancy of cancers. On the other hand, judgment of a grade of malignancy of cancers requires not only precision but also speed. That is to say, high therapeutic effect cannot be expected until determination of precise and rapid treatment policy is carried out. Development of techniques capable of determining a grade of malignancy of cancers precisely and speedily as well as without putting a burden on a patient would contribute to the treatment of cancers immeasurably and offer great benefit to patients with cancer.

The present invention addresses the problems discussed above, and aims to provide a means for determining a grade of malignancy of a cancer cell in a simple and easy way.

Means to Solve the Problems

Under the above-mentioned circumferences, the present inventors have focused on ATBF1 (AT motif binding factor 1) and have made various studies on localization of the protein in cells. ATBF1 includes two isoforms having different molecular amounts, which are formed by using different promoters and carrying out selective splicing: ATBF1-A (404 kDa, the amino acid sequence thereof is shown in SEQ ID NO: 2. The base sequence (see, GenBank accession number: L32832) coding for ATBF1-A is shown in SEQ ID NO: 3) and ATBF1-B (306 kDa, the amino acid thereof sequence is shown in SEQ ID NO: 4. The base sequence (GenBank accession number: L32833) coding for ATBF1-B is shown in SEQ ID NO: 5) (see, non-patent document 1). Note here that ATBF1-A has a structure in which N-terminal side of protein is longer by 920 amino acids than that of ATBF1-B.

Firstly, we investigated the relationship between nucleus/cytoplasm movement of ATBF1 and the cell cycle by using cultured cancer cells (basic experiment 1). That is to say, we made an experiment in which cultured cells of P19 mouse undifferentiated embryonic carcinoma cell line are used and stimulated by retinoic acid so that undifferentiated cancer cells are differentiated into nerve cells. As a result, (1) in an undifferentiated state in which differentiation stimulation is not particularly applied to p19 carcinoma cells, the ATBF1 expression was not observed in both the nucleus and the cytoplasm, showing that carcinoma cells were proliferated; (2) in a case where carcinoma cells still maintain the undifferentiated proliferation state even when differentiation of nerve was urged, the ATBF1 expression starts in the cytoplasm but proliferation state of carcinoma cells were still maintained; and (3) when carcinoma cells were changed into a group of differentiated cells having neurite, ATBF1 moved from the cytoplasm to the nucleus and the expression is changed into the expression carried out mainly in the nucleus. It was confirmed that the cell cycle was terminated and proliferation was suppressed. These experiment results indicate that ATBF1 is a protein that actually moves from the cytoplasm to the nucleus as is predicted from the presence of signals retained in the nuclei in two portions and that this movement is associated with the cell cycle arrest.

Next, we studied on the adjustment mechanism of the movement of ATBF1 from the cytoplasm to the nucleus and the export of ATBF1 from the nucleus to the cytoplasm by using cultured cancer cells (basic experiment 2). As a result, in the study on the relation of ATBF1 with respect to a control system relating to the movement between the cytoplasm and the nucleus using P19 cells, only when fibronectin, laminin, gelatin, poly-L-ornithine, and the like, are coated onto a culture dish, P19 cells can be attached well to the cultured dish. Under such conditions, the movement of ATBF1 to the nucleus was observed. This is a change from a floating state to an attached state and is involved in a receptor existing on the surface of the cell, suggesting that information in accordance with the extracellular environment is transmitted to the inside of the cells, thereby determining the intracellular localization of ATBF1. Next, study on the exporting mechanism of ATBF1 from the nucleus to the cytoplasm proved that ATBF1 was actually inhibited from being exported from the nucleus to the cytoplasm and the intranuclear concentration of ATBF1 was clearly increased by the action of inhibitor Leptomycin B of CRM1 (Exportin 1 or chromosome region maintenance 1) and that the number of cells undergoing apoptosis was clearly increased. From these experimental results, it can be determined that the state in which the ATBF1 concentration is increased in the nucleus is a state in which apoptosis of cancer cells is promoted. This is thought to give an important suggestion to the treatment policy of cancers. Furthermore, in the study on the adjustment mechanism of movement of ATBF1 to the nucleus, when two kinds of antagonists (Wortmannin, LY294002) of PI3K (phosphatidylinositol 3-kinase) were acted on P19 cultured cells that had been subjected to retinoic acid treatment in a state in which culture dish was attached, ATBF1 production itself of P19 cells were not affected. However, ATBF1 proteins were gathered around the nucleus in a ring form, but the movement of the proteins into the nucleus tended to be inhibited (the action is stronger in Wortmannin than in LY294002). At the same time, the cell itself maintained the proliferation state. This experiment result means that the movement of ATBF1 to the nucleus depends on PI3K and that when ATBF1 does not move to the nucleus, cells can maintain the proliferation state. Subsequently, in the study on what protein among the PI3K family proteins confirmed in the above-mentioned study is involved in the phosphorylation when ATBF1 moves to the nucleus, caffeine and drugs reported to particularly specifically inhibit the action of ATM (Ataxia Telangiectasia Mutated, causative gene of cerebellar ataxia telangiectasia) were acted on. As a result, the inhibition of the movement to the nucleus was insufficient when PI3K inhibitor, Wortmannin, and LY294002 were used. As compared to this, with caffeine, the movement of ATBF1 to the nucleus in almost all of the culture cells was inhibited. This result means that PI3K involved in phosphorylation in a signal site in the nucleus of ATBF1 is ATM. Furthermore, it means that the introduction of ATBF1 into the nucleus is promoted by the activation of ATM, that is, the perception of DNA disorder due to radiation.

The above-mentioned results of the basic experiments 1 and 2 showed that the movement of ATBF1 from the cytoplasm to the nucleus and further to the cytoplasm switched the time of cell cycle and proliferation state. In order to clarify whether the above-mentioned results were mainly caused by only ATBF1 or acted by some other causes, a forced expression test was carried out in Neuro 2A cells, which were culture cell line derived from mouse neuroblastoma by using an ATBF1 expression vector (basic experiment 3). As a result, in all the cells showing the forced expression of ATBF1, incorporation of BrdU (5-bromodeoxyuridine) was not observed without fail. It was clarified that ATBF1 induced the cell cycle arrest.

We studied on the relationship between the movement of ATBF1 to the nucleus and the proliferation potency in the nerve cells of 14-day embryonal fetal rat brain (basic experiment 4). Firstly, when we examined the 14-day embryonal rat fetal brain tissue, it was confirmed that neuroepithelium cells existing in the paraventricle region uptakes BrdU and ATBF1 was localized in the cytoplasm. Since the nerve cells existing in the differentiating field did not uptake BrdU, it was known that the cell cycle is terminated. ATBF1 was localized in the nucleus. Comparison and observation of intracellular localization of ATBF1 between the neuroepithelium cells having division and proliferation potency at the fetal stage and finally differentiated nerve cells losing its division ability is extremely referential when we consider the grade of malignancy of a cancer. Cancer cells are similar to the normal neuroepithelium cells in having division ability in an undifferentiated state and also in that ATBF1 exists in the cytoplasm. In normal neuroepithelium cells, when ATBF1 moves from the cytoplasm to the nucleus, the neuroepithelium cells change their nature by final differentiation into the nerve cells whose cell proliferation is terminated. Also in cancer cells, two modes as to intracellular localization of ATBF1 are observed. The cancer cells can be classified into a kind having a high grade of malignancy in which ATBF1 exists only in the cytoplasm and a kind having a relatively low grade of malignancy in which ATBF1 exists in the nucleus.

On the other hand, it was proved that the increase in the intracellular concentration of ATBF1 induced the cell cycle arrest and functioned as an index showing the tendency of differentiation of cells. It was experimentally confirmed that molecular mechanism of the movement of ATBF1 to the nucleus was involved in ATM that was a member of the PI3K family protein.

As described in the previous report (non-patent document 6), in cultured cells of gastric cancer, ATBF1 forms a protein-protein binding to tumor suppressor gene p53 and functions. It is thought that this complex of ATBF1 and p53 activates the promoter of tumor suppressor gene p21 so as to lead the increase of expression of p21 and to lead cancer cells to apoptosis. It is clear that when a DNA modification signal is actually activated by acting a kind of anticancer drug (alkylating agent), the ATBF1 expression is induced. The therapeutic effect of cancers largely depends upon the induction of ATBF1 and the effect of the movement of ATBF1 from the cytoplasm to the nucleus. This is a principle by which the present inventors evaluate the apoptosis of various kinds of cancer cells and efficacy of various treatment from the expression mode by applied clinical experiment.

Based on the facts such as the movement of ATBF1 from the cytoplasm to the nucleus, binding between ATBF1 and p53, further, expression induction of p21, and the activation of a DNA repairing signal, and the like, by ATM signal in the above mentioned experiments, the present inventors have examined the intracellular amount and localization of ATBF1 in various cancer cells (herein, cancer cells include benign tumor, benign-malignant borderline lesion, a series of cells toward a malignant tumor), for example, breast cancer, bladder cancer, gastric cancer, lung cancer, neuroblastoma, gastric stromal tumors (GIST), meningioma, prostate cancer (as a comparison material, the present inventors have examined normal human cells as well). Furthermore, as to the case in which prognosis of the patient can be examined, the present inventors have investigated the relationship between the expression mode of ATBF1 and the prognosis. As a result, the cases in which the ATBF1 expression was observed in various human cancer cells, regardless of whether the expression was observed in the nucleus or the cytoplasm, had more excellent prognosis than the case in which the expression was not observed. Furthermore, the localization of ATBF1 in the nucleus and the cytoplasm was also investigated. In the case in which the prognosis was poor, the intracellular amount of ATBF1 in the cells was reduced, showing that the grade of malignancy of a cancer was related with the intranuclear amount of ATBF1. Specifically, in the case in which the prognosis was poor, a larger amount of ATBF1 was present in the cytoplasm than in the nucleus, or ATBF1 was present only in the cytoplasm. Furthermore, some of the cases where the prognosis was poor showed lacking in ATBF1 in both the nucleus and the cytoplasm.

The above-mentioned results clarified that the staining pattern of ATBF1 in the whole cell, in the cytoplasm, or in the nucleus showed the different grades of malignancy of cancers in (1) a case where ATBF1 was localized mainly in the nucleus, (2) a case where ATBF1 was localized mainly in the cytoplasm, and (3) a case where ATBF1 tended to be absence in both the nucleus and the cytoplasm. It was shown that the above-mentioned discrimination enabled the grade of malignancy in cancer cells to be determined.

The present inventors have conducted a further detailed study on the relationship between ATBF1 and the grade of malignancy of cancer cells. That is to say, the present inventors studied on the localization site of ATBF1 protein in various cancer cells by using two kinds of antibodies (antibody name; NT440 and 1-12, see FIG. 31) capable of specifically recognizing the N-terminus side of the ATBF1-A protein (a region corresponding to exon 3 of ATBF1 gene) and an antibody (antibody name; AT6, see FIG. 31) capable of specifically recognizing the C-terminus side of the ATBF1 protein (a region corresponding to exon 11 of ATBF1 gene) in addition to the antibody D1-120 (an antibody specifically recognizing a central portion of the ATBF1 protein, that is, a region corresponding to exon 10 of ATBF1 gene) which was used in the above-mentioned experiments. As a result, the following findings have been obtained.

(1) The sites in which the localization is largely different by the grade of malignancy of cancers are a site recognized by D1-120 (D1-120 site) and a site recognized by AT6 (AT6 site). Therefore, detecting these sites are very important in determining the grade of malignancy of cancers. Furthermore, it is clear that the examination of D1-120 alone is an index for determining the grade of malignancy of cancers (see the below-mentioned Examples). Therefore, it is thought that it is the most important to detect the D1-120 site in determining the grade of malignancy of cancers. On the other hand, it was shown that by examining the localization of the D1-120 site and the AT6 site simultaneously, a method of determining the grade of malignancy having higher specificity can be provided.

(2) In accordance with the study using antibodies other than D1-120, ATBF1 does not always exist as a macro protein in accordance with the kinds or malignancy of a tumor. It was clarified that there was a pathologic condition in which ATBF1 is subjected to processing or ATBF1 undergoes skipping of exon by alternative splicing of mRNA when ATBF1 gene is transcribed, resulting a change in the protein structure (see FIG. 47).

(3) The staining properties of NT440 and 1-12 tended to be localized mainly in the nucleus. Therefore, the detection of a site recognized by these antibodies, that is, a site at the N-terminus of ATBF1 corresponding to exon 3 of ATBF1 gene becomes an index showing that the amount of ATBF1 is increased or decreased or ATBF1 is absent. Furthermore, that fact that NT440 remains in the cytoplasm and 1-12 exists in the nucleus means that the movement in which serine at the 148th position undergoes the phosphorylation and the N-terminus of ATBF1 moves to the nucleus exists. Therefore, by calculating the ratio of protein amount stained by NT440 and I-12, the ratio of movement of the portion to the nucleus can be obtained. Furthermore, a comparison of the presence, absence, or localization of the NT440 site and the 1-12 site with the staining pattern of the antibody (D1-120) recognizing the center of the ATBF1 protein and/or the antibody recognizing the side of C-terminus makes it possible to determine the conditions of processing of ATBF1 protein, furthermore, the skip of exon by abnormal splicing caused in the mRNA level. From the above-mentioned reasons, in order to precisely understand the entire image of a genome structure of ATBF1 that is a huge transcription factor, it is effective that by staining not only by an important antibody corresponding to exon 10 coding for DNA binding domain but also by an antibody corresponding to exon 3 coding for N-terminus (furthermore, antibody exon 11 coding for C-terminus), respectively, and comparison is carried out. Examination of the staining pattern of the antibody recognizing the N-terminus side of ATBF1-A in this way provides an auxiliary but useful information in determining the grade of malignancy of cancer.

(4) The study results to date are classified into two cases, that is, the case where the D1-120 site exists mainly in the nucleus and the case where the D1-120 site exists mainly in the cytoplasm or is absent. Firstly, the case where the D1-120 site exists mainly in the nucleus is further classified into two cases, that is, the case in which the AT6 site is mainly in the nucleus and the case in which the AT6 site is mainly in the cytoplasm. When the expression in the tumor expressing Bcl-2 and Bcl-$x_L$ is related to the ATBF1 expression, [A] when the AT6 site is mainly in the nucleus, it is clear that the expression of Bcl-2 and Bcl-$x_L$ tends to be suppressed, so that it can be determined that the grade of malignancy is low; and [B] when the AT6 site is mainly in the cytoplasm, the expression of Bcl-2 and Bcl-$x_L$ is not suppressed depending upon tumors, so that it can be determined that the grade of malignancy is higher than the case where the AT6 site is mainly in the nucleus.

Next, when the D1-120 site is mainly in the cytoplasm or when the D1-120 tends to be absent, the AT6 site in most of the tumors is mainly localized in the cytoplasm. In general, the D1-120 site and the AT6 site are simultaneously detected in the cytoplasm. However, even in the case where the D1-120 site is absent, exception in which the staining pattern of the AT6 was localized not in the cytoplasm but in the nucleus in some tumors was observed (in the examination to date, as mentioned below, in a specific site of B-cell lymphoma). In this case, only from the observation of the absence of the D1-120 site, it may be determined that the grade of malignancy is extremely high. However, actually, it is theoretically predicted that when the AT6 is localized in the nucleus and that Bcl-2 is suppressed, which is proved by the observation itself. Therefore, in the tumor having the high grade of malignancy in which the same D1-120 site is absent, the diagnosis of a tumor in which the AT6 is localized in the nucleus should be done carefully. As compared with the tumor in which AT6 exists in the cytoplasm, it is thought to be necessary to determine that the grade of malignancy is low.

From the above description, it may be most important to examine the localization of the portion of ATBF1, which can be detected by D1-120 in determining the grade of malignancy of cancers. However, by adding the findings obtained by using AT6, 1-12, and NT440, more detailed determination can be achieved.

From the above-mentioned staining pattern of NT440, 1-12, D1-120 and AT6, in the same tumor, there is no unity that whether staining is localized mainly in the nucleus or mainly in the cytoplasm for each case, that is, a N-terminus site (NT440, 1-12), a site near the center (D1-120), and C-terminus site (AT6). It shows the presence of the pathologic conditions in which the change in the whole structure of ATBF1 protein occurs due to fragmentation by the protein processing, effect of change in the gene level by, for example, the way of exon to be used, mutation, and the like.

Herein, among the antibodies recognizing the region corresponding to exon 3, 1-12 recognizes a state in which serine at the 148th position is phosphorilated and NT440 recognizes the portion of ATBF1 at the N-terminus regardless of the presence or absence of phosphorylation. In the region corresponding to exon 3, it is shown that an nuclear localization signal exists but no nuclear exporting signal exist (see, FIGS. 31 and 33). When this region is separated from the other region, a specific state in which the ATBF1 exists only in the nucleus but does not exist in the cytoplasm is observed. The 1-12 antibody and the NT440 antibody can detect this specific state. On the other hand, AT-6 recognizes a region corresponding to exon 11. Since this region includes neither nuclear localization signal nor nuclear exporting signal in the structure (see FIG. 31 and FIG. 33), when this region is separated from the other region, this region becomes a fragment which cannot move to the nucleus, and may be mainly accumulated in the cytoplasm. AT-6 can specifically detect this state. From the above description, in all cancers (tumors) in which pathologic conditions, in which the entire structure of ATBF1 is changed because ATBF1 undergoes the processing, are predicted, it is preferable that findings of 1-12, NT440, and AT-6 in addition to D1-120 are totally investigated. As a conclusion, by using four antibodies at the same time, the finding of D1-120 and findings of other antibodies, in particular, the finding of AT6 are totally considered so as to make a determination of the grade of malignancy. Thus, the reliability of the determination can be more improved.

As a further theoretical aspect, when various mutations accumulated in ATBF1 genome observed in a prostate cancer and possibility of abnormality of Alternative splicing at the stage of mRNA are investigated in detail, the possibility in the presence of ATBF1 protein from which exon 10 including homeodomains 1 to 4 are skipped can be indicated (see non-patent document 9 and FIG. 37). That is to say, the absence of staining in the D1-120 site (corresponding to exon 10, see FIG. 31) in various tumors (see the below-mentioned Examples) can not only indicate the height of the grade of malignancy of tumor, but also indicate the presence of an abnormal protein from which exon 10 has been skipped. Moreover, the absence of staining of D1-120 has been observed in tumors other than prostate cancer. It is suggested that the mutation of ATBF1 genome and the abnormality in alternative splicing in the mRNA level that have already been recognized in a prostate cancer widely exist in common in other tumors. Furthermore, the examination of the intracellular expression in a particular site of the cell of ATBF1 using antibodies corresponding to exon 3, 10 and 11, the localizations in the nucleus and the cytoplasm are continued to be carried out in parallel to the examination of the sequence in the genome and abnormality in the sequence of mRNA, thereby not only the grade of malignancy of various tumors but also the abnormality in the gene level of the alternative splicing in the predictable mRNA can be detected easily.

The present invention has been completed based on the above-mentioned results and provides the following configurations. That is to say, the present invention relates to a method of determining a grade of malignancy of a test cancer cell, comprising a step of detecting the amount of ATBF1 in a test cancer cell separated from a living organism.

In one embodiment of the present invention, as the amount of ATBF1, at least one selected from the following (1) to (3) are detected.

(1) the intranuclear amount and/or intracytoplasmic amount of a region corresponding to exon 10 of an ATBF1 gene, (2) the intranuclear amount and/or intracytoplasmic amount of a region corresponding to exon 11 of an ATBF1 gene, and (3) the intranuclear amount and/or intracytoplasmic amount of a region corresponding to exon 3 of an ATBF1 gene.

In one preferable embodiment of the present invention, at least (1) is detected. In a further preferable embodiment of the present invention, the above-mentioned (1) to (3) are detected.

A method of the present invention preferably uses an immunohistochemical staining method as a detection method.

As another aspect, the present invention provides a reagent (a reagent for determining the grade of malignancy of a test cancer cell) and a kit (a kit for determining a grade of malignancy of a test cancer cell), which can be used for the method of the present invention. The reagent of the present invention comprises an anti-ATBF1 antibody. As the anti-ATBF1, (1) an antibody recognizing a region corresponding to exon 10 of the ATBF1 gene, (2) an antibody recognizing a region corresponding to exon 11 of the ATBF1 gene, or (3) an antibody recognizing a region corresponding to exon 3 of the ATBF1 gene can be used.

The kit of the present invention comprises one or more antibodies selected from the group consisting of the following (1) to (3).

(1) An antibody recognizing a region corresponding to exon 10 of the ATBF1 gene, (2) an antibody recognizing a region corresponding to exon 11 of the ATBF1 gene, and (3) an antibody recognizing a region corresponding to exon 3 of the ATBF1 gene.

In the preferable embodiment, the kit of the present invention additionally comprises ATBF1. Furthermore, when an antibody produced by using an antibody that is a fusion protein with a tag or a carrier protein is used for a kit, furthermore, the kit may additionally comprises the tag or the carrier protein.

Effect of the Invention

According to the present invention, the grade of malignancy of a test cancer cell can be determined in a simple way. The method of determining the grade of malignancy of the present invention can be used for predicting the proliferation potency of cancer that can be expressed by using an index such as proliferation rate, infiltration tendency and easily metastatic property. Furthermore, the results obtained by the present invention can be used for predicting the efficacy of chemotherapy or radiation treatment. Thus, by predicting and determining the two important factors for evaluating the cancer: (1) proliferation potency of cancer and (2) efficacy of various treatment, the present invention provide useful information in selecting treatment.

BRIEF DESCRIPTION OF DRAWINGS

FIG. 1 schematically illustrates a mechanism in which DNA damaging terminates the cell cycle.

FIG. 2a shows P19 cells on which no retinoic acid (RA) act. Neither ATBF1 nor β-tubulin are expressed. FIG. 2b shows p19 cells at 24 hours after retinoic acid (RA) act on, showing that β-tubulin is negative but staining of ATBF1 is observed in the cytoplasm. FIG. 2c shows P19 cells at four days of further culturing after the action of retinoic acid (RA) was terminated. The staining of ATBF1 is concentrated on the nucleus. In the cytoplasm, in the periphery of the cell group, β-tubulin positive neurite is extending. FIGS. 2d, 2e, and 2f show the analysis results of flow cytometry of P19 cells shown in FIGS. 2a, 2b, and 2c, respectively. Only FIG. 2f shows the cell cycle arrest.

FIG. 3a shows a potential position of a nuclear reserve signal in ATBF1 by computer analysis. The presence of sequence similar to the consensus sequence are predicted in two positions (respectively start from the 277th position of amino acid and 2987th position of amino acid). FIG. 3b shows a potential position of nuclear exporting signal in ATBF1. The presence of the nuclear exporting signal are predicted in three positions (respectively start from the 1267th, 2471st, and 2504th positions of amino acid).

FIG. 4a shows an ATBF1 expression in P19 cells when a culture dish is not coated. The cells are in a floating state and ATBF1 appears in the cytoplasm but does not move to the nucleus. FIG. 4b shows an ATBF1 expression of P19 cells at three hours of culturing after a culture dish is coated with fibronectin and poly-L-ornithine. The movement of ATBF1 to the nucleus is observed. FIG. 4c shows a state at 24 hours, showing that expression of ATBF1 in the nucleus is apparently enhanced.

FIG. 5a shows an expression state of ATBF1 in P19 cultured cells when Leptomycin B is not allowed to act on. ATBF1 is observed in the nucleus. FIG. 5b shows an expression state of ATBF in P19 cultured cells when Leptomycin B is allowed to act on. It is clearly shown that the intranuclear concentration of ATBF1 has increased.

FIG. 6a shows an ATBF1 expression in the nucleus of P19 cells. FIG. 6b shows a state in which ATBF1 is inhibited from moving into the nucleus by the action of Wortmannin and ATBF1 is mainly present in the cytoplasm. FIG. 6c shows a state in which that ATBF1 is partially inhibited from moving into the nucleus by the action LY294002. However, it is understood that this inhibition effect is smaller than that by Wortmannin. FIG. 6d shows the effect of caffeine. It is shown that ATBF1 was more completely inhibited from moving to the nucleus as compared with the cases using Wortmannin and LY294002.

FIG. 7c shows the result of experiment only HA tags are introduced without ATBF1 and shows that about 40% BrdU positive cells exhibit double-positive for HA tag and shows yellow as shown in hatched portion. On the other hand, all of the HA tagged gene introduced cells containing cDNA of ATBF1 show red and shows exhibit negative for BrdU. In addition to the results of gene introduction experiment, the cell cycle of each group of cells was detected furthermore by using FACScan. As compared with the cell cycles in the gene introduction group containing only HA tags shown in FIGS. 7d and 7e, the cell cycle of the gene introduction group containing ATBF1 cDNA is completely terminated in the G1/G0 stage by the forced expression of ATBF1. This is shown because of the fact that cell group in M1 region, that is, in the G1/G0 stage are increased by 10% or more and DNA introduction efficiency.

FIG. 8a is a BrdU-stained image. The expression of the BrdU is apparently different between the position of the paraventricle region (solid line) and the differentiating field (dotted line). The paraventricle region includes a large number of BrdU positive cells. Meanwhile, most of the differentiating field is negative to BrdU. FIG. 8b is an ATBF1-stained image. In the paraventricle region (solid line), the localization of ATBF1 is observed also in the cytoplasm. On the contrary, in the differentiating field (dotted line), ATBF1 is mainly in the nucleus. FIGS. 8c and 8d is a magnified view showing the sites. As shown by black arrows in FIG. 8c, DAB reacted products (black) are present mainly in the nucleus. FIG. 8e is a fluorescence stained image (white: positive). As shown by white arrows, it is apparent that ATBF1 is present mainly in the nucleus. As shown by black arrows of FIG. 8d, DAB reacted products (black) are also localized in the cytoplasm. In the fluorescence stained image of FIG. 8f (white: positive), it is apparent that ATBF1 is present in the cytoplasm and as shown by white arrows, the nucleus are shown in black in which no expression is observed.

FIG. 9 shows the differences of staining properties by antigen activation methods carried out with respect to non-infiltrating cancer and infiltrating cancer cases in urothelial carcinoma of the urinary bladder. Autoclave treatments using various buffers were carried and ATBF1 staining was carried out. Black circle mark (●) represents that staining was observed mainly in the nucleus and white circle mark (○) represents that staining was observed mainly in the cytoplasm.

FIG. 10 shows the differences of staining properties by antigen activation methods carried out with respect to non-infiltrating cancer and infiltrating cancer cases in urothelial carcinoma of the urinary bladder. Microwave oven treatments using various buffers were carried and ATBF1 staining was carried out. Black circle mark (●) represents that staining was observed mainly in the nucleus and white circle mark (○) represents that staining was observed mainly in the cytoplasm.

FIG. 11 shows the differences of staining properties by antigen activation methods carried out with respect to non-infiltrating cancer and infiltrating cancer cases in urothelial carcinoma of the urinary bladder. Pressure cooker treatments using various buffers were carried and ATBF1 staining was carried out. Black circle mark (●) represents that staining was observed mainly in the nucleus and white circle mark (○) represents that staining was observed mainly in the cytoplasm.

FIG. 13a (HE stained image) and FIG. 13b (ATBF1-stained image) show sites a 53-year-old woman case in which the staining is localized in the lactiferous duct of the papillary duct adenocarcinoma. When the site in the mammary gland (a portion surrounded by a square in FIG. 13a) in the mammary gland is histologically stained with ATBF1, it is apparently shown that cells in which ATBF1 is localized in the nucleus as shown by black arrows are observed together with cells in which ATBF1 is localized in the cytoplasm as shown by white arrows (FIG. 13b). FIG. 13c (HE stained image) and FIGS. 13d and 13e (ATBF1-stained images) show a 66-year-old woman case in which papillary duct adenocarcinoma exists in the lactiferous duct and central part induces necrosis and so-called comedocarcinoma (FIG. 13c). ATBF1 is localized in the nucleus in most part of the lactiferous duct as shown by arrows (FIGS. 13d and 13e). FIG. 13f (HE stained image) and FIG. 13g (ATBF1-stained images) show a 50-year-old woman case of papillary duct adenocarcinoma in which infiltration is localized in the mammary gland (FIG. 13f). ATBF1 is localized in the cytoplasms in almost all the cells (FIG. 13g) showing the large granular staining. FIG. 13h (HE stained image) and FIG. 13i (ATBF1-stained images) show a 73-year-old woman case of the papillary duct adenocarcinoma in which of in filtration is observed from the mammary gland tissue to the surrounding tissue. ATBF1 is localized in the cytoplasm as shown by arrows (FIG. 13i). As compared with the staining pattern shown in FIG. 13g, the amount of ATBF1 tends to be apparently small. FIG. 13j (HE stained image) and FIG. 13k (ATBF1-stained images) show a 53-year-old woman case of scirrhous carcinoma in which infiltration is observed in a way in which tumors are separately present in the mammary gland (FIG. 13j). ATBF1 is partially localized in the cytoplasm as shown by black arrow but a site cancer cells lacking ATBF1 is observed (FIG. 13k).

In FIG. 15, HE-stained images (a1, b1, c1, and d1) and ATBF1-stained images (a2, b2, c2, d2, and d3) are shown. FIG. 15a shows a papillary intraepithelial carcinoma in which nuclei are small in size and regularly arranged, so that the carcinoma is judged to be in WHO Grade I (a1). The expression of ATBF1 in a site surrounded by black is localized in the nucleus as shown by black arrow (a2). FIG. 15b shows a papillary intraepithelial carcinoma in which nuclei are small in size and regularly arranged, and that carcinoma of WHO Grade I (upper part in b1) and carcinoma of WHO Grade II (lower part of b1) in which nuclei are large and less regulated are mixed. When ATBF1 expression at the boarder site surrounded by black is examined, ATBF1 is localized mainly in the nucleus shown by black arrow in the site of Grade I while ATBF1 is localized mainly in the cytoplasm shown by white arrow in the site of Grade II (b2). In an infiltrating cancer shown in FIG. 15c, from a state that tumors are infiltrated and developed in the subepithelial connective tissue and vessels and that small cells and large cells are included, it can be that the tumor is in WHO Grade II (c1). When the ATBF1 expression in the cells infiltrating in the connective tissue surrounded by black is observed, the large granular staining is shown in the cytoplasm (c2) as shown in black arrow. FIG. 15*d* shows an infiltrating cancer of WHO Grade III in which cells are arranged with high density and extremely large nuclei are included (d1). When the ATBF1 expression in the two infiltrated sites surrounded by black is examined, a site in which ATBF1 is localized in the cytoplasm as shown in white arrow (d2) and a site that has a small amount of ATBF1 expression and tends to lack ATBF1 expression both in the nucleus and the cytoplasm as show in black arrow (d3) are included together.

FIG. 16*a*1 shows gastric type adenoma or an atypical epithelial nest showing dense proliferation in an atypical tubular adenoma including cubic eosinophilic cells. ATBF1 is localized in the nucleus shown by arrows (a2), apparently showing the expression of p53 in the nucleus (a3) and the expression of p21 in the nucleus (a4). FIG. 16*b*1 shows moderately atypical adenoma or atypical epithelial nest in which not-aligned intestinal type small tubular adenomas are gathered. ATBF1 is localized mainly in the nucleus as show by arrow (b2) and the expression of p53 and p21 is also observed (b3 and b4). FIGS. 16*c*1, *c*2, *c*3 and *c*4 show highly atypical adenoma or an adenoma of boarder region or an atypical epithelial nest of an intestinal type tubular adenoma in which the nucleus has a long shape and highly layered. ATBF1 is localized mainly in the cytoplasm as show by arrow (c2), staining of p53 is observed but p21 is not expressed (c4).

FIG. 17*a*1 (HE-stained image) shows a well-differentiated tubular adenocarcinoma having a structure including small and large tubular adenocarcinomas developed in a state in which they infiltrate into the subepithelial portion in an esophagus flat epithelium (dotted line arrow). In some sites (black square frame), as shown by arrow, a site in which ATBF1 is localized in the cytoplasm (a2, ATBF1-stained image) and a site lacking ATBF1 (a3, ATBF1-stained image) are present together. FIG. 17*b*1 (HE-stained image) shows a moderately-differentiated tubular adenocarcinoma having a structure including small and large tubular adenocarcinomas existing in a state in which they are densely and irregularly adhered. In most of the cells, ATBF1 shows localization of the cytoplasms as shown by arrows (b2, ATBF1-stained image).

FIG. 18*a*1 (HE-stained image) shows adenocarcinoma showing solid growth. FIGS. 18 *a*2 and *a*4 (HE-stained images) are magnified views of a site surrounded by square in FIG. 18*a*1 showing that the adenocarcinoma is solid and lacks tubular adenocarcinoma formation. Although HE-stained images show similar structures, a site lacking ATBF1 (a3, ATBF1-stained image) and a site in which ATBF1 is localized in the cytoplasm as shown by arrow (a5, ATBF1-stained image) are present together. FIG. 18*b*1 (HE-stained image) shows separate infiltration of anaplastic carcinomas with high ratio of nucleus/cytoplasm. As shown by arrow, ATBF1 is localized in the cytoplasm (b2, ATBF1-stained image).

FIG. 19*a*1 (HE-stained image) shows the infiltration of a signet ring cell in which the nucleus is put aside by mucus drop. There are a case in which ATBF1 is localized in the cytoplasm of the signet ring cell as shown by black arrows and a case in which ATBF1 lacks staining as shown by dotted line arrows. Such cells are mixed so as to form an infiltration portion. FIG. 19*b*1 (HE-stained image) shows the inside of the lymph duct of the gallbladder wall (square in the left upper part) and shows a signet ring cell showing infiltration in the connective tissue (square in the right lower part). ATBF1 are absent inside the lymph duct (b2, ATBF1-stained image) and the infiltrated portion (b3, ATBF1-stained image).

FIG. 20*a* (HE-stained image) shows a site in which Paget cells are present in the epidermis of the penis skin (site at the left side in a) and a site in which cells gradually infiltrate so as to form a tumor (site at the right side in a). FIG. 20*b*1 (HE-stained image) shows that the Paget cells localized in the epidermis are scattered. In the site, ATBF1 is localized mainly in the nucleus (b2, ATBF1-stained image). FIG. 20*c* 1 (HE-stained image) shows a site in which the infiltration tendency is shown in a portion lower than the epidermis. In this site, as shown by arrow, ATBF1 is localized in the cytoplasm (c2, ATBF1-stained image). In the tumor formation portion (a, HE-stained image), ATBF1 expression is observed mainly on the entire surface of the tumor (d, a site shown by arrows in the ATBF1-stained image), showing the tendency in which ATBF1 is absent in a deep inner part of the tumor. FIGS. 20*e*1 and 20/1 (both are HE-stained images) show the infiltration of the funicular tumor. FIG. 20*e*2 (ATBF1-stained image) shows that ATBF1 is highly localized in the cytoplasm on the surface of the tumor as shown by arrows. FIG. 20/2 (ATBF1-stained image) shows that ATBF1 is absent in a deep inside part of the tumor as shown by arrows.

FIG. 20*g*1 (HE-stained image) shows that tumor metastasis is observed in the lymphoid tissue and the lymph duct (dotted line arrow) in the groin lymph node. FIG. 20*g*2 (ATBF1-stained image) shows that Paget cells existing in the lymph duct (dotted line arrow) lack ATBF1 as shown by arrows.

FIG. 21*a* is a structural image of a HE-stained image of bone marrow, showing marrow cells (bone marrow cells) with slightly hyperplasia. Although not apparent from the drawing, three kinds of hematopoietic cells, that is, leukocyte, erythrocyte and platelet hematopoietic cells are present. FIG. 21*b* (ATBF1-stained image) shows that ATBF1 is positive in a part of the cell group of bone marrow. The magnified part thereof is shown in FIG. 21*c* (ATBF1-stained image). Cells in which ATBF1 is localized mainly in the cytoplasm as shown by a dotted line arrow is observed and the cell group in which staining of ATBF1 is strong both in the nucleus and the cytoplasm is apparently present shown by arrows.

FIG. 22*a*1 (ATBF1-stained image) shows the formation of tumor having a diameter of about 1 cm existing in the lung as shown by arrows. The magnified image thereof is shown in FIG. 22*a*2 (ATBF1-stained image), showing that the tumor cells are proliferated in a way which they are substituted for pulmonary alveolus epithelium and intestinal connective tissue is increased. Since the tumor cells tend to be flat and regularly arranged and the nucleus swelling of the tumor remains slight, the tumor can be diagnosed to be low grade atypical adenomatous hyperplasia (low-grade AAII). When the drawing is further magnified, as shown in FIG. 22a3 (ATBF1-stained image), ATBF1 is observed in the nucleus in the tumor cell. FIG. 22b1 (HE-stained image) shows the formation of tumor having a diameter of about 7 cm existing around the bronchioles of the lung as shown by arrows. FIG. 22b2 (HE-stained image) is a magnified view of FIG. 22b1, showing that the tumor cell is present in a way in which it is substituted for the pulmonary alveolus epithelium, interstitial tissue is increased, lymphocyte infiltrates, the sizes of the tumor cells are not uniform, and the cell density is higher and the cell length is longer than those of the low-grade AAH shown in FIGS. 22a1, a2 and a3. As a result, the tumor can be diagnosed to be high grade atypical adenomatous hyperplasia (high-grade AAH). FIGS. 22b3 and b4 (ATBF1-stained images, arrow) show that ATBF1 is localized mainly in the nucleus in almost all the tumor cells. FIG. 22c1 (HE-stained image) shows the formation of tumor having a diameter of about 1.8 cm existing in a range shown by arrow, showing that a site in which the pulmonary alveolus collapses to form fibrosis is mixed as shown by dotted line arrow. FIG. 22c2 (HE-stained image) is a magnified view of FIG. 22c1, which is similar to the structural image of FIG. 22b2 but the cell density is somewhat higher and in which cells having remarkable nucleus swelling are mixed. As shown it FIG. 22c3 (HE-stained image), in the tumor in which the pulmonary alveolus collapse and fibrosis are observed, the cells are arranged with high density. FIG. 22c2 has a problem in discrimination with respect to AAH. By comprehensively judging together with FIG. 22c2, the tumor can be diagnosed to be a bronchiolus alveolar cell carcinoma (BAC) and Noguchi's classification B. In the site in which the tumor cells are arranged in a way in which they are substituted for a pulmonary alveolus epithelium, as shown by white arrows in FIG. 22c4 (ATBF1-stained image), ATBF1 staining is observed in the cytoplasm in most part although a site in which staining is partially present in the nucleus is mixed as shown by black arrows. Furthermore, FIG. 22c5 (ATBF1-stained image) apparently shows that in the site in which pulmonary alveolus collapse and fibrosis are observed, ATBF1 is localized in the cytoplasm in almost all the cells as shown by arrows.

As shown in FIG. 26a, histologically, the tumor includes small circular or short spindle cells, which increase with high density and in a solid state, accompanying a small amount of blood vessel connective tissues. The tumor is shown to have many nucleus mitosis images and proliferate fast. The arrangement has a solid and alveolus state. FIG. 26b is a low magnification ATBF1-stained image, showing that the amount of ATBF1 expression of the tumor is larger as compared with that of the other kinds of tumor cells. As shown in FIGS. 26c and 26d, depending upon the sites, a site in which the staining is mainly observed in the nucleus (c) and a site in which the staining is mainly observed in the cytoplasm (d) are mixed. FIG. 26e shows that the staining is observed mainly in the nucleus, showing strong ATBF1 expression in the nucleus as shown by white arrows. At the same time, ATBF1 staining is observed in the cytoplasm around the nucleus. It is clear that both the nucleus and the cytoplasm may be stained in the tumor cells. FIG. 26f shows a site in which staining is observed in the nucleus (dotted line arrows) and staining is observed in the cytoplasm (arrows); and FIG. 26g shows a site in which staining is observed mainly in the cytoplasm (arrows).

FIG. 27a shows a left adrenal tumor image of eight-month-old girl. The tumor is histologically diagnosed to be poorly differentiated neuroblastoma, low MKI and favorable histology group. As shown by arrows in FIG. 27b, ATBF1 is localized in the nucleus in almost all the cells except for small number of cells. On the contrary, FIG. 27c is a tumor tissue image of retroperitoneal lymph node of 2-year-old boy. In the image, tumor cells invading into the vessel are observed. The tumor is histologically diagnosed to be poorly differentiated neuroblastoma, low MKI and unfavorable histology group (in detail observation, the tumor is low MKI but anaplasia is remarkable. The about 10 points/high power field of mitosis are recognized). As shown by arrows in FIG. 27d, ATBF1 tends to be localized in the cytoplasm in almost all the cells.

FIG. 29a1 shows fibrous meningioma including long fibrous tumor cells, showing that ATBF1 is localized only in the nucleus of the long cell as shown by arrows (a2). FIG. 29b1 is meningocortical meningioma showing a partial whorl formation in which ATBF1 is localized in the nucleus of the tumor cell (b2). FIG. 29c1 shows partial brain infiltration, which is atypical meningioma having apparently higher density compared with the meningioma shown in FIGS. 29a1 and 29b1 and in which ATBF1 is localized in the cytoplasm in most of the tumor cells as shown by arrow (c2). FIG. 29d1 shows clear cell meningioma having bright cytoplasm and cells rich in glycogen. As shown by arrows, ATBF1 is localized in the cytoplasm in most of the tumor cells (d2).

FIG. 31 shows brief explanations of NT440 and 1-12 recognizing the N-terminus, D1-120 recognizing the central part, and AT6 recognizing the C-terminus of ATBF1; the corresponding relationship between each exon of the ATBF1 gene and sequence of protein; and amino acid sequence of the polypeptide used for immunization, respectively. As to NT440 and 1-12, the difference in the sequence of ATBF1 between human and mouse is shown.

FIG. 32A shows distribution of Bcl-2 in the lymphoid follicle and a site including a marginal region. FIG. 32B-1 shows AT6 staining in the site, FIG. 32B2 shows a magnified view of the lymphoid follicle site, and FIG. 32B3 is a magnified view of a marginal region. The staining of ATBF1 other than AT6 with respect to a site including both the marginal region and the lymphoid follicle portion is shown in FIG. 32C (NT440), FIG. 32D (1-12) and FIG. 32E (D1-120).

FIG. 33A schematically shows the positions of antibodies in an ATBF1-A protein. FIGS. 33B and 33C schematically show the staining strength of each antibody in the sites including the lymphoid follicle and the marginal region, localization ratio of the nucleus and the cytoplasm, positions of protein processing assumed from the staining pattern, and further a state in which the localization of AT6 site mainly in the nucleus suppresses the transcription of the bcl-2 gene and does not suppress the transcription of the bcl-2 gene when the localization of AT6 site is changed to the cytoplasm.

FIG. 43 shows an esophagus tumor formation image (A, HE), a NCAM (CD56) positive image (B), lymph duct invasion (C, HE), a site histologically showing funicular and tenioid arrangements (D, HE, black arrow), and a site showing a solid arrangement (D, HE, white arrow).

FIG. 44 shows the results of staining of HE (A1, 2), NT440 (B1, 2), 1-12 (C1, 2), D1-120 (D1, 2) and AT6 (E1, 2) in a site showing a funicular and tenioid well-differentiated arrangements (A1-E1) and a site showing a dense and focal poorly-differentiated arrangement (A2-E2) and the summary thereof (F, G).

FIG. 48 shows the difference in ATBF1 expression and Bcl-2 staining between the central portion (A) of the tumor and the marginal portion (B) of the tumor. FIG. 48 shows the stained image of the tumor with NT440 (A1, B1), 1-12 (A2, B2), D1-120 (A3, B3), AT6 (A4, B4), and Bcl-2 (A5, B5).

FIG. 49 summarizes and shows the staining properties of the central part of the tumor (A) and the marginal portion of the tumor (B).

FIG. 50 is a sequence showing each exon (exon 2 to 11) of ATBF1. The underlined parts show the exon regions. On the right upper part of the sequence of each exon, exon number is given. The exon numbers are given as follows: an untranslated region specific to ATBF1-B existing in the 5' most upstream of the ATBF1 gene is defined as number 1, the following exon of an untranslated region specific to ATBF1-A following to the exon 1 is defined as number 2, an exon including the first ATBF1-A translated region is defined as number 3, and to the following exons, numbers 4 to 11 are given.

FIG. 51 shows a continuation part of FIG. 50.
FIG. 52 shows a continuation part of FIG. 51.
FIG. 53 shows a continuation part of FIG. 52.

BEST MODE FOR CARRYING OUT THE INVENTION

In the present invention, the term "test cancer cell" refers to a subject cell whose grade of malignancy is to be determined by the method of the present invention. The test cancer cell is separated from a living organism. That is to say, the present invention is applied to a test cancer cell in a state in which it is separated from a living organism. The term "separated from a living organism" refers to a state in which a test cancer cell is completely isolated from a living organism from which the test cancer cell is derived by extracting a part of the living organism in which the test cancer cell exists. The test cancer cell is generally prepared in a state in which it exists in a living organism, that is, a state in which it is bound to surrounding cells and used in the present invention. Note here that after the test cancer cell is separated (isolated) from the surrounding cells, it may be used in the present invention.

The test cancer cell in the present invention includes a cell that is determined to be a cancer by the other diagnostic method, a cell that is determined to have a high probability of being a cancer, and a cell having a probability of being a cancer. Preferably, a cell that is determined to be a cancer by another diagnostic method or a cell that is determined to have a high probability of being a cancer is used. Herein, an example of the other diagnostic method includes X-ray contrast radiography, endoscopy, an ultrasonic diagnostic method, computed tomography, MRI examination, PET examination, a diagnostic method using a tumor marker, and the like. In general, a test cancer cell is collected from a tissue that is suspected to be a cancer by one or more of these methods.

In the present invention, "cancer" is broadly interpreted and includes carcinoma and sarcoma. Furthermore, the term "cancer" used in the present invention the present invention is used compatibility with "tumor." Furthermore, a state before pathological diagnosis is established, that is, before the tumor is determined whether benign or malignant, the cancer may comprise comprehensively benign tumor, benign-malignant borderline lesion, and malignant tumor.

"ATBF1" refers to AT motif binding factor 1. ATBF1 is known to be bound to AT-rich domain of an AFP (alpha fetoprotein) regulation factor so as to downregulate the expression of AFP genes (see, non-patent document 1). As mentioned above, "ATBF1" has two isoforms (ATBF1-A and ATBF1-B). In the present application, the term "ATBF1" is intended to include these two isoforms. Therefore, unless otherwise mentioned, the "amount of ATBF1) means the total amount of each isoform. In the method according to the present invention, in principle, the total amount is employed for detection. However, the amount of either isoform may be employed for detection. Note here that when simply specified "ATBF1" is used, except for the case where it is clear to have other meanings, it means an ATBF1 protein.

Figure 47:
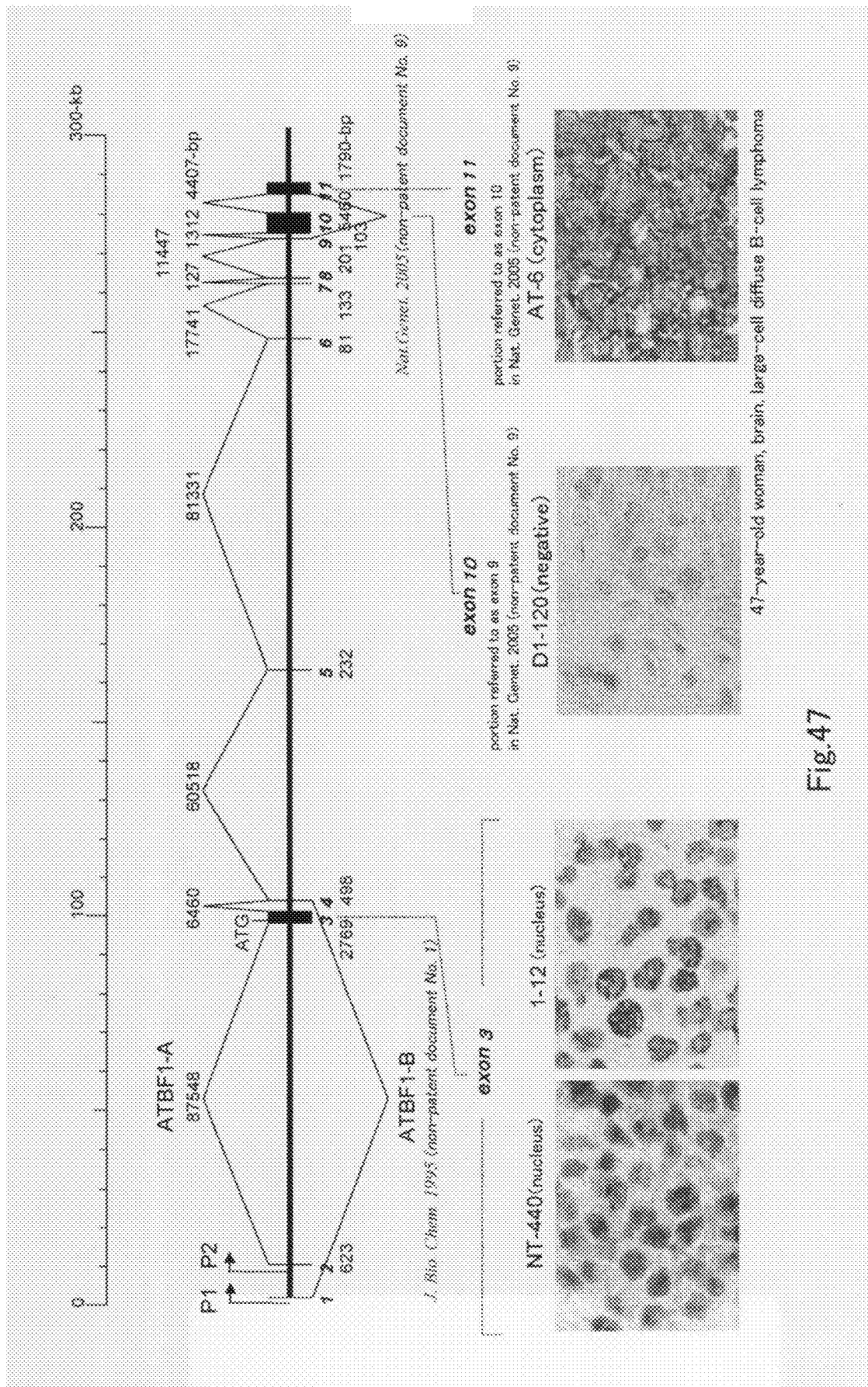
FIG. 47 is a view to illustrate the outline of the use of different promoters shown in the non-patent documents 1 and 9, the mechanism in which two kinds of mRNA of ATBF1-A, B2 are produced by Alternative splicing, and production of mutant protein by abnormal skipping of exon 10 in a human malignant tumor. The lacking of staining of the D1-120 site is shown by taking the case of cerebral large-cell diffuse B lymphoma of a 47-year-old woman described in FIG. 46 as an example.

A structure of an ATBF1 gene is shown in FIG. 47 (see, non-patent document 1 and non-patent document 9). Furthermore, the sequence of exons 2 to 11 of ATBF1 gene are shown in FIGS. 50 to 53. The ATBF1 gene includes exons 1 to 11. As a result of selective splicing, mRNAs of ATBF1-A and ATBF1-B are formed. In FIG. 47, regions shown as exons 10 and 11 are described as exons 9 and 10 in non-patent document 9, respectively.

The amino acid sequences and the base sequences corresponding to exon 3, exon 10 and exon 11 are described as the following SEQ ID numbers in the attached sequence list.

The amino acid sequence (SEQ ID NO: 11) of the region corresponding to exon 3, the base sequence (SEQ ID NO: 12) of exon 3, the amino acid sequence (SEQ ID NO: 13) of the region corresponding to exon 10, the base sequence (SEQ ID NO: 14), amino acid sequence (SEQ ID NO: 15) of the region corresponding to exon 11, and base sequence (SEQ ID NO: 16) of exon 1.

An "amount of ATBF1 in a test cancer cell" refers to the total amount of internuclear ATBF1 and intercytoplasmic ATBF1 in a test cancer cell. In this specification, specification, the "amount of ATBF1 in a test cancer cell" also refers to an "amount of ATBF1 in a whole cell." On the other hand, the "amount of ATBF1 in the nucleus" refers to the amount of ATBF1 existing in the nucleus of the test cancer cell. Similarly, the "amount of ATBF1 in the cytoplasm" refers to the amount of ATBF1 existing in the cytoplasm of the test cancer cell.

The term "detect an amount of ATBF1" refers to finding the amount of ATBF1 as an absolute amount or relative amount. The reference of the relative amount may be an amount of ATBF1 of a standard sample prepared in accordance with the grade of malignancy. Alternatively, when the subject to be detected is ATBF1 in the nucleus, the amount of ATBF1 in the cytoplasm can be used as a standard of the amount of ATBF1 amount. Similarly, when the subject to be detected is the amount of ATBF1, the amount of ATBF1 in the nucleus can be used as a standard of the amount of ATBF1 amount. Note here that "the amount of ATBF1 is detected" may be examining whether or not ATBF1 exists. In general, the presence or absence of ATBF1 and the amount of ATBF1 if any are examined. It is not always necessary to precisely quantify the amount of ATBF1. For example, by compared with the ATBF1 of control that is to be an index for the grade of malignancy, the amount of ATBF1 can be measured to the level in which the grade of malignancy of the test cancer cell can be determined.

The first aspect of the present invention relates to a method of determining a grade of malignancy of a test cancer cell (malignancy grade determination method).

In the present invention, "malignancy grade determination method" refers to a method of determining a grade of malignancy of a test cancer cell. In general, the grade of malignancy of a cancer is conventionally classified (determined) based on the cellular atypia, heteromorphic property in construction of cells and tissues, proliferation property, infiltration property, metastatic property, and the like. In general, it is thought in cancers with low grade of malignancy that there is a case where the proliferation rate of cells is slow, so that infiltration metastasis is not likely to occur and surgical excision is easy, and a case where chemotherapy and radiation treatment are effective, so that the size of a tumor can be reduced. The combination thereof makes prognosis good. On the contrary, it is thought in cancers with high grade of malignancy that there is a case where the proliferation rate of cells is fast, so that infiltration metastasis is likely to occur and surgical excision is difficult, and a case where chemotherapy and radiation treatment are not effective, so that the size of the tumor cannot be reduced. The combination thereof makes prognosis poor. In the case of a cancer with particularly high grade of malignancy, rapid and exact surgical excitation is desired, and combined modality treatment including exact auxiliary treatment (radiation treatment or chemotherapy) becomes essential. The present invention can use, as a reference of the grade of malignancy, prediction of the ease in infiltration and metastasis caused by the proliferation rate of a cancer, that is, prediction of the proliferation potency, and prediction as to whether or not the therapeutic effect of chemotherapy or radiation treatment is obtained. Therefore, when a cancer shows low proliferation potency (cell cycle is likely to be terminated) and is predicted that chemotherapy or radiation treatment is effect (apoptosis is likely to be introduced by DNA damaging), it can be said that the cancer has low grade of malignancy. On the contrary, when a cancer shows high proliferation potency (cell cycle is not likely to be terminated) and is predicted that chemotherapy or radiation treatment is not effect (apoptosis is not likely to be introduced even by DNA damaging), it can be said that the cancer has high grade of malignancy. Herein, the reason why two factors, that is, proliferation potency and the effect of chemotherapy or radiation treatment should be considered and points to be noted therefor will be described by taking small cell carcinoma of the lung (oat cell carcinoma) as an example. In general, small cell carcinoma of the lung is known to be highly malignant and have poor prognosis. However, in rare cases, by carrying out chemotherapy at the early stage, the carcinoma can be completely cured. According to the research by the present inventors, small cell carcinoma of the lung exhibits the strong expression of ATBF1 in both the nucleus and the cytoplasm (an antibody corresponding to exon 10 is used). When high proliferation potency is predicted from the strong staining of the cytoplasm, it is meant that the carcinoma progresses due to rapid infiltration and metastasis, so that surgery is impossible in many cases. Thus, the carcinoma is determined to have a high grade of malignancy. However, on the contrary, when it is predicted that because of DNA damaging due to the strong staining of the nucleus, the apoptosis is likely to be introduced, the carcinoma easily response to the chemotherapy and cancer cells can be perfectly killed. As a result, the carcinoma is determined to have a low grade of malignancy. Therefore, when the grade of malignancy is determined, it is realistic, actual, and practical to always consider two factors, that is, proliferation potency and effectiveness of chemotherapy or radiation treatment. Furthermore, it is a point to be notified in considering the grade of malignancy. However, either of two factors as mentioned above may be used as an index in evaluating the cancer.

In the present invention, a) a step for detecting the amount of ATBF1 in a test cancer cell is carried out. Based on the amount of ATBF1 detected as a result of the step, a grade of malignancy of the test cancer cell is determined. As shown in the below-mentioned Examples, for example, when the case in which the amount of ATBF1 is small in the whole cell (both nucleus and cytoplasm) shows extremely high grade of malignancy, meanwhile, when the expression amount of ATBF1 is high, the case has a good prognosis and easily responds to various treatment. Therefore, firstly, the amount of ATBF1 in the whole cell is effective as determination index of the grade of malignancy. As the investigation on breast cancer as mentioned below, when immunohistological staining is not carried out, a method of measuring the quantity of ATBF1 mRNA using a PCR method also enables the quantification of ATBF1 in the whole cell. In the present invention, when a grade of malignancy of a test cell is determined, it is preferable that the amount of ATBF1 in the whole cell including the nucleus and cytoplasm of the test cancer cell is firstly considered.

In one embodiment of the present invention, b) a step for detecting the amount of ATBF1 in a test cancer cell is carried out. Based on the amount of ATBF1 detected as a result of the step, a grade of malignancy of the test cancer cell is determined. Specifically, for example, in the case where a large amount of ATBF1 is detected in the nucleus, it can be determined that the proliferation potency of the cell is low and the case is expected to have high sensitivity with respect to chemotherapy or radiation treatment and that a grade of malignancy of the test cancer cell, in general, is low. However, as in the above-mentioned lung small cell carcinoma, when ATBF1 is expressed both in the nucleus and cytoplasm simultaneously, it is desired to comprehensively determine the grade of malignancy with individually considering the proliferation potency and the sensitivity with respect to chemotherapy or radiation treatment.

In one embodiment of the present invention, c) a step for detecting the intracytoplasmic amount of ATBF1 in a test cancer cell is carried out. In this embodiment, based on the amount of ATBF1 in the cytoplasm in a test cell, a grade of malignancy of the test cancer cell is determined. Specifically, for example, in the case where a large amount of ATBF1 is detected in the cytoplasm, it can be determined that the proliferation potency in the test cancer cell is maintained. Furthermore, even in the case where ATBF1 is not detected in the cytoplasm or small amount of ATBF1 is detected, under the condition where ATBF1 is not expressed in the nucleus, it can be determined that the proliferation potency in the test cancer cell is maintained. Herein, it is preferable to make a comprehensive determination with considering the state of expression in the nucleus.

In one preferable embodiment of the present invention, after carrying out (a) the step for detecting the amount of ATBF1 in a test cancer cell, (b) the step for detecting the intranuclear amount of ATBF1 in a test cancer cell, and (c) the step for detecting the intracytoplasmic amount of ATBF1 in a test cancer cell, a step (d) of comparing the intranuclear amount of ATBF1 obtained in the step (b) with the intracytoplasmic amount of ATBF1 obtained in the step (c) is carried out. In this embodiment, the amount of ATBF1 is compared between the nucleus and the cytoplasm in a test cell. Then, mainly based on the localization of ATBF1, the grade of malignancy of a test cell is determined. Thus, when the amount of ATBF1 in the nucleus is compared with that in the cytoplasm, more precise evaluation of grade of malignancy can be achieved. As shown in the below-mentioned Examples, in the cancer cell in which it can be predicted and determined that the proliferation potency is low, or sensitivity with respect to chemotherapy or radiation treatment is high and the grade of malignancy is low, it was proved that ATBF1 tended to be localized in the nucleus. On the other hand, in the case where ATBF1 is limited to the cytoplasm (that is to say, in the case where the amount of ATBF1 in the nucleus is relatively small), histologically, subepithelial infiltration of carcinoma was highly progressed and the sensitivity with respect to chemotherapy or radiation treatment tended to be low. It was proved that the grade of malignancy was increased. Furthermore, through the examination of cancers having high malignancy or the examination of general cancers in the metastatic focus, when ATBF1 is absent both in the nucleus and the cytoplasm, the tendency in which the grade of malignancy becomes higher is clearly shown.

In the method of the present invention, typically, it is determined which section a test cancer cell is classified in a plurality of sections in which the grade of malignancy becomes sequentially higher. Herein, the number of sections is not particularly limited. For example, three sections can be provided. A specific example of the three sections includes: grade of malignancy 1 (low): ATBF1 tends to be localized in the nucleus, grade of malignancy 2 (middle): ATBF1 tends to be localized in the cytoplasm, and grade of malignancy 3 (high): ATBF1 tends to be absent in the nucleus and the cytoplasm. Alternatively, four sections can be provided (specifically, for example, grade of malignancy 1 (low): ATBF1 tends to be highly localized in the nucleus, grade of malignancy 2 (middle): ATBF1 tends to be slightly to moderately localized in the cytoplasm, grade of malignancy 3 (high): ATBF1 tends to be limited to the cytoplasm and is the expression in the nucleus is small, and grade of malignancy 4 (very high): ATBF1 tends to be absent in the nucleus and the cytoplasm. Note here that as in lung small cell carcinoma before chemotherapy, it is predicted to be difficult to uniformly determine which category of the above-mentioned grades of malignancy 1 to 3 or 1 to 4 cancers, in which ATBF1 is highly expressed in both nucleus and cytoplasm; and the proliferation potency is high, and the sensitivity with respect to chemotherapy is high, is included. In such a case, it is preferable to consider two indices of grade of malignancy, that is, proliferation potency and the sensitivity with respect to chemotherapy or radiation treatment.

The kinds of cancers tested in the present invention is not particularly limited. For example, the present invention can be applied to the judgment of the grade of malignancy of various tumors including, for example, breast cancer, bladder cancer, gastric cancer, lung cancer, neuroblastoma, gastrointestinal stromal tumor (GIST), prostate cancer, meningioma, and the like.

As shown in the below-mentioned Examples, the present inventors have investigated and clarified that various kinds of cancers have the relationship between the grade of malignancy and the amount of intracellular expression of ATBF1. Furthermore, the relationship between the grade of malignancy of a cancer and the amount of ATBF1 in the nucleus and cytoplasm in a cancer cell (localization of ATBF1 in the nucleus/the cytoplasm) was observed. Hereinafter, the outline of the results of the investigation on various human cancers (tumors) is shown (see, example 1 to example 12).

Example 1) Human breast cancers (153 cases) were investigated by using the expression amount of ATBF1 mRNA as an index. It was determined that in the case group in which the expression amount of ATBF1 mRNA was large had better prognosis than the case group in which the expression amount was low or absent. For this result, in the method of the present invention, for example, when the intercellular amount of ATBF1 in a suspected breast cancer cell as the test cancer cell is measured, in the case where the expression amount is large, it can be determined that the grade of malignancy is low (or the subject from which the test cancer cell is derived has good prognosis). On the contrary, when the amount of ATBF1 in the test cancer cell is small, it can be determined that the grade of malignancy is high (or the subject from which the test cancer cell is derived has poor prognosis).

Example 2) In a cell line which is one of cultured bladder cancer cells in which mutation of tumor suppressor gene p21, p53 and the effect of an anti-cancer drug cisplatin have been already confirmed (Int J Cancer. 1996 Nov. 15; 68(4):501-5), and which is capable of inducing apoptosis of the tumor in the anti-cancer drug, ATBF1 was present in the nucleus. On the contrary, in the cell line in which an anti-cancer drug does not exhibit the effect, the expression amount of ATBF1 was small or the expression was localized in the cytoplasm even if the total amount of expression was large, and thus, staining was not observed in the nucleus. From these results, in the method of the present invention, for example, intracellular amount of ATBF1 is measured in a suspected bladder cancer cell as a test cancer cell, it can be determined that the grade of malignancy is low when the expression amount of ATBF1 is large. Alternatively, when ATBF1 is localized in the nucleus in the test cancer cell, it can be determined that the grade of malignancy is low. On the other hand, when the amount of ATBF1 in the test cancer cell is small, it can be determined that the grade of malignancy is high. Furthermore, when the amount of ATBF1 is localized in the cytoplasm in test cancer cell, it can be determined that the grade of malignancy is high.

Example 3) In a clinical example of human bladder cancer, that is, papillary urothelial carcinoma, ATBF1 tended to be localized in the nucleus. However, in a cancer infiltrated to subepithelium, ATBF1 tended to be localized in the cytoplasm. From these results, in the method of the present invention, for example, when the presence state of ATBF1 in a suspected papillary urothelial cancer cell or suspected infiltration type bladder cancer cell, which are used as the test cancer cells, is examined, when ATBF1 is localized in the nucleus, it can be determined that the grade of malignancy is low. On the other hand, when ATBF1 is localized in the cytoplasm in the test cancer cell, it can be determined that the grade of malignancy is high.

Example 4) In an examination of series from adenoma to carcinoma in the stomach (biopsy diagnosis, Group III to V), in a slight aberrant type and a moderate aberrant type of adenoma of Group III, ATBF1 was localized in the nucleus. However, in a high aberrant type of adenoma of Group III, ATBF1 was localized in the cytoplasm. In a carcinoma of Group V, a case where ATBF1 was present in the cytoplasm and a case where ATBF1 was absent were observed. An AFP producing gastric cancer that is said to have a high grade of malignancy lacked ATBF1 as shown in the previous reports (non-patent documents 2, 5 and 7). Furthermore, in cases of primary gastric adenocarcinoma mucocellulare, cancer cells lacking ATBF1 and cancer cells in which ATBF1 was localized were observed. Furthermore, when a site in which a primary gastric adenocarcinoma mucocellulare was metastasized to the gallbladder and which exhibited an infiltration property was observed, a case of adenocarcinoma mucocellulare cells completely lacking ATBF1 was observed. In this example, cancer cells with higher metastaticity seemed to metastasize to be lymphogenous, resulting that the infiltration was shown. It was possible to determine that the lacking of ATBF1 enhanced the grade of malignancy. From these results, in the method of the present invention, for example, when the intracellular amount of ATBF1 in a suspected adenocarcinoma cell as a test cancer cell was measured, when the amount of ATBF1 is large, it can be determined that the grade of malignancy is low. Alternatively, when ATBF1 is localized in the nucleus in the test cancer cell, it can be determined that the grade of malignancy is low. On the other hand, when the intracellular amount of ATBF1 in a test cancer cell is small, it can be determined that the grade of malignancy is high. Alternatively, also when ATBF1 is localized in the cytoplasm in a test cancer cell, it can be determined that the grade of malignancy is high.

Example 5) In the example of pulmonary adenocarcinoma showing a response to chemotherapy and the size of tumor has been reduced, the amount of ATBF1 expression in the whole cell is large, and the expression was observed both in the nucleus and the cytoplasm. In the cases that do not show the response to treatment, the expression itself of ATBF1 is small, and the expression is localized to only the cytoplasm. From this result, in the method of the present invention, the intracellular amount of ATBF1 is measured by using, for example, a suspected pulmonary adenocarcinoma cell as a test cancer cell. As a result of the measurement, when the amount of ATBF1 is large, it can be determined that the grade of malignancy is low. Alternatively, when ATBF1 is present in the nucleus in the test cancer cell, or when ATBF1 is localized in the nucleus, it can be determined that the grade of malignancy is low. On the other hand, when the amount of ATBF1 is small, it can be determined that the grade of malignancy is high. Alternatively, ATBF1 is localized in the cytoplasm in the test cancer cell, it can be determined that the grade of malignancy is high.

Example 6) In atypical adenomatous hyperplasia that is said to be a precancerous lesion of pulmonary adenocarcinoma, ATBF1 was present not only in the cytoplasm but also in the nucleus. On the contrary, in the case that is determined to be adenocarcinoma, in the most cases, staining was not observed in the nucleus and ATBF1 tended to be localized in the cytoplasm. From this result, in the method of the present invention, as a result of the examination of the state of presence of ATBF1 in, for example, a suspected pulmonary adenocarcinoma cell used as a test cancer cell, when ATBF1 is present also in the nucleus, it can be determined that the grade of malignancy is low. On the other hand, when ATBF1 is localized in the cytoplasm in the test cancer cell, it can be determined that the grade of malignancy is high.

Example 7) In a normal hematopoietic cell of the spinal cord, ATBF1 was highly expressed both in the nucleus and the cytoplasm. This fact supports that a bone marrow hematopoietic cell is a cell group in which proliferation and division are actively carried out and that a marrow cell having a hematopoiesis function is the most susceptible cell group (which is referred to as myelosuppression and which tends to undergo apoptosis in DNA damage) in normal cells in various cancer treatment.

Example 8) Similar to a bone marrow hematopoietic cell, also in a small cell carcinoma of the lung (oat cell carcinoma), an extremely large amount of ATBF1 are present both in the nucleus and the cytoplasm. This also supports the high speed of the proliferation of small cell carcinoma and the susceptibility to chemotherapy. From this result, in the method of the present invention, for example, when a suspected lung small cell carcinoma cell is used as a test cancer cell and the state of presence of ATBF1 in the cell is examined, and then ATBF1 is localized in the cytoplasm as a result, it can be determined that the grade of malignancy is high. On the other hand, when the amount of ATBF1 is localized in the nucleus in the test cancer cell, it can be determined that the grade of malignancy is low.

Example 9) In a well-differentiated prostate cancer, it was observed that ATBF1 was localized in the nucleus. In moderately-differentiated and poorly-differentiated cancers, it was observed that ATBF1 was localized in the cytoplasm or the expression tended to be absence. From this result, according to the method of the present invention, for example, when a suspected prostate cancer cell is used as a test cancer cell, and the intercellular amount of ATBF1 is measured, and then the amount of ATBF1 is large as a result, it can be determined that the grade of malignancy is low. Alternatively, when ATBF1 is localized in the nucleus in the test cancer cell, it can be determined that the grade of malignancy is low. On the other hand, when the intercellular amount of ATBF1 is small (in particular, the ATBF1 expression is not observed), it can be determined that the grade of malignancy is high. Alternatively, when ATBF1 is localized in the cytoplasm in the test cancer cell, it can be determined that the grade of malignancy is high.

Example 10) In neonatal and infantile adrenal tumors, neuroblastomas, some of which result in the termination of death and some of which are spontaneously lost, are known. To predict the prognosis is important to doctors and parents of the child with neuroblastoma. In almost all the tumor cells in the cases that result in benign and finally can survive, ATBF1 is localized in the nucleus. On the contrary, in the case that did not finally survive, as a result of dissection, the tumor showed infiltration, metastasis, vascular invasion, and the like. In the cases clearly showing that the tumor death was caused by the grade of malignancy itself of the tumor, in most of the tumor cells, ATBF1 was localized in the cytoplasm. This means that the progress of the tumor and the prognosis of a patient can be predicted at the time of biopsy. From the results, according to the method of the present invention, for example, when the state of the presence of ATBF1 in the cell is examined by using a suspected neuroblastoma cell as a test cell, and ATBF1 is localized in the nucleus as a result, it can be determined that the grade of malignancy is low. On the other hand, when ATBF1 is localized in the cytoplasm in the test cancer cell, it can be determined that the grade of malignancy is high.

Example 11) In gastrointestinal stromal tumor (GIST), in general, ATBF1 is localized in the nucleus. However, in the cases that died from liver metastasis and diagnosed as having highly malignant GIST, ATBF1 was present in the cytoplasm. From this result, according to the method of the present invention, for example, when the state of the presence of ATBF1 in the cell is examined by using a suspected GIST cell as a test cancer cell, and then ATBF1 is localized in the nucleus as a result, it can be determined that the grade of malignancy is low. On the other hand, when ATBF1 is also preset in the cytoplasm in the test cell, it can be determined that the grade of malignancy is high.

Example 12) In a tumor cell of meningioma (WHO Grade I) that is classified in a benign tumor, ATBF1 was localized in the nucleus. However, atypical meningioma (WHO Grade II) and clear cell meningioma (WHO Grade II) that are said to be deteriorated to malignant, the ATBF1 expression was observed in the cytoplasm. From this result, according to the method of the present invention, for example, when the state of the presence of ATBF1 in the cell is examined by using a suspected meningioma cell as a test cancer cell, and then ATBF1 is localized in the nucleus as a result, it can be determined that the grade of malignancy is low. On the other hand, when ATBF1 is localized in the cytoplasm in the test cancer cell, it can be determined that the grade of malignancy is high.

According to the investigation by the present inventors, it was proved that detecting a specific region of ATBF1 was effective in determining the grade of malignancy of a test cancer cell. Based on this finding, in one preferable embodiment of the present invention, as the amount of ATBF1 in a test cancer cell separated from the living organism, at least one of the following (1) to (3) can be detected.

(1) the intranuclear amount and/or intracytoplasmic amount of a region corresponding to exon 10 of an ATBF1 gene.

(2) the intranuclear amount and/or intracytoplasmic amount of a region corresponding to exon 11 of an ATBF1 gene (C terminal region).

(3) the intranuclear amount and/or intracytoplasmic amount of a region corresponding to exon 3 of an ATBF1 gene (N terminal region).

(1) Detection of the Intranuclear Amount and/or Intracytoplasmic Amount of a Region Corresponding to Exon 10 of an ATBF1 Gene In this detection, in a test cancer cell, the amount in the nucleus and/or the amount in the cytoplasm of a region corresponding to exon 10 of ATBF1 gene (Partial protein. Hereinafter, referred to as "first region of ATBF1 protein" or also abbreviated as "first region." The amino acid sequence of this region is shown in SEQ ID NO: 13 and a base sequence coding for the region is shown in SEQ ID NO: 14, respectively.) are detected. As shown in the below-mentioned Examples, when the relationship between the amount and localization mode of the first region and the grade of malignancy was investigated by using some test cancer cells, the following (a) to (c) were generally observed. (a) When the first region is localized mainly in the nucleus, the grade of malignancy is low. (b) When the first region is localized mainly in the cytoplasm, the grade of malignancy is high. (c) When the first region is absent (in the cytoplasm and in the nucleus), the grade of malignancy is high. That is to say, it was proved that (a) to (c) were preferable and important indices for determining the grade of malignancy of a cancer cell. Therefore, for example, when a large amount of the first region is detected in the nucleus in a test cancer cell (or the first region is localized in the nucleus), it can be determined that the grade of malignancy of the test cancer cell is low. Similarly, for example, when a large amount of the first region is detected in the cytoplasm nucleus in a test cancer cell (or the first region is localized in the cytoplasm), it can be determined that the grade of malignancy of the test cancer cell is high. Furthermore, for example, in the test cancer cell, when the first region is absent (or the amount of the first region is extremely small), it can be determined that the grade of malignancy of the test cancer cell is high.

Herein, when the determination is carried out by using the localization mode of the first region in a test cancer cell as an index, in general, the intranuclear amount and the intracytoplasmic amount of the first region are detected simultaneously. Then, by comparing the detection results with each other, the localization mode of the first region is examined. When the first region was localized mainly in the cytoplasm or the first region was absent, the grade of malignancy of the test cancer cell is determined to be high. In this way, comparison between the detection amount in the nucleus and the detection amount in the cytoplasm makes it possible to clearly find the localization mode of the first region in the cell. Note here that from either of the detection results of the amount of the first region in the nucleus and the amount of the first region in the cytoplasm, intercellular localization of the first region may be predicted and determined. In this case, either of the detection meets the need.

(2) Detection of the Intranuclear Amount and/or Intracytoplasmic Amount of a Region Corresponding to Exon 11 of an ATBF1 Gene (Positioned at the C Terminal Region of ATBF1-A Protein).

In this detection, in a test cancer cell, the amount in the nucleus and/or the amount in the cytoplasm of a region corresponding to exon 11 of ATBF1 gene (Partial protein. Hereinafter, referred to as "second region of ATBF1 protein" or also abbreviated as "second region." The amino acid sequence of this region is shown in SEQ ID NO: 15 and a base sequence coding for the region is shown in SEQ ID NO: 16, respectively.) are detected. As shown in the below-mentioned Examples, when the relationship between the amount and localization mode of the second region and the grade of malignancy was investigated by using some test cancer cells, the following (a) and (b) were generally observed. (a) When the second region is localized mainly in the nucleus, the grade of malignancy is low. (b) When the second region is localized mainly in the cytoplasm, the grade of malignancy is high. That is to say, it was proved that (a) and (b) were preferable and important indices for determining the grade of malignancy of a cancer cell. Therefore, for example, when a large amount of the second region is detected in the nucleus in a test cancer cell (or the second region is localized in the nucleus), it can be determined that the grade of malignancy of the test cancer cell is low. Similarly, when, for example, when a large amount of the second region is detected in the cytoplasm in a test cancer cell (or the second region is localized in the cytoplasm), it can be determined that the grade of malignancy of the test cancer cell is high.

Herein, when the determination is carried out by using the localization mode of the second region in a test cancer cell as an index, in general, the intranuclear amount and the intracytoplasmic amount of the second region are detected simultaneously. Then, by comparing the detection results with each other, the localization mode of the second region is examined. When the second region was localized mainly in the cytoplasm, the grade of malignancy of the test cancer cell is determined to be high. In this way, comparison between the detection amount in the nucleus and the detection amount in the cytoplasm makes it possible to clearly find the localization mode of the second region in the cell. Note here that from either of the detection results of the amount of the second region in the nucleus and the amount of the second region in the cytoplasm, intercellular localization of the second region may be predicted and determined. In this case, either of the detections meets the needs.

(3) Detection of the Intranuclear Amount and/or Intracytoplasmic Amount of a Region Corresponding to Exon 3 of an ATBF1 Gene (Positioned in the N Terminal Region of ATBF1-A Protein).

In this detection, in a test cancer cell, an amount in the nucleus and/or an amount in the cytoplasm of a region corresponding to exon 3 of ATBF1 gene (Partial protein. Hereinafter, referred to as "third region of ATBF1 protein" or also abbreviated as "third region." The amino acid sequence of this region is shown in SEQ ID NO: 11 and a base sequence coding for the region is shown in SEQ ID NO: 12, respectively.) are detected.

As shown in the below-mentioned Examples, the detection of the third region (region recognized by NT440, 1-12) makes an index for showing whether the amount of ATBF1 in the whole cell is increased, decreased, or absent. Furthermore, by detecting the state of the phosphorylation at the 148th serine in the third region, it is possible to know the rate of the third region moving to the nucleus. Furthermore, when the presence, absence, the localization positions in the nucleus and the cytoplasm of the third region are compared with the localization state in of the central region (that is, the first region) of the ATBF1 protein, it is possible to determine the processing of the ATBF1 protein and furthermore, skip of the exon due to the abnormal splicing generated in the mRNA level. As mentioned above, the detection of the third region can provide useful information, although it is auxiliary information, in determining a grade of malignancy of cancers.

Preferably, two or more of the above-mentioned (1) to (3) are detected. Then, by considering each of the detection results, the grade of malignancy of a test cancer cell is determined. When two or more of the (1) to (3) are detected in this way, more detailed and precise determination and evaluation can be achieved.

It is preferable that the above-mentioned (1), that is, the detection of the first region is included in the detection items. The amount or intracellular localization mode of the first region detected in the above-mentioned (1) best characterizes the grade of malignancy of a cancer. Therefore, in the determination of the grade of malignancy, the detection of (1) is particularly important.

More preferable embodiments include an embodiment in which the above-mentioned (1) and (2) are detected, and an embodiment in which the above-mentioned (1) and (3) are detected. When the detection items are increased in this way, more precise determination can be carried out. Above all, it is the most preferable that the above-mentioned (1) to (3) are detected and the detection results are comprehensively evaluated. It is advantageous because detailed information can be obtained, and thus more precise determination can be carried out.

Herein, a specific example of the criteria in the embodiment in which the above-mentioned (1) and (2) are detected (embodiment in which the first region and the second region are detected) is shown below. The grade of malignancy 1 represents a section with the lowest grade of malignancy. As the number is increased, the grade of malignancy in the section becomes higher.

| Grade of malignancy | Amount or localization of first region | Amount or localization of second region |
| --- | --- | --- |
| 4 | Absence | Localize in the cytoplasm |
| 3 | Localize in the cytoplasm | Localize in the cytoplasm |
| 2 | Localize in the nucleus | Localize in the cytoplasm |
| 1 | Localize in the nucleus | Localize in the nucleus |

A representative example of the grade of malignancy 4 can include undifferentiated cancer of paranasal cavity, and part of diffuse malignant lymphoma. Similarly, a representative example of the grade of malignancy 3 can include a part of glioblastoma multiforme and a part of diffuse malignant lymphoma. A representative example of the grade of malignancy 2 can include a part of GIST (Bcl-2$^+$), a part of meningioma. A representative example of the grade of malignancy 1 can include a part of GIST (Bcl-2$^-$) and a part of meningioma.

The ATBF1 gene includes exons 1 to 11 (see FIG. 47). Among them, the exon 10 has the longest sequence and codes for all of the four homeodomains. As shown in the below-mentioned Examples, it was suggested that ATBF1 was cut into plural parts in a process after translation. Furthermore, it was reported that due to abnormal skipping of the exon 10, a mutant protein lacking a region corresponding to exon 10 was produced (non-patent document 9).

When ATBF1 is in a complete state (ATBF1 is present as a full-length protein) in a cell, "region corresponding to exon 10 of ATBF1 gene (that is, first region)," "region corresponding to exon 11 of ATBF1 gene (that is, second region)," and "region corresponding to exon 3 of ATBF1 gene (that is, third region)" are respectively present as a part of such an ATBF1. On the other hand, when ATBF1 is divided in a process after translation, each region is present as one of the partial ATBF1 generated after division (or one part therein).

Note here that the first region is recognized by antibody D1-120 produced by using a part of a central region of the ATBF1-A protein (a region other than a homeodomain of the exon 10) as an antigen. Similarly, the second region is recognized by antibody AT6 produced by using a part of the C-terminal region of the ATBF1-A protein as an antigen. The third region is recognized by antibodies NT440 and 1-12 produced by using a part of the N-terminal region of the ATBF1-A protein as an antigen. The production method of such antibodies will be described in the below-mentioned Examples.

The test cancer cell can be collected from a suspected cancer tissue. Specifically, a part of the suspected cancer tissue is collected in biopsy and it is subjected to the method of the present invention as a sample including a test cancer cell.

In the present invention, the detection of the amount of ATBF1, and the detection of the first region, second region and third region of ATBF1 protein are, although not particularly limited, preferably carried out by using an immunohistochemical staining method. The immunohistochemical staining method enables rapid and sensitive detection of the amount of ATBF1. Furthermore, the operation is simple. Therefore, the burden accompanying the detection of the amount of ATBF1 to the subject (patient) is reduced.

In the immunohistochemical staining method, antibodies for specifically recognizing the subject to be detected (anti-ATBF1 antibody, anti-first region antibody, and the like) are used, and the amount of ATBF1 is detected by using the binding property (binding amount) of the antibody as an index.

In the immunohistochemical staining method, in general, firstly, the antibodies specific to the subject to be detected (for example, anti-ATBF1 antibody) is made into contact with a test cancer cell. Thereafter, the amount of the antibody bound to the whole cell, nucleus, and/or cytoplasm was measured. Then, from the measurement result, the amount of the subject to be detected in the whole cell, nucleus and/or cytoplasm of the test cancer cell is calculated. Specifically, in accordance with the below-mentioned immunohistochemical staining method, the method of the present invention can be carried out.

An immunohistochemical staining method of a living tissue is generally carried out by the following procedures (1) to (9). Note here that the immunohistochemical staining method of a living tissue is described in various documents and publications (see, for example, "Kouso-Koutai Hou (Enzyme antibody technique, revised Vol. 3, K. Watanabe, K. Nakamura (ed.), Gakusai Kikaku)

(1) Fixation, Embedding in Paraffin

A tissue surgically removed from a living organism is fixed in formalin, paraformaldehyde, absolute ethanol, and the like. Thereafter, the tissue is embedded in paraffin. In general, the tissue is dehydrated with alcohol, then treated with xylene, and finally embedded in paraffin. The paraffin-embedded tissue specimen is sliced in a desired thickness (for example, 3 to 5 μm thick) and extended on a slide glass. Alcohol fixed specimen, dry-filled specimen, frozen specimen, and the like may be used instead of the paraffin embedded specimen.

(2) Deparaffinization

In general, treatment is carried out with xylene, alcohol and purified water, sequentially.

(3) Pretreatment (Antigen Activation)

Enzyme treatment, heat treatment and/or pressure treatment, and the like, are carried out for antigen activation, if necessary.

(4) Endogenous Peroxidase Removal

When peroxidase is used as a labeled material in dying, it is treated with a hydrogen peroxide solution so as to remove an endogenous peroxidase activity.

(5) Nonspecific Reaction Inhibition

The slice is treated with a bovine serum albumin solution (for example, 1% solution) for several minutes to several tens minutes so as to inhibit a nonspecific reaction. Note here that the following primary antibody reaction is carried out by using an antibody solution containing bovine serum albumin and this reaction may not be carried out.

(5) Primary Antibody Reaction

An antibody diluted to an appropriate concentration is dripped on a slice on the slide glass so as to react them for the following several tens minutes to several hours. After the reaction is completed, the reacted product is washed with a buffer solution such as a phosphate buffer solution.

(6) Addition of Labeled Reagent

Peroxidase is frequently used as a labeled material. A secondary antibody labeled with peroxidase is dripped on a slice on the slide glass so as to react them for the following several tens minutes to several hours. After the reaction is completed, the reacted product is washed with a buffer solution such as a phosphate buffer solution.

(7) Coloring Reaction

DAB (3,3'-diaminobenzidine) is dissolved in a Tris buffer solution. Then, a hydrogen peroxide solution is added. The thus prepared solution for coloring is allowed to penetrate into a slice for several minutes (for example, five minutes) so as to develop color. After coloring, the slice is sufficiently washed with tap water to remove DAB.

(8) Nucleus Staining

Nucleus is stained by reacting it with Mayer's Hematoxylin for several seconds to several tens second, and then washed with flowing water so as to develop color (in general, several minutes).

(9) Dehydration, Penetration and Inclusion

Dehydration with alcohol, penetration treatment with xylene are carried out, and finally inclusion is carried out with a synthetic resin, glycerine, and rubber syrup.

The kind and origin of an antibody used for an immunohistochemical staining method (a detection antibody) is not particularly limited as long as the antibody has a specific binding property with respect to a subject to be detected. The antibody for detection may be any one of a polyclonal antibody, an oligoclonal antibody (a mixture of several kinds to several tens kinds antibodies), and a monoclonal antibody. An example of the polyclonal antibody or the oligoclonal antibody can include an affinity purified antibody by an antigen in addition to an IgG fragment derived from antiserum obtained by animal immunization. An anti-ATBF1 antibody may be an antibody fragment such as Fab, Fab', F(ab')$_2$, scFv, dsFv antibody, and the like.

In the measurement of the amount of ATBF1, a D1-120 antibody shown in the below-mentioned Examples can be used. This antibody specifically recognizes a D1-120 site (a region corresponding to the exon 10 and including a small part of a homeodomain 1 and a region immediately before the homeodomain 1) that is a common region of ATBF1-A and ATBF1-B. Therefore, when this antibody is used, both ATBF1-A and ATBF1-B can be detected simultaneously. On the other hand, since this antibody specifically bound to the first region of ATBF1, the detection amount by this antibody reflects the amount of the first region. Therefore, when this antibody is used, it is possible to find the amount of the first region or the localization thereof. Similarly, when an antibody AT6 capable of recognizing a region corresponding to the exon 11 of ATBF1 gene is used, it is possible to find the amount of the second region that is a C-terminal region or the localization thereof. When an antibody NT440 or 1-12 capable of recognizing a region corresponding to the exon 3 of ATBF1 gene, it is possible to find the amount of the third region that is an N-terminal region or the localization thereof.

An anti-ATBF1 antibody and the like can be prepared by using an immunological technique, a phage display technique, a ribosome display technique, and the like.

Preparation of a Polyclonal Antibody by an Immunological Technique can be Carried out by the following procedure. An antigen (for example, D1-120 site of ATBF1 or a part thereof) is prepared and an animal such as a rabbit is immunized with this antigen. ATBF1 (or a part thereof) of species other than human (for example, mouse) can be used as an antigen. An antigen can be obtained by purifying a living organism. Furthermore, an antibody obtained by using a gene recombination technique can be used. Recombinant human ATBF1 is prepared by introducing a gene (a part of a gene may be employed) coding for, for example, ATBF1 into an appropriate host by using a vector, followed by allowing the gene to express in the obtained recombinant cell.

In the case where effective immune eliciting effect cannot be expected because the molecular weight is low, it is preferable to use an antigen to which a carrier protein is bound. An example of the carrier protein includes KLM (Keyhole Light Hemocyanin), BSA (Bovine Serum Albumin), OVA (Ovalbumin), and the like. For binding the carrier protein, a carbodiimide method, a glutaraldehyde method, a diazo condensation method, an MBS (maleimide benzoyl oxysuccinimide) method, and the like. On the other hand, an antigen obtained by expressing ATBF1 (or a part thereof) as a fusion protein with GST, $\beta$ galactosidase, maltose binding protein, or histidine (His) tag, and the like. Such a fusion protein can be simply purified by a general-purposed method.

The present inventors assayed the size of ATBF1 protein in an actual tissue by western blot in a brain tissue of an embryonic rat and an adult rat, an undifferentiated embryonic carcinoma cell line (P19 cell), and further two kinds of neuroblastoma cell lines (NB-1 and GOTO). The antibody used at this time was D1-120 for detecting a central portion of the ATBF1-A (404 kDa) protein. As a result of the western blot using these antibodies, the size of the protein (that is, the ATBF1 protein) recognized by the antibody is shown to be 404 kDa, about the half size thereof, that is, 210 kDa, and various shorter sizes depending upon tumor cells. However, when the present invention is practiced, an antibody corresponding to D1-120 is used for determining a grade of malignancy of a cancer cell, it is thought that the difference in this protein sizes is not necessarily considered. However, when a recombinant ATBF1 is used, in order to obtain the same level of results as the results (result of staining using D1-120) shown in the below-mentioned Examples, it is thought to be necessary to use an antibody prepared by using an antigen prepared by selecting a part of gene (the site corresponding to the exon 10) coding for a D1-120 site of the ATBF1-A amino acid sequence in the ATBF1 gene (or a part of the gene) and introducing the selected portion into an appropriate host by using a vector. As shown in the results of experiment using NT440, 1-12 and AT6, the detection results (localization embodiment, etc.) when an anti-ATBF1 antibody recognizing a site distant from the D1-120 site is used is utterly different from the detection results when D1-120 is used. However, even if an antibody recognizing a site other than the D1-120 site is used, if the site is in the vicinity of the D1-120 site, a site detected by D1-120 (the first region) can be similarly detected. Whether or not one antibody has specificity similar to that of D1-120 can be verified by a preliminary experiment using a P19 cell and the like, research experiment for localization of ATBF1 using a cancer cell (specifically, Western blotting, and the like). When the antibody is determined to have specificity similar to that of D1-120 from the experiment, the antibody can be used for the same purpose as D1-120.

Immunization is repeated if necessary, and blood is collected at the time when the antibody value is sufficiently increased so as to obtain serum by centrifugation and the like. The obtained antiserum is subjected to an affinity purification. On the other hand, a monoclonal antibody can be prepared by the following procedure. Firstly, immunization operation is carried out by the same procedure as mentioned above. Immunization is repeated if necessary, and at the time when the antibody value is sufficiently increased, antibody production cells are extracted from the immunized animal. Then, the obtained antibody production cell and a myeloma cell are fused to each other so as to obtain a hybridoma. Then, after this hybridoma is monocloned, a clone capable of producing an antibody having a high specificity with respect to a target protein is selected. By purifying a culture solution of the selected clone, the target protein can be obtained. On the other hand, after the hybridoma is proliferated to desired number or more, this is transplanted into the peritoneal cavity of an animal (for example, a mouse) and allowed to proliferate in abdominal dropsy. The abdominal dropsy is purified, and thereby the target antibody can be obtained. For the purification of the above-mentioned culture solution or the purification of the abdominal dropsy, an affinity chromatography using protein G, protein A, and the like, are preferably used. Furthermore, an affinity chromatography in which antigen is solid-phased can be also used. Furthermore, a method such as an ion exchange chromatography, a gel filtration chromatography, ammonium sulfate fractionation, and centrifugation, and the like, can be also used. These methods can be used alone or in any combination thereof.

The obtained antibody can undergo various modifications as long as the specific binding property with respect to a subject to be detected is maintained. In the present invention, such a modified antibody may be used.

When a labeled antibody is used for an anti-ATBF1 antibody, it is possible to directly detect the amount of the antibody binding using the amount of labels as an index. Therefore, a method becomes simpler. On the contrary, there is a problem that it is necessary to prepare an anti-ATBF1 antibody to which a labeled substance is bonded and detection sensitivity is generally lowered. Thus, it is preferable to use an indirect detection method such as a method for using a secondary antibody to which a labeled substance is bonded, a method for using a polymer to which a secondary antibody and a labeled substance are bonded, and the like. Herein, the secondary antibody is an antibody having a specific binding property with respect to the anti-ATBF1 antibody, and the like. For example, when the anti-ATBF1 antibody and the like is prepared as a rabbit antibody, anti-rabbit IgG antibody is used. Labeled secondary antibodies that can be used for antibodies of various species such as a rabbit, a goat, a mouse, etc., are commercially available (for example, Funakoshi Co., Ltd, COSMO BIO CO., LTD.). An antibody can be appropriately selected in accordance with the anti-ATBF1 antibody and the like used in the present invention.

For the labeled substance, any one arbitrarily selected from peroxidase, $\beta$-D-galactosidase, micro peroxidase, horseradish peroxidase (HRP), fluorescein isothiocyanate (FITC), rhodamine isothiocyanate (RITC), alkaline phosphatase, biotin and a radioactive substance can be preferably used. In particular, when a method for reacting avidin peroxidase by using biotin as a labeled substance is used, more sensitive detection can be carried out.

The second aspect of the present invention provides a reagent (a reagent for determining a grade of malignancy of a test cancer cell) and a kit (a kit for determining a grade of malignancy of a test cancer cell) for carrying out the method of the present invention.

One embodiment of the reagent of the present invention is an anti-ATBF1 antibody (including an anti-first region antibody, an anti-second region antibody and an anti-third region antibody. The same is true hereinafter) used in carrying out the method of the present invention by an immunological technique as mentioned above. Herein, the antibody may be any one of a polyclonal antibody, an oligoclonal antibody (a mixture of several kinds to several tens kinds antibodies), and a monoclonal antibody. An example of the polyclonal antibody or the oligoclonal antibody can include an affinity purified antibody by an antigen in addition to an IgG fragment derived from antiserum obtained by animal immunization. An anti-ATBF1 antibody may be an antibody fragment such as Fab, Fab', F(ab')$_2$, scFv, dsFv antibody, and the like. Furthermore, as mentioned above, it may be an antibody to which a desired label is provided.

An example of antibodies preferably used as the antibody for detection can include (1) an antibody recognizing a region corresponding to exon 10 of ATBF1 gene, (2) an antibody recognizing a region corresponding to exon 11 of ATBF1 gene, or (3) an antibody recognizing a region corresponding to exon 3 of ATBF1 gene.

The antibody of (1) can detect a region corresponding to exon 10 (the first region of ATBF1 protein). The antibody of (2) can detect a region corresponding to exon 11 (the second region of ATBF1 protein). The antibody of (3) can detect a region corresponding to the exon 3 (the third region of ATBF1 protein).

A specific example of the antibodies of (1), (2) and (3) can include the following antibodies.

The antibody of (1): D1-120, the antibody of (2): AT6, and the antibody of (3): 1-12, and NT440 (a mixture of NT440-1, NT440-2 and NT440-3).

The details of the properties of these antibodies, for example, a recognition site, correspondence to exons of ATBF1 gene, are shown in FIG. 31.

The kit of the present invention includes a reagent having a specific binding property with respect to ATBF1, or a part of ATBF1, for example, the first region. A preferable example of the reagent is an anti-ATBF1 antibody, but is not limited to this. By using a kit of the present invention, the method of the present invention can be carried out in a simple way and for shorter time.

As one preferable embodiment, an immunoassay (detection) kit including an anti-ATBF1 antibody is provided. In the case of a kit used for directly detecting the binding amount of the anti-ATBF1 antibody, a labeled anti-ATBF1 antibody is used. On the other hand, in the case of a kit used for an indirect detection method, a non-labeled anti-ATBF1 antibody is used. In this case, the kit may include a secondary antibody labeled with a labeled substance (labeled secondary antibody). In the case of a kit for detection method using a polymer obtained by binding the secondary antibody and the labeled substance, the kit may include the polymer.

On the other hand, a kit may further include ATBF1 (antigen). Typically, a kit includes ATBF1 that is substantially the same or same level as the ATBF1 used as an antigen when an anti-ATBF1 antibody used for the kit is prepared. Therefore, the ATBF1 may not be a full length ATBF1. Furthermore, it may be recombinant ATBF1. The ATBF1 is used for confirming the staining obtained by using a kit is based on the specific binding of an anti-ATBF1 antibody and the ATBF1. Specifically, firstly, an anti-ATBF1 antibody is treated with the ATBF1. By using an anti-ATBF1 antibody after treatment, immunostaining is carried out. The obtained staining image is compared with a staining image obtained by using an untreated anti-ATBF1 antibody. If stronger staining is obtained in the latter stained image, is can be confirmed the observed staining is based on the binding property of the anti-ATBF1 antibody and ATBF1.

On the other hand, in the case where an anti-ATBF1 antibody prepared by using a fusion protein with a tag or a carrier protein (hereinafter, referred to as "tag, and the like") as an antigen is used for a kit, the kit may further include the used tag, and the like. When an antibody having a reactivity with respect to a tag, and the like, which is used in the preparation process in the anti-ATBF1 antibody constituting the kit may be mixed, the tag, and the like, is needed. When the tag, and the like is as mentioned below, it can be confirmed that the staining image obtained by using a kit is based on the specific binding of an anti-ATBF1 antibody and ATBF1. Firstly, an anti-ATBF1 antibody is treated with this tag, and the like. By using an anti-ATBF1 antibody after treatment, immunostaining of the specimen is carried out. The obtained staining image is compared with a staining image obtained by using an untreated anti-ATBF1 antibody. If there is no difference between both images, it can be confirmed that staining pattern in the latter staining image is based on the binding property of the anti-ATBF1 antibody and ATBF1.

The kit of the present invention may include one or more reagents (for example, formalin or paraffin for fixing and embedding a tissue, BSA for inhibiting a non-specific binding, a coloring reagent such as DAB, a hematoxylin for staining nucleus) necessary for carrying out immunostaining such as an antigen antibody reaction, staining, etc. and instruments, and the like. Furthermore, in general, the kit of the present invention includes an instruction manual.

Hereinafter, the present invention will be described in detail with reference to Examples (including Experiment examples).

EXAMPLE 1

<Investigation on Relationship Between ATBF1 and Cell Cycle Control System>

The present inventors discovered a new fact, as a result of study of molecular interaction by a yeast two-hybrid method that is a molecular-biological technique, ATBF1 that is a DNA binding transcription regulation factor is bonded not only to DNA but also to cytoskeleton protein GFAP (glial fibrillary acidic protein) that is present in the cytoplasm. Conventionally, it has been naturally expected and observed that a DNA binding protein is present in the nucleus in a physiological state. However, ATBF1 is also expected to be nucleoprotein but probability has been shown that ATBF1 not only functions in the nucleus but also exists in the cytoplasm in a state in which it is bonded to a cytoskeleton protein. This is a starting point from which the present inventors found the movement between the nucleus and cytoplasm in the present time. Moreover, as shown in the previous publication (non-patent document 6), in the other experiment system using a cultured gastric cancer cell, the present inventors have invented that ATBF1 is bonded to p53 protein in the nucleus and activates the promoter of p21 so as to suppress the cell cycle (see, FIG. 1). Therefore, the present inventors have focused on the cell cycle control function of ATBF1 and examined the movement of ATBF1 in various cancer cells. As a result, the present inventors has noticed the importance of the new fact that in addition to cells in which ATBF1 is localized in the nucleus as a nucleoprotein, in the cancer cells in which a cell cycle control system is disturbed and proliferation property becomes strong, the movement of ATBF1 from the nucleus to the cytoplasm is observed and the staining of ATBF1 in the nucleus is extremely lowered (see, the below-mentioned various Examples).

EXAMPLE 2

<Production of Anti-ATBF1 Antibody>

2-1. Preparation of Antigen

A recombination peptide obtained by fusing mouse 41 amino acid residues (2114~2154: LQTLPAQLPPQLGPVE-PLPADLAQLYQHQLNPTLLQQQNKR: SEQ ID NO: 1) of ATBF1 (Ido et al., (1996). Gene, 168, 227-231) into glutathione S transferase (GST) was used as an antigen. Note here that the above-mentioned 41 amino acid residues completely agree with amino acid residues (2170 to 2147) of human ATBF1.

Specifically, the antigen was prepared by the below-mentioned (1) and (2). Details of preparation of antigen and production of antibody are descried in the previous document (J. Comparative Neurology (2003) 465: 57-71: non-patent document 3).

(1) As mentioned above, a part of the target amino acid was cut out from mouse cDNA and recombined (subcloned) into a vector, pGEX-KT, for producing GST fusion protein was carried out. (2) A gene was introduced into *Escherichia coli* AD202 and a protein expressed by AD202 was purified by a usual method by using Sepharose-glutathione beaded agarose (Sigma) (see, for example, "Handbook for First Purification of Recombinant Protein," 1999, Amersham Pharmacia Biotech).

2-2 Immunization and Separation/Purification of Antibody

By using the antigen (ATBF1-GST fusion protein) prepared in 2-1, an anti-ATBF1 antibody (D1-120) was obtained by the following procedures.

(1) Antigen (1 mg/ml) fused into PBS (pH 7.5) was mixed with an equal amount of Titer Max Gold (CytRx) so as to form an emulsion for immunization. (2) The emulsion (2 ml) was administered to the back of a rabbit by subcutaneous injection and immunization was carried out (five times, Days 0, 14, 28, 49 and 70). (3) When 91 days had passed, the rabbit was sacrificed and blood was collected and the serum was separated. (4) An antigen column by an antigen used for immunization was formed. The serum was subjected to antigen antibody column purification and then an anti-ATBF1 antibody was obtained (see, for example, (see, for example, "Handbook for first Antibody Purification," 2000, Amersham Pharmacia Biotech).

EXAMPLE 3

<Relationship Between ATBF1 Expression and Cell Cycle in Cultured Cancer Cells>

The present inventors carried out an experiment for differentiating undifferentiated cultured cancer cell to a nerve cell by using a P19 mouse embryonal carcinoma cultured cell and investigated the relationship between the ATBF1 expression and the cell cycle in the process.

3-1. ATBF1 Expression at Starting Time of Culturing P19 and Cell Cycle

The present inventors harvested cells in an undifferentiated proliferation state, to which stimulation had not been particularly applied, when at the starting time of culturing P19 carcinoma cells, and carried out an immunohistochemical staining method (ATBF1 staining using D1-120) by the following procedures. The cells were cultured in a chamber slide and fixed in 4% paraformaldehyde that had been adjusted with PBS, followed by washing. A primary antibody solution obtained by dissolving an anti-ATBF1 antibody in 0.05M Tris buffer solution (pH 7.6, containing 1% solution of bovine serum albumin and sodium azide) so that the concentration of the solution became 5 µg/ml was dropped on a slice to cause reaction at 37° C. for about 30 minutes (primary antibody reaction). After sufficiently washing, a secondary antibody Alexa Fluor 594-conjugated goat anti-rabbit IgG (as shown in the below-mentioned Examples, when double staining with other monoclonal antibody is carried out, Alexa Fluor 488-conjugated goat anti-mouse IgG is used simultaneously. Both are products by Molecular Probes.) was allowed to act on a specimen to cause a reaction at room temperature for about one hour (secondary antibody reaction). After sufficiently washing, inclusion was carried, which was observed by using a fluorescence microscope (AX70; Olympus) or a confocal laser scanning microscope (LSM5; ZWISS). As a result of staining, the ATBF1 expression was observed in neither the nucleus nor the cytoplasm (see, FIG. 2*a*). The flow cytometry examination shows cells in a proliferation state. Cells in the cell cycle S, G2, and M stages were mixed at high rate together with cells in the cell cycle G1 stage (see, FIG. 2*d*).

3-2. ATBF1 Expression in P19 after Retinoic Acid Treatment for 24 Hours, and Cell Cycle Twenty-four hours after retinoic acid that is a drug for promoting neurodifferentiation was administered to cultured cells, ATBF1 staining and further flow cytometry examination were carried out by the method mentioned in the above-mentioned 3-1. As a form, although cells still maintained an undifferentiated proliferation state, the ATBF1 expression in the cytoplasm was observed (see, FIG. 2*b*). The flow cytometry examination still showed that cells were in a proliferation state. The rate of cells in the cell cycle S, G2, and M stages were high together with the rate of cells in the cell cycle G1 stage (see, FIG. 2*e*).

3-3. ATBF1 Expression Four Days after Administration of Retinoic Acid was Stopped, and Cell Cycle The administration of retinoic acid was stopped, and the cells were cultured for further four days, followed by carrying out ATBF1 staining and flow cytometry examination by the method described in the above 3-1. As a form, the cultured cells were changed in the group of differentiated cells having neurite. Then, ATBF1 moved from the cytoplasm to the nucleus, the ATBF1 expression was changed into the expression mainly in the nucleus (see, FIG. 2*c*). According to the examination using flow cytometry, the rate of the cells in the S stage, cells in the G2 and M stages were extremely reduced and the cells group was changed into a group of cells almost all of which were cells in the G1 stage (see, FIG. 2*f*). This means clear cell cycle arrest and the stop of the G1 stage, in other words, proliferation suppression was observed. This experimental results not only proved that ATBF1 was a protein that was actually moved from the cytoplasm to the nucleus but also showed that the movement of ATBF1 to the nucleus stopped the cell cycle as expected from the presence of potential nuclear localization signals at two points starting from positions 277 and 2987 of the amino acid sequence, respectively (see, FIG. 3a).

EXAMPLE 4

<Investigation on Regulation Mechanism of Movement of ATBF1 from Cytoplasm to Nucleus And Export from Nucleus to Cytoplasm in Cultured Cancer Cells>

4-1. Investigation on Promoting Mechanism of Movement of ATBF1 into Nucleus

When retinoic acid or the inducing chemical substance thereof is allowed to act on P19 cells, an amount of mRNA transcription and an intracellular amount of protein of ATBF1 are increased. However, as long as P19 cells are cultured in a state in which they are floating in a culture solution, ATBF1 remains in the cytoplasm and the movement into the nucleus is not observed. Herein, under the condition in which cells were attached to a culture dish, the investigation was carried out in order to examine the change of the ATBF1 expression. The localization of ATBF1 was observed in cells after fibronectin, laminin, gelatin, poly-L-ornithine and poly-L-lysine, having the characteristics similar to extracellular environment in the living organism, were attached to the culture dish. By the same method as described in 3-1, ATBF1 was stained (using D1-120). In the case where fibronectin and the like is not coated on a culture dish, cells are in a floating state, and ATBF1 appears in the cytoplasm but does not move to the nucleus (see, FIG. 4a). On the contrary, when fibronectin and poly-L-ornithine were coated on the culture dish so that cells can be attached thereto, within three hours after culture was started, in not a few cells, the movement of ATBF1 to the nucleus was observed (see, FIG. 4b), and 24 hours after culture was started, the movement of ATBF1 to the nucleus was observed in almost all the cells (see, FIG. 4c). Also when laminin or gelatin was attached to the culture dish, P19 cells can be well attached on the surface of the culture dish. Also in this condition, the movement of ATBF1 to the nucleus was observed. This means that the movement of ATBF1 from the cytoplasm to the nucleus was adjusted by a factor (or adhesive stimulation per se) such as fibronectin for promoting the attachment of cells to a culture dish. The receptors existing on the surface of the cell are may be involved in the change from the floating state to the attached state. It was thought that by transmitting information corresponding to the extracellular environment into the cell, intracellular localization of ATBF1 was changed.

Figure 5:
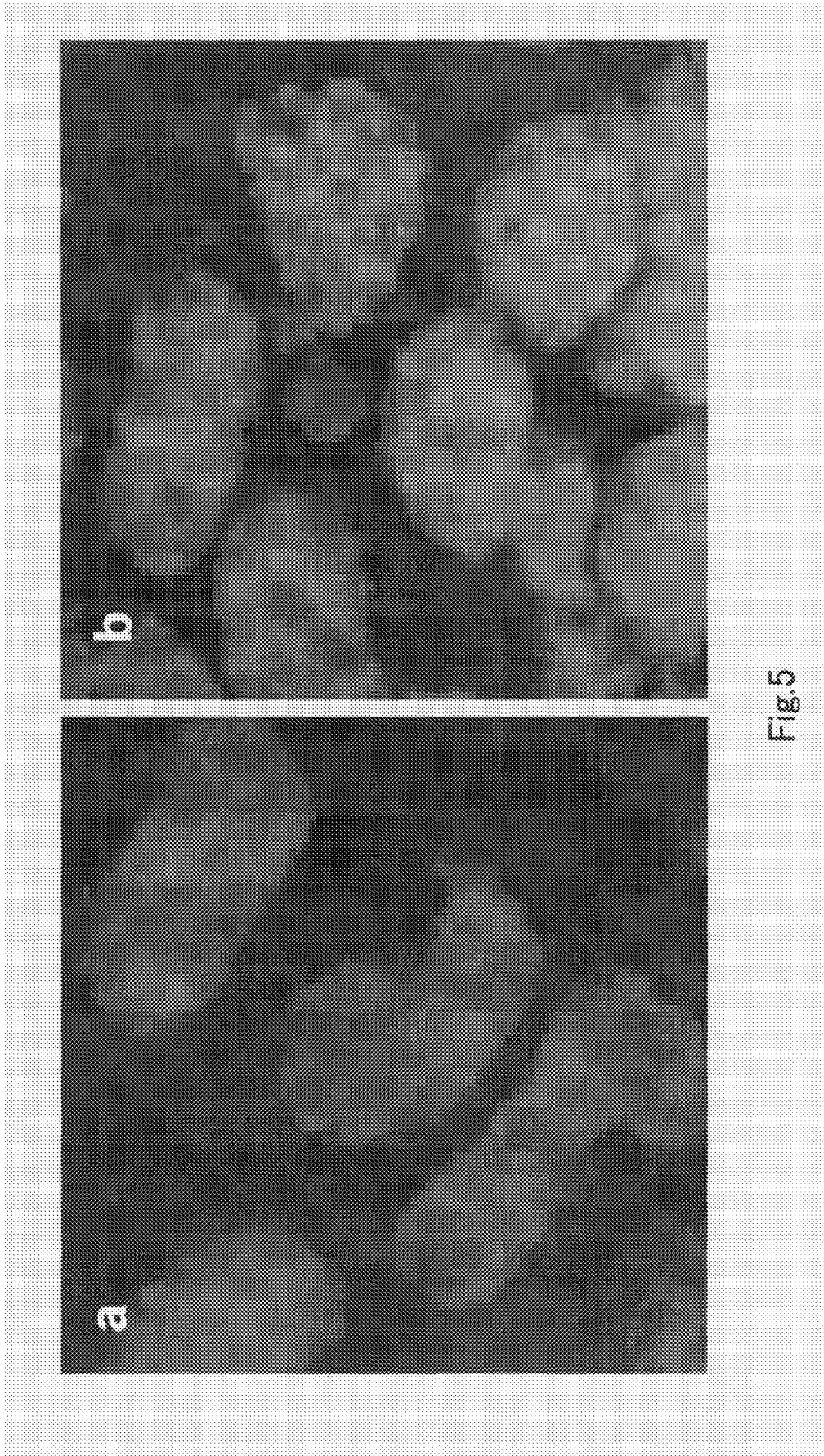
FIG. 5 shows an effect of Leptomycin B on the movement of ATBF1 in P19 cultured cells.

4-2. Investigation of Mechanism of Exporting Mechanism of ATBF1 from Nucleus to Cytoplasm Recently, the fact that transport and export of various factors from the nucleus to the cytoplasm is adjusted with CRM1 (Exportin 1 or chromosome region maintenance 1) has been reported. ATBF1 is assumed to have a target sequence of CRM1, that is, nuclear exporting signals existing in three positions (portions starting from the 1267th, 2471th and 2504th positions in the amino acid sequence, respectively) (see FIG. 3b). Therefore, it was expected that by the action of an antimicrobial drug Leptomycin B that was an inhibitor of CRM1, the export of ATBF1 from the nucleus to the cytoplasm was assumed to be inhibited. This time, by using P19 cells, an experiment was carried out, in which retinoic acid was allowed to act on a culture dish coated with the above-mentioned fibronectin and poly-L-ornithine and furthermore an antimicrobial drug Leptomycin B was added, and ATBF1 staining was carried out by the method described in the above 3-1. Then, the movement of ATBF1 was observed. As a result, as compared with the amount of ATBF1 expression in the case where Leptomycin B is not allowed to act on (see FIG. 5a), by allowing Leptomycin B to act on, the intranuclear concentration of ATBF1 in the P19 cells are clearly increased (see FIG. 5b). At the same time, the number of cells undergoing apoptosis was clearly increased. Furthermore, in the case where one more day of culture was added, the following day, almost all the cells died. This experiment results show that the nuclear exporting of ATBF1 is controlled by CRM1 and that a state in which the concentration of ATBF1 is increased in the nucleus is a state for promoting apoptosis of cancer cells. At the same time, this experiment results were thought to suggest an important policy for treating cancers.

Figure 6:
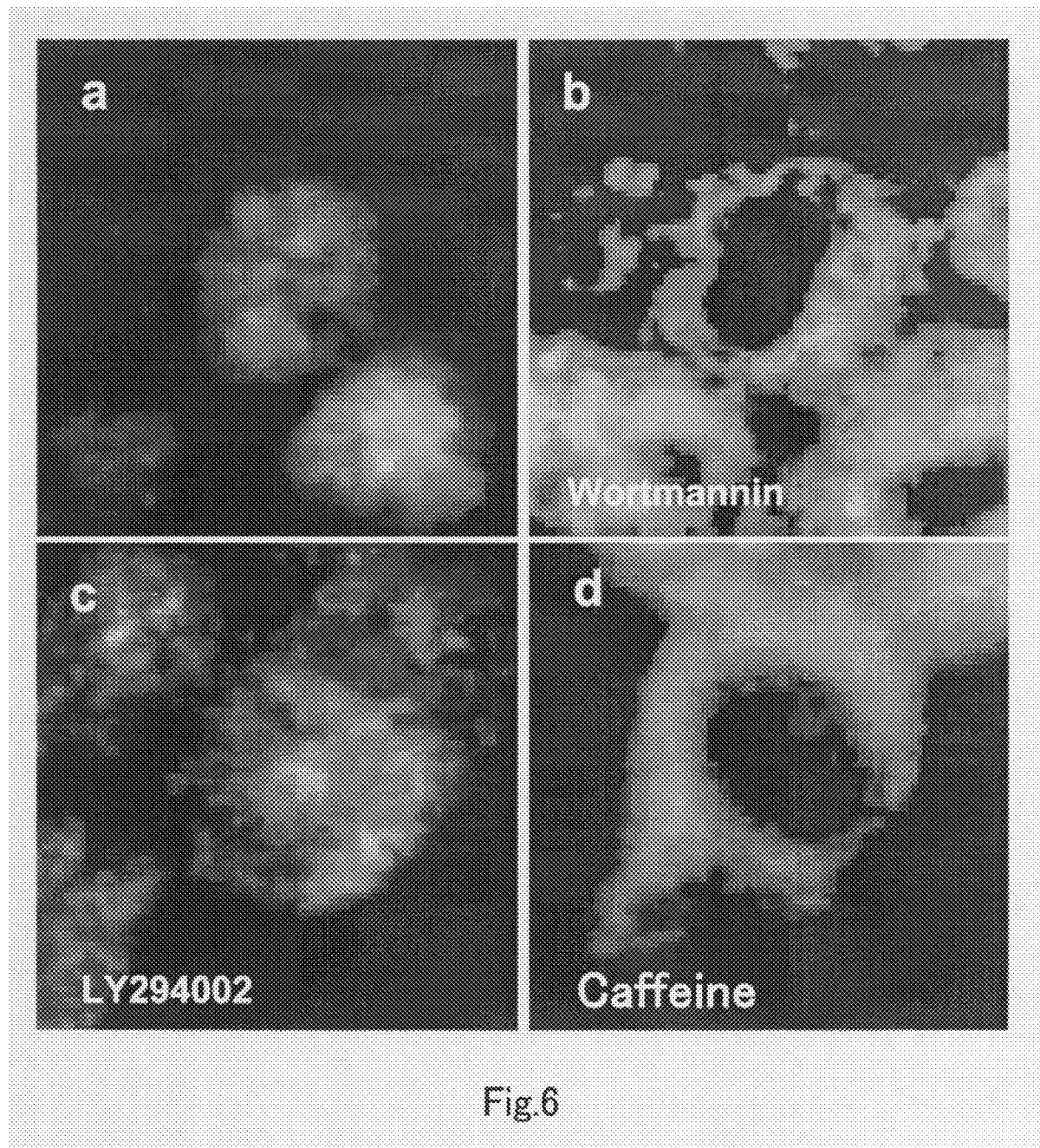
FIG. 6 shows the results of experiment for examining the effect when three kinds of antagonists (Wortmannin, LY294002, and caffeine) of PI3K family protein are allowed to act on with respect to the movement of ATBF1 to the nucleus in P19 cells.

4-3. Investigation on Regulating Mechanism of Movement from Cytoplasm to Nucleus From the fact about various factors relating to the cell cycle, which was investigated in the past, the movement of proteins between the nucleus and the cytoplasm is known to relate to phosphorylation of amino acid. In particular, it was determined that, for the movement to the nucleus, phosphorylation and dephosphorylation of nuclear localization signals were important. In enzymes capable of catalyzing the phosphorylation reaction, PI3K (phosphatidylinositol 3-kinase) family proteins have been much studied. Recently, similar to ATBF1, it has been reported that when N-CoR (the nuclear receptor co-repressor) that moves between the nucleus and the cytoplasm moves from the nucleus to the cytoplasm, the phosphorylation of the 401st serine was involved in PI3K (2002, Nature 419, 934-939). The present inventors predicted that from the fact that ATBF1 expression and N-CoR expression are complementary to each other in rat embryonic cerebral nerve cells, on the contrary to the case where N-CoR is exported from the nucleus to the cytoplasm, when ATBF1 moves from the cytoplasm to the nucleus, phosphorylation of nuclear localization signal by PI3K is involved. Then, similar to the above, after retinoic acid was allowed to act on P19 cells on a culture dish coated with fibronectin, an experiment of allowing two kinds of antagonists of PI3K (Wortmannin and LY294002) to act on, ATBF1 was stained by the method described in the above 3-1, and thereby the movement of ATBF1 was observed. As a result, ATBF1 in the P19 cells to which the drugs were not added was shown to move to the nucleus (see, FIG. 6a), on the contrary, in the case of the P19 cells to which the drugs were added, although ATBF1 production itself was not affected, the movement of proteins into the nucleus tended to be inhibited (the effect was stronger with Wortmannin than with LY294002) (see, FIGS. 6b and 6c). At this time, cells maintained the proliferation state in which mitoses were dispersed. It was observed that ATBF1 in the cytoplasm forms an image in a ring form in a portion in the cytoplasm around the nucleus (predicted to be endoplasmic reticulum). This means that the movement of ATBF1 from the cytoplasm (endoplasmic reticulum) to the nucleus is dependent upon PI3K and that when ATBF1 does not move to the nucleus, cells can maintain a proliferation state.

Then, the present inventors examined which protein in the PI3K family proteins confirmed in the above-mentioned experiment was involved in phosphorylation when ATBF1 moved to the nucleus. ATM (Ataxia Telangiectasia Mutated) is a causative gene of ataxia telangiectasia and a representative example of the gene coding for PI3K family protein. ATM has various functions. In particular, as a monitoring system of DNA damaging due to radiation and the like, ATM is known to control the cell death or cell cycle. This time, the present inventors carried out an experiment using a drug, caffeine, capable of specifically inhibiting the effect of ATM. Firstly, the present inventors cultured P19 cells and confirmed that the P19 cells were attached to a culture dish, thereafter, P19 cells were treated with retinoic acid, followed by allowing caffeine to act on P19 cells. As a result, when PI3K inhibitors, Wortmannin and LY294002, were used, the inhibition of the movement of ATBF1 to the nucleus was not complete (see, FIGS. 6b and 6c). On the contrary, with caffeine, the movement of ATBF1 to the nucleus was inhibited in almost all of the cultured cells (see, FIG. 6d) and the proliferation of cells was completely maintained. This result means that PI3K involved in phosphorylation of the nuclear localization signal of ATBF1 is ATM. Furthermore, the result suggests that the introduction of ATBF1 into the nucleus be promoted by the perception of the activation (phosphorylation) of ATM, that is, DNA damaging due to radiation.

EXAMPLE 5

<Investigation on Relationship Between ATBF1 Forced Expression and Cell Cycle>

Figure 7:
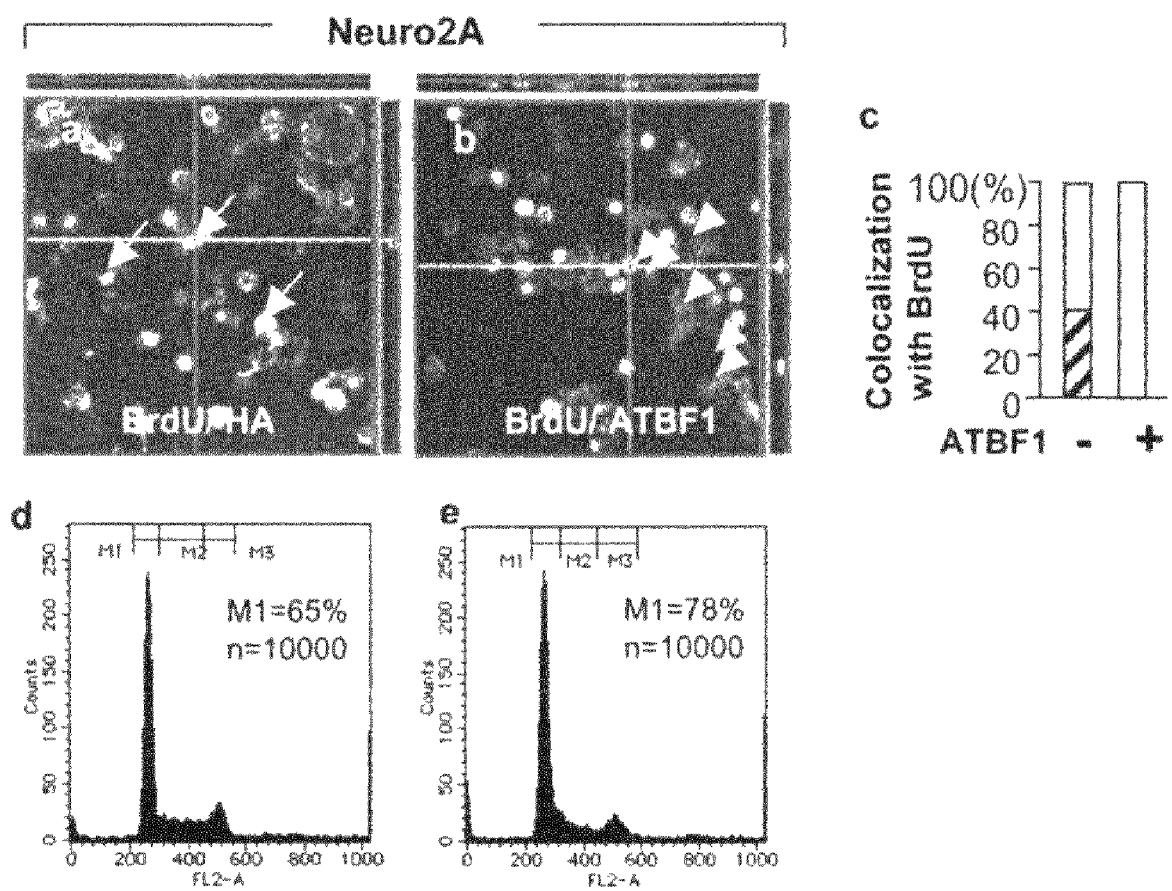
FIG. 7 shows findings of photographs taken by using a confocal laser microscope, showing that full-length ATBF1 cDNA is forcedly expressed in Neuro2A cells of a cell line derived from mouse neuroblastoma. DNA synthesized cells were labeled by adding BrdU into a culture solution for only one hour right before the cells were fixed and observed. BrdU incorporation cells were detected by using a secondary antibody emitting green fluorescence and at the same time, HA tag added to a forced expression vector was detected by using a secondary antibody emitting red fluorescence. As shown in arrows in FIG. 7a, green color of BrdU positive cells are overlapped with red color of the HA tag and cell group emitting a color of yellow were detected. On the other hand, as shown by arrow heads in FIG. 7b, all of ATBF1 introduced cells with HA tag present red and are not overlapped with green color of BrdU positive cells. This experimental result shows that forced expression of ATBF1 cDNA completely suppresses the cell cycle. These facts are summarized as bar graph in FIG. 7c.
Figure 8:
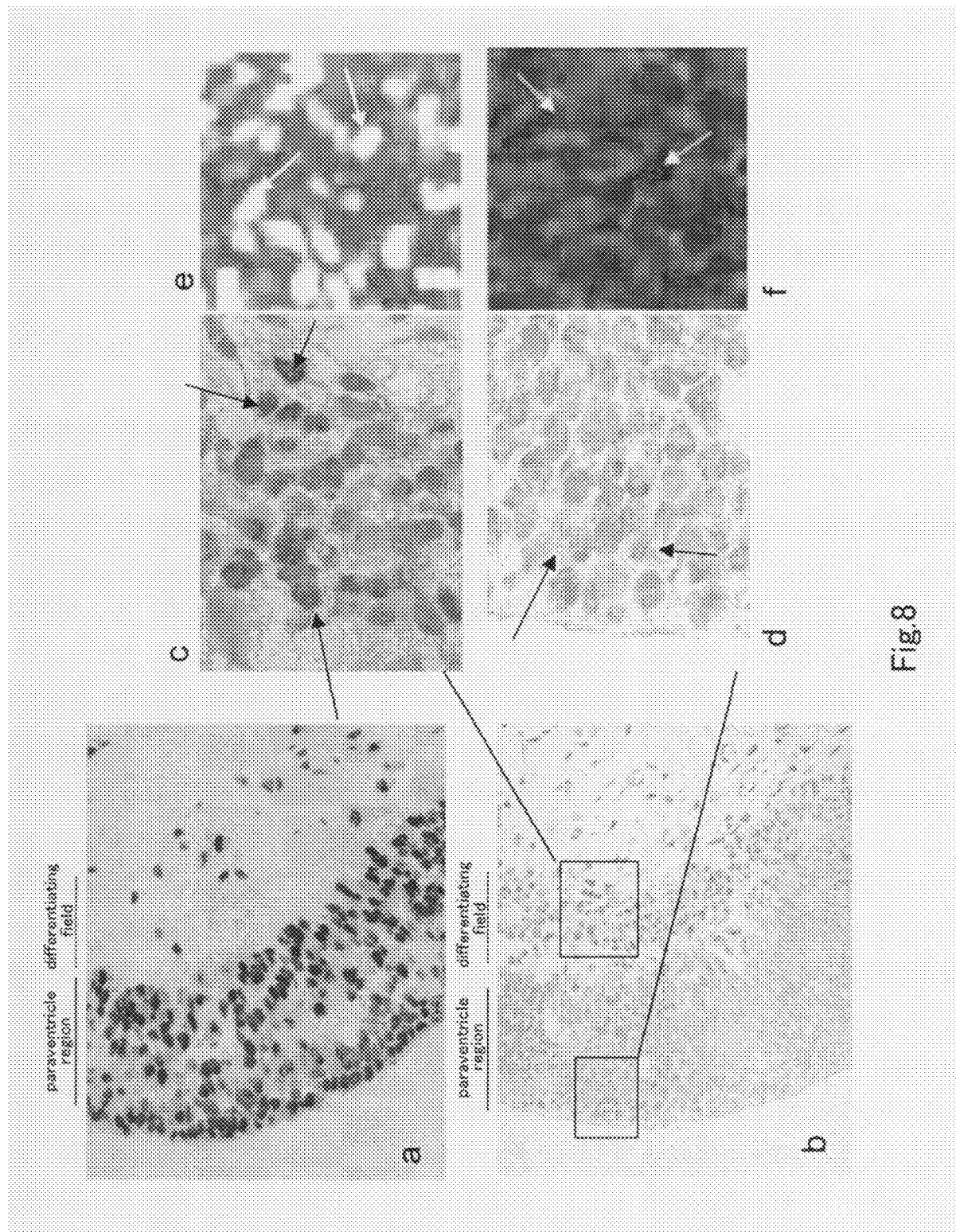
FIG. 8 shows findings of tissue of a isthmus portion of the rat brain at the 14th day of the fetal period.

According to Examples 3 and 4, it was clarified that the time or proliferation state of the cell cycle is changed by the movement of ATBF1 from the cytoplasm to the nucleus and further to the cytoplasm. In order to clarify whether such events occurred only because of ATBF1 or occurred as a results of the effect of some other factors, the present inventors carried out a forced expression experiment in Neuro2A cell in the cultured cell line derived from a mouse neuroblastoma by using an ATBF1 single expression vector. By introducing the ATBF1 expression vector into Neuro2A, ATBF1 was forcedly expressed, and then ATBF1 was stained by the method described in the above 3-1. Thereby, the movement of ATBF1 was observed and a cell cycle was examined by flow cytometry. Furthermore, at the same time, the present inventors mixed BrdU (5-bromodeoxyuridine) in the culture solution and examined whether or not thymidine for DNA replication was incorporated. As a result, it was clear that BrdU was not incorporated into cells recognized to be gathered into the nucleus by allowing ATBF1 to express forcedly (see, FIG. 7b). In a whole cultured cell structure, the rate of cells which stops the cell cycle was increased (see, FIG. 7c). This experiment result means that ATBF1 expression in the nucleus is a direct cause to the stop of DNA replication and stop of the cell cycle.

On the other hand, at the same time when an ATBF1 expression vector was introduced into a gene, BrdU (5-bromodeoxyuridine) was added to a cultured solution and cells in DNA replication were labeled. As a result, it was clarified that in the cells in which the forced expression of ATBF1 was observed, the incorporation of BrdU was not observed without exception. Thus, it was clarified that main cause of the stop of the cell cycle was ATBF1.

EXAMPLE 6

<Relationship Between Movement of ATBF1 to Nucleus and Proliferation Potency in 14-Day Embryonal Fetal Rat Cerebral Nerve Cells>

Furthermore, the present inventors examined the relationship between the movement of ATBF1 to the nucleus and the proliferation potency by using 14-day embryonal fetal rat brain. The nerve cells in the embryonal cerebral base maintain an undifferentiated state (which is referred to as "neuroepithelium cells") in paraventricle region right under the cerebral ventricle. Cells, which finished the final division in the region, pass through a region under the cerebral ventricle and moves into a differentiating field where they are terminally differentiated into the nerve cells. In order to examine the relationship between the ATBF1 expression and the incorporation of BrdU, BrdU was administered to the peritoneal cavity of a mother rat, and three hours later, the mother rat was killed and fetuses were examined. In order to confirm the actual staining properties of ATBF1 and BrdU, an immunohistochemical staining method was carried out by the following procedures. Firstly, the collected fetus tissue was fixed in 4% paraformaldehyde and embedded in paraffin, sliced to the thickness of about 3 µm, and expanded on a slide glass. After deparaffinization, by using a citrate buffer solution (pH 6.0), the tissue specimen was heat treated in an autoclave for four minutes (110° C.) (the reason why the antigen activation method was selected will be seen in Example 7). Then, the tissue specimen was treated with a hydrogen peroxide solution so as to remove endogenous peroxidase. Then, a primary antibody solution, which had obtained by dissolving the anti-ATBF1 antibody prepared in Example 2 in 0.05M Tris buffer (pH 7.6, containing 1% solution of bovine serum albumin and sodium azide) so that the concentration was 5 µg/ml, was dripped on a slice (specimen section) and reacted at room temperature for one hour (primary antibody reaction). After sufficiently washing, a secondary antibody (DAKO Enivision, Labelled polymer, HRP [Code No. K1491] Anti-mouse and Anti rabbit) was allowed to act on the specimen so as to be reacted at room temperature for one hour. After sufficiently washing, a color solution obtained by dissolving DAB in Tris buffer and adding a hydrogen peroxide solution was allowed to permeate to the specimen so as to color (coloring reaction). After coloring, the specimen was sufficiently washed with tap water to remove DAB. Subsequently, the specimen was stained with Mayer's Hematoxylin for about 15 seconds and then, washed with flowing water for eight minutes so as to carry out coloring. Finally, the specimen was allowed to pass through alcohol system and xylene system, and penetration and inclusion were carried out. Fetus rat brain tissue was stained by the above-mentioned procedures, and thereby localization of ATBF1 (using D1-120) in the nucleus and the cytoplasm can be clarified. The BrdU staining was carried out by the same staining technique by using anti-BrdU antibody as a primary antibody. Since the difference in the staining properties between the nucleus and the cytoplasm may be understood easier by fluorescence coloring method than by the DAB coloring, fluorescence staining was also carried out by the same method as shown in Example 3 (3-1) and observation by using a fluorescence microscope (AX70; Olympus) was carried out simultaneously. As a result, it was observed that the neuroepithelium cells existing in the paraventricle region were incorporated BrdU and ATBF1 was localized in the cytoplasm (see, FIGS. 8a, 8b, 8d and 8f). Since the nerve cells existing in the differentiating field did not have incorporate BrdU, it was found that the cell cycle stopped. ATBF1 was localized in the nucleus (see, FIGS. 8a, 8b, 8c and 8e). According to this time results, normal neuroepithelium cells having the similarity to cancer cells in that they are undifferentiated and have division potency are finally differentiated into nerve cells whose cell proliferation was stopped and change their characteristic when ATBF1 moves from the cytoplasm to the nucleus. Comparative observation between the neuroepithelium cells having the division and proliferation potency in the fetus stage and the nerve cells that have lost the division potency and been finally differentiated is extremely useful in considering the grade of malignancy of cancers. As described in detail in the following Examples, in the point that two modes regarding the intracellular localization of ATBF1 are observed in cancer cells and that the cancer cells are classified into a type in which ATBF1 exist in only the cytoplasm and the grade of malignancy is high and a type in which ATBF1 exist in the nucleus and the grade of malignancy is relatively low, it can be determined that the results in the cancer cells are the same as those obtained in the observation of the nerve cells in the fetus stage.

EXAMPLE 7

<Investigation of Optimum Conditions for Detecting ATBF1 (Conditions for Activating Antigen) when Anti-ATBF1 Antibody is Used>

In order to precisely detect ATBF1 by using an antibody from a normal pathological specimen that has been surgically collected, fixed in fixation, and then embedded in paraffin, it is important to determine the activation reaction conditions of antigen. In examining the movement of ATBF1 between the nucleus and cytoplasm, it is important to activate the antigen moderately both in the nucleus and the cytoplasm. Herein, in bladder cancers surgically collected and diagnosed, by using each one case of epithelium papillary non-infiltrating vesicourethral carcinoma (abbreviated as "non-infiltrating cancer") and subepithelial infiltration vesicourethral carcinoma (abbreviated as "infiltrating cancer"), the following investigation was carried out in order to optimum antigen activation method. Firstly, the specimen was fixed in formalin and then, paraffin slice (specimen section) was prepared. By the same technique as that in Example 6, ATBF1 staining (using D1-120) was carried out. As the antigen activation method, as shown below, combination of three kinds of heat treatments and nine kinds of activator solutions (total combination number: 27) and three kinds of enzyme treatments were used so as to investigate the staining pattern thereof. The three kinds of heat treatment include: (1) autoclave, 121° C., 15 minutes; (2) pressure cooker, four minutes, and (3) microwave oven, temperature adjusted to not to be boiled, 15 minutes. The nine kinds of antigen activator solution include: (1) DAKO Target Retrieval Solution PH 6.0, (2) DAKO Target Retrieval Solution High pH, pH 10.0, (3) 10 mM citrate buffer, pH 6.0, (4) 10 mM NaOH-added citrate buffer, pH 7.0, (5) TE buffer (1 mM EDTA+10 mM Tris-HCl buffer), pH9.0, (6) 50 mM Tris-HCl buffer, pH 10.0, (7) 20 mM Tris/0.65 mM EDTA/ 0.0005% Tween 20, (8) 1 mM EDTA solution, pH8.0, and (9) 5% Urea solution. The three kinds of the enzyme treatments include: (1) trypsin, (2) pepsin, and (3) proteinase K.

Figure 12:
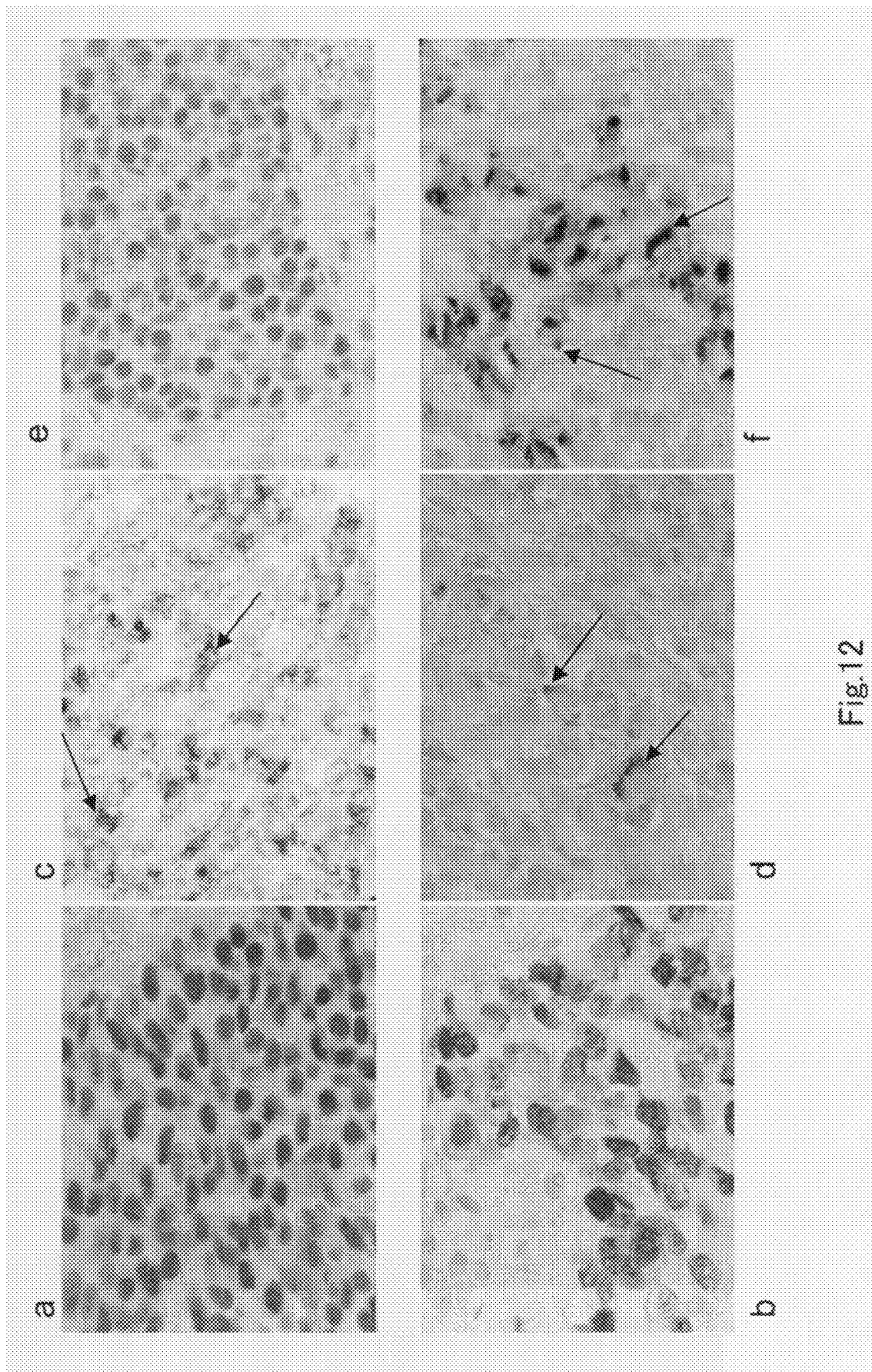
FIG. 12 shows representative examples of the differences of staining properties by antigen activation methods carried out with respect to non-infiltrating cancer and infiltrating cancer cases in urothelial carcinoma of the urinary bladder. The upper part images (FIGS. 12a, 12c, and 12e) show an example of a non-infiltrating cancer; and the lower part images (FIGS. 12b, 12d, and 12f) show an example of an infiltrating cancer. The left side images (FIGS. 12a and 12b) show a case using 50 mM Tris-HCl buffer (pH 10.0) and in which autoclave treatment was carried out. Both in the non-infiltrating cancer case (FIG. 12a) and the infiltrating cancer case (FIG. 12b), staining of ATBF1 in the nucleus was observed. The middle part images (FIGS. 12c and 12d) show a case using DAKO TRS (pH 6.0) in which microwave oven treatment was carried out. Both in the non-infiltrating cancer case (FIG. 12c) and the infiltrating cancer case (FIG. 12d), the staining pattern of ATBF1 in the cytoplasm around the nucleus as in the cell shown by arrows. Right side images (FIGS. 12e and 12f) shows a case using 10 mM citrate buffer (pH 6.0) and in which pressure cooker treatment was carried out. In the non-infiltrating cancer (FIG. 12e), ATBF1 is observed in the nucleus and in the infiltrating cancer (FIG. 12f), ATBF1 is observed in the cytoplasm surrounding the nucleus as shown by arrows, showing that it is possible to differentiate the difference between the localization of staining in the nucleus and the cytoplasm.

The results of staining is described. Depending upon the heat treatment method and kinds of buffers, the staining strength in the non-infiltrating cancer and the infiltrating cancer and the staining patterns of the nucleus and cytoplasm in the cell were changed. The staining pattern of all of the 27 kinds were different from each other but had large tendency. When autoclave treatment is carried out, the staining pattern of the nucleus tends to be outstanding. Depending upon the selection of buffer, the cytoplasm was not stained (see, FIG. 9). On the contrary, with the treatment using microwave oven, it was difficult to stain the nucleus and the staining of the cytoplasm tended to be outstanding (see, FIG. 10). Treatment using a pressure cooker was carried out at temperatures between the temperature by an autoclave and that by a microwave oven and the nucleus and the cytoplasm tended to be stained (see, FIG. 11). Furthermore, in any enzyme treatments, no staining was obtained in non-infiltrating cancers or infiltrating cancers. Depending upon the antigen activation method and kinds of buffers, ATBF1 was localized in both in the nucleus and the cytoplasm in non-infiltrating cancers (see FIGS. 12a and 12c) as well as ATBF1 was localized in both the nucleus and the cytoplasm in infiltrating cancers (see FIGS. 12b and 12d), which made it difficult to make an evaluation. It seemed to be apparently impossible to make an objective evaluation, however, the evaluation of the tendency throughout the staining pattern of 27 kinds was possible as shown in the following (1) and (2). (1) ATBF1 is a protein capable existing both in the nucleus and the cytoplasm and does not exist in membrane or plasma component. (2) In non-infiltrating cancers and infiltrating cancers used in this time, ATBF1 is observed both in the nucleus and the cytoplasm. However, there is a difference in the nucleus/cytoplasm ratio of proteins in the cell. It can be determined that the proteins exist mainly in the nucleus in non-infiltrating cancers, and the proteins exist mainly in the cytoplasm in infiltrating cancers. Based on these two evaluations, it is possible to decide a response to a specimen surgically sectioned and fixed in formalin. That is to say, in order to determine the grade of malignancy of a cancer after ATBF1 staining, it was thought to be important to realize not only the presence of ATBF1 expression in a cancer cell, but also relative comparison of the amount of ATBF1 in the nucleus and the cytoplasm. It was determined to be optimum that 10 mM citrate buffer solution (pH 6.0) was used so as to carry out heat treatment in a pressure cooker for four minutes (110° C.) (FIGS. 12e and 12f). Furthermore, heat treatment by using a microwave (95° C.) or an autoclave (121° C.) was not able to clearly represent the detection of localization of ATBF1 moving between the nucleus and the cytoplasm. Therefore, it was thought that such heat treatment was not suitable for staining ATBF1.

EXAMPLE 8

<Investigation on Relationship Between Grade of Malignancy and ATBF1 in Breast Cancer>

8-1. Evaluation of Expression Amount of ATBF1 mRNA and Prognosis by Using 153 breast Cancer Cases In order to examine the expression amount of ATBF1 mRNA in clinical specimens of 153 operative cases of breast cancers, real-time semi-quantity PCR was carried out. Note here that the real-time semi-quantity PCR was carried out by usual method by using LightCycler ver. 3.0 (Roche Diagnostics K.K.) with reference to attached manual. As a result, it was proved that important parameters as a conventional factors of prognosis, for example, the size of primary lesion, the presence or absence of lymph node metastasis, the presence or absence of the expression of estrogen receptors, and the like, and the change in the expression amount of ATBF1 mRNA had statistically significant correlation (results are not shown). Briefly, it was clear that prognosis of a patient was good in the case of tumors having a large expression amount of ATBF1 and that the reduction in the expression amount meant to be malignant.

Figure 13:
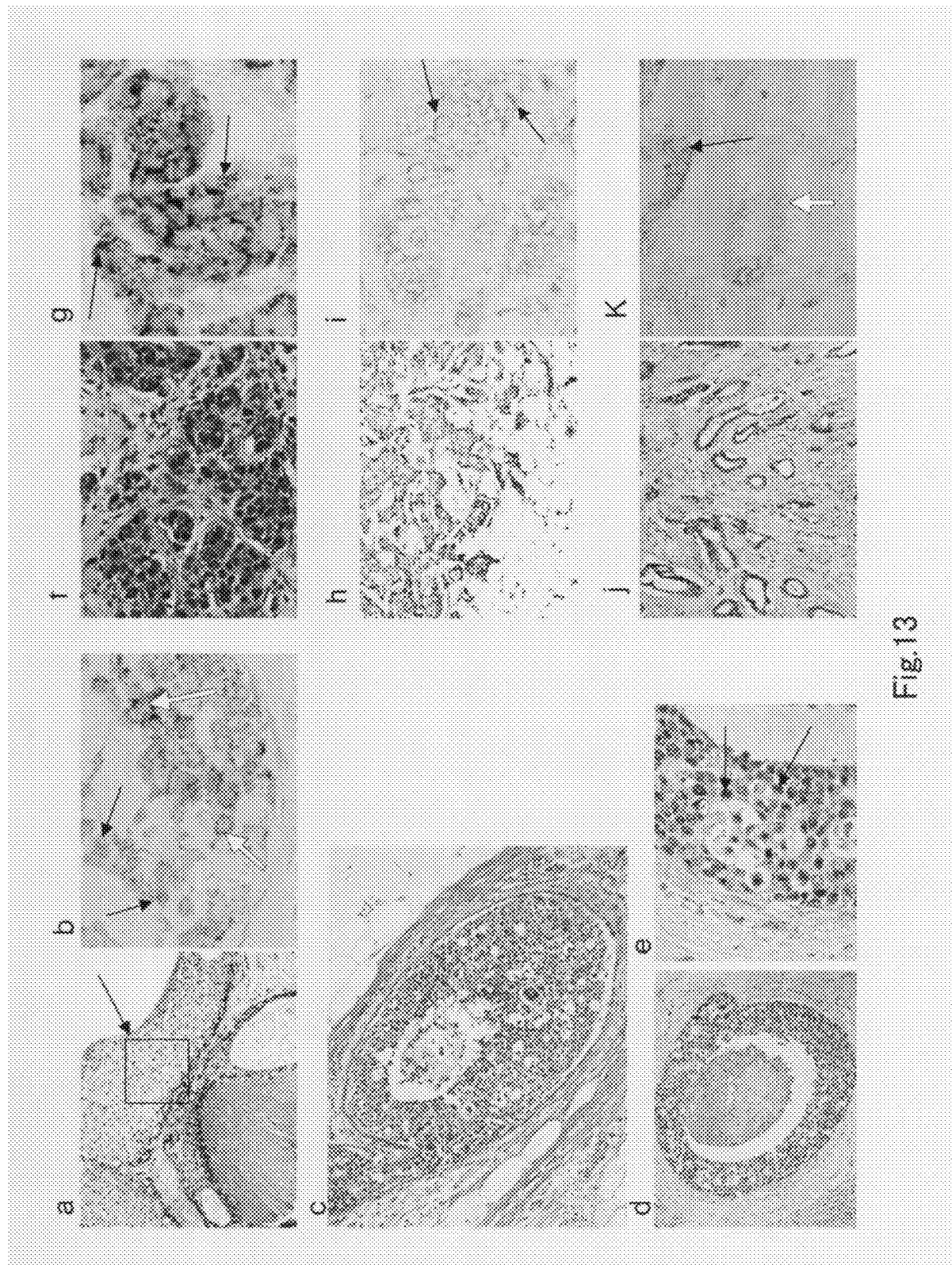
FIG. 13 shows the results of the ATBF1 staining in an excision case and a biopsy case of breast cancer.

8-2. Relationship Between ATBF1 Localization and Histological Infiltration of Tumor in Breast Cancer In order to confirm the actual staining pattern of ATBF1 on a tissue slice (sectioned slice) with respect to 4 breast cancer cases (73, 66, 53, and 50 years old), ATBF1 staining (using D1-120) was carried out by the procedures shown in Example 6. The cases of papillary duct adenocarcinoma and scirrhous carcinoma will be exemplified. In carcinoma that was histologically localized in the lactiferous duct and did not show infiltration to the surrounding of the lactiferous duct (see FIGS. 13a and 13c), the staining of ATBF1 tended to be obtained mainly in the nucleus (see FIGS. 13b, 13d and 13e). In sites showing infiltration growth in the mammary gland and fatty tissue (see FIGS. 13f, 13h and 13j), in some cases, ATBF1 was localized only in the cytoplasm (see FIGS. 13g, 13i and 13k), and in some cases, the staining of ATBF1 was absent (see FIG. 13k). When the intracellular localization of ATBF1 was compared in terms of the histological infiltration, in the state in which carcinoma was localized in the lactiferous duct epithelium and did not show the infiltration, that is, in the state in which the grade of malignancy was low, ATBF1 was localized also in the nucleus. However, when infiltration tendency and progress toward the fatty acid were observed, the tendency was clearly shown that ATBF1 was localized in the cytoplasm or expression was not occurred. This result that is not contradictory to the fact that the presence of the expression amount of ATBF1 mRNA, shown in 8-1 of Example 8, effects on the prognosis. It can be determined that investigation on the localization of ATBF1 is useful for predicting the grade of malignancy of a breast cancer.

EXAMPLE 9

<Investigation on Relationship Between Grade of Malignancy and ATBF1 Expression in Various Human Cancers>

All the examples mentioned below are investigations on the relationship between ATBF1 staining and the grade of malignancy of a tumor in human cancer cells, and the results of the investigation. In all the investigations, ATBF1 staining (using D1-120) was carried out in accordance with procedures shown in Example 6.

9-1. Cultured Bladder Cancer Cell (Difference in ATBF1 Expression in Three Kinds of Human Bladder Cancer Cell Lines)

As Miura (one of the present inventors) has already reported (non-patent document 6: Microbilo. Immunol. 48(2), 137-145, 2004), it has been understood that ATBF1 functions in a state in which it forms a protein-protein binding with p53 in the nucleus of a tumor, and may be involved in the grade of malignancy of a tumor. That is to say, the first function is suppressing transcription of an alpha fetoprotein gene. The second function is suppressing a cell cycle by activating p21 gene. In particular, the function of suppressing the cell cycle by activating p21 gene is triggered when cell DNA is damaged by, for example, radiation, chemical substances, and the like (see, FIG. 1).

In actual tumors, the movement of ATBF1 to the nucleus or the cytoplasm is observed. In the case of considering a grade of malignancy of a cancer, in order to exactly elucidate the meaning of the observation, the relation with respect to the other factors is also important. As the first step, the present inventors investigated where in these cultured cells ATBF1 is localized by staining ATBF1 by using three cultured cell lines (RT4, T24 and HT1376) derived from human bladder cancer in which abnormality in two kinds of tumor suppressor genes, p21 and p53, having the close relation to ATBF1 has been already clarified (see, FIG. 1 again). These three kinds of cultured cell lines have already been examined for the presence or absence of the effect of an anti-cancer drug, cisplatin, and whether or not p21 is to be introduced (Int J Cancer. 1996 Nov. 15; 68(4):501-5). Therefore, it is thought that they are suitable materials for evaluating the grade of malignancy of a tumor in which ATBF1 is expressed.

Figure 14:
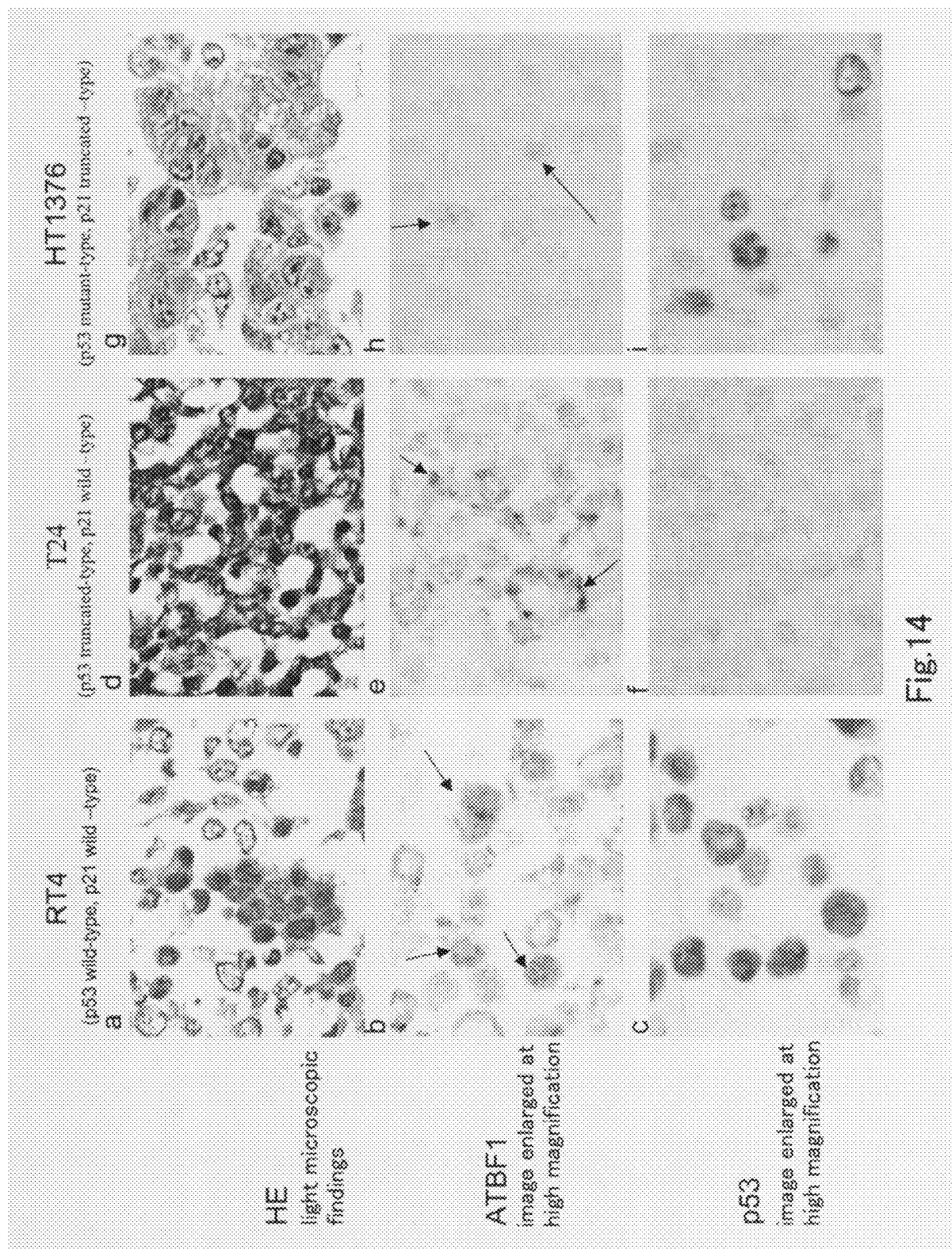
FIG. 14 shows a HE stained image (upper line: a, d, and g; stained images of RT4, T24 and HT1376 from the left side), an ATBF1 stained image (middle line: b, e, and h; stained images of RT4, T24 and HT1376 from the left side), and a P53 stained image (lower line: c, f, and 1; stained images of RT4, T24 and HT1376 from the left side) of human bladder cancer cell line. In RT4, ATBF1 is present also in the cytoplasm but cells showing the localization of ATBF1 in the nucleus as shown by black arrow (FIG. 14b). P53 also shows the strong staining with respect to the nucleus (FIG. 14c). In T24, as shown by black arrow, ATBF1 is almost localized in the cytoplasm and the staining pattern shows a large granular (FIG. 14e). P53 shows an extremely slight staining in the nucleus (FIG. 14f). In HT1376, as shown by black arrow, small amount of ATBF1 is localized in the nucleus (FIG. 14h). P53 shows staining in the nucleus (FIG. 14i).

The result of ATBF1 staining is shown in FIG. 14 (see, FIG. 14). In FIG. 14, the left line pictures show a HE stained image (picture in the upper row), ATBF1 stained image (picture in the middle row) and p53 stained image (picture in the bottom row) of RT4, respectively. RT4 is derived from human papilloma of the urinary bladder and includes not-mutated (wild-type) p21 and p53. Apoptosis can be induced by cisplatin. The grade of malignancy is lowest in the three cultured cell lines. The staining of ATBF1 observed in a small amount in the cytoplasm but mainly in the nucleus, showing that ATBF1 is introduced in the nucleus. Not-mutated p53 can be introduced in the nuclei of almost all the cells.

In FIG. 14, the middle line pictures show a HE stained image (picture in the upper row), ATBF1 stained image (picture in the middle row) and p53 stained image (picture in the bottom row) of T24, respectively. T24 has not-mutated (wild-type) p21 but p53 nonsense mutant. P53 protein is truncated in the middle. Since the usual routes of p53 and p21 do not work (see FIG. 1), apoptosis cannot be induced by cisplatin in this cell. The grade of malignancy is higher than that of RT4. In T24, ATBF1 is observed in the nucleus but staining of ATBF1 is observed in granular state mainly in the cytoplasm. Mutated p53 is hardly introduced in the nuclei of cells.

In FIG. 14, the right line pictures show a HE stained image (picture in the upper row), an ATBF1 stained image (picture in the middle row) and a p53 stained image (picture in the bottom row) of HT1376, respectively. HT1376 has p53 missense mutant in which point mutation of protein is present. In addition, HT1376 has p21 frame shift mutation. Therefore, apoptosis cannot be induced by cisplatin. Therefore, similar to T24, HT1376 is cultured cell line having high grade of malignancy. In this cell line, unlike RT4 nor T24, weak expression of ATBF1 was observed in the nucleus. In a part of the nucleus of the cell, p53 having missense mutation is introduced.

In the above-mentioned three kinds of cultured cell lines, in the stationary state, a small amount of p21 is introduced. When an anti-cancer drug cisplatin is acted on, only RT4 can introduce p21 so as to make cells to apoptosis. In accordance with the idea that ATBF1 introduced in the nucleus of a tumor forms a protein-protein binding with wild-type p53 and is stabilized so as to increase the promoter activity of p21, since p53 is a wild-type in RT4, p53-ATBF1 is stably present in the nucleus. Thus, it can be thought that p21 is normally activated and apoptosis can be introduced. However, since p53 is truncated in the middle in T24, it is assumed that ATBF1 does not easily remain in the nucleus but moves to the cytoplasm. Thus, it can be judged that p21 cannot be introduced. Furthermore, also in HT1376, since p53 protein includes mutation, unlike RT4, a large amount of ATBF1 cannot be present in the nucleus. In addition, since p21 has mutation, p21 does not normally function. Therefore, as a result, in these two cell lines, apoptosis cannot be introduced. Thus, it can be interpreted that the grade of malignancy is high. Anyway, the fact that a large amount of ATBF1 is stained in the nucleus is an index indicating that the grade of malignancy is low. Furthermore, by understanding the localization of ATBF1 in the cell, it is possible to predict the presence or absence of introduction of p53 or the presence or absence of mutation. It can be judged that the relationship between the staining pattern of the cultured bladder cancer cells and the expression of p53 can provide very important information in considering the grade of malignancy of a cancer after ATBF is stained in actual bladder cancers.

9-2. Bladder Cancer (Usefulness of ATBF1 in Determining Grade of Malignancy of Human Bladder Cancer)

Figure 15:
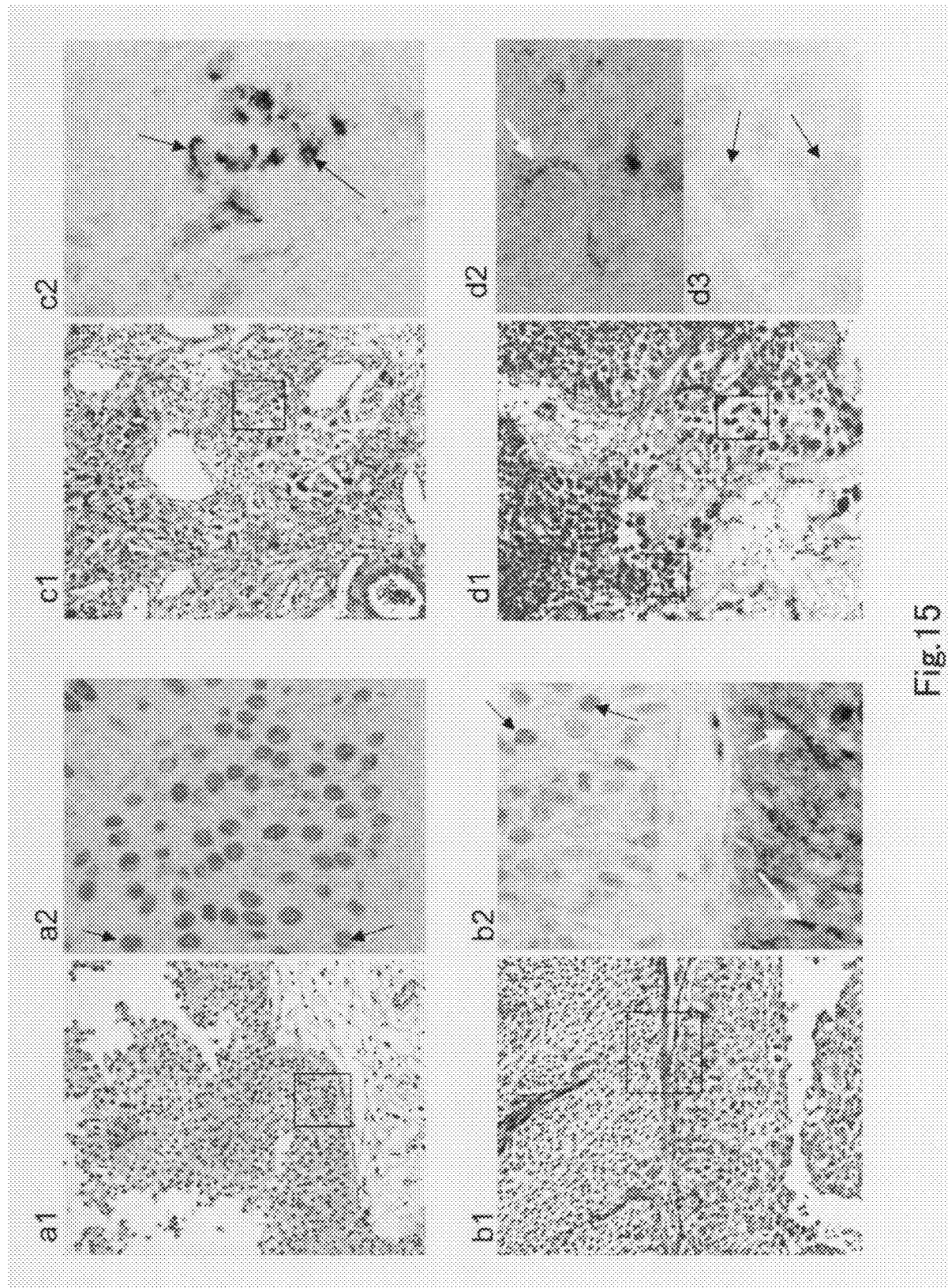
FIG. 15 shows human vesicourethral carcinoma tissue (a: papillary intramucosal carcinoma, WHO Grade I, low atypical case; b: papillary intramucosal carcinoma, case including WHO Grade I (low atypical) and WHO Grade II (middle grade of malignancy); c: submucous infiltrating cancer, WHO Grade II, moderately atypical case; and d: submucous infiltrating cancer, WHO Grade III, highly atypical).

In order to investigate the usefulness of ATBF1 staining in determining the grade of malignancy of human vesicourethral carcinomas, staining properties of ATBF1 were examined in cases in various WHO grades classified based on the degree of histological atypical of tumor cells that are thought to be one of the indices of the grade of malignancy (see FIG. 15). FIG. 15a shows stained images (a1: HE stained image, a2: ATBF1 stained image) of papillary intramucosal carcinoma of 65-year-old man case (WHO Grade: I, histological atypical: low). The stained ATBF1 is observed only in the nucleus. This staining pattern is similar to that of the cultured cell RT4 (see 9-1 mentioned above and FIG. 14b).

Figure 1:
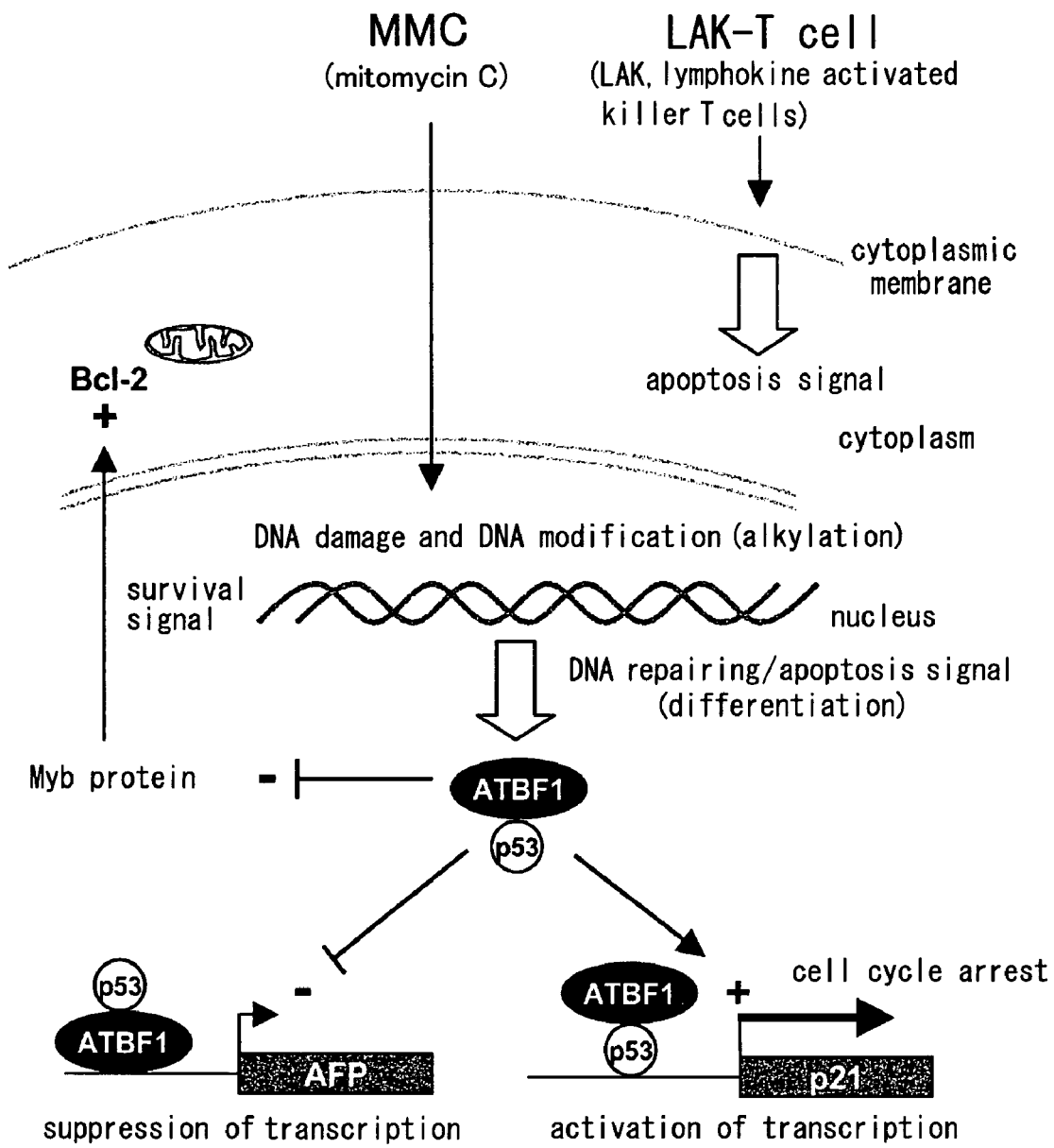
FIG. 1 is a schematic view showing the relationship between ATBF1 and both p21 and p53.

FIG. 15b shows stained images (FIG. 15b1: HE stained image, FIG. 15b2: ATBF1 stained image) of a papillary intramucosal carcinoma of 81-year-old man case (WHO Grade: I, histological atypical: low; and WHO Grade: II, histological atypical: moderate are mixed). In a portion of Grade I, the stained ATBF1 is observed only in the nucleus. In a portion of Grade II, the stained ATBF1 is observed in the cytoplasm. Also herein, the staining pattern in the nucleus is similar to that of the cultured cell RT4 (see 9-1 mentioned above and FIG. 14b). On the other hand, the staining pattern in the cytoplasm is similar to that of the cultured cell T24 (see 9-1 mentioned above and FIG. 14e).

FIG. 15c shows stained images (FIG. 15c1: HE stained image, FIG. 15c2: ATBF1 stained image) of a submucosal infiltrating cancer of 55-year-old man case (WHO Grade: II, histological atypical: moderate). The stained ATBF1 is observed in the cytoplasm. This staining pattern is similar to that of the cultured cell T24 (see 9-1 mentioned above and FIG. 14e).

FIG. 15d shows stained images (FIG. 15d1: HE stained image, FIGS. 15d2, d3: ATBF1 stained image) of a submucosal infiltrating cancer of 84-year-old man case (WHO Grade: III). In some cells, the stained ATBF1 is observed in the cytoplasm (FIG. 15d2. The staining pattern is similar to that of the cultured cell T24. In some cells, the staining of ATBF1 is thin and tends to be absent (FIG. 15d3. The staining pattern is closer to HT1376 in the three kinds of cultured cells.).

It cannot be said that the tissue atypical degree, which is WHO grade, completely corresponds to the ATBF1 expression. However, as the WHO grade is increased, and as papillary epithelial urothelial carcinoma moves to infiltrated urothelial carcinoma, the following movement tends to be observed sequentially: ATBF1 is localized in the nucleus; ATBF1 is localized in the cytoplasm; and furthermore, ATBF1 is absent. Therefore, by considering the results of 9-1 mentioned above, it is possible to determine the grade of malignancy of bladder cancers based on the localization of ATBF1.

9-3. Gastric Adenoma and Gastric Cancer (Gastric Biopsy Diagnosis, Investigation on the Series of Group III to Group V and ATBF1 Expression)

As to gastric adenomas with different atypical degrees and gastric cancers that is securely malignant, ATBF1 was stained (using D1-120), the relationship between the staining of ATBF1 and the localization of expression was examined.

Figure 16:
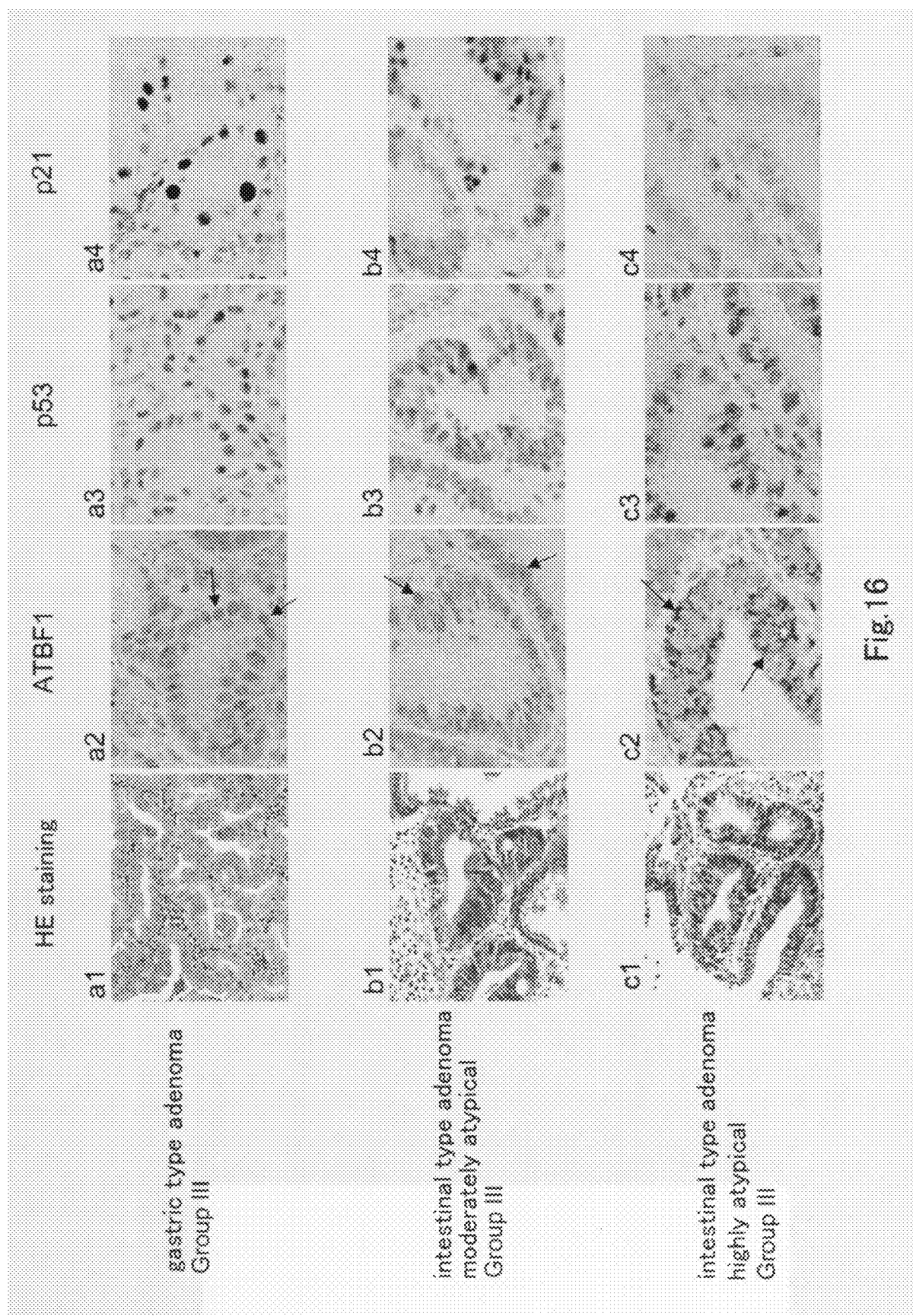
FIG. 16 shows the expression of ATBF1 in adenoma diagnosed to be Group III.

In gastric adenomas (herein, 55-year-old female case is shown, in which several polyps in one stomach have undergone polypectomy), most gastric-type atypical epithelial nests or adenomas (Group III, see FIG. 16a1) are benign lesions whose progresses are slow. In the follow-up for several years, much change may not be observed. In this case, the staining pattern of ATBF1 is localized in the nucleus (see FIG. 16a2). The staining pattern of p53 in the nucleus is observed (see FIG. 16a3) and introduction of p21 into the nucleus can be observed (see FIG. 16a4). Also in intestinal type atypical epithelial nests or adenoma lesions (Group III) with moderately atypical degree (see FIG. 16b1), ATBF1 was localized mainly in the nucleus (see FIG. 16b2). Although there was difference in the strength with respect to gastric type adenoma, expression of p53 and p21 was observed (see FIGS. 16b3 and 16b4). On the contrary, in the intestinal type atypical epithelial nests or adenomas (Group III, see FIG. 16c1) that is thought to be a borderline lesion with highly atypical degree, a granular form of staining of ATBF1 was observed in the cytoplasm (see FIG. 16c2). The expression of p53 was also slightly diffused (see FIG. 16c3) and the introduction of p21 into the nucleus was not observed (see FIG. 16c4).

As shown in FIG. 1, when it is thought that ATBF1 introduced in the nucleus forms a protein-protein binding with p53 to introduce p21 and is involved in the cell cycle arrest or apoptosis, in the case where adenoma is in the slight or moderate degree of atypical in the same adenomas, while ATBF1 is localized in the nucleus, p21 can be introduced. However, in the case where adenoma is diagnosed as having high degree of atypical, it can be thought that ATBF1 moves to the cytoplasm and p21 cannot be introduced and that the proliferation of adenoma cannot be suppressed. According to this result, it can be said that the staining of ATBF1 can predict the grade of malignancy of adenoma (since the adenoma is not a malignant tumor, the provability of proliferation potency or incidence of apoptosis rather than the grade of malignancy can be predicted). It can be said that this result is useful for differentiating an adenoma that remains as a benign lesion from a borderline lesion that is required to be differentiated from cancer.

Hereinafter, the results of ATBF1 staining in gastric cancer cases in various histological patterns will be described.

Figure 17:
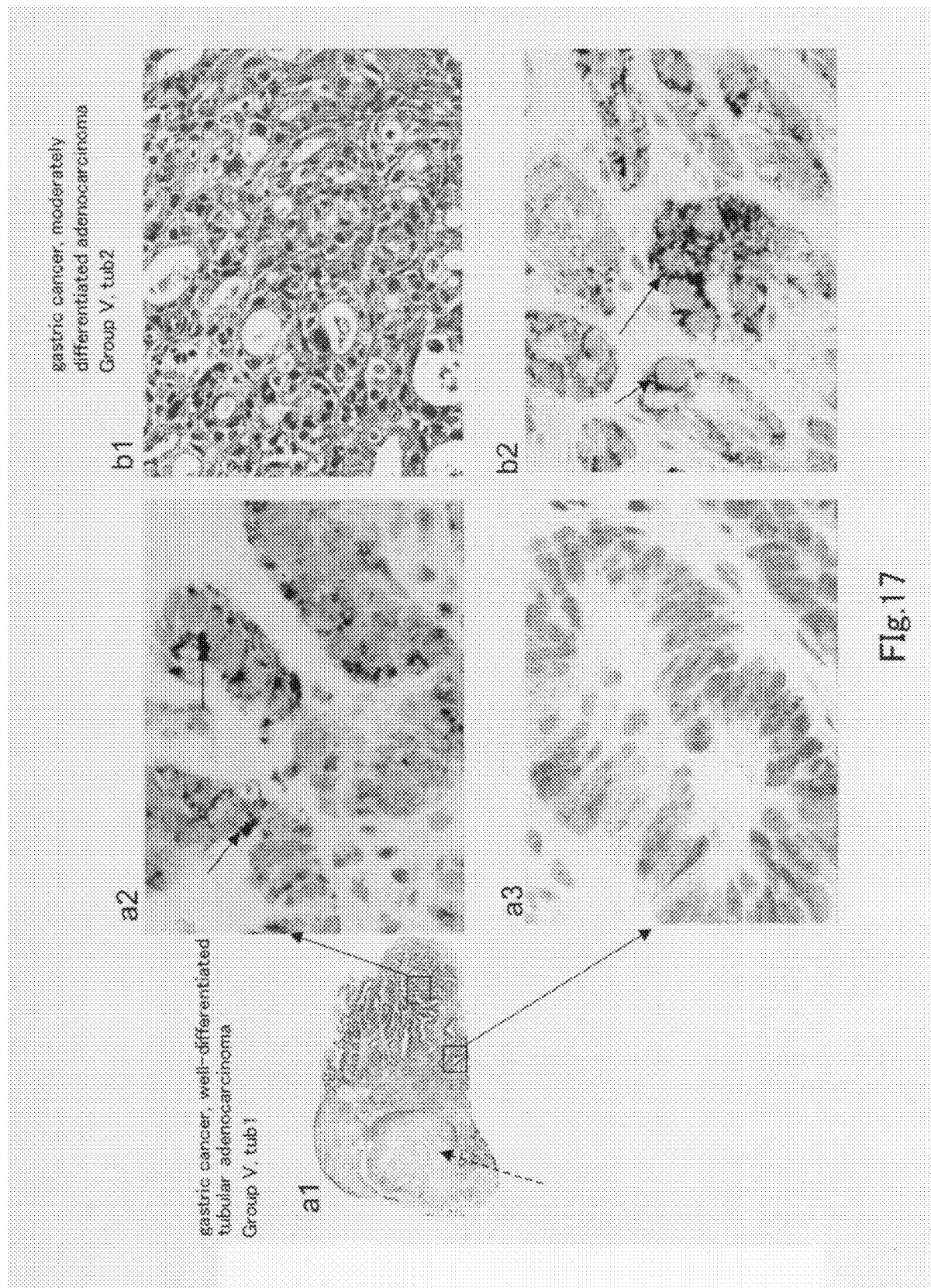
FIG. 17 shows ATBF1 expression in a histologically well-differentiated or moderately differentiated tubular adenocarcinoma among gastric cancers diagnosed to be in Group V.

(1) Well-differentiated adenocarcinoma (tub1, Group V): One case of a gastric cancer developed in the esophagus subepithelial and cardiac regions (78-year-old man, see FIG. 17a1) is shown. ATBF1 exists both in a site in which a cancer cell exists in the cytoplasm (see FIG. 17a2) and a site lacking the ATBF1 expression (see FIG. 17a3).

(2) Moderately Differentiated Adenocarcinoma (tub2, Group V)

An example of biopsy of a 44-year old woman (see FIG. 17b1) is shown. In this case, ATBF1 exists mainly in the cytoplasm (see FIG. 17b2).

(3) Poorly-Differentiated Adenocarcinoma, Solid Type (por 1, Group V)

Figure 18:
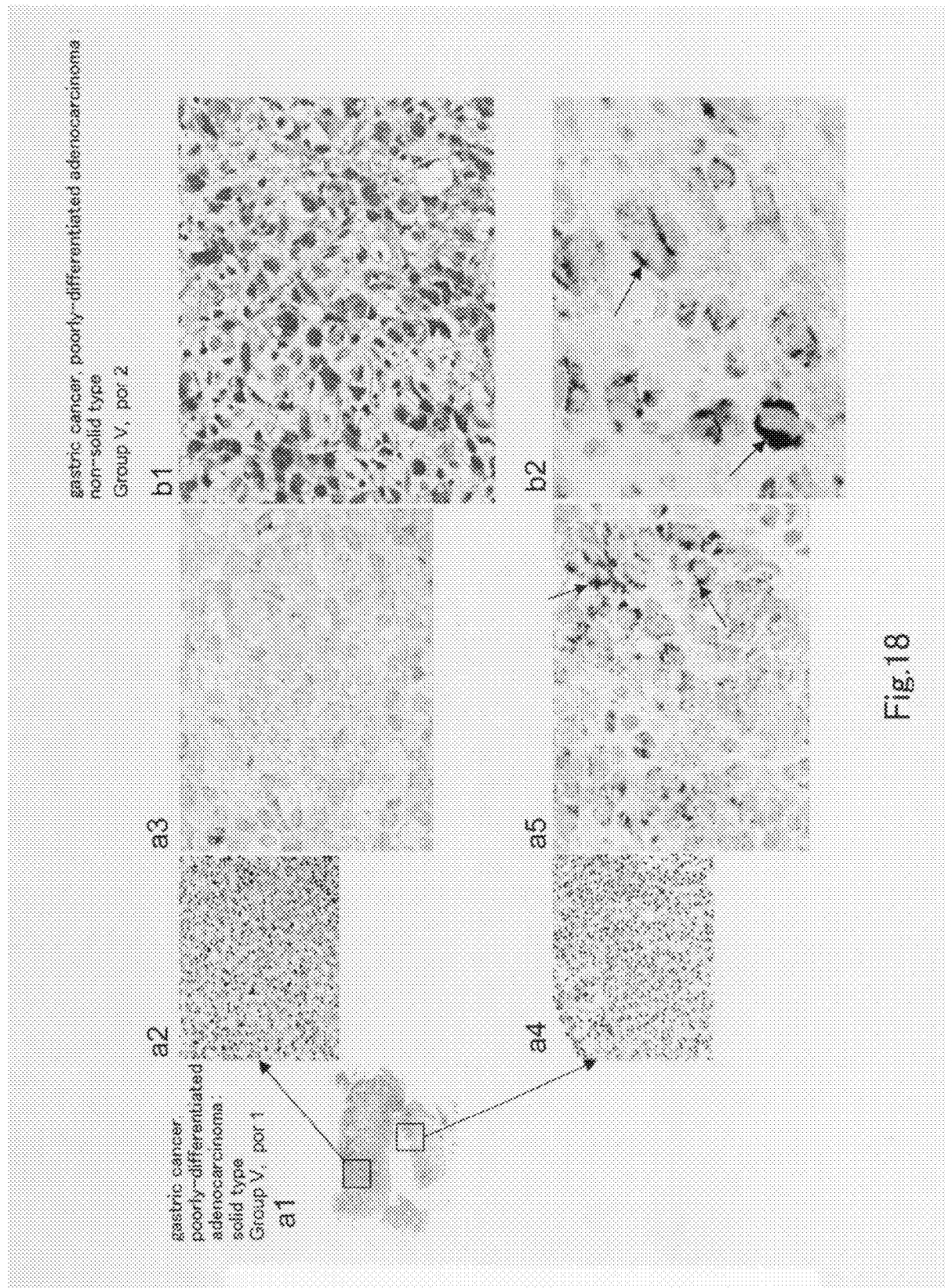
FIG. 18 shows ATBF1 expression in a poorly-differentiated adenocarcinoma among gastric cancers diagnosed to be in Group V.

An example of biopsy of a 68-year old woman is shown. In por1 in which an expansive development is shown in the mucosa (see, FIG. 18a1, 18a2, and 18a4), the staining of ATBF1 exists both in a site in which whole cell lacks staining (see, FIG. 18a3) and in a site in which staining is localized in the cytoplasm (see, FIG. 18a5).

(4) Poorly-Differentiated Adenocarcinoma, Non-Solid Type (por2) and Adenocarcinoma Mucocellulare (Signet Ring Cell Carcinoma, sig)

Figure 19:
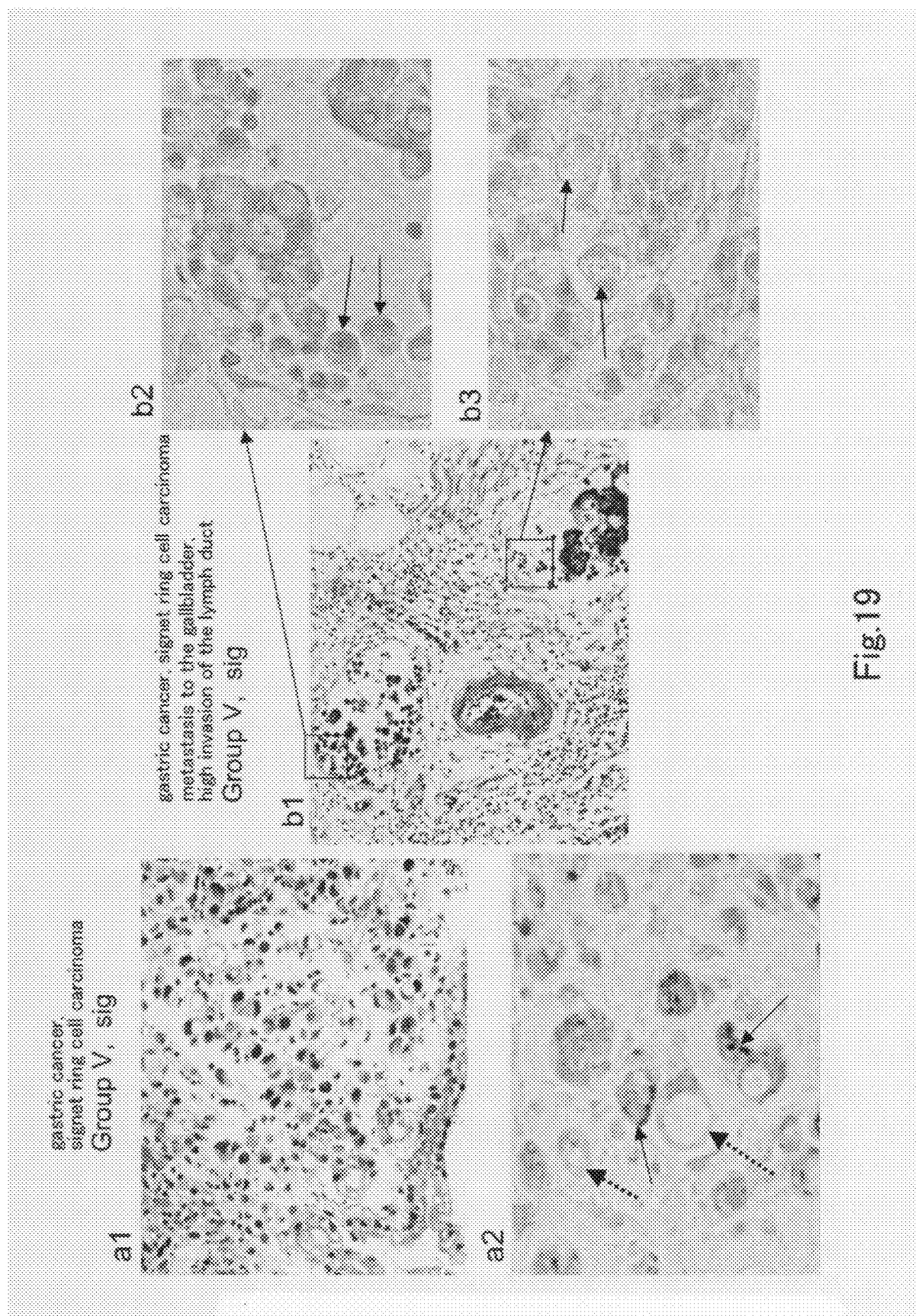
FIG. 19 shows ATBF1 expression in an infiltration portion in adenocarcinoma mucocellulare (FIGS. 19*a*1 and *a*2) and a metastasis infiltration portion to the gallbladder (FIGS. 19*b*1, *b*2 and *b*3) among gastric cancers diagnosed to be in Group V.

An example of biopsy of a 72-year old woman is shown. In por2, sig in which an infiltrating development is shown in the mucosa and the whole cell of the gastric wall (see, FIG. 18b1), staining of ATBF1 was localized mainly in the cytoplasm and no staining was observed in the nucleus (see, FIG. 18b2). In a site of adenocarcinoma mucocellulare (see, FIG. 19a1), cells in which ATBF1 existed in the cytoplasm and cells lacking ATBF1 were included together (see, FIG. 19a2).

(5) Metastatic Adenocarcinoma Mucocellulare (sig)

Not-resectable case of scirrhous stomach cancer (age 74) is shown. When the gallbladder was extracted because of cholelithiasis, the metastasis to the gallbladder was found. The ATBF1 expression is shown in a site of metastasis to which cancer moved and infiltrated to the gallbladder wall via invasion of the lymph duct (see FIG. 19b1). In adenocarcinoma mucocellulare in a usual primary site of the gastric cancer, cells in which ATBF1 is localized in the cytoplasm and cells lacking ATBF1 exist together (see FIG. 19a2). However, the site of this case, showing the metastasis to the gallbladder (see FIG. 19b1), both in the lymph duct invasion site (see FIG. 19b2) and the infiltration site to the connection tissue of the gallbladder wall (see FIG. 19b3), completely lacked ATBF1.

(6) AFP Producing Gastric Cancer

As described in the previous documents (non-patent documents 2, 5 and 7), an AFP production site of an AFP producing gastric cancer lacked ATBF1 expression completely (results are not shown).

Firstly, when the fact that an AFP producing gastric cancer has extremely high grade of malignancy is taken into consideration, it can be predicted that lacking ATBF1 expression can significantly enhance the grade of malignancy of a gastric cancer. In the examination of the ATBF1 expression in a large number of cases mentioned above and cases continuing at present, a site in which ATBF1 is localized only in the nucleus can be found, although locally, in a part of the well-differentiated cancers and a part of the solid type poorly-differentiated cancers. However, in various cancers of any histological patterns in the most cases, the most of ATBF1 is present in the cytoplasm or ATBF1 is absent. This result shows that a gastric cancer is a tumor with high grade of malignancy in general. At the same time, the result shows that lacking staining of ATBF1 mainly in the cytoplasm can indicate the further increase in the grade of malignancy. Throughout examination of a series of expression in the gastric adenoma and the gastric cancer, also in the stomach, it was judged that ATBF1 staining can play an important role for predicting the grade of malignancy of a tumor or prognosis thereof.

9-4. Extramammary Paget's Disease of Penis

A case of a 72-year-old man, in which extraction of the penis and radical groin resection were carried out, is shown. Paget's disease is a concept of dermatosis in a papillary area of the mammary gland, which was originally suggested by Dr. Paget in 1874. In fact, Paget's disease is an adenocarcinoma developing in various sites other than the mammary gland. In the early stage, a large-sized Paget cells, having the nucleus that is histologically rich in chromatin and a plenty of bright cells, are localized in epidermis (so-called, intraepithelial carcinoma, carinoma in situ). The adenocarcinoma is a malignant disease that infiltrates into the dermis, causes lymphogenous metastasis and in turn, multiorgan infiltration in accordance with the progress of the pathologic conditions. In this case, since pathologic conditions in various stages having different grades of malignancy, including a site in which the Paget cell is localized in the epidermis of the penis skin, a site in which the cell infiltrates into the dermis, a site having tumor formation, and a site of lymph node metastasis of the groin, can be observed simultaneously, ATBF1 expression in each site was examined (using D1-120) (see FIG. 20a).

Figure 20:
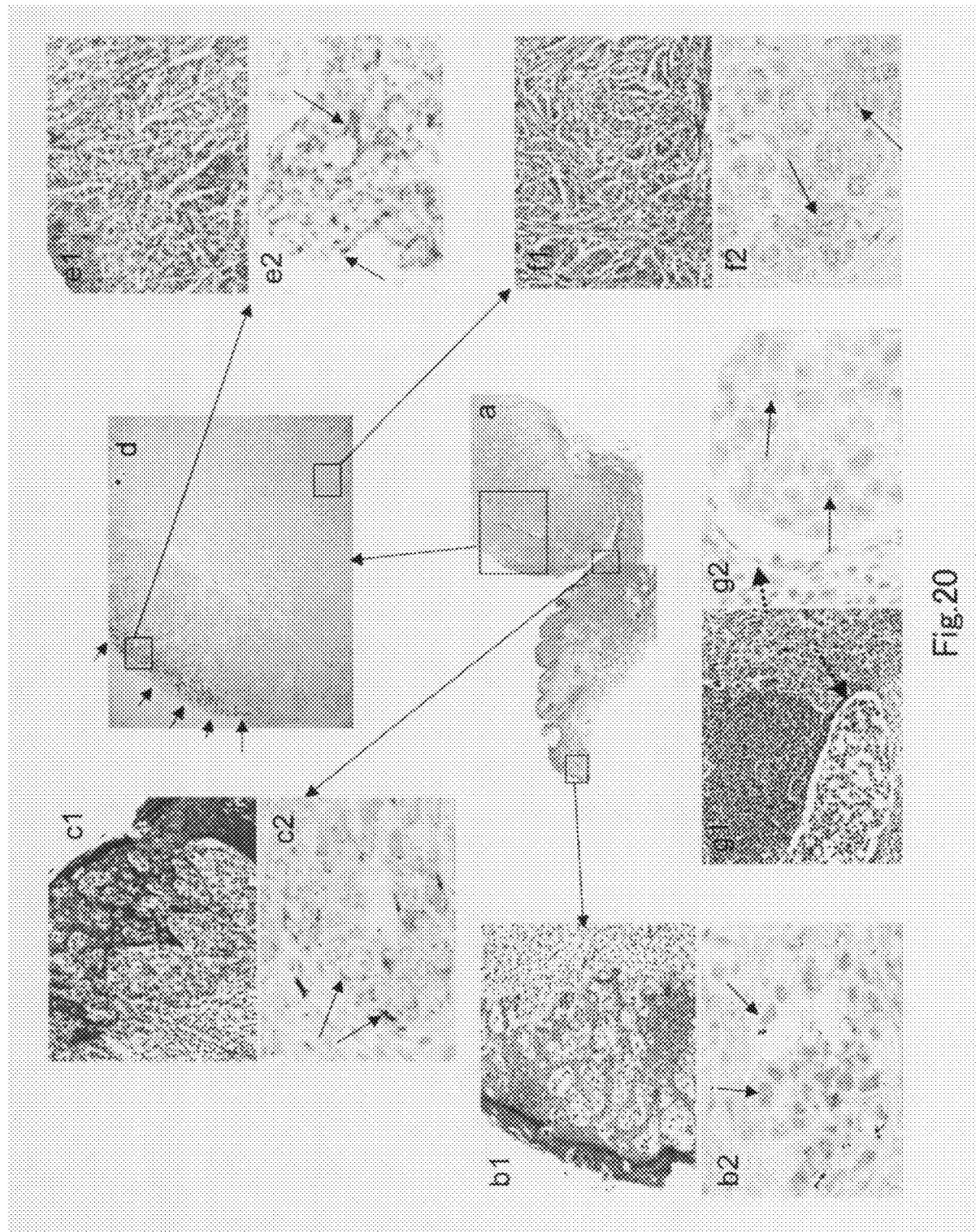
FIG. 20 shows ATBF1 expression in various grades of malignancy of extramammary Paget's disease developed in the penis.

The epithelium of the penis skin in the site somewhat distant from the portion in which the tumor was formed was observed (see FIG. 20). According to HE stained image, a large-size and bright cells were observed, and the dispersion of Paget cells containing mucus were observed. Slightest amount of cells was not infiltrated to the dermis, showing a state that can be judged to be a cancer localized in the epithelium (see FIG. 20b1). Staining of ATBF1 was observed mainly in the nucleus of the Paget cell (see FIG. 20b2). Next, also in the epidermis in the vicinity of the portion in which a tumor is formed, Paget cells continuously exist. In a site in which slight cells ere infiltrated to the dermis (see FIG. 20c1), staining of ATBF1 was observed in the cytoplasm (see FIG. 20c2) and staining was not observed in the nucleus at all. Furthermore, in a site in which high infiltration was observed, the epidermis was erosive and a tumor was formed (see FIGS. 20a and 20d), presence of ATBF1 in the cytoplasm was more clearly observed (see FIG. 20e2). However, in the surface and inner deep portion of the tumor, the situation of the ATBF1 expression was utterly different. As the portion moves to the inside, ATBF1 tended to be absent (see FIG. 20ef2). In most of the tumors metastasized to the inside of the lymph node in the groin, cells lacks ATBF1 (see FIG. 20g2) and a small amount of cells in which a small amount of ATBF1 existed in the cytoplasm exist together. From the viewpoint that cancer cells showing the distant metastasis has a high grade of malignancy, with comparison with the results obtained by the ATBF1 staining, it can be judged that a cancer cell in the lymph node metastasis site that tended to lack ATBF1 and cancer cells existing inside the tumor showing the tumor formation property have the highest grade of malignancy. The site in which infiltration to the dermis starts, or the site in which ATBF1 on the surface of the tumor exists in the cytoplasm has the next highest grade of malignancy. It can be judged that the site in which ATBF1 is localized in the nucleus of the epidermis has the lowest grade of malignancy. That is to say, Paget cells remain in the epithelium while the ATBF1 is localized in the nucleus, cells infiltrates to the cytoplasm, forms tumor, and further the cells lack expression to cause the metastasis. This result shows that in adenocarcinoma like extramammary Paget's disease, ATBF1 staining is useful for predicting the progress of tumors and prognosis.

9-5. Investigation on Relationship Between Normal Human Bone Marrow Hematopoietic Cell and ATBF1

A specimen of the case (67-year-old woman) that was suspicion of blood disease and underwent bone marrow aspiration, resulting in being diagnosed to be normal was used. The specimen was fixed in formalin and then stained with ATBF1 staining (using D1-120) was carried out.

Figure 21:
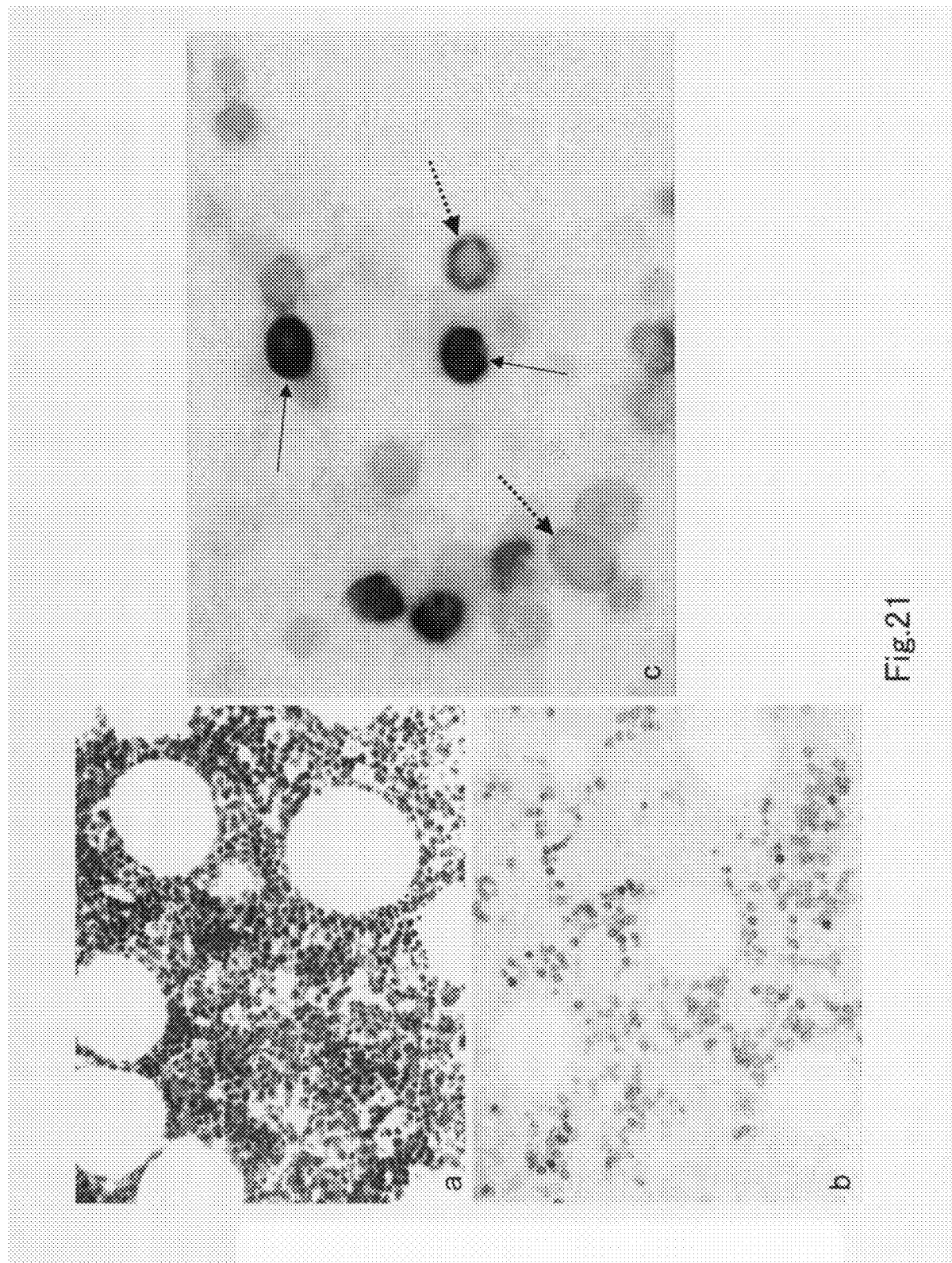
FIG. 21 shows ATBF1 expression in bone marrow.

Since the normal human bone marrow is hematopoiesis, the cell proliferation and apoptosis thereof are active. It is thought to be useful to know the ATBF1 expression in the cell group in considering the grade of malignancy of the cancer and the effect of various kinds of treatment. In matured human tissue other than the tissue in the fetal period, as long as it is considered immunohistologically, a large amount of ATBF1 is expressed in the bone marrow. Stained ATBF1 was highly observed not only in the cytoplasm but also in the nucleus (see FIGS. 21b and 21c). In the current study, the ATBF1 expression in the cytoplasm means that proliferation potency is maintained and the ATBF1 expression in the nucleus means that it is easy to cause the cells to apoptosis in accordance with the DNA damage. Therefore, it is thought that the staining of ATBF1 in the bone marrow is compatible with the fact that the bone marrow hematopoietic cells are cell group maintaining the proliferation potency and being susceptible to the influence of chemotherapy and radiation (which is referred to as "myelosuppression") and provides important information in understanding the staining pattern of a cancer.

The ATBF1 expression in blood cells, which had been proliferated and moved to the periphery (the lymph node, peripheral blood) without undergoing apoptosis, was utterly different from that in the bone marrow. The ATBF1 expression was not observed in the nucleus at all and the expression was observed in the cytoplasm only in a small amount of cells (the lymph node and the veins in the various organs were examined, not shown).

9-6. Small Peripheral Type Lung Cancer (Investigation on Usefulness of ATBF1 in Judging Development of Small Peripheral Type Lung Cancer, Investigation of Progressing Process and Grade of Malignancy)

Recently, in accordance with the progress in diagnostic imaging technology and the prevalence of diagnosis using CT, a large number of extremely small peripheral occurrence type adenocarcinomas have been discovered. They are known to be gland glass opacity (GGO) on CT and pathologically diagnosed as having atypical adenomatous hyperplasia (adenomatous atypical hyperplasia, AA H), and local bronchioloalveolar epithelial cancer (Bronchiolo-Alveolar Carcinoma, BAC), Noguchi's classification A to C). Data on the prognosis have been accumulated.

AAH was described in WHO classification of lung cancers in 1999 and the idea of adenoma-carcinoma sequence (AAH corresponds to large bowel adenoma) as suggested in the large bowel cancers was introduced. To date, it has been shown that all of AAHs do not progress to adenocarcinoma, or de novo BACs developing without passing through the AAH have been present. In the case of GGO diagnosed as having AAH, it is difficult to select surgical operation and follow-up may be selected.

On the other hand, to BAC with 2 cm or less, Noguchi's classification is employed. In types A and B by Noguchi's classification, metastasis is not observed in the lymph node and the five-year survival rate is 100%, so that types A and B correspond to a non-infiltrating cancer. In type C, 30% of cells show lymph node metastasis and the five-year survival rate is 75%, so that type C corresponds to an infiltrating cancer.

In this way, at present, since a large number of precancerous lesions and early stage pulmonary adenocarcinoma have been discovered as GGO, it is clearly important to consider a carcinogenesis mechanism in the peripheral pulmonary adenocarcinoma tissue-morphologically, cell-biologically and molecular biologically and to describe pathologically in determining the treatment policy and predicting the prognosis. However, it lacks definite criteria in judging whether AAH or BAC in rapid diagnosis such as biopsy diagnosis, cytologic diagnosis, rapid diagnosis at the time of operation, or the like. It is not so easy, which annoys pathologists and surgeons.

At this time, ATBF1 staining (using D1-120) was carried out in lung tumors in four cases (low-grade AAH to BAC, to type B by Noguchi's classification) that had been diagnosed has having GGO by CT examination. Then, by using a localization of ATBF1 in the nucleus and cytoplasm, it was possible to show probability for clearly discriminating between a disease group of precancerous lesions including low grade of atypical adenomatous hyperplasia (low-grade AAH) and high grade of atypical adenomatous hyperplasia (high-grade AAH) and a group of local bronchioloalveolar epithelial cancers (lesions corresponding to BAC, types A and B by Noguchi's classification), so-called early stage non-infiltrating cancers, in which cells were proliferated in a way in which they are substituted for alveolar epithelium and did not include active fibroblast in interstitial tissue in the lesion. Therefore, much attention has been focused on the usefulness of the staining of ATBF1 in judging the study on development and progressing process of small peripheral type adenocarcinoma, and the grade of malignancy of carcinomas discovered in the early stage.

Figure 22:
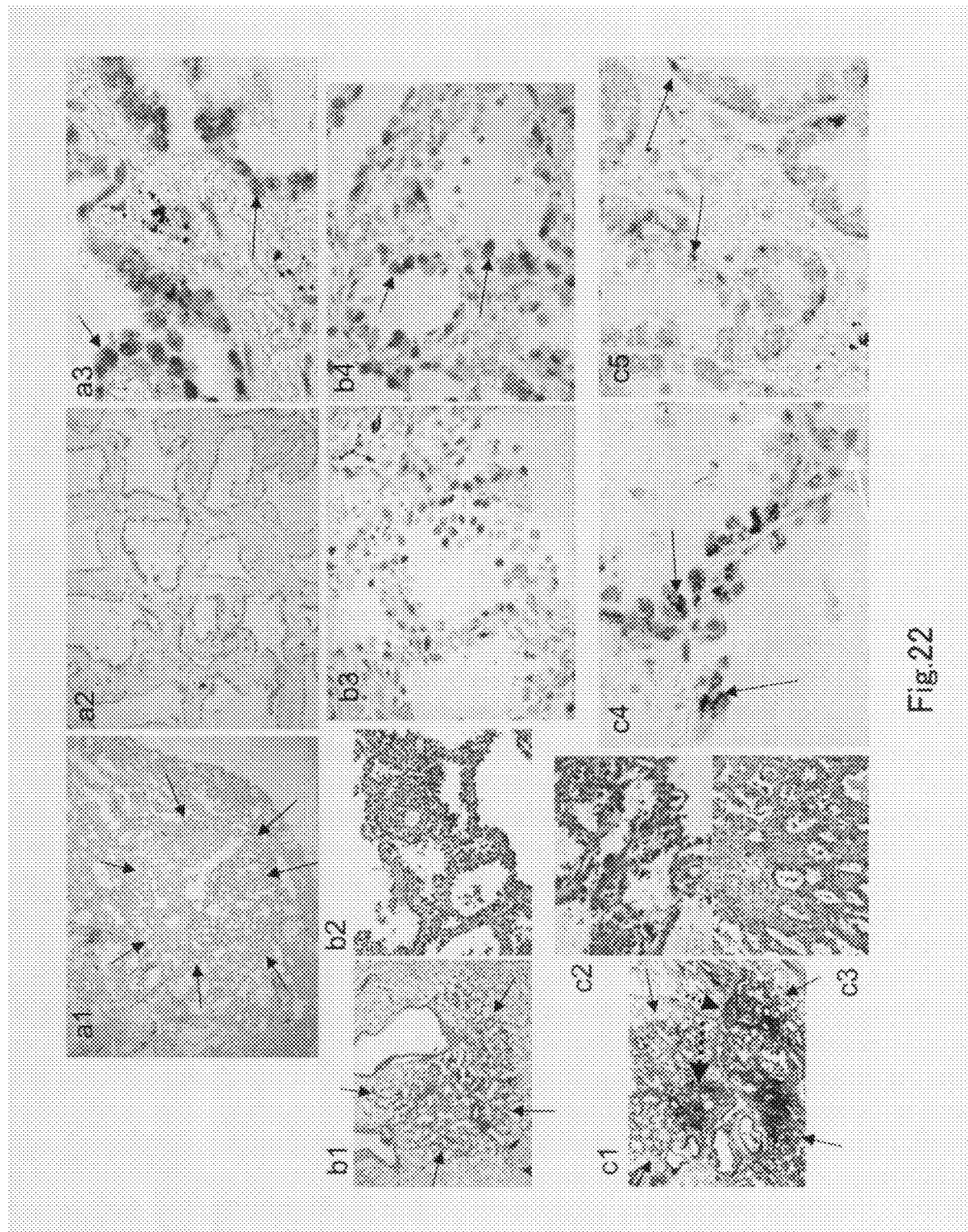
FIG. 22 shows structural image and ATBF1 expression in a small peripheral type pulmonary tissue.

Firstly, as a case of the precancerous lesion AAH, a case of a 78-year-old woman with Low-grade AAH (see FIG. 22a) was used and ATBF1 staining was carried out so as to examine the localization site of ATBF1. Localization of ATBF1 in the cytoplasm was observed in some cells. However, ATBF1 was localized mainly in the nucleus in most of cells (see FIG. 22a3). Next, as to tumor with slightly higher grade, by using a case of a 57-year-old woman with high-grade AAH was examined (see FIG. 22b). Similar to low-grade AAH, also in the high-grade AAH, although a site in which staining of ATBF1 existed in the cytoplasm was observed, the staining was mainly observed in the nucleus.

As to BAC (adenocarcinoma corresponding to types A and B by Noguchi's classification) corresponding to an early stage non-infiltrating pulmonary cancer, a case of tumor of a 77-year-old woman (see FIG. 22c) and a case of tumor of 64-year-old man (not shown) were examined. In a site in which the proliferation is carried out in a way which is substituted for alveolar cell epithelium (see FIG. 22c4) and in a site in which a surrounding pulmonary alveolus tissue was collapsed and fibrosis occurred (see FIG. 22c5), the localization site of ATBF1 was utterly different from that of the case of AAH. That is to say, in BAC corresponding to types A and B by Noguchi's classification, localization of ATBF1 in the nucleus was observed n some cells, but localization of ATBF1 was observed mainly in the cytoplasm.

The following is a description for reference. As to adenocarcinomas that can be judged to be BAC in early stage infiltrating cancers corresponding to type C by Noguchi's classification and in further progressed infiltrating cancers, other investigations have been done. As a result, in any cases, ATBF1 is localized in mainly in the cytoplasm (results are not shown).

According to studies performed to date, it was thought that the presence of ATBF1 in the nucleus meant the cell cycle arrest via p21 and good efficacy of chemotherapy and radiation treatment. On the contrary, the presence of ATBF1 in the cytoplasm is assumed to mean that cells have strong proliferation property and that various treatment and therapies are not effective. As mentioned above, in the low-grade AAH and high-grade AAH, ATBF1 expression is localized mainly in the nucleus. In BAC (type B by Noguchi's classification), ATBF1 expression is localized mainly in the cytoplasm. Thus, there is a clear difference in the site where ATBF1 is expressed.

Any of the cases selected for investigation at this time are GGO having a tumor with diameter of 2 cm or less, and undergoing a partial section of or lobectomy of the lung portion. Therefore, in all the cases, lymph node metastasis is not caused and it can be predicted that the five-year survival rate is nearly 100%. Furthermore, since the results of staining of ATBF1 with respect to cases that have been finally diagnosed to be histologically low-grade AAH, high-grade AAH, and BAC (types A and B) are shown, there may be question whether or not the results can have clinically significant meaning even if the localization of ATBF1 enables AAH and BAC to be discriminated from each other. However, the actual clinical field is not only an ideal situation, for example, determination of diagnosis with respect to completely sectioned tumors. Moreover, it has not been easy to discriminate AAH from BAC. For example, with respect to a small specimen, which has been diagnosed to have extremely small tumor by CT examination and then has undergone cytological diagnosis or biopsy, situation of suggesting to predict the future prognosis and suggestion to adapt an operation throughout the histological observation may be necessary. In such a case, it is complicated to discriminate AAH from BAC. However, it is thought that ATBF1 staining makes it possible to make quality diagnoses such as: "since ATBF1 is localized in the nucleus, the probability of being AAH is high and tumor diameter is particularly small, with taking the age into consideration, follow-up may be carried out" or "since ATBF1 is localized in the cytoplasm, the probability of being BAC is high, it is assumed that the proliferation rate of the tumor is fast in the future. Therefore, operation is recommended." In the future, with respect to peripheral small lung tumors surgically sectioned, carrying out ATBF1 staining in addition to the judgment of AAH and BAC and Noguchi's classification is useful in investigating not only the study on prognosis but also investigation on cell-biological property, resulting in enhancing the precision of quality pathological diagnoses and preventing extra surgical treatment.

9-7. Alveolar Cell Carcinoma

Figure 23:
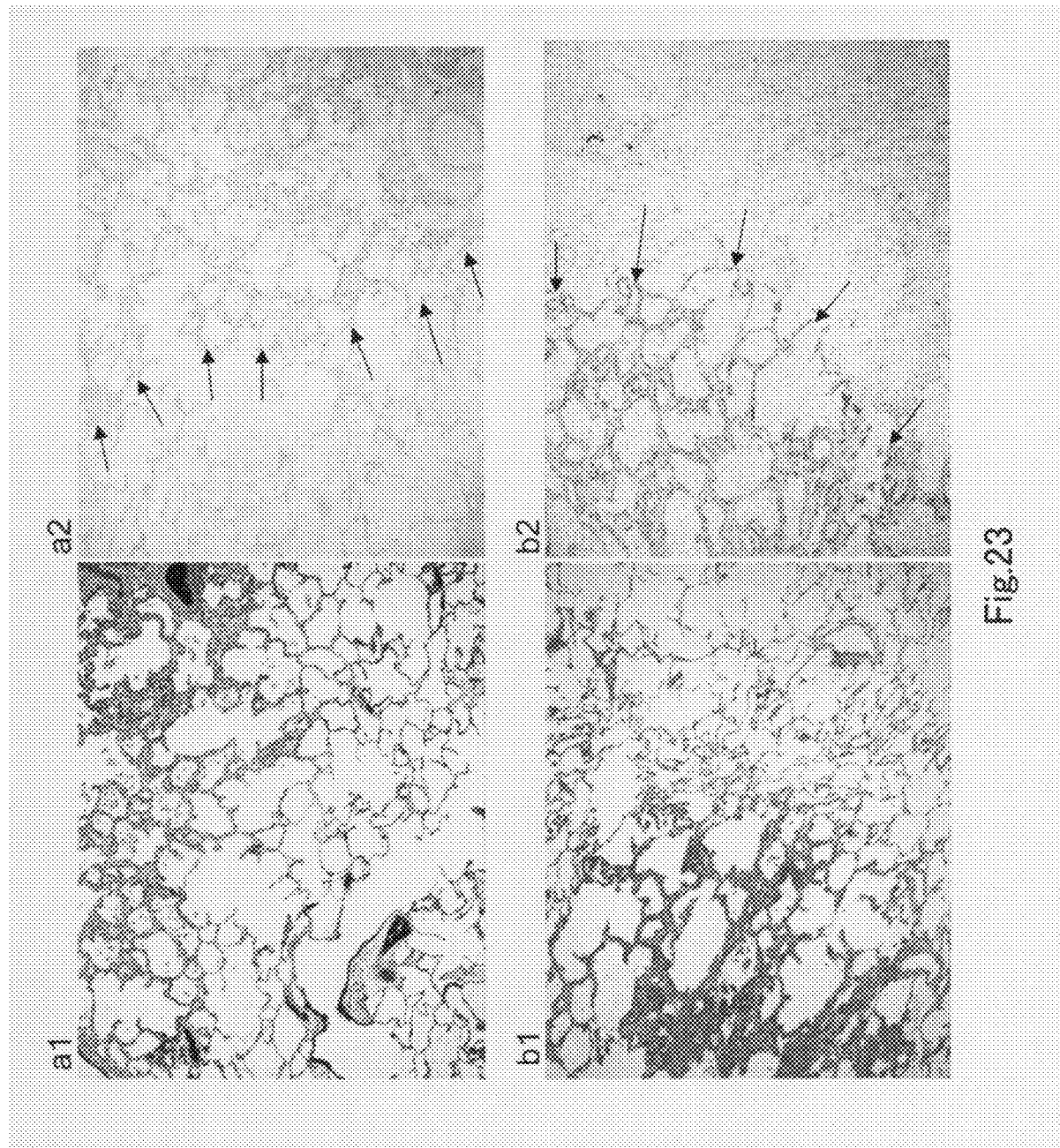
FIG. 23 shows ATBF1 expression in atypical adenomatous hyperplasia (a1, HE-stained image) and localized bronchiolus alveolar cell carcinoma (b1, HE-stained image). In the atypical adenomatous hyperplasia, ATBF1 is strongly localized in the nucleus in the range shown by arrows (a2, ATBF1-stained image), which clarifies the border to the normal tissue. Furthermore, in the alveolar cell carcinoma, ATBF1 is strongly localized in the cytoplasm in the range shown by arrows (b2, ATBF1-stained image), which clarifies the border to the normal tissue.

The normal lung is a tissue originally expressing a large amount of ATBF1. The normal lung tissue, 2-type alveolar cell, and the like, also shows the staining pattern of ATBF1 (using D1-120) although the amount is small. In the case of alveolar cell carcinoma (or atypical adenomatous hyperplasia), it was observed by low magnification microscopy that the amount of ATBF1 in the whole cell of a cancer cell is overwhelmingly increased (64-year-old man case and 57-year-old woman case are presented, see FIG. 23). Therefore, only by the fact that the staining of ATBF1 is strong, it was expected that it was possible to discriminate a cancer tissue or a precancerous lesion from a normal tissue. Thus, it was shown that ATBF1 staining would become a useful discriminating means for beginners of pathological diagnosis.

9-8. Pulmonary Adenocarcinoma (Probability of being an Index for Selecting and Determining Chemotherapy with Respect to Advanced Pulmonary Adenocarcinoma)

An advanced lung cancer has the high possibility of recurrence after operation. It is becoming more and more important to select treatment to recurrence and metastasis for providing patients with life lengthening or high quality life of their remaining years. Among them, at present, there is no stereotyped treatment to increasing adenocarcinomas. Depending upon cases, cases show complete response to chemotherapy or ineffective response to chemotherapy. With respect to local recurrence, lymph node metastasis or metastasis to other organs, there is no index in selecting a chemotherapy. In some cases, useless chemotherapy may burden a patient. In some cases, a doctor may regret after realizing that surgical extraction was the first option rather than chemotherapy. At this time, by using four cases of recurrence pulmonary adenocarcinoma (complete response to chemotherapy: one case (65-year-old man), and ineffective response to chemotherapy: three cases (53-year-old man, 65-year-old woman, and 78-year-old man), ATBF1 immunostaining was carried out with respect to the specimens extracted at the initial operation, and comparison investigation was carried out.

Figure 4:
FIG. 4 shows an expression site of ATBF1 in P19 cells when a culture dish is coated with fibronectin and poly-L-ornithine after treatment with retinoic acid is carried out and when a culture dish is not.
Figure 24:
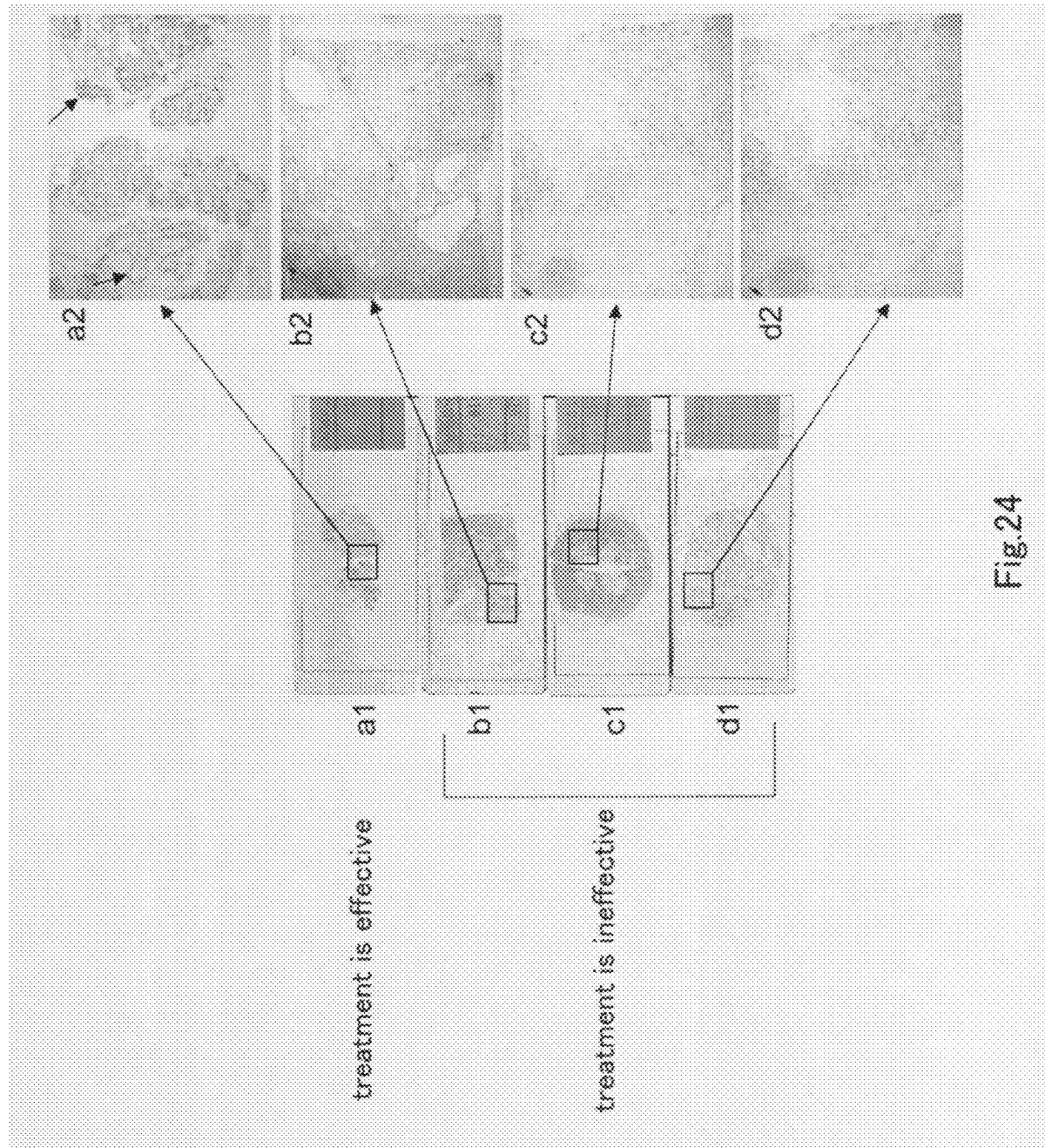
FIG. 24 shows gross observation preparation images (a1 to d1) and ATBF1-stained images of low magnificent microscopy of the pulmonary adenocarcinoma tissue of one case showing effective response to chemotherapy (a1, ATBF1-stained image) and three cases showing ineffective response to chemotherapy (b1, c1, d1, ATBF1-stained image). The brown staining of DAB is extremely slight in the gross observation (b1, c1, and d1) in the preparation of three cases showing ineffective response. On the other hand, the brown staining is deep in the preparation of one case showing effective response. The brown staining in preparation is not clearly observed by gross observation, however, a low magnification ATBF1-stained image clearly shows the deep staining of ATBF1 (a2, b2, c2, d2) in the case showing effective response as shown by arrows.
Figure 25:
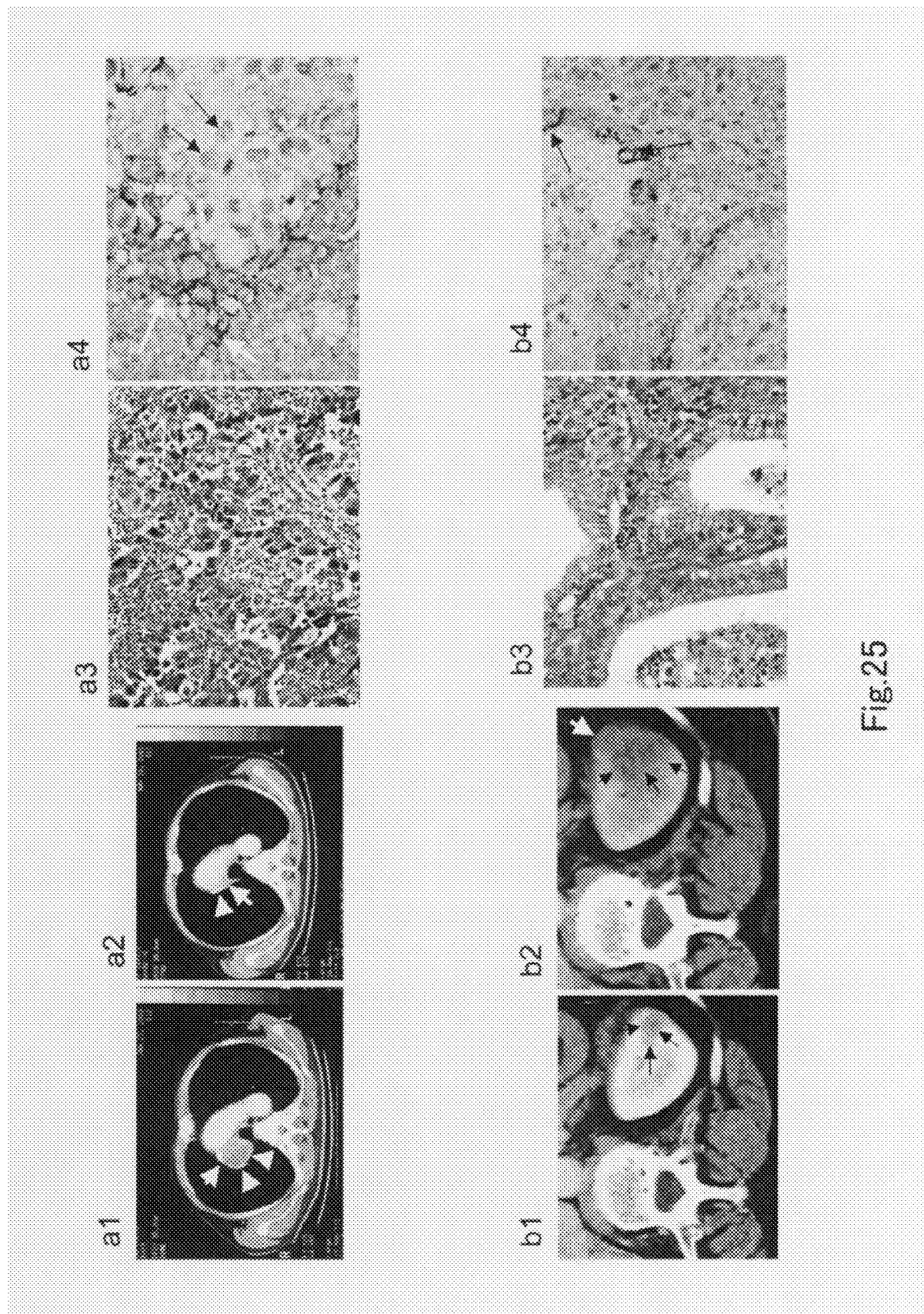
FIG. 25 shows CT images before treatment (a1 and b1) and after treatment (a2 and b2) of a case showing an effective response to chemotherapy (a, 65-year-old man) and a case showing an ineffective response to chemotherapy (a, 65-year-old woman), tissue images of pulmonary adenocarcinoma at the time of onset (a3 and b3, HE-stained image) and an ATBF1 expression site (a4 and b4, ATBF1-stained image). The CT image of the case showing effective response shows the swelling (a1, white arrow) and disappear (a2, white arrow) of tracheobronchial lymph node. The tumor is poorly-differentiated adenocarcinoma (a3) having a partial lumen. The tumor cell includes a site in which ATBF1 expression (a4) is localized in the cytoplasm (white arrow) and a site in which ATBF1 expression is localized in the nucleus (black arrow). The CT image of the case showing ineffective response shows the presence (b1, black arrow) and increase (b2, white and black arrows) of metastatic tumor in the superior part of the left kidney. Histologically well-differentiated tubular adenocarcinoma (b3) is shown. The amount of ATBF1 expression is small and the whole amount is localized in the cytoplasm (b4, black arrow) and localization in the nucleus is not observed.

After the extracted specimen was subjected to ATBF1 immunostaining (using D1-120, DAB coloring), at the stage before the actual microscopic examination, each preparation state was subjected to gross observation (see FIGS. 24*a*1 to 24*d*1 and FIGS. 24*a*2 to 24*d*2). In one case showing complete response, it was apparent that brown coloring in DAB was strong only from the gross observation. The amount of ATBF1 expression in the tumor was apparently larger as compared with that of the three cases showing ineffective response. By the observation after microscopic examination, in the case showing complete response to chemotherapy, the amount of ATBF1 in the tumor was large, and in some sites, the localization of ATBF1 in the nucleus was observed (see FIG. 25*a*4, showing the same case as shown in FIG. 24*a*). On the contrary, in the case showing ineffective response to chemotherapy, the amount of ATBF1 in the tumor was small, and the localization of ATBF1 in the cytoplasm was observed (see FIG. 25*a*4, showing the same case as shown in FIG. 24*a*) or the tendency of lacking ATBF1 was observed (details are not shown).

Taken a case showing complete response to chemotherapy (see FIGS. 25*a*1 to 25*a*4, 65-year-old man) and a case showing ineffective response to chemotherapy (see FIGS. 25*b*1 to 25*b*4, 65-year-old woman) as examples, a CT image before chemotherapy, a CT image after chemotherapy, a HE stained image and an ATBF1 stained image were investigated.

Figure 2:
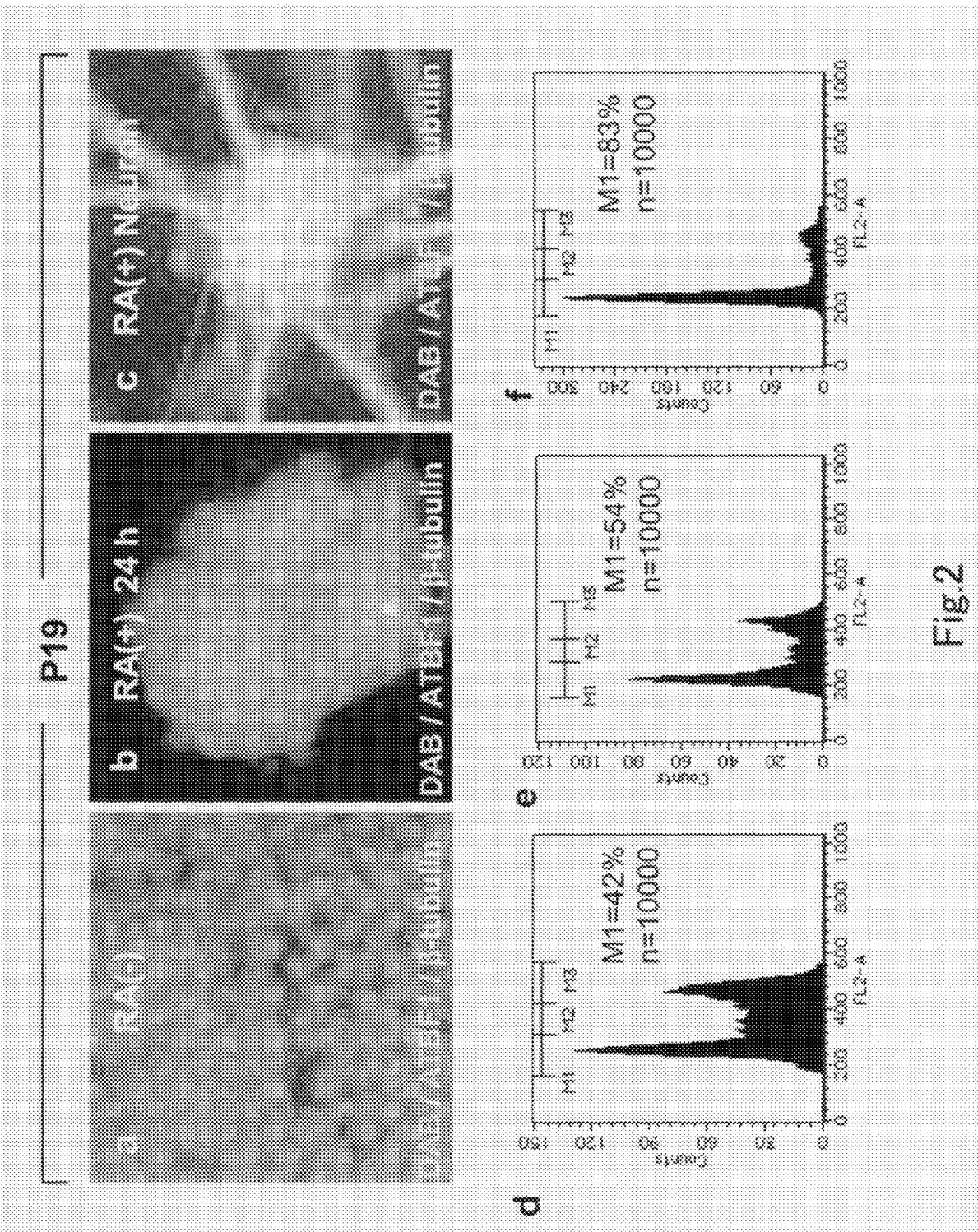
FIG. 2 shows ATBF1 expression and the flow cytometry examination in a P19 cell. Upper pictures show triple stained image of DAPI (staining the nucleus DNA), ATBF1, and β-tubulin.

In the case showing complete response to chemotherapy, in histologically poorly-differentiated adenocarcinoma (see FIG. 25*a*3), by CT examination, a tumor in the tracheobronchial lymph node was observed (see FIG. 25*a*1), but four months after the chemotherapy, the tumor was almost disappeared (see FIG. 25*a*2). A site in which the staining of ATBF1 was apparently shown in the cytoplasm and a site in which the staining of ATBF1 was shown in the nucleus were present together (see FIG. 25*a*4).

In the case showing ineffective response to chemotherapy, in histologically well-differentiated adenocarcinoma (see FIG. 25*b*3), by CT examination, a tumor was observed in the superior part of the left kidney (see FIG. 25*b*1). Although chemotherapy was carried out, four months after the chemotherapy, the tumor was apparently expanded (see FIG. 25*b*2). ATBF1 expression was small and all of the expression was localized in the cytoplasm and no straining was observed in the nucleus were present together (see FIG. 25*b*4).

According to the study performed to date, it is thought that the presence of ATBF1 in the nucleus means the cell cycle arrest via p21 and the efficacies of chemotherapy and radiation treatment. On the contrary, it is thought that the presence of ATBF1 in the cytoplasm means that the proliferation property of cells is strong and various treatment do not easily exhibit efficacy. At this time, in the case showing complete response to chemotherapy, ATBF1 expression in the tumor cell was extremely large and tumor cells in which ATBF1 was localized in the nucleus were present. On the contrary, in the case showing complete response to chemotherapy, it was observed that the amount of ATBF1 expression was small and ATBF1 tended to be localized in the cytoplasm or tended to lack expression. Therefore, based on the result of the staining of ATBF1, it was thought to be possible to predict success or failure of the selection of chemotherapy with respect to adenocarcinoma, to reduce a burden of the chemotherapy (systemic adverse effect such as myelosuppression, epilation, or the like) on a patient, and to make an appropriate judgment of the selectin of the other treatment methods such as surgical operation. Furthermore, the results of this time demonstrate that only the gross observation of the preparation makes it possible to determine the amount of ATBF1 and to roughly predict the effect of chemotherapy, so that simple material on the selection of chemotherapy is provided to doctors who are not familiar with detailed observation by using a microscope.

9-9. Lung Small Cell Carcinoma

Lung small cell carcinoma occupies about 15 to 20% of total lung cancers. As compared with non small cell carcinoma, metastasis is observed in lung small cell carcinoma. At the time of diagnosis, mediastinal lymph node metastasis was observed in 70% or more of lung small cell carcinoma. About 60% has distant metastasis. At the time of pathological anatomy, only 4% of lung small cell carcinoma does not show the distant metastasis.

In general, in most cases, surgical operation is not adaptive. If lung small cell carcinoma is left, it is rapidly expanded. The lung small cell carcinoma is a tumor with high grade of malignancy in which unless effective treatment is provided, most cases result in death within one year. Although the lung small cell carcinoma proliferates at high rate, it has high sensitivity with respect to anti-cancer drug and radiation therapy. Thus, it has clinical features that are significantly different from those of adenocarcinoma, squamous carcinoma, large cell carcinoma, and the like. According to the recent progress in the treatment including chemotherapy, the treatment performance of the lung small cell carcinoma has been improved. Therefore, the effect of life lengthening has been expected and some cases have been cured although its number is small. On the other hand, it is known that not a few small cell carcinomas show the same tissue image but are not suitable for chemotherapy.

Figure 26:
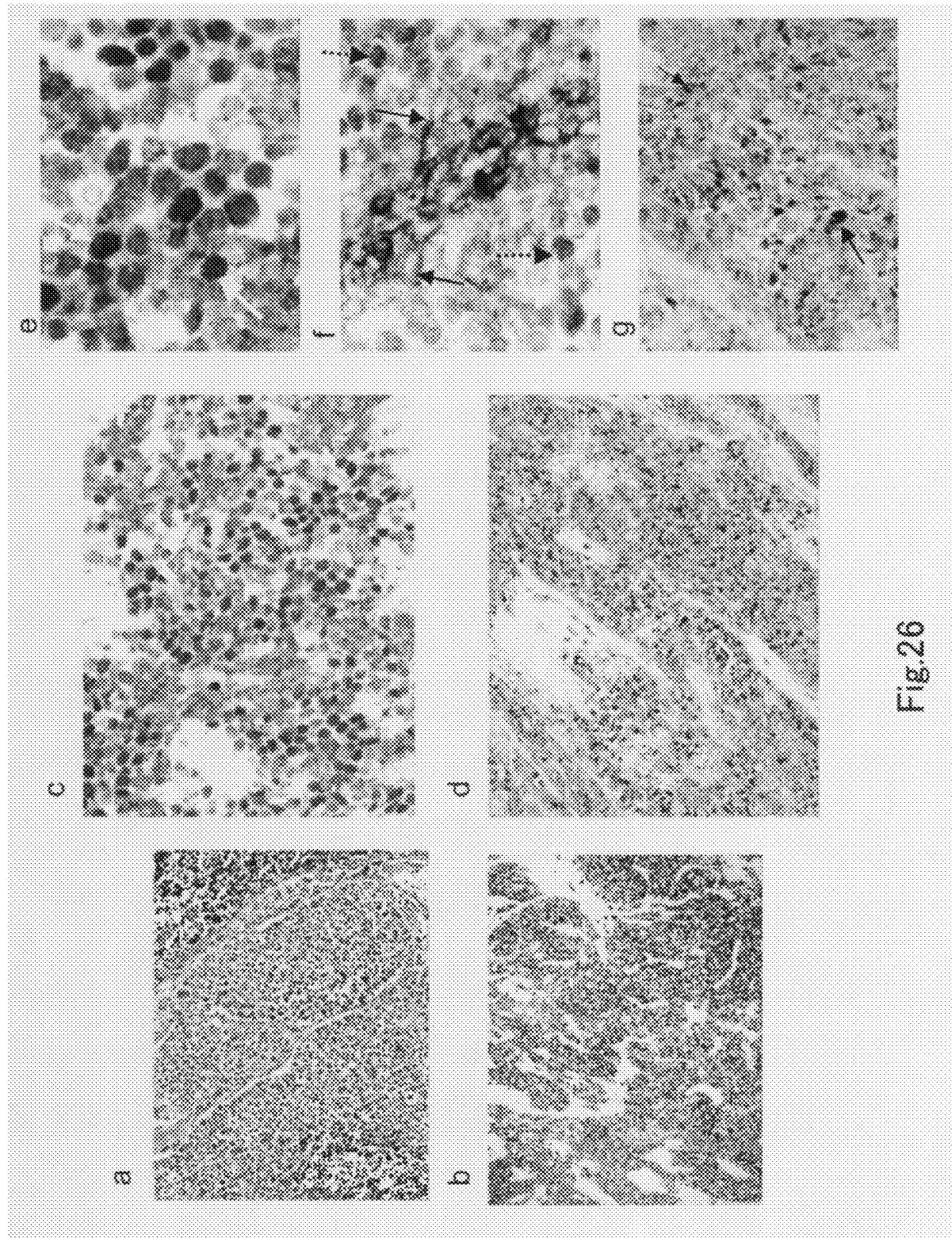
FIG. 26 shows a tissue image (a, HE-stained image) and ATBF1 (b-g, ATBF1-stained image) of a case of small cell carcinoma of 74-year-old man.

The present inventors carried out staining of ATBF1 (using D-120) with respect to four cases (for 78, 52, 67, and 70-year-old men) that had undergone long biopsy for the purpose of diagnosis. The present inventors investigated the localization of ATBF1 in a tumor cell. In any cases, the amount of ATBF1 in the cell of the small cell carcinoma was large, and a site in which the cytoplasm was stained, a site in which the nucleus was stained and site in which both cytoplasm and the nucleus were stained were observed (see FIG. 26). Depending upon the cases, the rate varied and the rate was not constant.

According to studies performed to date, it is assumed that the presence of ATBF1 in the nucleus means the cell cycle arrest via p21 and good efficacy of chemotherapy and radiation treatment. On the contrary, the presence of ATBF1 in the cytoplasm is assumed to mean that cells have a strong proliferation property and that various treatment and therapies are not effective. In the lung small cell carcinoma examined at this time, as compared with other various tumor cells which had been examined, the amount of ATBF1 expression is significantly large. Not only tumor cells in which ATBF1 exists in the cytoplasm but also tumor dells in which ATBF1 exists in the nucleus are mixed at various ratios. This examination result agrees with the feature that although the lung small cell carcinoma proliferates at high rate, it has high sensitivity with respect to anti-cancer drug and radiation therapy. Thereafter, sliced specimen of tumor that underwent biopsy is subjected to ATBF1 staining and the ratio of tumor cells in which ATBF1 is localized in the nucleus with respect to the whole tumor is examined. Thereby, it is possible to indicate curable cases (which are expected to show the staining in the nucleus in most cells) or cases showing not suitability to chemotherapy (which are expected to show the staining in the cytoplasm in most tumor cells).

9-10. Neuroblastoma

Neuroblastoma has the highest number in infantile malignant solid tumors. The treatment method and prognoses are effected depending upon the known prognosis factors such as age, stage, occurrence site, gene number, chromosomal aberration, and the like. Depending upon the judgment of the prediction of the grade of malignancy, the treatment policies are utterly different from each other. There are cases in which the treatment is completed only by surgical operation and cases which can be healed only by chemotherapy. In addition, recently, there have some cases in which progress has been observed while expecting self-healing. On the contrary, advanced neuroblastomas or neuroblastomas with high grade of malignancy need strong and long-period chemotherapy. In order to save the life, supermass chemotherapy using transplantation of bone marrow is sometimes required. Therefore, at present, there is the following tendency: for infantile neuroblastoma with good prognosis, light treatment is intended; and for advanced neuroblastoma with poor prognosis, a protocol for stronger chemotherapy is intended.

When examination of various prognosis factor is added in addition to clinical prognosis factors such as age, stage, and site, the presence of amplification of N-myc, examination of DNA ploidy (tumor of aneuoloid shows good prognosis, and tumor of diploid or tetraploid shows poor prognosis), analysis of chromosome aberration (short arm deficiency of the first chromosome shows poor prognosis), analysis of the expression of Trk-A and Ha-ras (when the expression amount of these proteins is large, prognosis is good), and the like, in addition to the tissue image of a tumor are examined.

Figure 27:
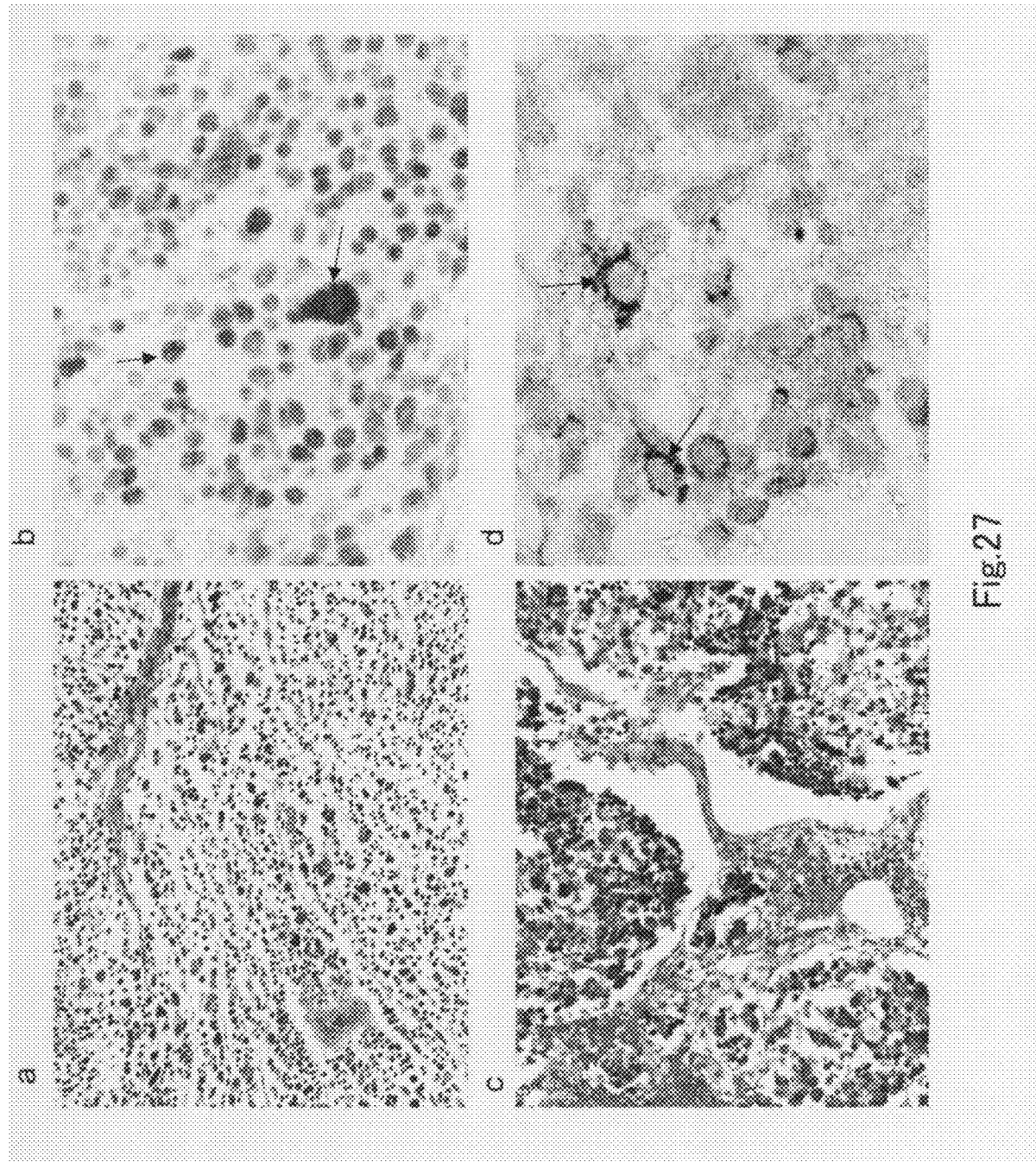
FIG. 27 shows tissue images (a, c, HE-stained image) and intercellular localization of ATBF1 (b, d, ATBF1-stained image) of survival cases (a and b) and death cases (c and d) of neuroblastoma.

At this time, as a cofactor for examining the prognosis factors, for the purpose of investigating whether or not the judgment of localization in the ATBF1 cells is effective, nine survival cases (Boy and girl cases. Age at the discovery of tumor was 1-year-old and 0-year-old) and three death cases (Boys. Ages at death are 10-year-old, 3-year-old and 2-year-old), staining of ATBF1 (using D1-120) was carried out. As a result, in the nine survival cases, in almost all tumor cells, the staining of ATBF1 was localized mainly in the nucleus. On the contrary, among three cases, which had died and had been subjected to pathological anatomy, one case of 2-year-old boy which had been thought to be died from tumor itself, in which histological infiltration, metastasis, vascular invasion of tumor, and the like, were shown and died for such a short time as 11 months, ATBF1 was localized in the cytoplasm in almost all the tumor cells (see FIG. 27). This result suggests that the presence of staining of ATBF1 that is localized mainly in the cytoplasm will be one of the materials for judging the tumor group with high grade of malignancy.

9-11. Gastrointestinal Stromal Tumor (GIST). Investigation of Usefulness of ATBF1 in Prediction of Prognosis of GIST In a mesenchymal tumor occurring in the gastrointestinal tract, it has been clear that tumors histologically having characteristics of the smooth muscle or the nerve cell, tumors that do not have any characteristics have been present. Accordingly, the concept of the gastrointestinal stromal tumor (GIST) has been established. GIST is said to be derived from a Cajal intervening cell that is a pacemaker cell of the spontaneous activity of the gastrointestinal tract. CD34 and c-kit proteins (CD117) that are undifferentiated mesenchymal cell antigens are used as a marker at the time of diagnosis. The mechanism for the formation of tumor is involved in sustained activity of tyrosine kinase by gain-of-function mutation of the c-kit gene. The first option for the effective treatment to GIST is a surgical operation. Even if complete excision can be carried out, it has been known that metastasis recurs. Recently, it has been reported that a tyrosine kinase inhibitor (imatinib mesilate) has been effective for metastasis recurring case of GIST whose primary cancer is a gastric cancer. Clinical use of the tyrosine kinase inhibitor (imatinib mesilate) started for prevention of recurrence, treatment drug for not-resectable cases. Absolute criterion on benign and malignant GIST is presence or absence of metastasis to distant organs and infiltration to surrounding organs. However, from the viewpoint of necessity to predict the prognosis, at present, the size of the tumor is used as an important criterion. According to the criteria, when the size of tumor is 2 cm or less, the risk is super low (treatment option; follow-up); when the size of tumor is 2 to 5 cm, the risk is low to middle (treatment option; surgical operation is also considered); and when the size of tumor is 5 cm or more, the risk is high (treatment option; surgical operation). Besides, usefulness of the cell density, the presence or absence of the nucleus mitosis, age of a patient, site of tumor, DNA aneuploidy, MIB 1 labeling index, and the like, has been indicated. At this time, the prediction of prognosis has to be done by combining these indices.

Figure 28:
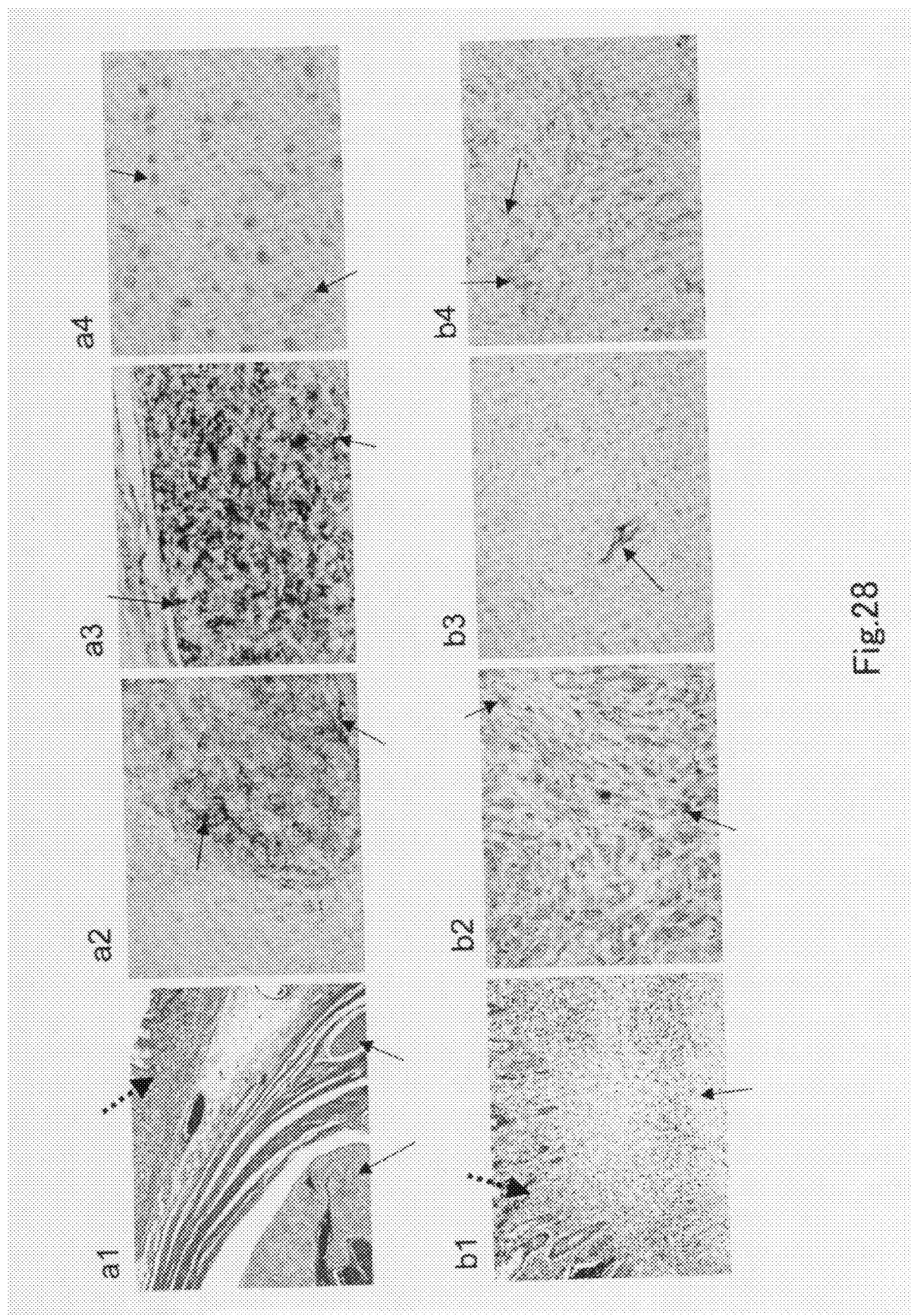
FIG. 28 shows HE stained images (a1 and b1), c-kit stained images a2 and b2), CD34-stained images (a3 and b3) and ATBF1 stained images (a4 and b4), sequentially from the left side, in the GIST tissue (a: GIST whose primary cancer is a gastric cancer, b: GIST whose primary cancer is a colon cancer). In the survival case of GIST whose primary cancer is a gastric cancer, tumor formation is observed in the muscularis existing in the lower part of the gastric mucosa shown by dotted line arrow in FIG. 28a1 (arrows). The boundary with respect to the surrounding is relatively clear. As shown by arrows in FIGS. 28a2 and 28a3, the most of the tumor cells are present in the cytoplasm and show positive for c-kit and CD34. As shown by arrows in FIG. 28a4, ATBF1 is localized in the nucleus in the most of the tumor cells. On the contrary, in the death case of GIST whose primary cancer is a colon cancer, infiltration growth is observed in the submucous tissue existing in the lower part of the colon mucosa shown by a dotted line arrow in FIG. 28b1. The boundary to the surrounding tissue is less clear than that of the survival case (see FIG. 28a1). The tumor cell shows positive for c-kit (arrow in FIG. 28b2) but negative for CD34 (note here that as shown by arrow in FIG. 28b3, only small blood vessel shows positive for CD34). As shown by arrows in FIG. 28b4, ATBF1 is localized in the cytoplasm in most of the tumor cells.

At this time, two cases of GIST were subjected to ATBF1 staining (using D1-120) so as to examine the staining properties of the nucleus and the cytoplasm and investigated the probability that staining of ATBF1 was a new marker for predicting the prognosis of GIST. ATBF1 staining properties of one case (52-year-old man) in which the size of the tumor at the time of discovery was 2.0×1.8 cm, progressed to benign, and no recurrence was observed, and one case of GIST whose primary tumor was in the colon (58-year-old woman) in which the size of the tumor at the time of discovery was 3.3×2.9 cm, progressed to peritoneal metastasis and died 5 months later are shown in FIG. 28. In both and lower pictures of FIG. 28, a HE stained image, a c-kit (CD117) stained image, a CD34 stained image and an ATBF1 stained image are shown sequentially in this order form the left.

In GIST whose primary tumor was gastric tumor and which did not clinically tend to recur (upper pictures in FIG. 28, positive for CD117, positive for CD34), the staining of ATBF1 in the nucleus was observed in all the tissue portions and the staining of ATBF1 in the cytoplasm was slightly observed. On the contrary, in GIST case whose primary tumor was colon tumor and which resulted in death from peritoneal metastasis (lower pictures in FIG. 28, positive for CD117: negative for CD34), the staining of ATBF1 in the nucleus remained but staining of granular ATBF1 was observed in the cytoplasm in the majority of cells.

According to studies performed to date, it is assumed that the presence of ATBF1 in the nucleus means the cell cycle arrest via p21 and the presence of ATBF1 in the cytoplasm means that cells have a strong proliferation property. According to this time examination, there is a clear difference in ATBF1 expression between GIST which did not have tendency of recurrence and GIST in which proliferation was significantly increased and patient already died. GIST specimen, which had undergone surgical excision and biopsy, was subjected to staining of ATBF1 so as to make it clear whether the staining was observed in the nucleus or in the cytoplasm. Thereby, it is thought that recurrence of tumor and tendency of growth can be known, so that it is possible to predict the necessity of addition of various treatment.

9-12. Meningioma (Investigation on Usefulness of ATBF1 in Predicting Pathological Diagnosis and Prognosis of Meningioma)

Meningioma, one of brain tumors, is derived from meningothelial cells and progresses relatively slowly, and therefore it is a tumor having good prognosis in all brain tumors. A majority of meningiomas are a benign tumor but some meningiomas progress to a malignant tumor depending upon the histological patterns although unusually. WHO provides Grading including from a low atypical degree to a highly atypical degree in accordance with the histological patterns. For example, MIB1 labeling index is used for predicting the prognosis. However, in a current state, it is not easy to predict the prognosis. This time, two cases of low atypical meningioma which progress to benign tumor and no recurrence was observed, 60-year-old woman (fibrous meningioma, WHO grade: I) and 68-year-old man (meningothelial meningioma, WHO grade: I), and one case of moderately atypical meningioma which repeated the recurrence and severe hemorrhage, 52-year-old woman (atypical meningioma, WHO grade: II), one case of moderately atypical meningioma that needs the future follow-up from the histological pattern, 63-year-old man (clear cell meningioma, WHO grade: II) were subjected to ATBF1 staining (using D1-120).

Figure 29:
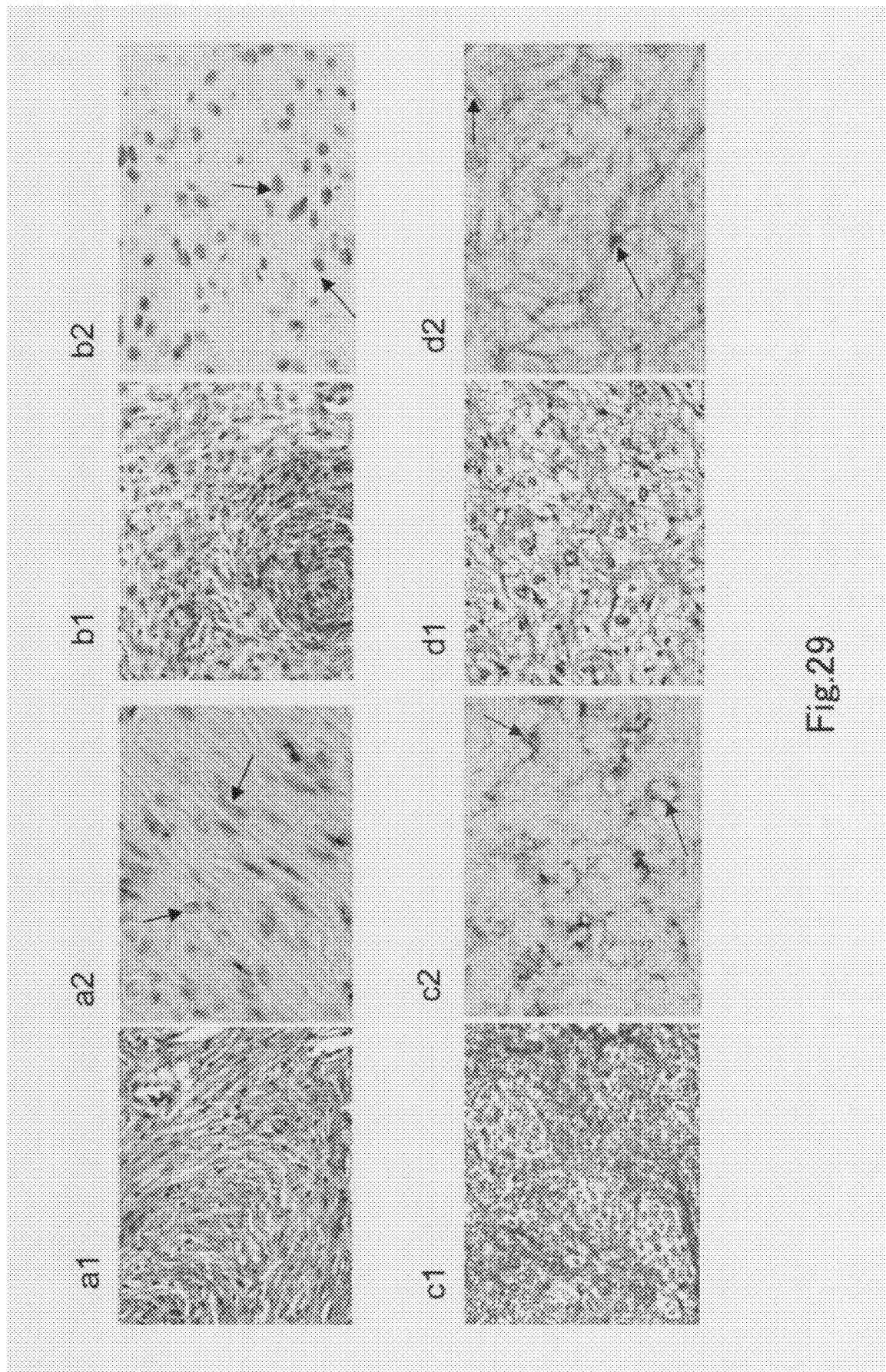
FIG. 29 shows HE stained images (a1, b1, c1, and d1) and ATBF1 stained images (a2, b2, c2, and d2) in various meningioma tissue; fibrous meningioma, WHO grade: I (a), meningothelial meningioma, WHO grade: I (b), atypical meningioma, WHO grade: II (c), and clear cell meningioma, WHO grade: II (d).

The result of staining is shown in FIG. 29. FIG. 29 shows HE stained images (a1, b1, c1 and d1) and ATBF1 stained images (a2, b2, c2 and d2) of cases. In fibrous meningioma (low atypical, grade I, FIGS. 29a1 and a2) and meningocortical meningioma (low atypical, grade I, FIGS. 29b1 and b2) having no tendency of clinical recurrence, staining of ATBF1 was observed in the nucleus and staining of ATBF1 in the cytoplasm was not observed in all tissues.

On the other hand, in atypical meningioma (moderately atypical, grade II, FIGS. 29c1 and c2) in which haemorrhage had already been repeated and clear cell meningioma (moderately atypical, grade II, FIGS. 29d1 and d2) in which, histologically, the proliferation rate is fast and probability of future recurrence is predicted to be high, staining of ATBF1 in the nucleus, staining of ATBF1 in the nucleus and the cytoplasm, and staining of ATBF1 only in the cytoplasm were observed.

According to studies performed to date, the presence of ATBF1 in the nucleus means the cell cycle arrest and good efficacy of chemotherapy and radiation treatment. On the other hand, the presence of ATBF1 in the cytoplasm means that cells have strong proliferation property and that various treatment and therapies are not effective. This time, the difference in the sites of ATBF1 expression was clearly observed between a tumors of Grade I and a tumors of Grade II. In the future, it is thought that surgically excised meningioma is subjected to ATBF1 staining, thereby, probability of predicting the grades of meningioma regardless of histological patterns (for example, when staining in the cytoplasm is observed, it is possible to suspect a tumor in at the moderately atypical or more), furthermore, probability of predicting the necessity of adding various treatments by considering the probability of recurrence, can be suggested.

9-13. Prostate Cancer

Lifestyle, western-style diet, and the like, in addition to aging, have caused the increase in the number of prostate cancer cases year by year. Since a prostate gland specific antigen Prostate-specific antigen (PSA) test has been introduced into routine diagnosis, the prostate cancer can be discovered at early stages, which is one of the causes of the increased in the number of the cases. In general, the progress of the prostate cancer is reported to be slow. To prostate cancers of the aged, sometimes a treatment policy including only follow-up without treatment may employed. However, the usefulness of local treatment including surgical operation, endocrine therapy, radiation treatment, or the like, performed in order to prevent the increase in the death rate after follow-up for a long time, has been proved. In general, recent diagnosis includes screening of the increase of PSA value in the serum and carrying out Systematic biopsy (14 points) under transrectal ultrasonotomography. A prostate cancer is generally adenocarcinoma and generally uses Gleason's grade system. This system well describes the determination of a treatment policy and the relation with respect to prognosis. However, sometimes, it is not correct. Therefore, as to an ideal grade system, there has been an argument among pathologists.

Figure 30:
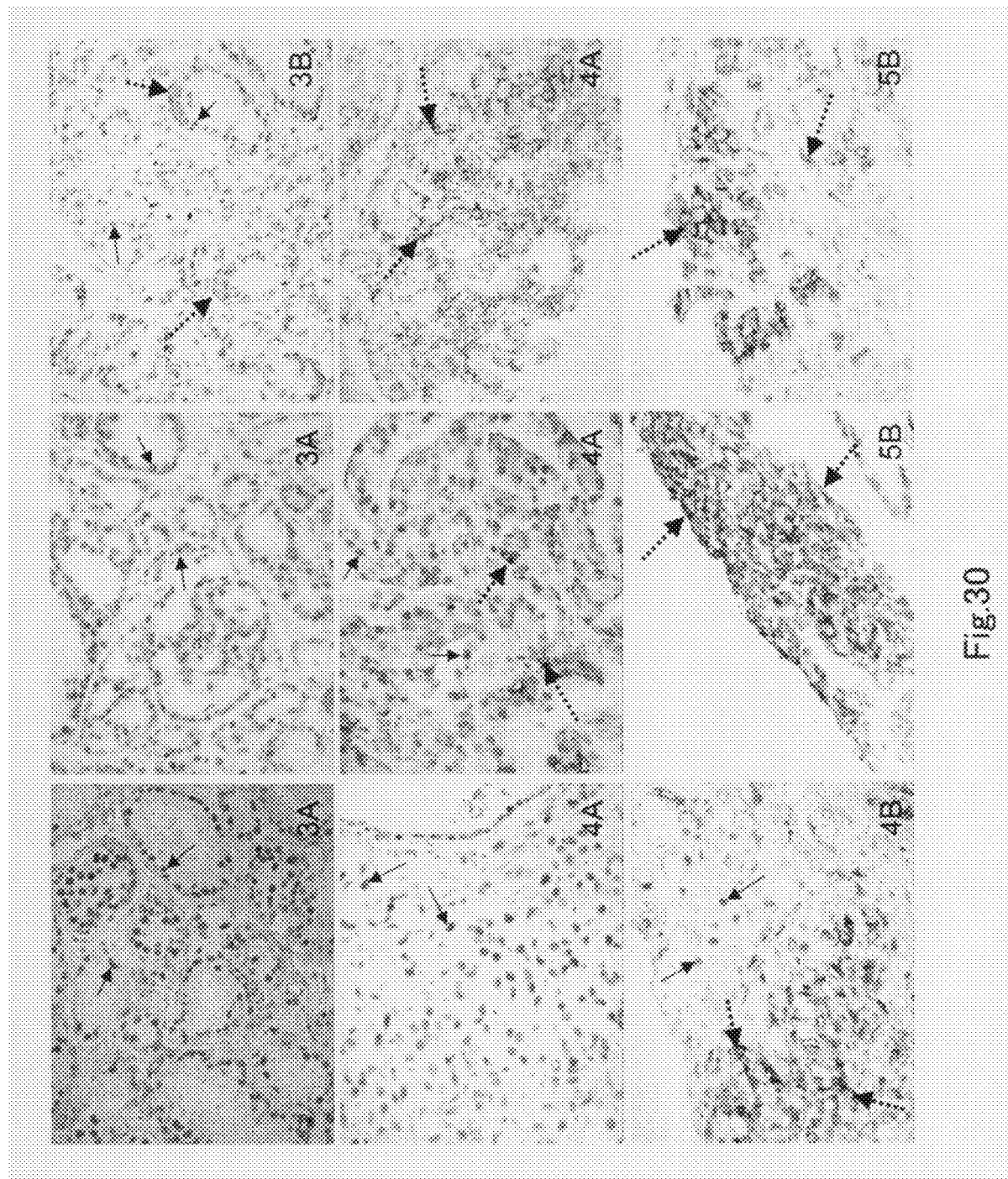
FIG. 30 shows microscope images of cases of 61-year-old man, 66-year-old man, 76-year-old man. In all images, the specimens of prostate cancer biopsy were stained with ATBF1. The images are arranged histologically in the order of Gleason grade, and stating properties of ATBF1 were compared. Reference numerals 3A to 5B in FIG. 30 show Gleason grades, respectively. Grades are determined as follows: the grade 3A represents the state in which although the size of tubular adenoma is irregular, tendency of adhesion is not shown; the grade 3B represents that small tubular adenoma is contained together; the grade 4A represents that tubular adenoma tends to be adhered; and the grade 4B represents that hypernephroid pattern is shown. When cancer cells forms a solid conglomerate or shows isolated infiltration tendency, the grade is determined to be grade 5B. Black arrow shows an example in which ATBF1 is localized in the nucleus of the tumor cell, and dotted line arrow shows an example in which ATBF1 is localized in the cytoplasm of the tumor cell. In Gleason grade 3A, ATBF1 is localized in the nucleus; and in the grade 5B, ATBF1 is localized in the cytoplasm. From the grade 3B to the grade 4B, a tumor cell showing the localization of ATBF1 in the nucleus and a tumor cell showing the localization of ATBF1 in the cytoplasm are mixed.

At this time, in order to examine the probability that the evaluation of localization sites of ATBF1 by ATBF1 staining contributes to the judgment of the grade of malignancy of a prostate cancer, biopsy specimens of 61-year-old, 66-year-old and 76-year-old men prostate cancer cases were subjected to ATBF1 staining (using D1-120) and comparison between the Gleason grade and staining pattern was carried out (see FIG. 30). In a prostate cancer (Gleason grade 3A) having a low Gleason grade and being histologically well-differentiated, the tendency of ATBF1 localizing in the nucleus was observed. In prostate cancer (Gleason grade 5B) having a high Gleason grade, being poorly-differentiated and showing clear tendency of infiltration, the tendency of ATBF1 localizing in the cytoplasm was observed. However, in prostate cancers (Gleason grades 3B-4B) having middle Gleason grade and being judged to be histologically moderately differentiated, localization site of ATBF1 staining was observed in both the nucleus and the cytoplasm depending upon the cases and sites. Gleason grade and the localization of ATBF1 do not completely corresponded to each other. However, as a main tendency, it was judged that the difference in the localization of ATBF1 might be considerably parallel with the level of the Gleason grade.

According to studies performed to date, the presence of ATBF1 in the nucleus means the cell cycle arrest and good efficacy of chemotherapy and radiation treatment. On the other hand, the presence of ATBF1 in the cytoplasm means that cells have strong proliferation property and that various treatment and therapies are not effective. This time results show the probability that it is possible to provide a more precise index in determining the prognosis judgment and the treatment policy of a patient, by combining the examination of localization of ATBF1 in cells with the judgment of Gleason grade when the biopsy prostate cancer tissue is examined.

9-14. Analysis of ATBF1 Expression in Other Tumors

The results of ATBF1 staining in various tumors other than those examined to date (any cases are not shown).

(1) A case of malignant lymphoma (Mature B-cell neoplasm, Mantle cell lymphoma) of a 64-year-old man; a site in which ATBF1 exists in the cytoplasm was observed but most tumor cells tended to lack ATBF1.

(2) A case of left testicular tumor (Embryonal carcinoma 80%, Yolk sac tumor 20%) of a 40-year-old man; ATBF1 was localized in the cytoplasm or was absent.

(3) A case of a hepatic cancer accompanied by type C liver cirrhosis (moderately to poorly differentiated hepatocellular carcinoma) of a 62-year-old man; in a site in which the tumor is brought into contact with the surrounding membrane at the marginal portion thereof, the tendency of ATBF1 existing in the cytoplasm was observed. In the middle portion of the tumor, tumor cells tended to lack ATBF1.

(4) A case of nasal neuroblastoma (olfactory neuroblastoma of high grade malignancy) of an 85-year-old woman; ATBF1 was localized in the cytoplasm in almost all the cells.

(5) A case of malignant lymphoma (Mature B-cell neoplasm, Follicular lymphoma, Grade I) of an 88-year-old woman; ATBF1 was localized in the cytoplasm in almost all the cells.

(6) A case of anterior mediastinal tumor (Seminoma) of a 48-year-old man; ATBF1 was localized in the cytoplasm in almost all the cells.

(7) A case of pleural tumor (Malignant mesothelioma) of a 56-year-old man; ATBF1 was localized in the cytoplasm in almost all the cells.

(8) A case of recurrent brain tumor (Hemangiopericytoma, WHO Grade III) of a 33-year-old man; ATBF1 was localized in the cytoplasm in almost all the cells.

(9) A case of thyroid carcinoma (Papillary carcinoma) of a 43-year-old woman; a site in which ATBF1 is localized in the nucleus and a site in which ATBF1 is localized in the cytoplasm were observed.

(10) A case of pituitary tumor (pituitary adenoma) of a 54-year-old man; a site in which ATBF1 is localized in the cytoplasm was observed in a part of the tumor cells. However, in most tumor cells, ATBF1 is localized in the nucleus.

(11) A case of pancreatic tumor (Endocrine tumor) of a 25-year-old man; in most tumor cells, ATBF1 is localized in the nucleus.

(12) A case of palmar aponeurosis tumor (Dupuytren's palmar fibromatosis) of a 58-year-old man; in most tumor cells, ATBF1 is localized in the nucleus.

EXAMPLE 10

<Judgment of Grade of Malignancy by Using Four Kinds of Antibodies (D1-120, NT440, 1-12, and AT6)>

10-1. Preparation of Two Kinds of Antibodies (NT440, 1-12 (see FIG. 31)) Recognizing N-Terminus of ATBF1-A and an Antibody (AT6 (see FIG. 31)) Recognizing C-Terminus of ATBF1-A Firstly, each antigen was prepared by the following procedures.

(1) Case of Antibody NT440 (Polyclonal Antibody)

A synthesized peptide was prepared by mixing three kinds of amino acid residues (4 to 15: CDSPVVSGKDNG: SEQ ID NO: 6), (429 to 445: CKSSEGKDSGAAEGEKQE: SEQ ID NO: 7), (500 to 516: CPSELDEELEDRPHEEPG: SEQ ID NO: 8) of human ATBF1-A (see non-patent document 1). The synthesized peptide was used as a peptide antigen. Note here that an underlined portion, C at N-terminus of the synthesized peptide shown in SEQ ID NO; 7 and 8 is added to the natural human amino acid sequences in order to secure the stability of the peptide.

(2) Case of Antibody 1-12 (Monoclonal Antibody).

A synthesized peptide of amino acid residues (143 to 155: CIVESLS$^{148}$QLTQGGG: SEQ ID NO: 9) of human ATBF1-A was used. The peptide, in which C (underlined) had been added to the N-terminus and the 148th serine (underlined, 148 was put on the right shoulder portion) had been phosphorylated, was used as an antigen. Therefore, this antibody is designed so as to recognize only the case where the 148th serine of ATBF1-A had been phosphorylated.

(3) Case of Antibody AT6 (Polyclonal Antibody)

A recombination peptide obtained by fusing amino acid residues (3405 to 3549: PGAPSPDKDPAKESPKPE-EQKNTPREVSPLLPKLPEEPEAESKSAD-SLYDPFIVPKVQYK LVCRKCQAGFSDEEAARSHLK-SLCFFGQSVVNLQEMVLHVPTGGGGGGSGGGGGGG GGGGGGGSYHCLACESALCGEEALSQHLE: SEQ ID NO: 10) into glutathione S transferase (GST), was used as an antigen.

By using each of the prepared antigens, an antibody (polyclonal antibody or monoclonal antibody) was produced and purified. Production and purification of a polyclonal antibody were carried out by the same method as described in the section of D1-120 antibody. Production and purification of a monoclonal antibody were carried out by the same method as described in various documents and texts (see, for example, "Kouso koutai hou" (Enzyme antibody method), the revised 3rd version," K. Watanabe, K. Nakane, Gakusai Kikaku).

The below mentioned Examples are results obtained by immunohistological investigation. In the case where staining was carried out using antibodies (NT440, 1-12, and AT6) other than D1-120, the same conditions and same antigen activation conditions used for the case of using D1-120 were selected. Thereby, it was possible to stain the difference in the localizations of ATBF1 in the nucleus and the cytoplasm in cells (including normal cells and cancer cells). Therefore, it was judged to be optimum that four kinds of anti-ATBF1 antibodies were used by using 10 mM citrate buffer solution (pH 6.0) and being heated in a pressure cooker for four minutes (110° C.).

10-2. Investigation on Relationship Between Expression of ATBF1 and AT6 Portion and Expression in Bcl-2 in Normal Lymph Node B Lymphocyte.

Figure 32:
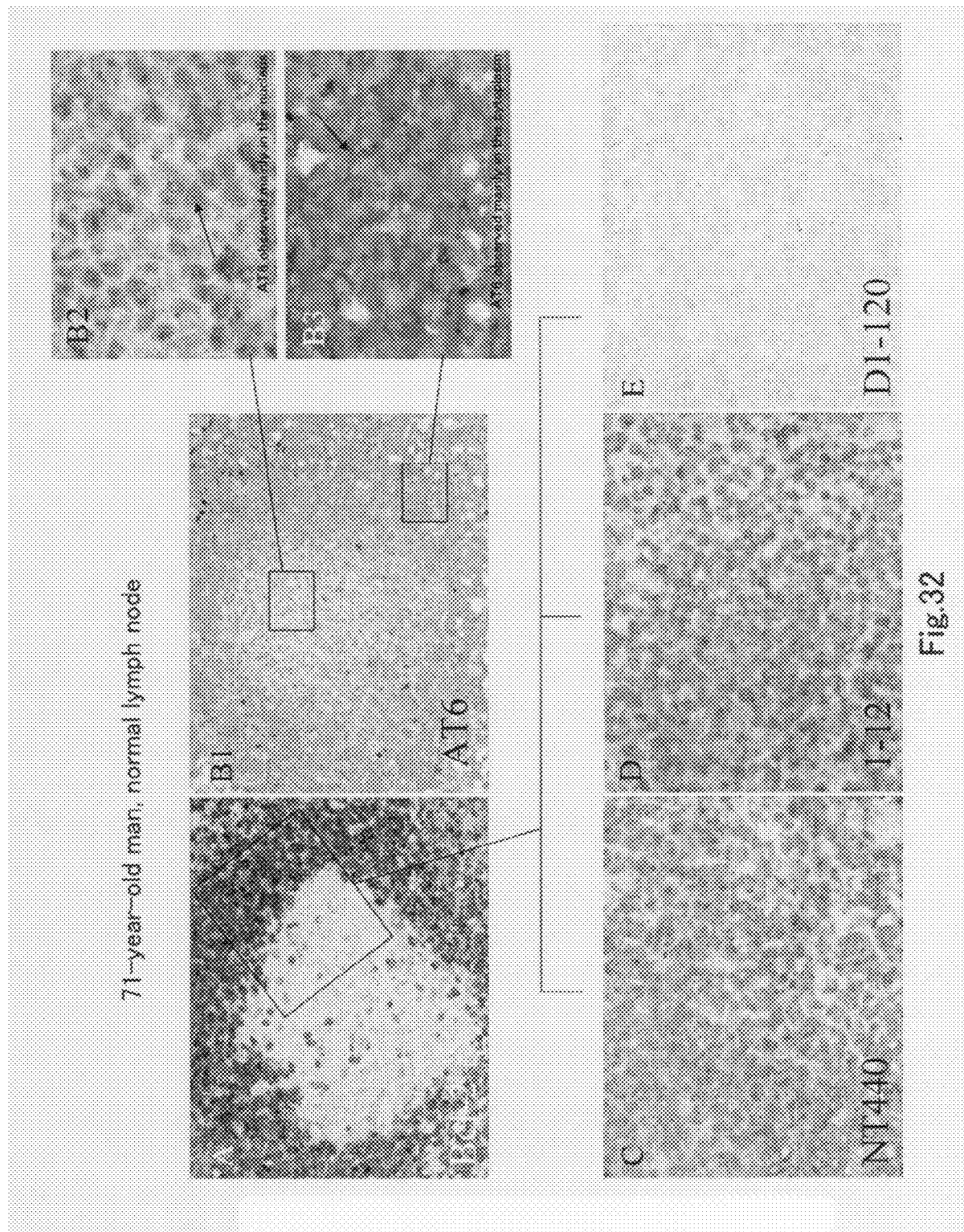
FIG. 32 shows a finding of tissue of normal lymph node of a 71-year-old man.
Figure 33:
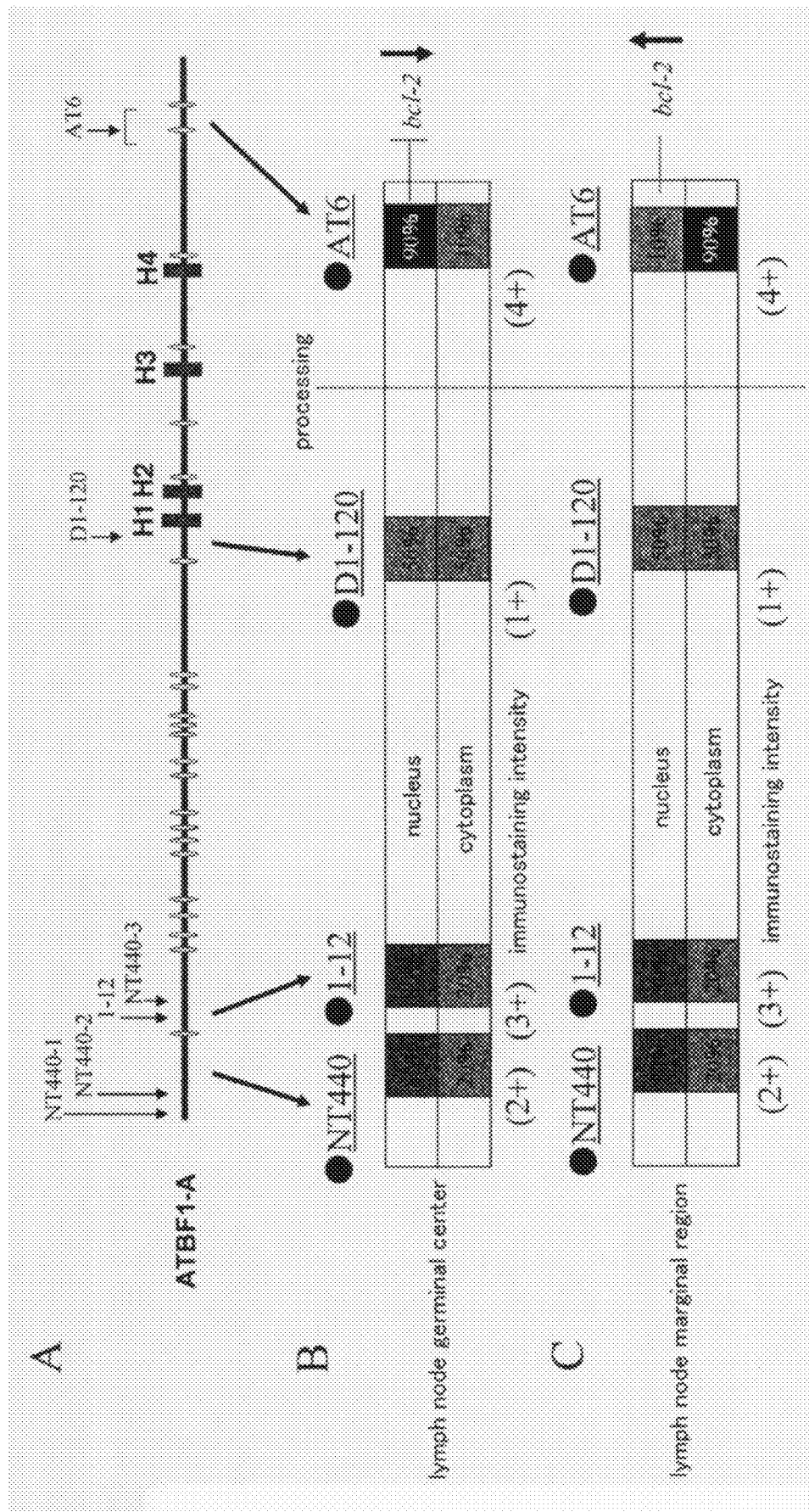
FIG. 33 summarizes the staining properties of ATBF1 in the case of normal lymph node of 71-year-old man.

ATBF1 expressions (NT440, 1-12, D1-120, and AT6) in the lymphocytes in normal lymphoid tissue around the bronchopulmonary region in a 71-year-old man were examined. The lymphoid tissue includes the lymphoid follicle in which B lymphocytes are grown. The center portion of the lymphoid follicle has germinal center in which B-lymphoblast exists and carried out division growth. This site lacks Bcl-2 expression (see FIG. 32A). In this site, division and growth of cells are actively carried out and at the same time, the frequency that cells move to apoptosis is high, and macrophages are regularly disposed. The macrophages (Tingible body macrophages) can carry out phagocytosis with respect to foreign substance for treating cells that underwent apoptosis. On the other hand, in a surrounding marginal region, mature B-lymphocytes, which finished differentiated, are accumulated. In these B-lymphocytes, high-degree of Bcl-2 expression was observed (see FIG. 32A). Bcl-2 protein suppresses the apoptosis by suppressing the release of cytochrome c from the mitochondria to the cytoplasm. That is to say, normal B-cells stored in the marginal region gains the function of suppressing the apoptosis. Note here that staining properties of ATBF1 obtained by NT440, 1-12, and D1-120 are not different in the germinal center, the marginal region B-lymphocyte. The staining properties of NT440 and 1-12 were observed mainly in the nucleus. The staining pattern of D1-120 was observed in the cytoplasm and the nucleus although the staining amount is extremely small (see FIGS. 32C, D and E, and FIGS. 33 B and C). On the other hand, the staining pattern of AT6 exhibited the clear difference between in the germinal center and in the marginal region (see FIG. 32B1). The stating in the germinal center was observed mainly in the nucleus and the stating in the marginal region was observed mainly in the cytoplasm (see FIGS. 32B, B3, and FIGS. 33B and C).

It is known that ATBF1 makes a protein-protein binding with an oncogene protein c-myb and suppresses the function thereof (see non-patent document 8). As to the cell cycle arrest and the movement to apoptosis, it is thought that Myb protein family incorporates Bcl-2 so as to suppress the apoptosis of a cell (see Grassilli, E. et al. Resistance to Apoptosis in CTLL-2 Cells Overexpressing B-Myb Is Associated with B-Myb-dependent bcl-2 Induction, CANCER RESEARCH 59, 2451-2456, 1999). Although it has not directly proved in the range of the addition examination, the present inventors understand that the examination results in normal B-lymphocytes at this time may be involved in the suppression of bcl-2 gene via interaction between AT6 portion corresponding to exon 11 of the ATBF1 gene and Myb oncogene protein in the nucleus (see FIG. 33B). Furthermore, in accordance with the mature and movement of B-cells, when the AT6 portion functioning in the nucleus moves to the cytoplasm, suppression with respect to the bcl-2 gene is displaced, it is suggested that the B-lymphocyte may express the Bcl-2 protein (see FIG. 33C). From the movement of the AT6 portion of ATBF1 from the nucleus to the cytoplasm, it is assumed that ATBF1 is processed to function in the middle position between the D1-120 and the AT6. In tumors expressing the Bcl-2 protein and gaining a mechanism for escaping from, when the AT6 site exists in the nucleus, the Bcl-2 expression is suppressed, the grade of malignancy of the tumor is judged to be low. When the AT6 site moves to the cytoplasm, since the suppression of Bcl-2 expression is released, the grade of malignancy is judged to be higher (see FIG. 33).

10-3. Expression of ATBF1 Protein in Cultured Tumor Cell (Investigation of Protein Fragment by Western Blotting Using D1-120)

In order to confirm the probability that the ATBF1 assumed in 10-2 is cut at some sites and it can function as each fraction of the cell, by using three kinds of cultured cells, that is, the cultured cell lines derived from human neuroblastoma, NB1 and GOTO; a mouse undifferentiated embryonic carcinoma cell line p19 and SDS-PAGE and western blotting using an anti-ATBF1 antibody (D1-120) were carried out. A control group and a nerve cell differentiation inducing group were examined, separately. As to the control group, cells of P19, NB1 and GOTO that have been cultured in a serum-containing culture solution were collected and examined. As to the nerve cell differentiation inducing group, retinoic acid treatment was carried out (P19: four days; NB1 and GOTO: 24 hours). However, a culture method of P19 cells is different from that of the other two cell lines. Firstly, in a state in which cells were allowed to float on a bacterial grade dish for four days, retinoic acid (concentration: $5 \times 10^7$ mol) treatment was carried out, and then a serum-containing culture solution from which the retinoic acid had removed was prepared and transferred to a usual tissue culture dish. Then, culture was continued for three days. According to this method, P19 cells were differentiated and induced to neuron in which neurite was observed.

Hereinafter, the outline of the technology of Immunoblot analysis is described. The detail of the technology is described in non-patent document 3.

(SDS-PAGE, Western Blotting (Immunoblot Analysis))

1) Any of cultured cells of P19, NB1 and GOTO were attached to and cultured in a tissue culture dish, and then subjected to neurodifferentiation induction with retinoic acid. The neurodifferentiation induction of P19 cells was carried out by the procedure as described in 3-1.

2) Cells that had finished a culture process were peeled off from the culture dish and allowed to float in PBS (pH 7.4). The floating cells were subjected to centrifugation (200 g, 10 minutes) so as to be collected in a shape of pellet, and allowed to float again in a lysis buffer (10 mM Tris-HCL, pH 7.4, 150 mM NaCl, 5 mM EDTA, 1% Triton X-100) that had been supplemented with a proteinase inhibitor and cooled on ice. The cell floating solution was left on ice for ten minutes and then subjected to centrifugation (15,000 g for 20 minutes). A fraction portion soluble in Triton was employed as a sample and used for sodium dodecyl sulfate-polyacrylamide gel electrophoresis (SDS-PAGE).

3) The sample was mixed with a SDS-PAGE sample buffer (0.0625 M Tris-HCl, pH 6.8, 2% SDS, 10% glycerol, and 5% β-mercaptoethanol) and boiled for two minutes. The sample was subjected to centrifugation (21, 880 g, at 4° C. for 30 minutes), the supernatant was separated, and then electrophoresis was carried out on a polyacrylamide gel. Since the full-length molecular weight of ATBF1-A was 404 kDa, the gel for the SDS-PAGE selected to be 4%. Protein was mounted in an amount of 20 µg each on the respective lanes of the gel.

4) After electrophoresis, the protein in the gel was electrically transferred to a polyvinyldifluoride (PVDF) membrane, and subjected to immunostaining.

5) The membrane was subjected to blocking at room temperature for one hour with Block Ace (SNOW BRAND MILK PRODUCTS CO., LTD., Japan).

6) An anti-ATBF1 antibody, D1-120 was dissolved in Block Ace so that the concentration was 0.5 µg/ml. The membrane was impregnated with a primary antibody solution and reacted at room temperature for two hours (primary antibody reaction).

7) After washing, reaction with DAKO Envision+ (DAKO, Denmark) was carried out for 30 minutes and washed, followed by coloring with ECL-kit. Finally, photoresist treatment and observation were carried out by using Hyperfilm ECL (both are product by Amersham Pharmacia Biotech, Buckinghamshire, England).

(Results)

Figure 34:
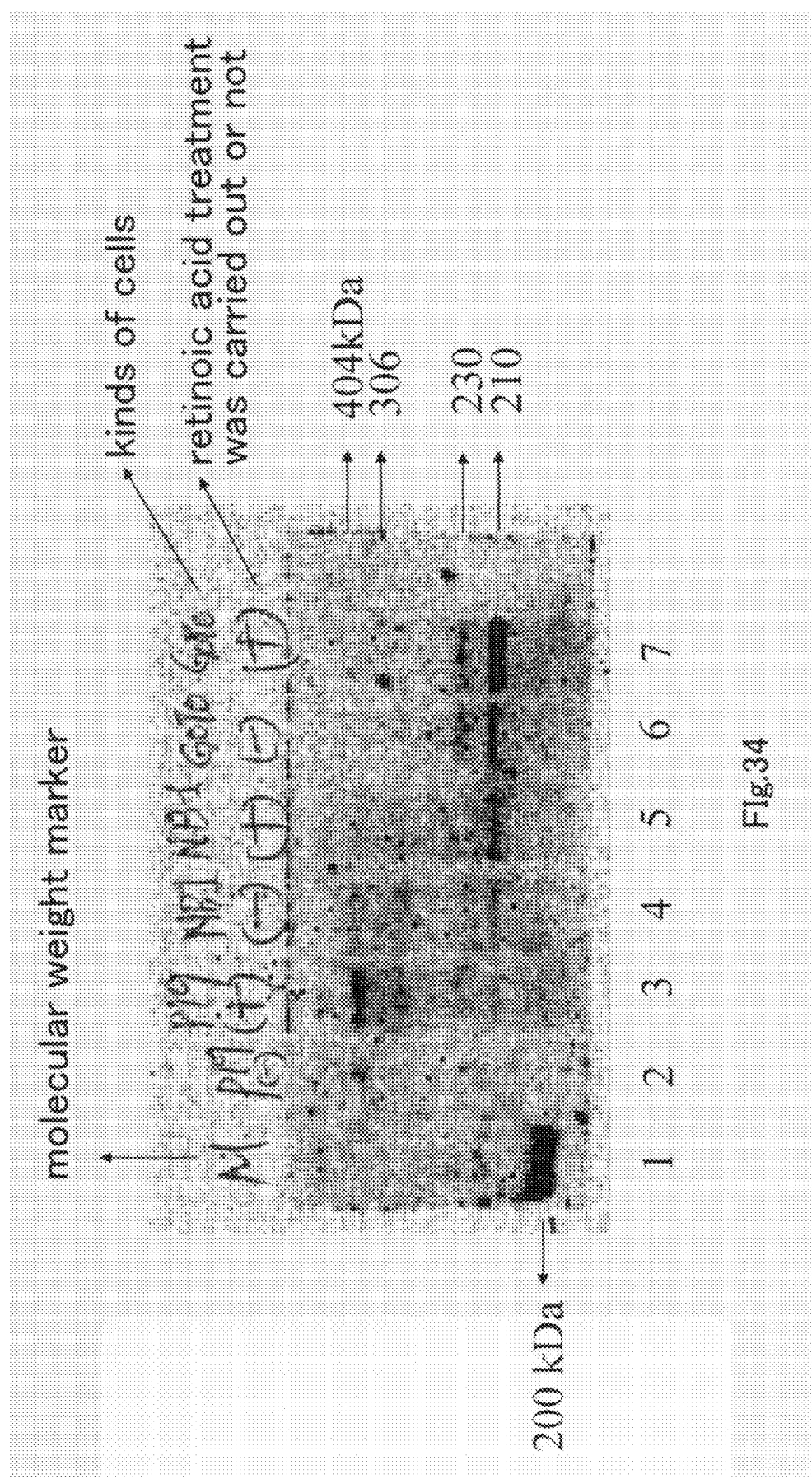
FIG. 34 shows western blotting for examining the change in the molecular weight of ATBF1 protein with or without the retinoic acid treatment of three kinds of cultured cells (P19, NB1, and GOTO). The antibody to be used is D1-120 corresponding to exon 10.

In p19 cells, when the retinoic acid treatment was not carried out, the expression of ATBF1 (indicated by D1-120 site) was hardly observed (see the lane 2 in FIG. 34). However, when the retinoic acid treatment was carried out, the expression of protein at the site of 404 kDa (corresponding to the full size ATBF1-A) was increased (see the lane 3 in FIG. 34). The fact that p19 cells in an undifferentiated state does not shows the ATBF1 expression and that p19 shows the ATBF1 expression dramatically at the time when differentiation to the nerve cell due to the retinoic acid treatment, is a fact reported in the mRNA level. It was predicted that 404 kDa protein (corresponding to ATBF1-A) and 306 kDa protein (corresponding to ATBF1-B) were detected. At this time, it has been clarified as a new fact that band was observed in further smaller fragments (230, 210 kDa).

Next, in NB1, before the retinoic acid treatment was not carried out, similar to P19, the expression of full length 404-kDa protein was observed (see the lane 4 in FIG. 34). Furthermore, it was clear that after the retinoic acid treatment was carried out, 210 kDa protein, which was smaller than the full-length 404-kDa protein, was mainly observed (see the lane 5 in FIG. 34).

GOTO did not respond to the retinoic acid treatment. The expression amount of protein was not different before and after the treatment. From the first, proteins having the smaller size (230 kDa and 210 kDa) are mainly expressed (see lanes 6 and 7 in FIG. 34). The fact that the ATBF1 expression of mainly small size proteins in GOTO and 404-kDa ATBF1 cannot be detected suggests the probability that as soon as proteins are produced, all the proteins are subjected to processing and divided and the probability that there is a mechanism in which depending upon the way of using the GOTO specific exon, mRNA coding for smaller size proteins is produced, so that 404-kDa proteins cannot be expressed.

Figure 35:
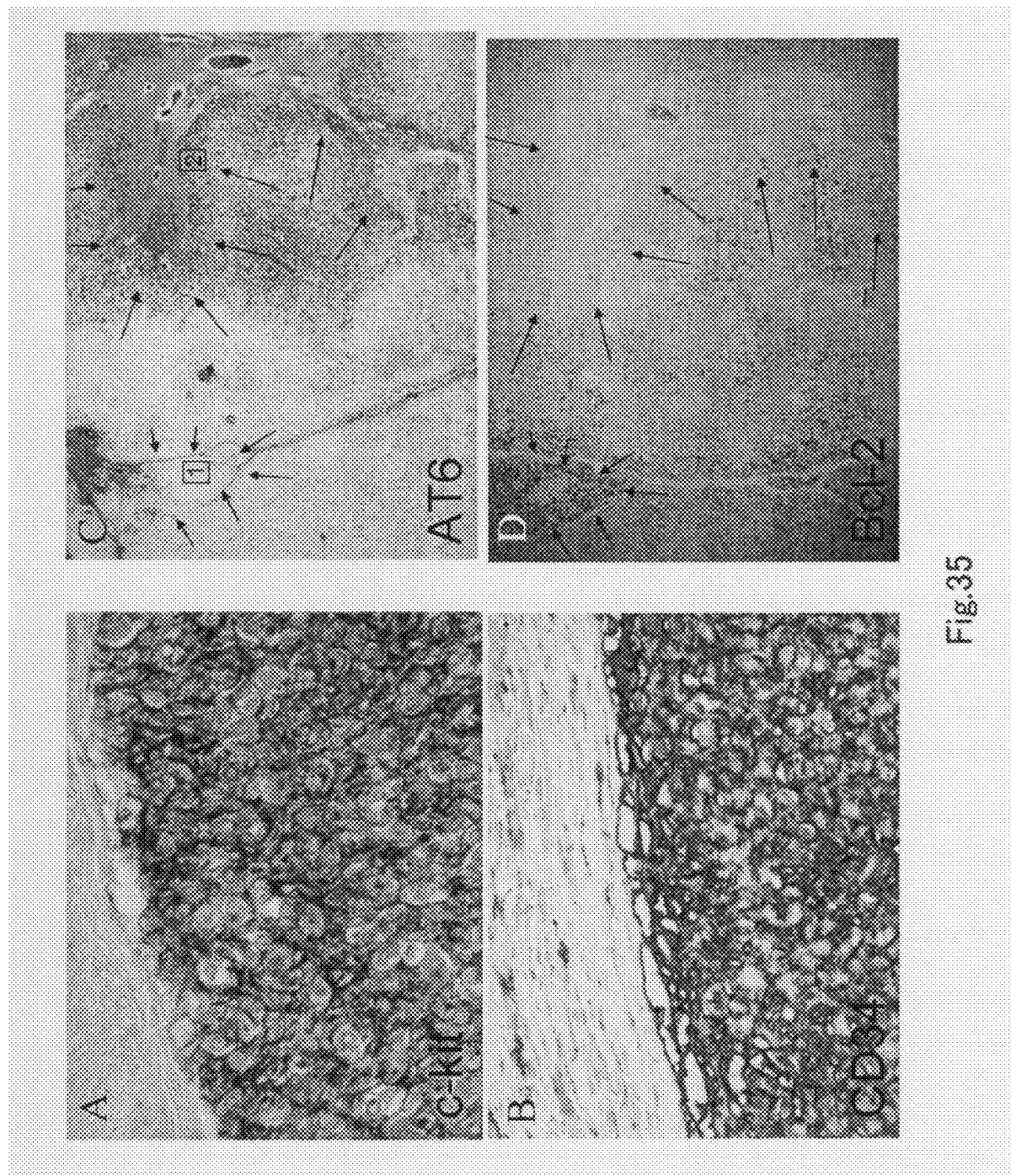
FIG. 35 shows a tissue image of gastric GIST of a 52-year-old man. The localization of the respective proteins are shown in FIG. 35A (c-kit), FIG. 35B (CD34), FIG. 35C (AT6 portion of ATBF1), and FIG. 35D (Bcl-2). The arrows in FIGS. 35C and 35D show that the localization of AT6 and Bcl-2 are complementary. The staining properties of ATBF1 and Bcl-2 sites shown by the number 1 surrounded by a square circle and the number 2 surrounded by a square circle are examined in detail in FIG. 36.
Figure 36:
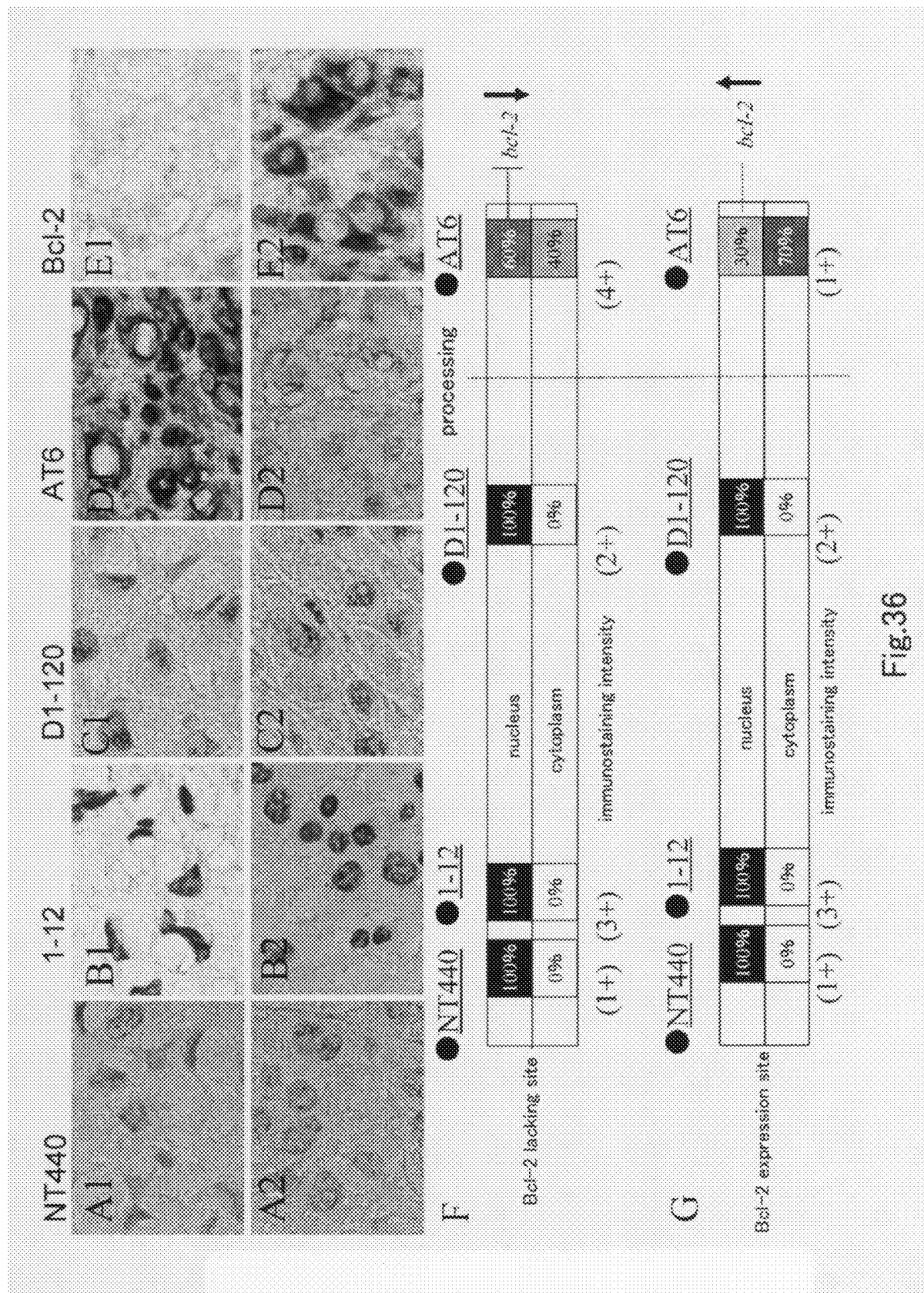
FIG. 36 summarizes a detail of the tissue image of gastric GIST of a 52-year-old man. The staining properties in the sites shown by the number 1 surrounded by a square circle (A1-E1) and the number 2 surrounded by a square circle (B2-E2) in FIG. 35 and the staining properties in sites (A) NT440, (B) 1-12, (C) D1-120, (D) AT6, and (E) Bcl-2, (F) a site lacking the expression of Bcl-2, and (G) a site in which Bcl-2 expression is observed, are summarized.

10-4. Investigation of Relationship Between Expression of ATBF1 and AT6 and Bcl-2 Expression Gastric GIST In GIST (Gastrointestinal stromal tumor) occurred in stomach (52-year-old man), the ATBF1 expression (NT440, 1-12, D1-120 and AT6) was investigated and compared with the expression of Bcl-2 proteins. In this case, the tumor shows positive for c-kit, positive for CD34 (see FIGS. 35A and B) and is localized in the gastric submucosa and has diameter of 20×18×20 mm. The metastasis to the other organs is not observed. Two nucleus mitoses are observed in the high power field 50. Neither necrosis nor hemorrhage are observed. Therefore, it is judged that the tumor may be treated as clinically benign tumor. In the ATBF1 site detectable by using D1-120, in any sites in the whole tumor, the staining was localized mainly in the nucleus (see FIGS. 36C1 and C2), so that it was determined that the grade of malignancy of the tumor was low. Furthermore, in more detailed investigation, when the expression of the Bcl-2 proteins in the tumor is compared with the ATBF1 expression using four kinds of antibodies, similar to the case of the D1-12, the NT440 and 1-12 showed the expression mainly in the nucleus (see FIGS. 36A, B and C). However, some sites in which the staining pattern by AT6 was different from the staining pattern by the other antibodies were obtained. That is to say, depending upon the site of the tumor, a site showing the staining pattern by AT6 and a site lacking the AT6 staining pattern were observed in a dispersion form, respectively (see FIG. 35C). When the tendency of staining in spots is compared with the Bcl-2 expression, the expression was complementary (see FIG. 35D). The site in which the expression of AT6 was observed lacked staining of Bcl-2. On the contrary, in the site lacking the expression of AT6, staining of Bcl-2 was observed. Next, the detail of the localization of AT6 was confirmed in the cellular level. In the site in which the AT6 expression was observed, although staining was observed in the cytoplasm in the cells, the staining was mainly in the nucleus (see FIG. 36D1). Bcl-2 expression was almost completely suppressed (see FIG. 36E1). On the other hand, in the site in which a small amount of AT6 were localized in the cytoplasm or the site in which AT6 was absent in the nucleus and the cytoplasm (see FIG. 36D2), the Bcl-2 expression was not suppressed at all, and the expression around the nucleus was obtained (see FIG. 36E2).

This phenomenon can be explained by thinking that, similar to the above-mentioned lymphoid follicle site, the AT6 portion corresponding to an exon 11 of the ATBF1 gene suppresses a bcl-2 gene via the interaction with Myb oncogene protein in the nucleus (see non-patent document 8). The variation of the localization of this AT6 portion and the presence or absence of staining shows that ATBF1 is processed in the middle position between the D1-120 and the AT6 (see FIGS. 36F and G). It was assumed that AT6 portion that could not move to the nucleus but was localized in the cytoplasm was then subjected to proteolysis so as to be disappeared, and that the function carried by this site was lost. That is to say, in the tumor like GIST in which only a certain portion expresses the Bcl-2 protein and gaining a mechanism for escaping from the apoptosis, when the expression amount is large in the AT6 site and the expression occurs mainly in the nucleus, the Bcl-2 expression is suppressed. Therefore, the grade of malignancy of the tumor is determined to be low in the whole tumor. When the AT6 site moves to the cytoplasm or AT6 site is absent, since the suppression of the Bcl-2 expression is released, the grade of malignancy of the tumor portion can be determined to be high in the whole tumor. Even in the tumor which is determined to be clinically benign and in which it can be determined that since D1-120 site in the ATBF1 exists in the nucleus in the D1-120 staining, it is clear that the grade of malignancy of the whole tumor is not high, the examination results of the grade of malignancy obtained when AT6 was added is more detailed judgment. It is suggested that to examine the amount of the sites in which the AT6 is localized in the cytoplasm or AT6 is absent becomes an index for predicting the probability of the recurrence and the metastasis of this kinds of tumors.

10-5. Investigation on Relation of Processing Position of ATBF1, Expression of AT6 Portion and Expression of Bcl-2 in Malignant Lymphoma (Large-Cell Diffuse B-Cell)

Figure 37:
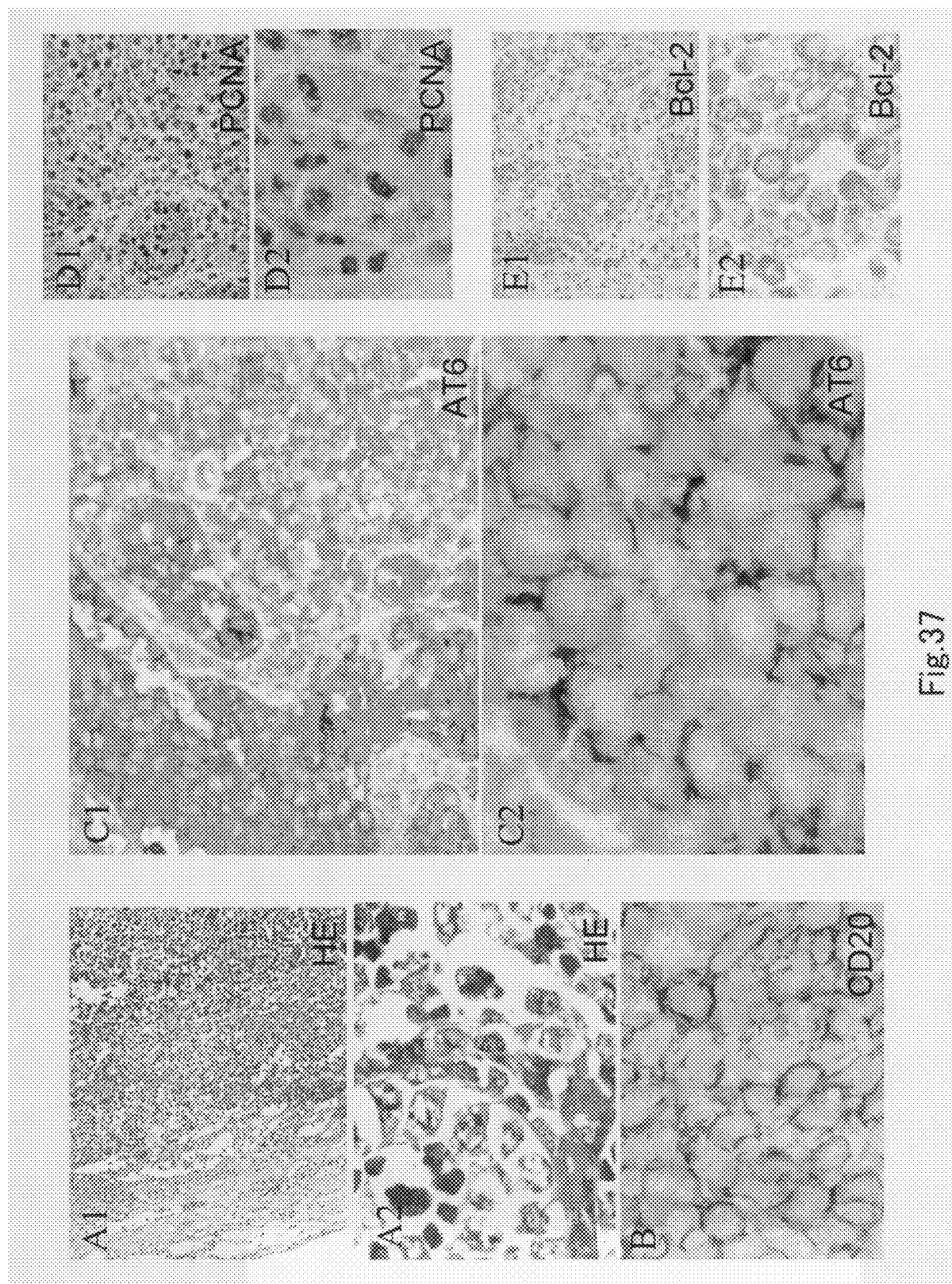
FIG. 37 is a tissue image of large-cell diffuse B-cell lymphoma of a 56-year-old woman. The staining properties of HE (A1: low magnification image, A2: high magnification image), CD20 (B), AT6 (C1: low magnification image, C2: high magnification image), PCNA (D1: low magnification image, D2: high magnification image), Bcl-2 (E1: low magnification image, E2: high magnification image) are shown.

A lymphoma case of 56-year-old woman in which 3 cm-diameter swelling was observed in the upper part of the right clavicle and in the right axillary lymph node. The swelling was the pathological proliferation of diffuse large cells (see FIG. 37A). LCA and CD20 including a marker of B-lymphocyte (see FIG. 37B) and showed positive for CD79a. The expression of Bcl-2 proteins was observed in almost all the tumor cells (see FIG. 37E). Therefore, it was judged that the swelling was a malignant lymphoma (large-cell diffuse B-cell). The ATBF1 expression (NT440, 1-12, D1-120, and AT6) in this malignant lymphoma was investigated and compared with the expression Bcl-2 proteins.

Figure 38:
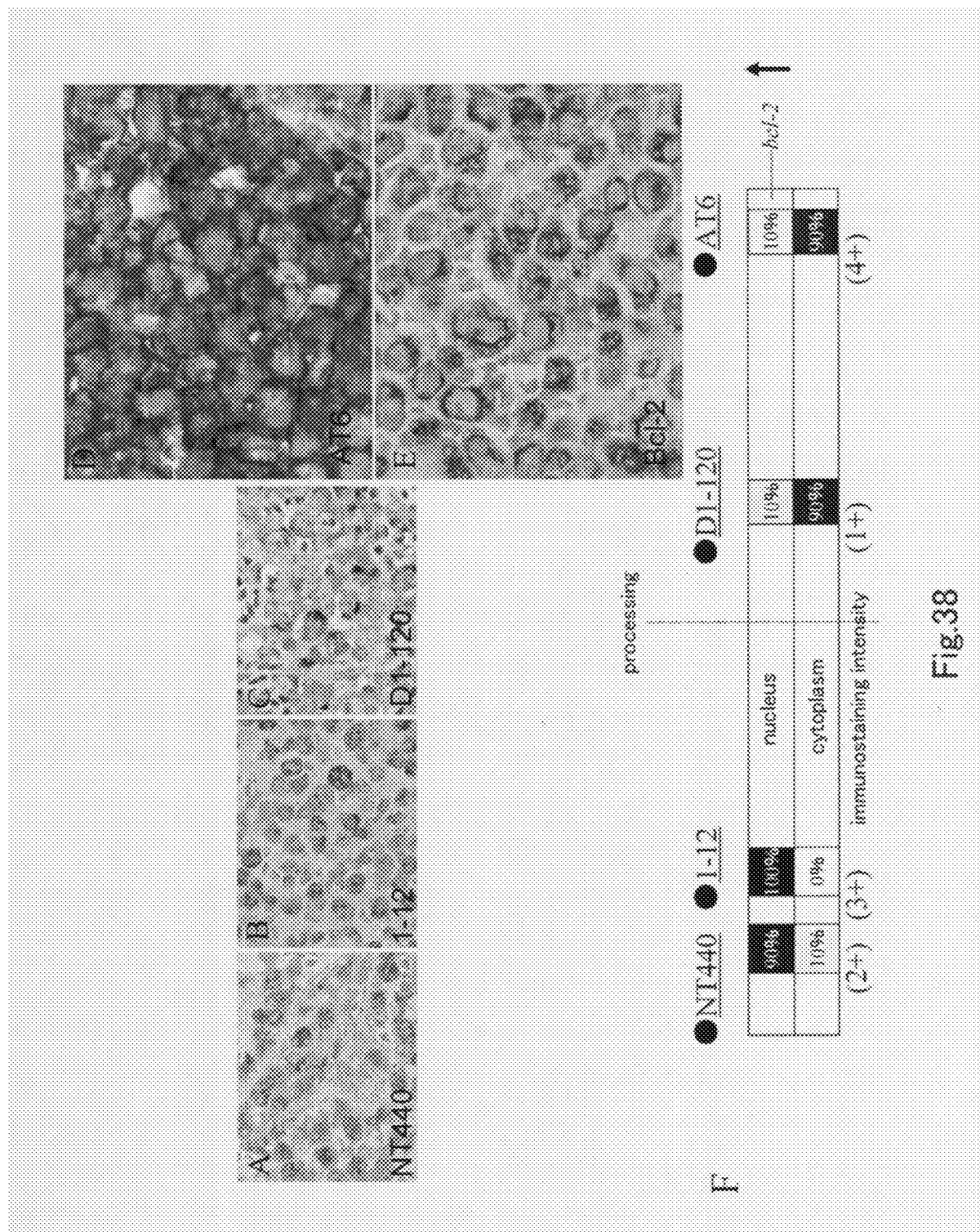
FIG. 38 shows summary and details of staining properties of ATBF1 and Bcl-2 of large-cell diffuse B-cell lymphoma of a 56-year-old woman. The staining images of NT440 (A), 1-12 (B), D1-120 (C), AT6 (D), and Bcl-2 (E) and the summary of the staining properties (F) are shown.

NT440 and 1-12 recognizing the N-terminus of ATBF1 showed staining mainly in the nucleus of the tumor cell (see FIGS. 38A and 38B) and D1-120 recognizing the central portion of ATBF1 and AT6 recognizing the C-terminus of ATBF1 showed the staining properties mainly in the cytoplasm (see FIGS. 38C and 38D). The fact that staining of D1-120 is observed mainly in the cytoplasm means that the grade of malignancy of this tumor is high. The malignant lymphoma is generally known to have a high grade of malignancy. The fact that almost all the cells show positive for PCNA (see FIG. 37D) also supports that judgment of the grade of malignancy in D1-120 is exact. The fact that all the staining of AT6 exists in the cytoplasm is similar to the above-mentioned lymphoid follicle marginal portion or a part of the GIST tumor. It is possible to explain by thinking that since AT6 portion corresponding to the exon 11 of the ATBF1 gene is not present in the nucleus, it is not possible to suppress the bcl-2 gene (non-patent document 8).

In conclusion, in the malignant lymphoma, D1-120 staining is observed mainly in the cytoplasm. Furthermore, AT6 staining is also observed mainly in the cytoplasm. Thus, it was able to be determined that the grade of malignancy was high. Furthermore, by comparing the localization of staining of four antibodies, it is possible to indicate that the ATBF1 protein is subjected to processing in the middle portion (see FIG. 38F).

10-6. Investigation on Relationship Between GFAP Expression and Processing Portion of ATBF1 Protein as Well as Relationship Between Localization of Staining of AT6 and Expression of Bcl-2 and Bcl-xL in Brain Glioblastoma Multiforme A glioblastoma multiforme case of 63-year-old man developed in the cerebral hemisphere. The ATBF1 expression (NT440, 1-12, D1-120, and AT6) in this tumor was investigated and compared with the expression of GFAP, Bcl-2, Bcl-xL proteins and with the expression of MIB1 that is a marker of the cell proliferation.

Glioblastoma occurs in middle and aged persons with high-incidence and is a high-incidence malignant gliocystoma among brain tumors. Since glioblastoma shows various images by gross observation and by histological observation, it is referred to as glioblastoma multiforme. The tumors of tissues include large and small focuses of necrosis and are characterized by pseudopalisading necrosis. In general, in the glia malignant tumor, a Glial fibrillary acidic protein (GFAP) is used for the purpose of identifying the glia cell. According to the protocol for treating brain tumors, "Immunohistochemically, GFAP is expressed in a part of the cells. The incidences and morphologies of positive cells are extremely various." It is thought that the fact that the incidences and morphologies are various as the protocol says means that the relationship between the GFAP expression and the tumor site has not clarified.

As mentioned above, a clue for elucidating the mechanism of the movement of ATBF1 between the nucleus and the cytoplasm was that a protein-protein binding between ATBF1 and GFAP had been proved by Yeast two-hybrid method. It has been clarified that the binding sites are substantially the center of ATBF1-A and C-terminus of the GFAP protein. Furthermore, a luciferase analysis has revealed that ATBF1 increased the promoter activity of GFAP. By using four antibodies, the theoretically predicted molecular mechanism was able to be confirmed by an actual clinical specimen of glioblastoma multiforme.

Figure 39:
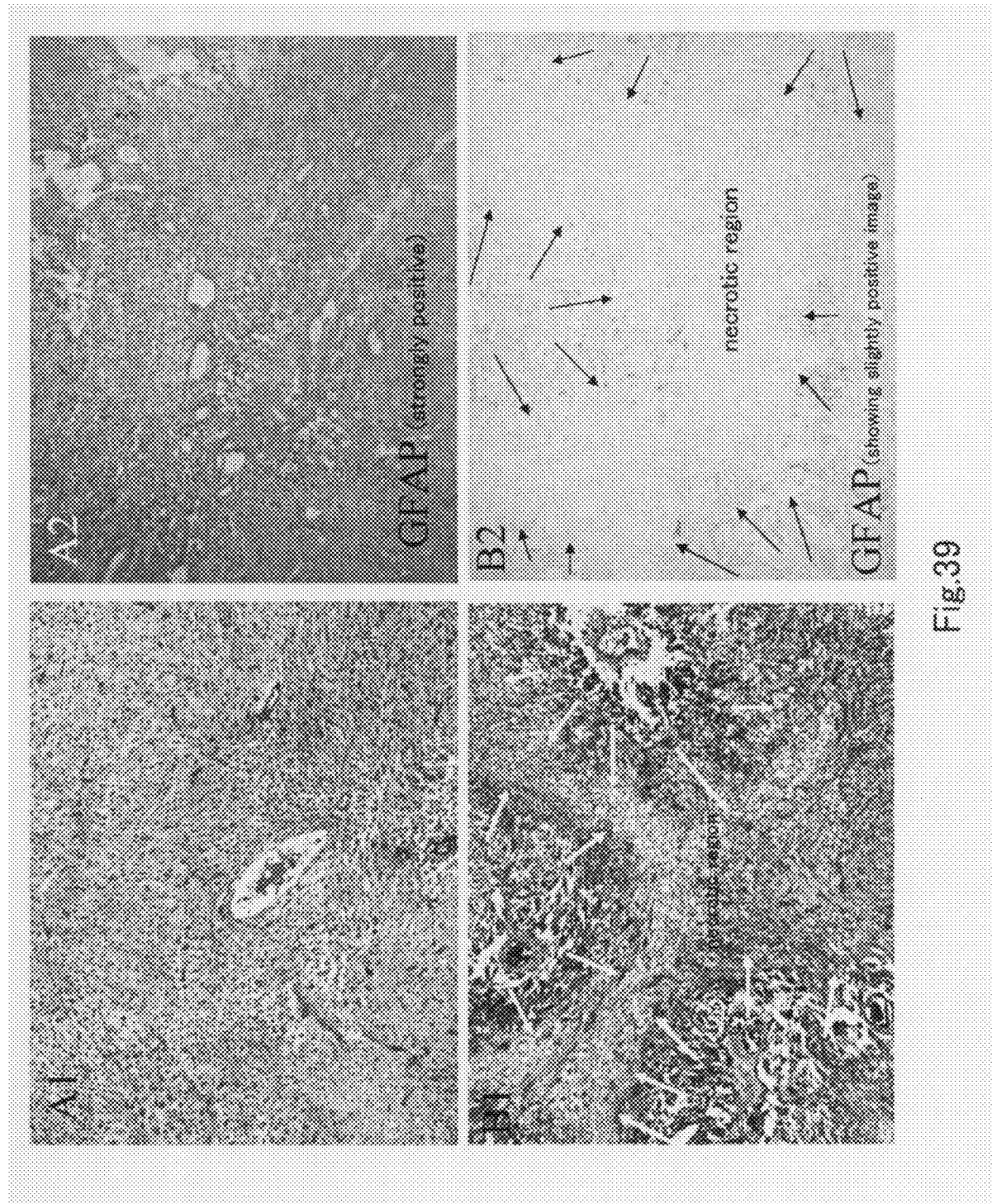
FIG. 39 is a tissue image cerebral glioblastoma multiforme of a 63-year-old man. The localization of GFAP (A2, B2) in a solid tumor site (A1, HE) and a site in which necrosis is scattered (B1, HE) are shown. The arrows of B1 and B2 show the range of necrotic tissue.

At this time, firstly, the present inventors made a comparison of GFAP expression in a tumor site forming a solid alveolus, focus of necrosis and the surrounding site thereof. As shown in FIG. 39A1, in the solid proliferation site, in almost all the cells, strong expression of GFAP was observed (see FIG. 39A2). This tumor is known to have high incidence of hemorrhage and necrosis. A site surrounded by arrows in FIG. 39B1 shows a site that is a so-called necrotic tissue, which is understood to occur as a result that the proliferation is so strong that the blood flow for supplying nutrition was insufficient (ischemia), so that necrosis or exfoliation occurred. When the GFAP expression in the focus of necrosis and in the vicinity thereof was observed, as compared with a solid site that is poor in necrosis, GFAP expression is weaker in living cells. Furthermore, in the necrotic tissue, GFAP proteins were not detected at all (see FIG. 39B2). This means that staining of GFAP is not observed in debris of cells that underwent necrosis. This suggests that the cells that underwent necrosis may be originally cells not capable of expression GFAP.

Figure 40:
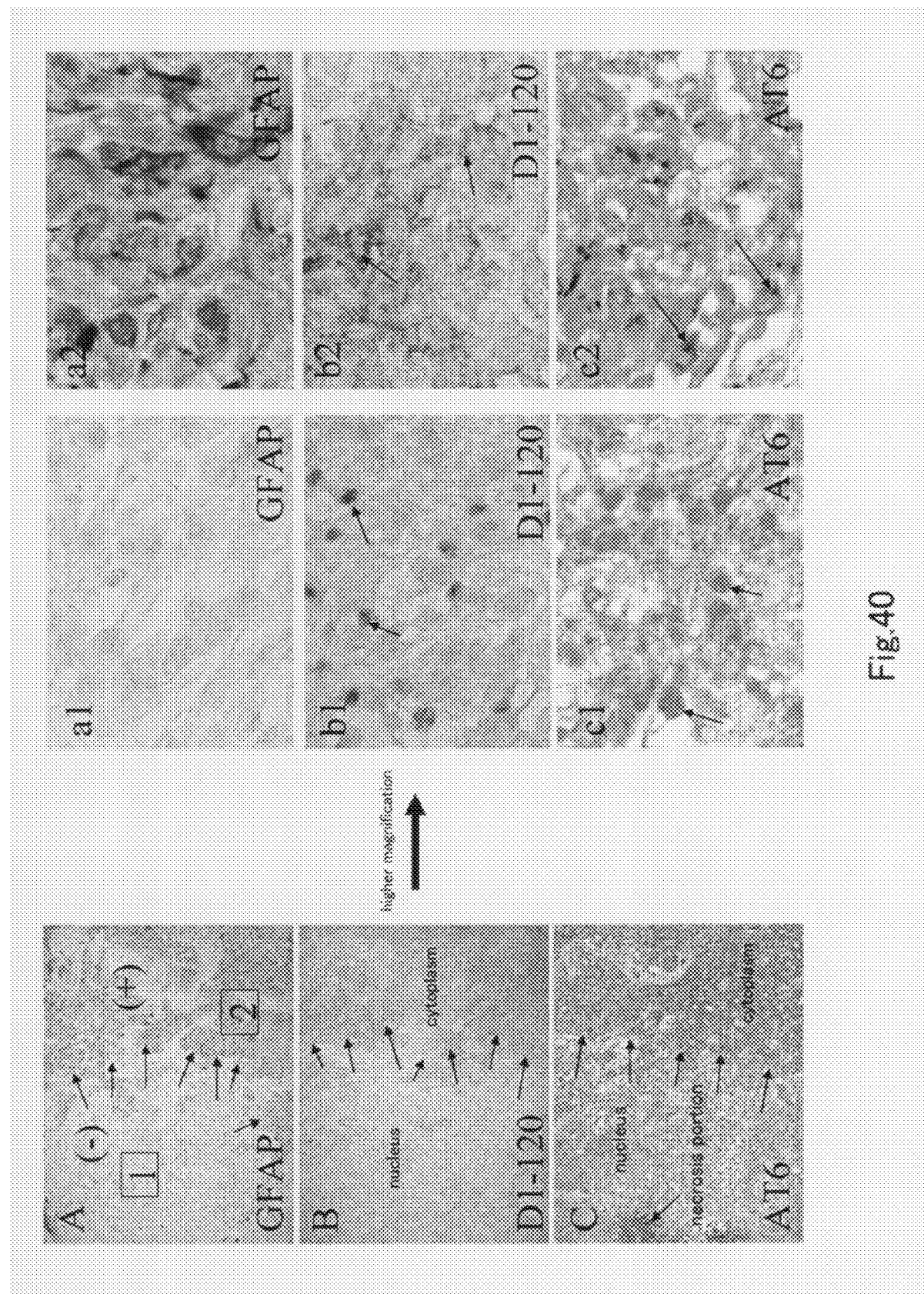
FIG. 40 shows stained images of cerebral glioblastoma multiforme of a 63-year-old man with GFAP, D1-120, and AT6. The detailed staining properties of the lacking portion of GFAP (A, square surrounding 1) and a positive portion of GFAP (A, square surrounding 2) are shown in FIGS. 40*a*1 and 40*a*2 respectively. At the same time, it is shown that the difference in the staining patterns (A, arrow) is similar to the staining patterns of D1-120 (B) and AT6 (C) (B, arrow, C, arrow). In the lacking portion of GFAP (A, square surrounding 1), the staining properties of D1-120 (b1) and AT6 (c1) are observed mainly in the nucleus (b1, c1, arrows). In the GFAP positive sites (A, square surrounding 2), the staining properties of D1-120 (b1) and AT6 (c1) are observed mainly in the cytoplasm (b2, 2, arrows).
Figure 41:
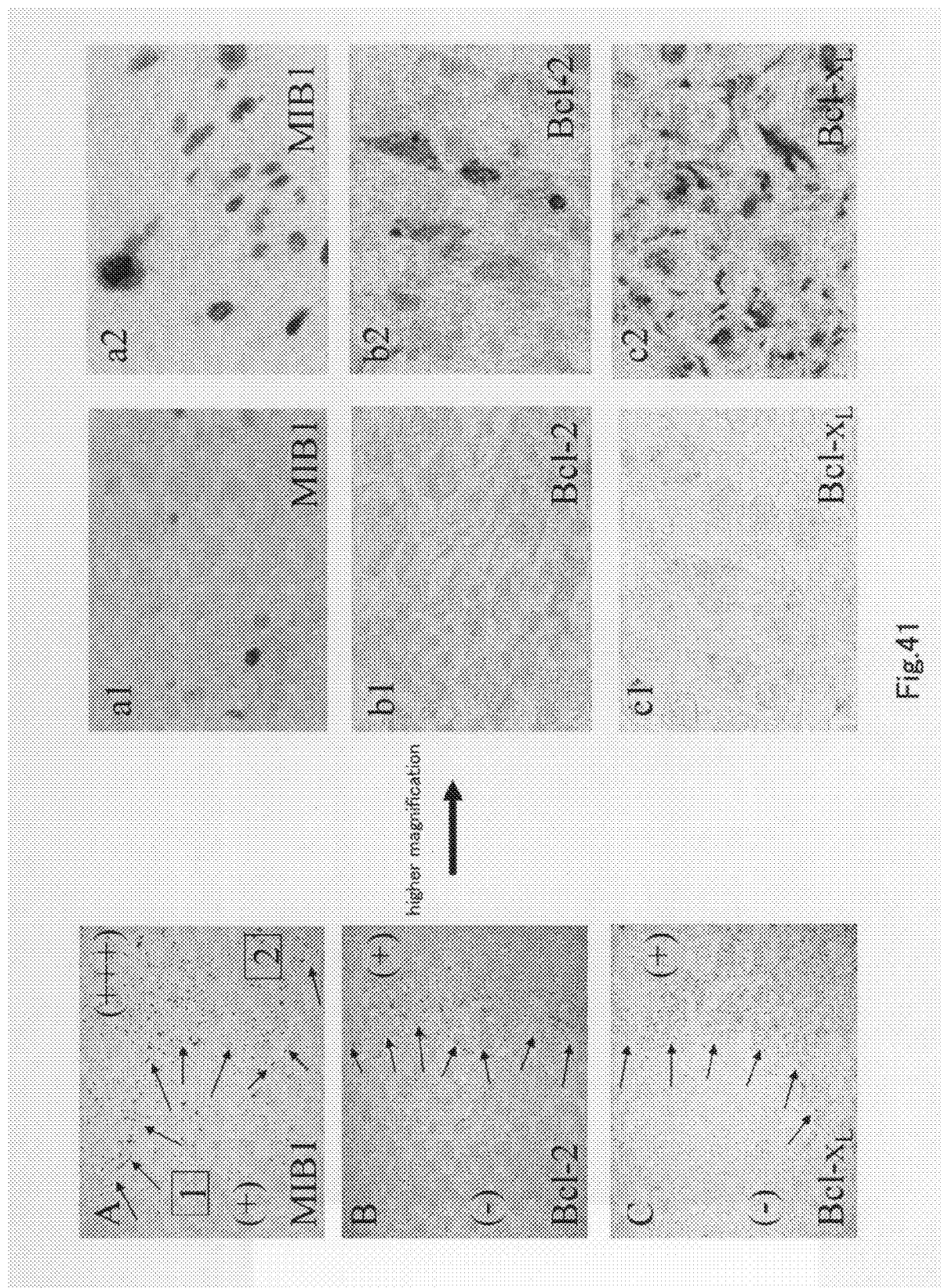
FIG. 41 shows stained images of cerebral glioblastoma multiforme of a 63-year-old man with MIB1, Bcl-2, and Bcl-xL. It is shown that staining patterns in the lacking portion of GFAP (FIG. 40A, square surrounding 1) and the GFAP positive sites (FIG. 40A, square surrounding 2) are similar to the staining properties of MIB1 (A), Bcl-2 (B), and Bcl-xL (C). Furthermore, the details of the staining of MIB1 (a1, a2), Bcl-2 (b1, b2), and Bcl-xL (c1, c2) in the lacking portion of GFAP (A, square surrounding 1) and the GFAP positive sites (A, square surrounding 2) are shown.

Next, sites in which the presence or absence of the GFAP expression can be clearly divided in the tumor are selected. Comparison was carried out between both sites in ATBF1 expression (NT440, 1-12, D1-120, and AT6), Bcl-2, Bcl-xL protein expression, and MIB1 expression. Stained patterns (FIG. 40A) due to the difference between the presence and absence of the GFAP expression observed in the tumor were extremely similar to the staining patterns observed by D1-120 (FIG. 40B), AT6 (FIG. 40C), MIB1 (FIG. 41A), Bcl-2 (FIG. 41B), and Bcl-xL (FIG. 41C). According to the detailed observation, in the site lacking the GFAP production (FIG. 40a1), staining of D1-120 was mainly in the nucleus (FIG. 40b1) and staining of AT6 was also mainly in the nucleus (FIG. 40c1); the MIB1 labeling index was low (FIG. 41a1); and the expression of Bcl-2 (FIG. 41b1) and Bcl-XL (FIG. 41c1) tended to be absent. On the contrary, the site showing the GFAP production (FIG. 40a2), D1-120 was observed mainly in the cytoplasm (FIG. 40b2) and AT6 was observed mainly in the cytoplasm (FIG. 40c2); the MIB1 labeling index was high (FIG. 41a2); and the expression of Bcl-2 (FIG. 41b2) and Bcl-xL (FIG. 41c2) tended to be high.

Figure 42:
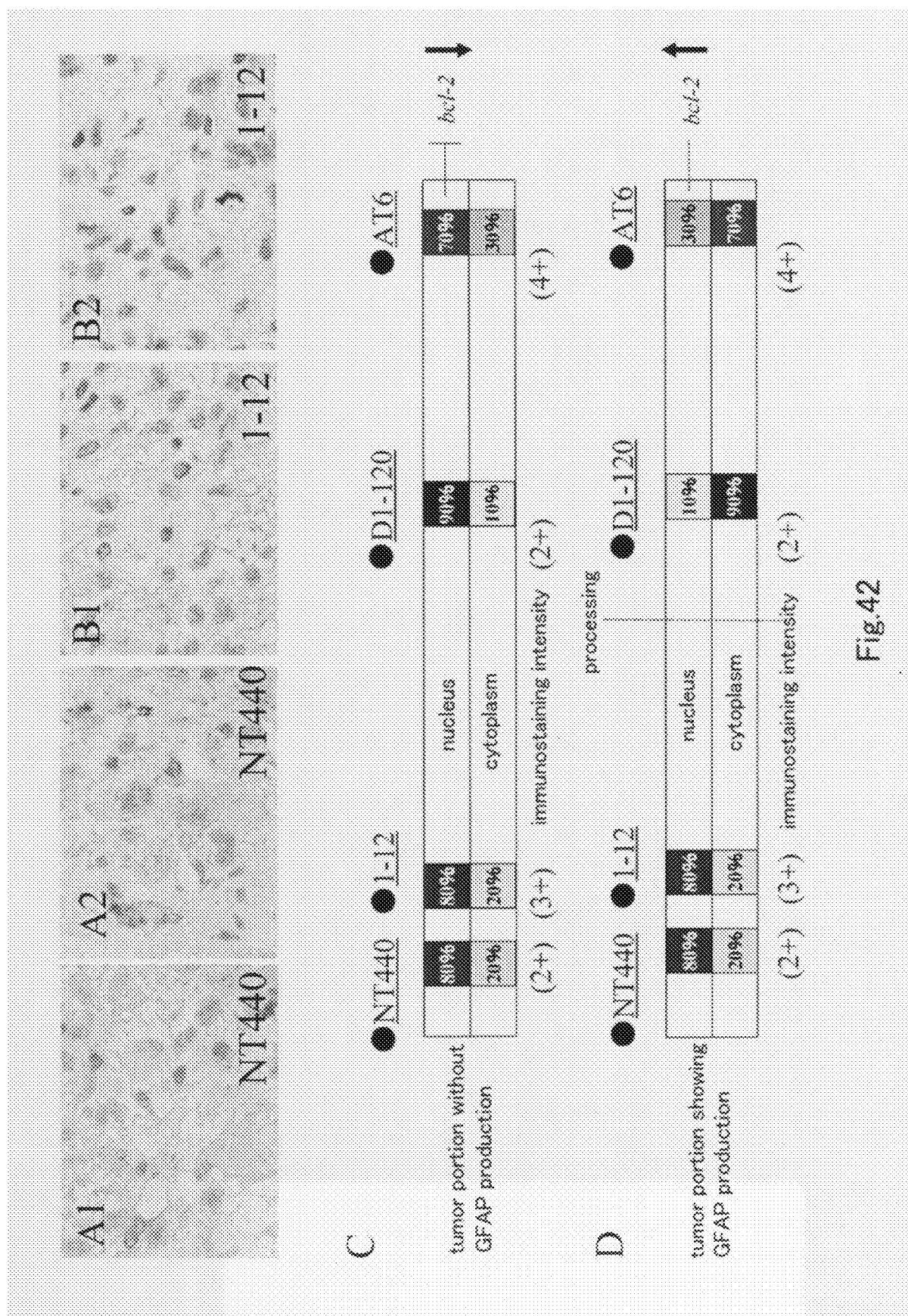
FIG. 42 shows NT440, 1-12 stained images of cerebral glioblastoma multiforme of a 63-year-old man, and summary of the ATBF1 staining properties. The details of the staining properties of NT440 (A1, A2) and 1-12 (B1, B2) in the lacking portion of GFAP (FIG. 40A, square surrounding 1) and the GFAP positive sites (FIG. 40A, square surrounding 2) are shown. The staining (C) of ATBF1 in a site in which GFAP production is not observed and the staining (D) of ATBF1 in a site in which GFAP production is observed are summarized.

In the ATBF1 expression, NT440 and 1-12 capable of detecting the N-terminus showed the expression mainly in the nucleus regardless of whether or not the GFAP production (see FIGS. 42A and 42B).

With respect to this tumor, when a malignancy grade determination method using ATBF1 was carried out, in the site expressing GFAP in the tumor, D1-120 and AT6 are present mainly in the nucleus. It is determined that the grade of malignancy is low. It is predicted that this site is easily moved to the apoptosis in response to chemotherapy and radiation treatment. On the contrary, in the site expressing GFAP, D1-120 and AT6 are mainly present in the cytoplasm. It is predicted that the grade of malignancy is high and that the response to chemotherapy and radiation treatment is poor. That is to say, since the glioblastoma multiforme is a tumor including a site with high grade of malignancy and site with low grade of malignancy, the glioblastoma multiforme is thought to have polymorphism.

An actual glioblastoma multiforme is a highly malignant tumor regardless of the development of surgical operations and chemotherapies. Within one year after discovery, 80% of patients died. The five-year survival rate has not also been improved currently. Although the tumor is temporarily reduced by chemotherapy, the remaining refractory cancer cells are re-proliferated, resulting in recurrence and development so as to make patient die. This mechanism can be understood from the ATBF1 staining.

10-7. Brain Glioblastoma Multiforme, GFAP Expression, and Tumor Malignancy Hypothesis A. Protein-protein binding between ATBF1 and GFAP (event in the cytoplasm)

B. Stimulation of a GFAP promoter by the introduction of ATBF1 (event in the nucleus)

C. Correlation between the change in the intracellular localization of the D1-120 and AT6 sites in ATBF1 depending upon the presence or absence of the GFAP production, and the cell proliferation (MIB1) and apoptosis resistant property (Bcl-2 and Bcl-$x_L$)

From the above-mentioned A, B, and C, the present inventors have considered the hypothesis from the oncogenesis to the proliferation development and investigated the relationship between the relationship between ATBF1 localization and GFAP (1) At early stage of the development of the gliosarcoma, the proliferation of the tumor starts. Needless to say, the tumor vessel also undergoes hyperplasia. However, when ischemia occurs and DNA damage is applied to the tumor cells, ATBF1 appears in the nucleus (ATBF1 appears mainly in the nucleus in any sites of NT440, 1-12, D1-120 and AT6.). This terminates the cell cycle and promotes the movement toward the apoptosis. Simultaneously, the expression of the ATBF1 in the nucleus causes the activation of a GFAP promoter. At this stage, many cells are introduced into the apoptosis before expressing GFAP (dispersion of the necrotic portions, the reason why the amount of cells positive for the GFAP is small in the vicinity of the necrotic portion).

(2) Gliosarcoma has then GFAP in the cytoplasm. Since the central portion of ATBF1 has characteristics of forming the protein-protein binding with the C-terminus GFAP. Even if ATBF1 is moving to the nucleus after proteins are produced in the cytoplasm, since ATBF1 is trapped by the cytoplasm, only the N-terminus side of the ATBF1 moves to the nucleus (NT440 and 1-12 have a staining ability with respect to the nucleus), however, the ATBF1 remains in the portion from the center to the C-terminus side (D1-120 and AT6. Both have a staining ability with respect to the cytoplasm). The cells in which D1-120 and AT6 are present in the cytoplasm have a high grade of malignancy as shown by the malignancy grade determination method, so that the cells do not easily move to apoptosis by chemotherapy. This is apparent from the fact that cell group showing positivity to GFAP has high MIB1 labeling index and expresses Bcl-2 and Bcl-$x_L$ (see FIGS. 42B and 42C).

(3) Since the processes (1) and (2) mentioned above occur in each portion of the tumor, in a small-sized gliosarcoma, GFAP production sites are then dispersed and have polymorphism in which hemorrhage and necrosis are mixed (glioblastoma multiforme).

(4) Furthermore, when a part of the cell in which whole ATBF1 exists in the nucleus and no GFAP expression is observed is moved to the apoptosis by, for example, chemotherapy, at first, the reduction of the tumor is observed. However, then the GFAP production is observed and the tumor changed to a tumor mainly including cells having resistance with respect to the apoptosis.

As mentioned above, although a tumor in which a site having a high grade of malignancy and a site having a low grade of malignancy are mixed in the grade of malignancy judgment using ATBF1, actually the tumor has extremely high grade of malignancy and bad prognosis. The following is the interpretation for the fact mentioned above.

(1) A glioblastoma multiforme is a tumor having particularly high grade of malignancy and poor prognosis. In a conventional pathological diagnosis, the molecular biological mechanism has been not clear. However, empirically, the GFAP production probability has been used as one index of the grade of malignancy.

(2) In the glioblastoma multiforme, the GFAP production is activated due to the expression of the ATBF1 in the nucleus. It is assumed that since a half part, that is, the C terminus site of ATBF1 is stabilized in the cytoplasm in a state of a protein-protein binding of ATBF1-GFAP, the movement of ATBF1 to the nucleus is prevented and then the grade of malignancy is increased.

(3) It is predicted that by providing a device for preventing ATBF1 from being trapped in the GFAP in a glioblastoma multiforme, ATBF1 can move to the nucleus, so that radiation therapy and chemotherapy become effective. In the future, new treatment method may be created.

As mentioned above, it was determined that simultaneous use of antibodies in each part of the ATBF1 protein was useful for estimating the abnormality in protein processing peculiar to tumors and a structural change in gene, in addition to determining the grade of malignancy of a cancer cell.

Figure 43:
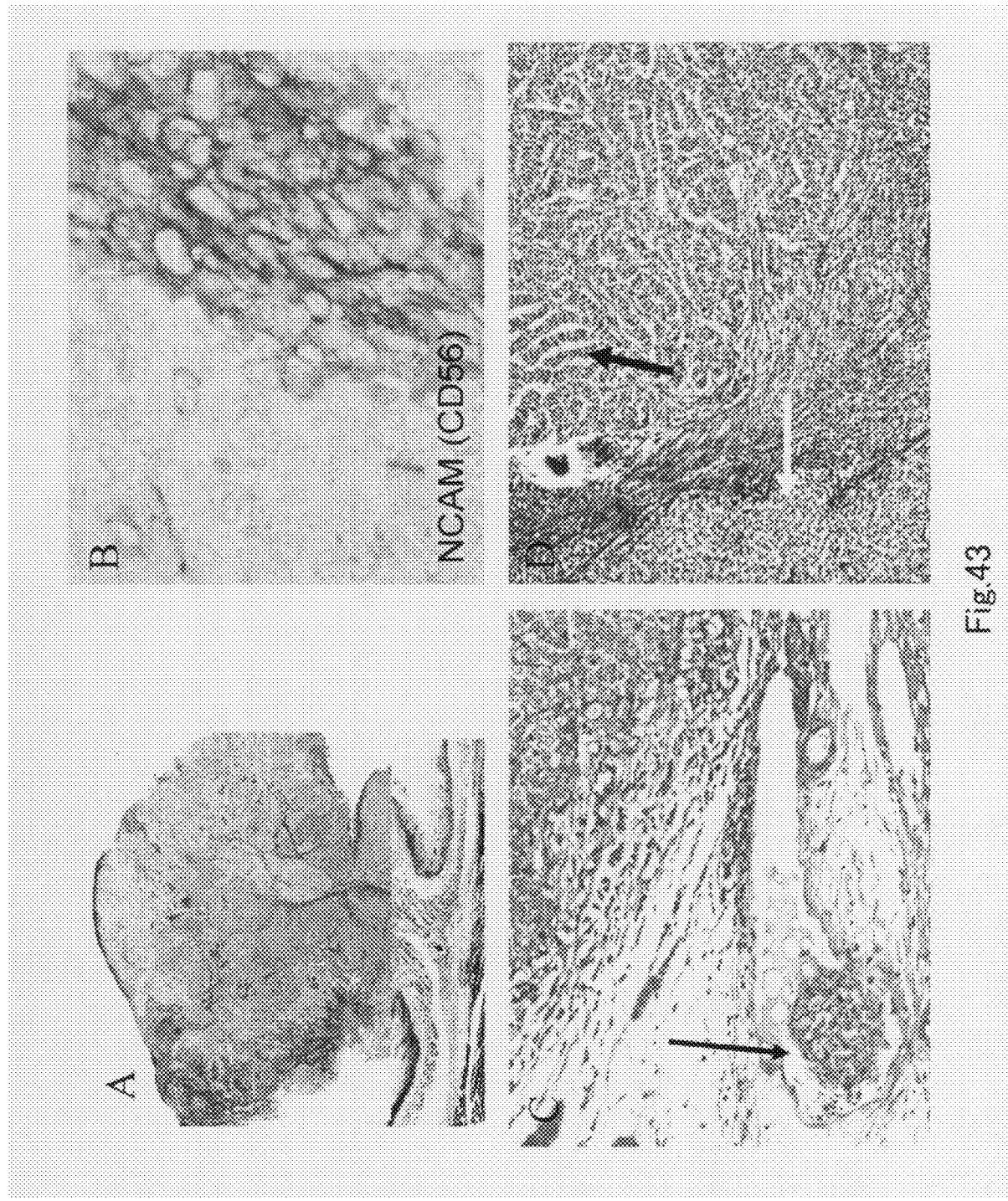
FIG. 43 shows findings of HE and NCAM of an esophagus neuroendocrine cancer of a 52-year-old man.

10-8. Investigation on Relationship Between Change in Localization of ATBF1 Protein and Tumor Morphology in a Highly Malignant Tumor, an Esophagus Neuroendocrine Cancer A case of highly malignant neuroendocrine cancer in the esophagus of a 52-year-old man. The ATBF1 expression (NT440, 1-12, D1-120, and AT6) in this tumor was investigated and comparison was made with respect to the morphological characteristics of the tumor. Most of the esophagus malignant tumors are squamous carcinomas and in rare cases, it is an undifferentiated cancer. Among them, the neuroendocrine cancer has a high grade of malignancy and poor prognosis. This case is a neuroendocrine cancer whose primary tumor was in the esophagus. Two months after the operation, the patient developed a liver metastasis and died. The tumor was a superficial protrusion tumor present at a site about 30 cm from the incisor and had a size of 4.0×2.8×1.7 cm (see FIG. 43A). According to the pathologic examination after operation, the tumor cell was positive for most of the NSE and S-100 proteins, was positive for chromogranin A, CD56 (NCAM) (see FIG. 43B), and Synaptophisin. As a result, the tumor was diagnosed to be a neuroendocrine cancer. Furthermore, infiltration into the lymph duct was observed (see FIG. 43C). It was determined that the tumor had variously differentiated directions in which a site which was positive for AE1/AE3 and CAM5.2 and had apparently epithelial characteristic and a site which was positive for Vimentin and like a sarcoma were present together.

When the tumor tissue was observed in detail, histologically, an epithelium-like well-differentiated site (see black arrow in FIG. 43D) in which a funicular arrangement and a tenioid arrangement of cells regularly arranged in one line were observed and a sarcoma-like site (see white arrow in FIG. 43D) showing a dense and focal poorly-differentiated arrangement can be clearly distinguished from each other and that the staining properties of ATBF1 were different in the sites.

In the site showing a funicular or tenioid and well-differentiated arrangement, in any of NT440, 1-12, D1-120 and AT6, stainign was observed mainly in the nucleus (see FIGS. 44A1 to 44E1 and 44F). On the contrary, in a site showing a focal and poorly-differentiated arrangement, in NT440 and 1-12, staining was observed mainly in the nucleus, and in D1-120 and AT6, staining was observed mainly in the cytoplasm (see FIGS. 44A2 to 44E2 and 44 G). When the grade of malignancy was determined by ATBF1, it was determined that in the well-differentiated site, D1-120 and AT6 were observed mainly in the nucleus, so that the grade of malignancy was low; and it was determined that in the poorly-differentiated site, D1-120 and AT6 were observed in the cytoplasm, so that the grade of malignancy was high.

Figure 44:
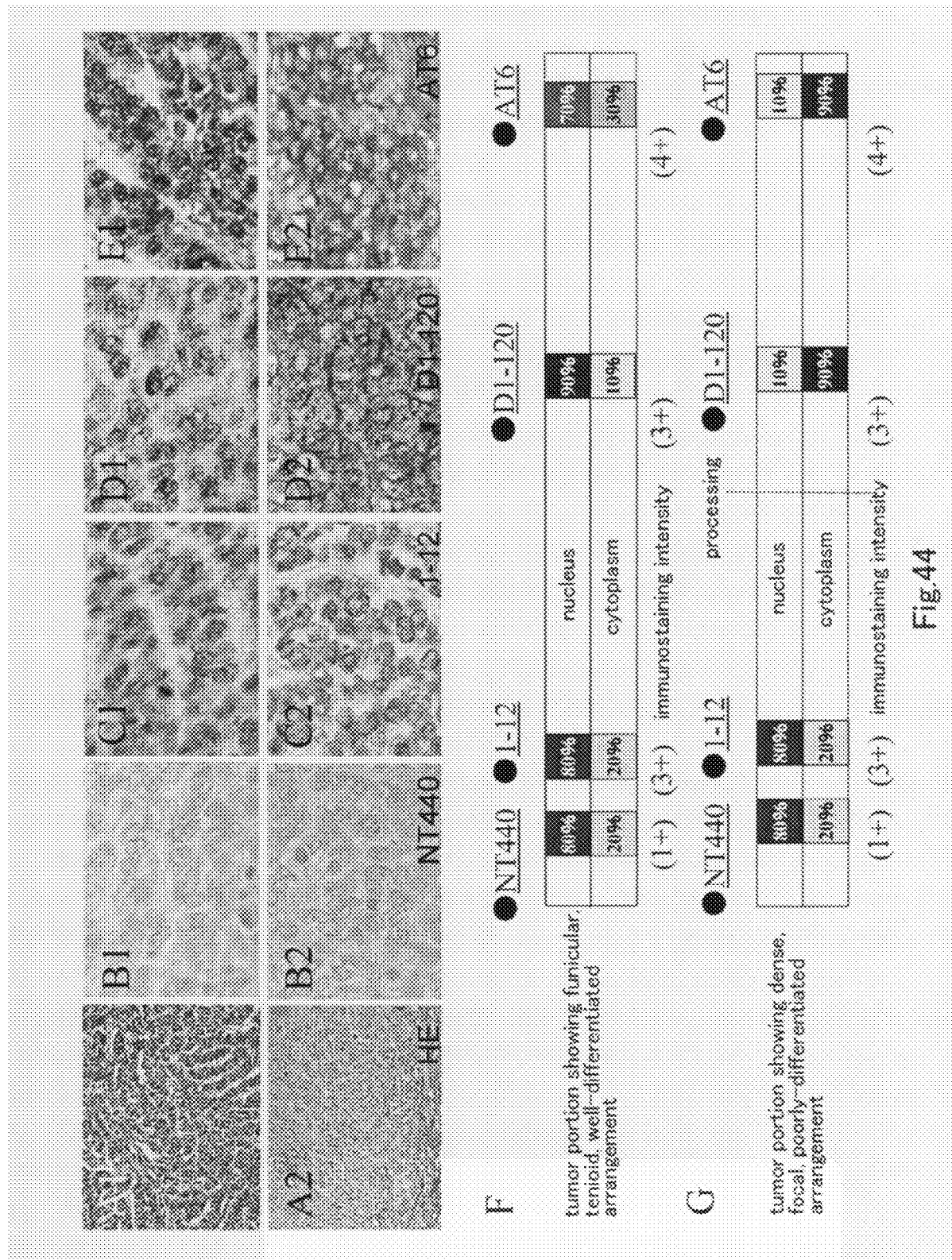
FIG. 44 shows a tissue construction of an esophagus endocrine cancer of a 52-year-old man and comparison of ATBF1 expression.

In general, from the viewpoint of tumor-pathology, it is thought that a tumor grows slowly in a morphologically well-differentiated site in the tumor. As the grade of malignancy of a tumor is increased, the growth rate of the tumor is becoming faster. The morphology of the tumor is changed mainly in a poorly-differentiated and dense site and then the tumor shows high development or distant metastasis. This time, in the judgment of grade of malignancy using ATBF1, a further well-differentiated site has a low grade of malignancy and a poorly-differentiated site has a high grade of malignancy. Therefore, it was able to be judged that the tumor included these sites. These can be interpreted that the conventional pathological observation results were confirmed by ATBF1. That is to say, it can be understood that when the D1-120 and AT6 sites of ATBF1 can be localized in the nucleus, since the tumor grows slowly and may move to the apoptosis, the structure of the tumor becomes well-differentiated; that when the protein processing occurs in the central portion of ATBF1 and the D1-120 and AT6 sites of ATBF1 are localized in the cytoplasm, since the tumor grows fast, the structure of the tumor becomes poorly-differentiated (FIGS. 44F and 44 G). From the fact that the tumor structure of the lymph duct of this case was poorly-differentiated, the tumor structure in a site of the liver metastasis may be mainly poorly-differentiated although it was not examined this time.

As mentioned above, it was judged that simultaneous use of antibodies corresponding to each part of the ATBF1 protein was useful for estimating the abnormality in protein processing peculiar to tumors and the relation with respect to the morphological characteristics and further, development form of the tumor, in addition to determining the grade of malignancy of a cancer cell.

Figure 45:
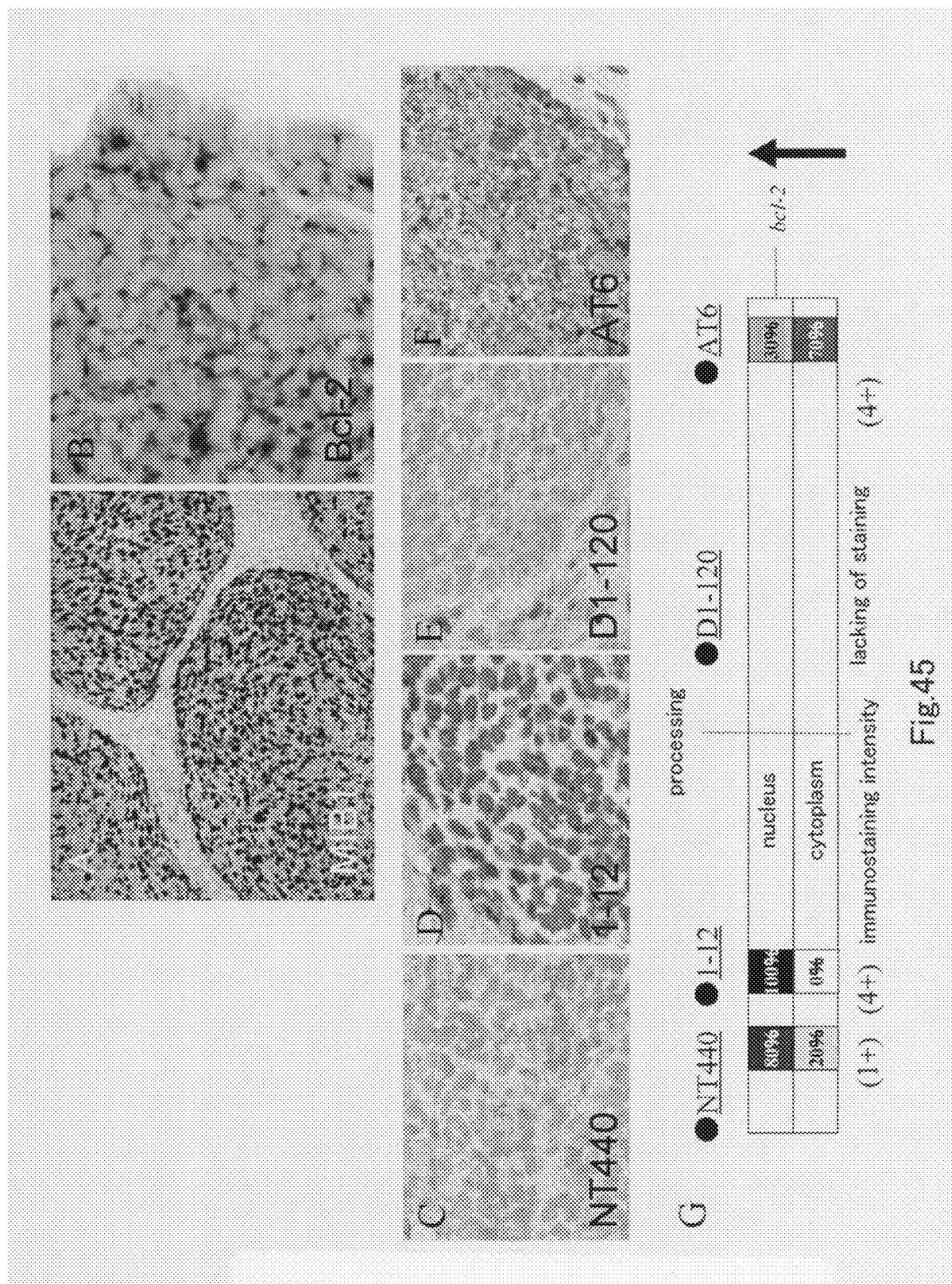
FIG. 45 shows a finding of an undifferentiated cancer of the paranasal cavity and a lymph node metastasis site of a 56-year-old man. The expression of MIB1 (A) and Bcl-2 (B) and the expression of NT440 (C), 1-12 (D), D1-120 (E) and AT6 (F) of the tumor and the staining properties thereof (G) are shown.
Figure 46:
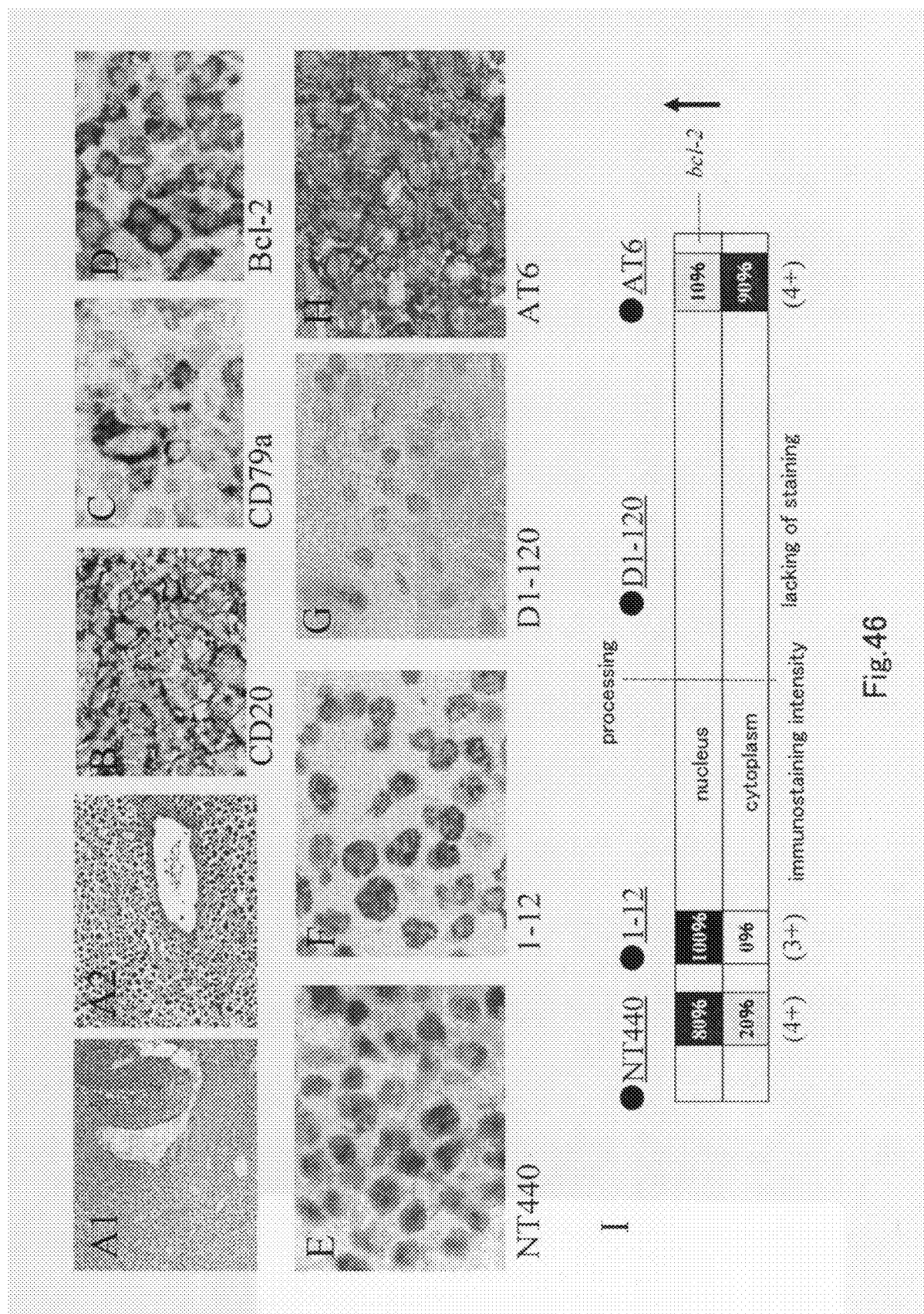
FIG. 46 shows a finding of cerebral large-cell diffuse B-cell lymphoma of a 47-year-old woman. The stained images of the tumor with HE (A1, 2), CD20 (B), CD79a (C), Bcl-2 (D), NT440 (E), I-12 (F), D1-120 (G), and AT6 (H) and summary of the staining properties of ATBF1 (I) are shown.

10-9. Investigation on Relationship Between ATBF1 Mutation Protein Production Due to the Abnormal Skipping of Exon 10 and the Localization of ATBF1 Protein in Undifferentiated Cancer in the Paranasal Cavity and Brain Large-Cell Diffuse B-Cell Lymphoma A first case is a lymph node metastasis site of an undifferentiated cancer in the paranasal cavity of a 56-year-old man. Almost all the tumor cells are labeled with MIB1 (see FIG. 45A). Extremely high expression of Bcl-2 proteins is observed and the tumor has a high grade of malignancy. A second case is a site of brain, large-cell diffuse B-cell lymphoma of a 47-year-old woman. Around the cerebral blood vessel, diffuse growth is shown (see FIG. 46A) and this case shows positive for CD20 and CD79a (see FIGS. 46B and 46C), so that it can be judged to be a B-cell malignant lymphoma. It is a tumor having a high grade of malignancy in which the expression of the Bcl-2 protein is strong (see FIG. 46D). In these two cases, staining properties of the ATBF1 (NT440, 1-12, D1-120, and AT6) were examined.

In both two cases, the staining properties of NT440 and 1-12 tended to be localized in the nucleus (see FIGS. 45C, 45D, and 46G, FIGS. 16E, 16F, and 16I). D1-120 was almost completely absent (see FIGS. 45E and 45G, FIGS. 16G and 16I). Furthermore, AT6 expression was observed mainly in the cytoplasm (see FIGS. 45F, ad 45G and FIGS. 16H and 16I).

When the grade of malignancy of a cancer was judged by using ATBF1, D1-120 was absent and AT6 was localized mainly in the cytoplasm. Therefore, it can be judged that the grade of malignancy was extremely high.

From this findings, when the protein structure or a processing site is considered, a site corresponding to the exon 3 is the nucleus, a site corresponding to the exon 10 is absent, and a site corresponding to the exon 11 is the cytoplasm. Both sides of the exon 10, the processing was carried out. Moreover, unless only the site corresponding to the exon 10 is disappeared, the explanation of the structure was thought to be difficult. However, in the non-patent document 10, when various mutations accumulated in the ATBF1 genome and the probability of abnormality of the Alternative splicing in the mRNA stage observed in the prostate cancer are investigated in details, it is possible to indicate the probability of the presence of ATBF1 protein in which exon 10 including the homeodomains 1 to 4 is skipped (see FIG. 47). That is to say, the absence of staining in the D1-120 sites (corresponding to exon 10, see FIG. 31) in various tumors the present inventors have already shown not only can indicate that the grade of malignancy of a tumor is high as shown in the two cases but also may indicate the presence of abnormal protein in which exon 10 is skipped.

Thus, the examination of the expression in the cells of ATBF1 site and the localization of the nucleus and the cytoplasm by using antibodies corresponding to exons 3, 10 and 11 are important in functionally evaluating the protein carried by corresponding ATBF1 genome regions. It was thought that as a molecular mechanism for determining the grade of malignancy, Alternative splicing or abnormality of the genome DNA structure of predicted mRNA was able to be detected in the protein level.

Figure 48:
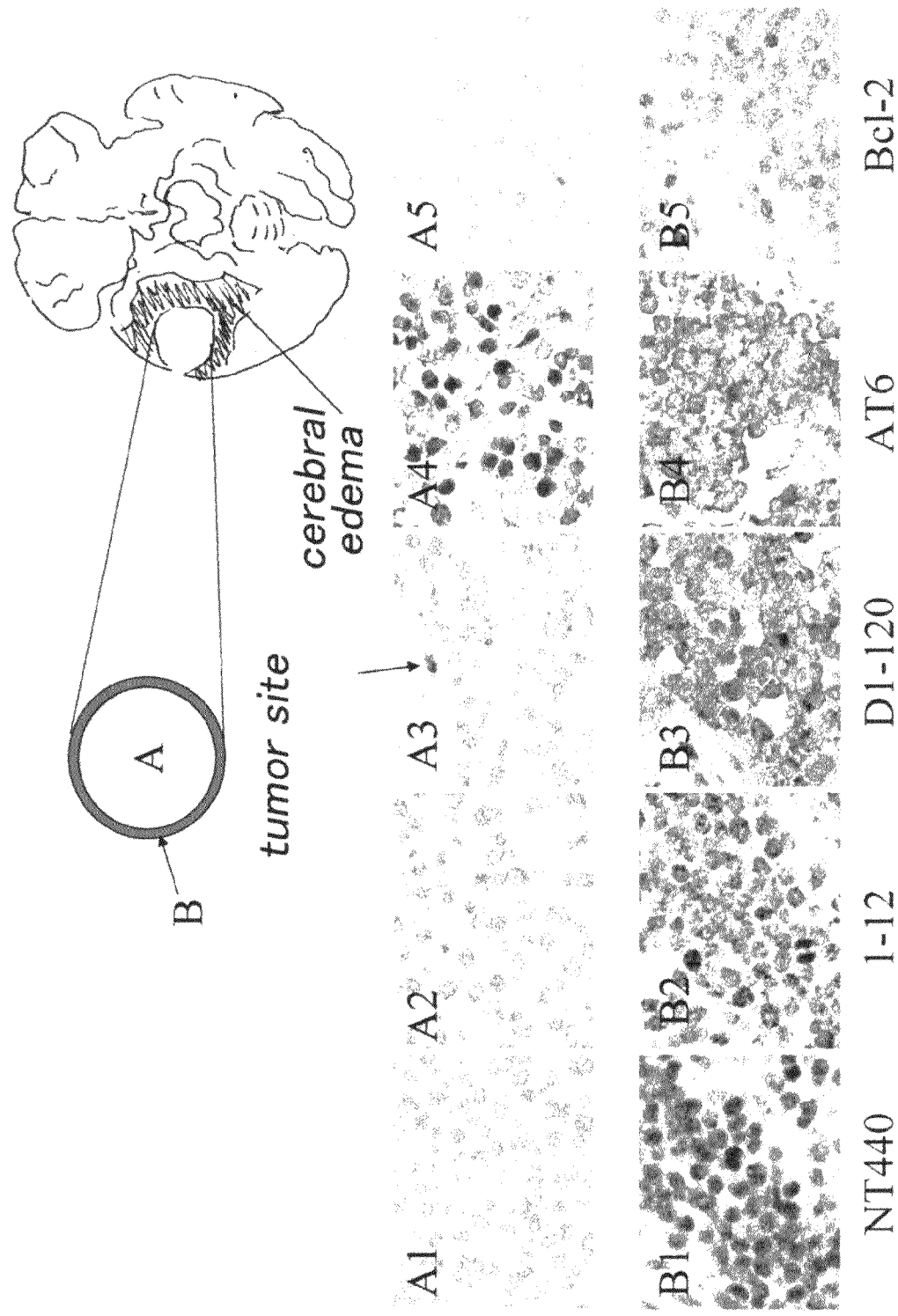
FIG. 48 shows a finding of cerebral large-cell diffuse B lymphoma of a 68-year-old woman.

10-10. Investigation on Relationship Between Change in Localization of ATBF1 Protein and Grade of Malignancy in the Same Tumor of Large-Cell Diffuse B-Lymphoma A case is a brain, large-cell diffuse B-cell lymphoma of a 68-year-old woman and is a malignant lymphoma being positive for CD20 and CD79a and showing diffuse growth. The Bcl-2 proteins were absent in most portions (site A in FIG. 48) but a small amount of expression was observed in the surrounding tumor (site B in FIG. 48). In the both sites, MIB1 label and PCNA expression were high and both are highly malignant. It was judged that the grade of malignancy of the site lacking the Bcl-2 expression was slightly lower.

Figure 49:
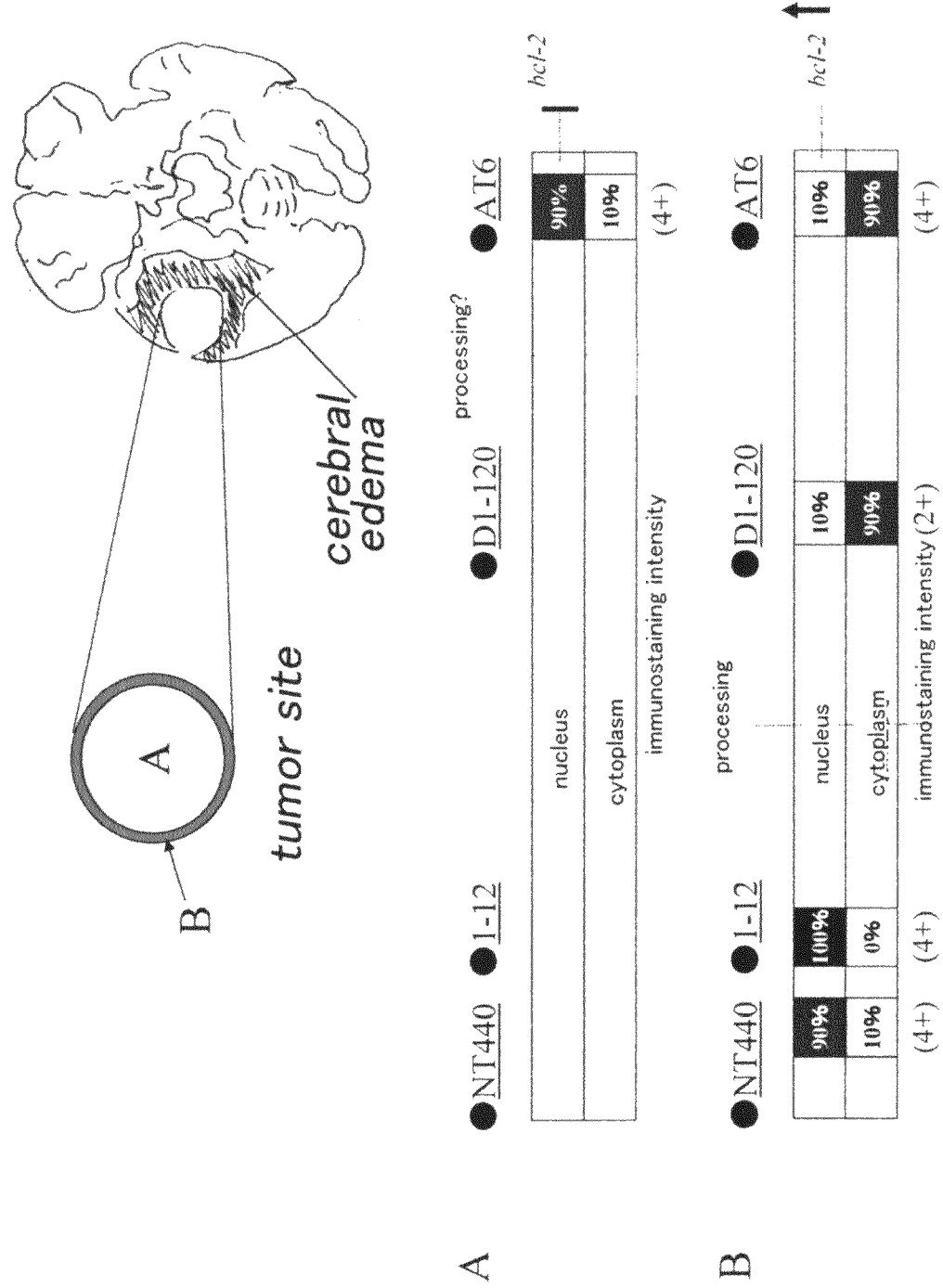
FIG. 49 summarizes a finding of ATBF1 expression of cerebral large-cell diffuse B lymphoma of a 68-year-old woman.

The ATBF1 expressions (NT440, 1-12, D1-120, and AT6) in the sites A and B were compared. In the site surrounding the tumor, NT440 and 1-12 were localized in the nucleus (see FIGS. 48B1 and 48B2 and FIG. 49B) and D1-120 and AT6 were localized in the cytoplasm (see FIGS. 48B3 and 48B4 and FIG. 49B). The fact that D1-120 is present in the cytoplasm means that this tumor has high grade of malignancy, which is not contradictory to the fact that AT6 is localized mainly in the cytoplasm and Bcl-2 expression is observed. On the other hand, in the central site of the tumor, NT440, 1-12, and D1-120 were absent (see FIGS. 48A1, A2 and A3, and FIG. A) and AT6 was localized mainly in the nucleus (see FIGS. 48A and 49A). The fact that the D1-120 is absent means that this tumor has high grade of malignancy, which is not contradictory to the fact that AT6 is localized mainly in the cytoplasm and the Bcl-2 expression is suppressed. However, staining, in which the sites corresponding to exon 3 and 10 were absent and only the site corresponding to exon 11 was localized in the nucleus, was a new pattern which the present inventors had never experienced.

The result of this examination means that, even in the same tumor, which seems to be apparently the same in the histological viewpoint, depending upon the sites, the grade of malignancy may be increased while processing of ATBF1 or localization of expression may be changed. Furthermore, various large-cell diffuse B-lymphomas presented at this time have different localization sites of ATBF1. This suggests the probability that ATBF1 may contribute to new classification of the grade of malignancy in the concepts of tumors which have been already been established.

In the pattern that only a site corresponding to the exon 11 is localized in the nucleus, a nuclear import signal is not detected in the exon 11 site in its own sequence However, since a protein interaction region with factor having other nuclear import signals such as Myb protein is reserved, the probability of moving to the nucleus in a form of a binding with some nuclear import proteins can be thought.

10-11. Conclusion

As shown in the previous report (non-patent document 6), in cultured cells of a gastric cancer, the ATBF1 functions in a form of a protein-protein binding with a tumor suppressor gene p53. It was assumed that this complex of the ATBF1 and p53 activated a promoter of the tumor suppressor gene p21 so as to increase the expression of p21 and to terminate the cell cycle, and at the same time to induce the apoptosis of cancer cells. Actually, the fact that when an alkylation agent (anti-cancer drug) is allowed to act on so as to activate a DNA modification signal, the expression of ATBF1 can be induced has been clarified [a route involved with p53 protein relating to cell cycle regulation].

As to the cell cycle arrest and movement to the apoptosis, it has been known that ATBF1 forms a protein-protein binding with oncogene protein c-myb so as to suppress the function thereof (see non-patent document 8). Furthermore, it is thought that a Myb protein family has a function of suppressing the apoptosis of cells by introducing Bcl-2 (see Grassilli, E. et al. Resistance to Apoptosis in CTLL-2 Cells Overexpressing B-Myb Is Associated with B-Myb-dependent bcl-2 Induction, CANCER RESEARCH 59, 2451-2456, 1999). Therefore, it is assumed that the suppression of the Myb protein family leads to the induction of the cell cycle arrest and apoptosis [a route involved in a RB (retinoblastoma) protein relating to regulation of the cell cycle]. Actually, as shown in the below-mentioned Example, there is an example in which the expression of Bcl-2 is suppressed in a site in which ATBF1 portion (detected by AT6) corresponding to exon 11 of ATBF1 gene is present in the nucleus in normal tissues and tumors, and the expression of Bcl-2 is activated in the above-mentioned site moves to the cytoplasm. The anti-ATBF1 antibody (AT6) recognizes, in an equistasis, the exon 11 of ATBF1 protein-protein binding with oncogene c-myb (see non-patent document 8). The result of this time histological examination suggests the probability that the movement of the ATBF1 protein to the nucleus can causes interaction with the Myb oncogene protein, so that it is involved in the suppression of bcl-2 gene.

According to the above-mentioned two previously reported studies and the examination carried out by the present inventors on the two suppression route of the cell cycle, it has been clarified that the cell cycle arrest in a cancer cell and the movement to the apoptosis are dependent upon not only the total amount of the ATBF1 expression but also the intercellular localization of functional fragment. This is a theoretical base of "a method of determining the grade of malignancy of a cancer cell" by using a plurality of antibodies to ATBF1.

Furthermore, the non-patent document 9 has clarified that various mutations are present in a gene coding for ATBF1 are present in a prostate cancer and reported that a functional disorder of the ATBF1 was one of the causes for the prostate cancer. In various cancer cells other than a prostate cancer, the 16th chromosomal aberration has been reported in many documents but the respective responsible genes involved in the canceration have not been identified. The non-patent document 9 clarifies that the ATBF1 existing in the 16th long arm plays an important role in determining the grade of malignancy of a tumor as one of the tumor suppressor genes.

<Construct of Kit for Determining Grade of Malignancy of Cancer Cell>

A kit includes a combination of reagents.
Reagent A: anti-ATBF1 antibody stock solution (D1-120)
Reagent B: ATBF1 antigen solution
Reagent C: GST antigen solution The reagent A can be obtained by adjusting the anti-ATBF1 antibody prepared in Example 2 to the concentration of 250 µg/ml. The reagent B can be obtained by adjusting a recombination peptide a recombination peptide. The recombination peptide is obtained by fusing 41 amino acid residues (2114 to 2154: LQTLPAQLPPQLGPVEPLPADLAQ-LYQHQLNPTLLQQQNKR: SEQ ID NO: 1) of mouse ATBF1, which have been adjusted when a D1-120 antibody is prepared, into GST. The reagent C can be obtained by adjusting the GST (for example, a product by Sigma) to the concentration of 2 mg/m.

Hereinafter, one example of a method of using the kit (immunohistological staining by DAB coloring) will be described.

(1) Test tissue section excised surgically or at the time of pathological anatomy is fixed in 10% formalin and embedded in paraffin by the same procedures as the usual pathological test. Specimen of an animal experiment using rat, mouse, and the like, may be subjected to paraformaldehyde fixation instead of formalin fixation. There is no particular difference in the staining pattern of ATBF1 between formalin fixation and paraformaldehyde fixation. Basically, a surgical pathological tissue material, which has been fixed in formalin right after collection, is used.

(2) Tissue embedded in paraffin is cut and sliced, followed by loading on a slide glass. As the slide glass, for example, Superfrost with MAS coated, S-9441 (Trade name, Matsunami) is used. The slide glass is excellent in durability with respect to heat treatment by using a pressure cooker.

(3) The sliced specimen is treated with usual deparaffinization system used in the usual preparation of pathological specimen and finally alcohol is replaced by purification water.

(4) During (3), two liters of citrate buffer solution is poured in a pressure cooker (a pressure cooker that can be used for general cooking can be used) and boiled with high heat. Commercially available citrate buffer solution (for example, instant citrate buffer solution [20 times concentrated solution RM-102C], pH 6.0, product by Mitsubishi Kagaku Iatron) can be used. In principle, the buffer solution that has been used for heat treatment once is not used again.

(5) The sliced specimen is put in a metallic basket, a lid of the pressure cooker is removed and the sliced specimen in the basket is put in a buffer solution in the transverse direction with the surface having the sliced specimen facing upward.

(6) The lid is put and the pressure cooker is heated with high heat until sound of steam starts to be generated. Thereafter, the heat is lowered and heating is continued for four minutes. The heating is stopped and allowed to stand for one minute.

(7) The entire pressure cooker is cooled with flowing water (tap water). After about 40 minutes have passed, the lid of the pressure cooker is removed, the specimen is taken out from the basket and substituted with purification water. Then, in order to block endogenous peroxidase, the specimen is treated with a hydrogen peroxide solution, then substituted with purification water. After the hydrogen peroxide solution is removed, the specimen is put in 20 mM Tris buffer and then substituted with 0.05M Tris buffer (pH 7.6).

(8) Tris buffer (0.05M, pH 7.6) supplemented with 1% solution of bovine serum albumin containing sodium azide is prepared. With this, reagent A is 50 times diluted (antibody solution). An antibody solution is added to the sliced specimen and allowed to be reacted with each other under humidity conditions (in a moist changer) at room temperature for one hour (primary antibody reaction). For usual specimen, about 40 µl of antibody solution is used for one reaction. For relatively large specimen, about 80 µl of antibody solution is used. By putting a tip of the pipette to the front of the preparation, the antibody solution is well introduced into the sliced specimen without bringing into contact with the sliced specimen.

(9) By using 0.05M Tris buffer (pH 7.6), the sliced specimen is washed (5 minutes, total twice). After washing, excess washing solution is wiped out.

(10) HRP labeled secondary antibody (DAKO Enivision, Labelled polymer, HRP (Code No. K1491) Anti-mouse and Anti-rabbit) is added to the sliced specimen and reacted for one hour at room temperature (secondary antibody reaction).

(11) Washing similar to (9) is carried out.

(12) Two tablets of DAB Chromogens (DAKO, Code. S3000) are dissolved in 40 ml of 0.05M Tris buffer (pH 7.6). To this, 30 µl of hydrogen peroxide solution is added and allowed to penetrate to the sliced specimen (5 minutes) and to color.

(13) DAB solution is washed with flowing water (tap water) to be removed.

(14) The sliced specimen is stained with Mayer's hematoxylin for about 15 seconds.

(15) The slice specimen is allowed to sand still in flowing water for eight minutes (washing for coloring).

(16) Similar to the usual preparation of a pathological specimen preparation, the specimen is allowed to pass through an alcohol system and a xylene system, and penetration and inclusion are carried out.

(17) The resultant specimen obtained by the above procedures was observed by using a microscope.

<Confirmation 1 of ATBF1 Specific Staining>

In order to confirm coloring (brown) by DAB is obtained by the result of ATBF1 specific immunostaining, the following operation is carried out.

(1) The reagent A (ATBF1 antibody stock solution) (10 µl), the reagent B (ATBF1 antigen) (1 µl), PBS (10 µl) and 5% BSA (4 µl) are mixed in a microtube.

(2) The entire tube (total amount: 25 µl) is rested at 37° C. for two hours.

(3) After reaction is finished, 25 µl of buffer solution (0.05M Tris buffer (pH 7.6) supplemented with 1% solution of bovine serum albumin containing sodium azide) used for diluting the antibody is added to the reacted product. The thus obtained solution (total amount: 50 µl) is used as a reagent for primary antibody reaction. Immunohistological chemical staining is carried out by the above-mentioned method. As a result, if no staining by DAB is observed, it can be confirmed that the ATBF1 specific immunostaining is carried out.

<Confirmation 2 of ATBF1 Specific Staining>

Since GST fused antigen was used for preparation, the anti-ATBF1 antibody (reagent A) may have a reaction property with respect to GST. In order to confirm that the coloring by DAB is not obtained by the result of the reaction property of the anti-ATBF1 antibody with respect to the GST, the following operation is carried out.

(1) The reagent A (ATBF1 antibody stock solution) (10 µl), the reagent C (GST) (1 µl), PBS (10 µl) and 5% BSA (4 µl) are mixed in a microtube.

(2) The entire tube (total amount: 25 µl) is rested at 37° C. for two hours.

(3) After reaction is finished, 25 µl of buffer solution (0.05M Tris buffer (pH 7.6) supplemented with 1% solution of bovine serum albumin containing sodium azide) used for diluting the antibody is added to the reacted product. The thus obtained solution (total amount: 50 µl) is used as a reagent for primary antibody reaction. Immunohistological chemical staining is carried out by the above-mentioned method. As a result, if no staining by DAB is observed, it can be confirmed that the ATBF1 specific immunostaining is carried out.

INDUSTRIAL APPLICABILITY

The present invention can be used for predicting the properties (grade of malignancy, prognosis, response to various treatment, and the like) of various cancers (including sarcoma). When the present invention is used, it is thought to be possible to indicate a tumor, which has been regarded as a benign tumor from the previous judging method although the probability of developing metastasis or recurrence is high, as, for example, middle malignant. On the contrary, it is thought that treatment focusing on the improvement of ADL (Activity of Daily Living) and QOL (Quality Of Life) of patients can be carried out to the cases in which unnecessary and excessive treatment had to be selected because a grade of malignancy of a tumor or prediction of the therapeutic effect cannot be obtained. In the future, the value of the present invention to the judgment of the grade of malignancy of neuroblastoma may be particularly important. As a means for providing an important index for determining vital prognosis and treatment policy of infant patients, it can be further predicted that the present invention would make world standard pathological criteria.

The present invention is not limited to the description of the above embodiments and Examples of the present invention. A variety of modifications, which are within the scopes of the claims and which can be easily achieved by a person skilled in the art, are included in the present invention.

All of the articles, publication of unexamined patent application, and Patent Gazette cited herein are hereby incorporated by reference.

The invention claimed is:

1. A method of determining a grade of malignancy of a test cancer cell, the method comprising the following steps:
   detecting an intranuclear amount and intracytoplasmic amount of a first region corresponding to exon 10 of an ATBF1 gene and/or a second region corresponding to exon 11 of an ATBF1 gene in the test cancer cell; and
   determining a grade of malignancy of the test cancer cell according to the following criteria: (a) the grade of malignancy is low when the first region is localized mainly in a nucleus, (b) the grade of malignancy is high when the first region is localized mainly in a cytoplasm, (c) the grade of malignancy is higher than that of (b) when the first region is absent both in the cytoplasm and in the nucleus, (d) the grade of malignancy is low when the second region is localized mainly in the nucleus, and (e) the grade of malignancy is high when the second region is localized mainly in the cytoplasm.

2. The method of determining a grade of malignancy according to claim 1, further comprising the step of:
   detecting the intranuclear amount and intracytoplasmic amount of a region corresponding to exon 3 of an ATBF1 gene.

3. The method of determining a grade of malignancy according to claim 1, wherein the detection is carried out by using an immunohistochemical staining method.

4. A method of determining a grade of malignancy of a test cancer cell, the method comprising the following steps:
   detecting an intranuclear amount and intracytoplasmic amount of a first region corresponding to exon 10 of an ATBF1 gene and/or a second region corresponding to exon 11 of an ATBF1 gene in the test cancer cell;
   detecting the intranuclear amount and intracytoplasmic amount of a third region corresponding to exon 3 of an ATBF1 gene in the test cancer cell; and
   determining a grade of malignancy of the test cancer cell wherein the grade of malignancy is high when the first region is absent both in the cytoplasm and in the nucleus.

5. The method of determining a grade of malignancy according to claim 4, wherein the detection is carried out by using an immunohistochemical staining method.

* * * * *

SEQUENCE LISTING

<160> NUMBER OF SEQ ID NOS: 27

<210> SEQ ID NO 1
<211> LENGTH: 41
<212> TYPE: PRT
<213> ORGANISM: Mus musculus

<400> SEQUENCE: 1

Leu Gln Thr Leu Pro Ala Gln Leu Pro Pro Gln Leu Gly Pro Val Glu
1               5                   10                  15

Pro Leu Pro Ala Asp Leu Ala Gln Leu Tyr Gln His Gln Leu Asn Pro
            20                  25                  30

Thr Leu Leu Gln Gln Gln Asn Lys Arg
        35                  40

<210> SEQ ID NO 2
<211> LENGTH: 3704
<212> TYPE: PRT
<213> ORGANISM: Homo sapiens

<400> SEQUENCE: 2

Met Glu Gly Cys Asp Ser Pro Val Val Ser Gly Lys Asp Asn Gly Cys
1               5                   10                  15

Gly Ile Pro Gln His Gln Gln Trp Thr Glu Leu Asn Ser Thr His Leu
            20                  25                  30

Pro Asp Lys Pro Ser Ser Met Glu Gln Ser Thr Gly Glu Ser His Gly
        35                  40                  45

Pro Leu Asp Ser Leu Arg Ala Pro Phe Asn Glu Arg Leu Ala Glu Ser
    50                  55                  60

Thr Ala Ser Ala Gly Pro Pro Ala Glu Pro Ala Ser Lys Glu Val Thr
65                  70                  75                  80

Cys Asn Glu Cys Ser Ala Ser Phe Ala Ser Leu Gln Thr Tyr Met Glu
                85                  90                  95

His His Cys Pro Ser Ala Arg Pro Pro Pro Leu Arg Glu Glu Ser
            100                 105                 110

Ala Ser Asp Thr Gly Glu Glu Gly Asp Glu Glu Ser Asp Val Glu Asn
        115                 120                 125

Leu Ala Gly Glu Ile Val Tyr Gln Pro Asp Gly Ser Ala Tyr Ile Val
    130                 135                 140

Glu Ser Leu Ser Gln Leu Thr Gln Gly Gly Gly Ala Cys Gly Ser Gly
145                 150                 155                 160

Ser Gly Ser Gly Pro Leu Pro Ser Leu Phe Leu Asn Ser Leu Pro Gly
                165                 170                 175

Ala Gly Gly Lys Gln Gly Asp Pro Ser Cys Ala Ala Pro Val Tyr Pro
            180                 185                 190

Gln Ile Ile Asn Thr Phe His Ile Ala Ser Ser Phe Gly Lys Trp Phe
        195                 200                 205

Glu Gly Pro Asp Gln Ala Phe Pro Asn Thr Ser Ala Leu Ala Gly Leu
    210                 215                 220

Ser Pro Val Leu His Ser Phe Arg Val Phe Asp Val Arg His Lys Ser
225                 230                 235                 240

Asn Lys Asp Tyr Leu Asn Ser Asp Gly Ser Ala Lys Ser Ser Cys Val
                245                 250                 255

Ser Lys Asp Val Pro Asn Asn Val Asp Leu Ser Lys Phe Asp Gly Phe
            260                 265                 270

```
Val Leu Tyr Gly Lys Arg Lys Pro Ile Leu Met Cys Phe Leu Cys Lys
            275                 280                 285

Leu Ser Phe Gly Tyr Val Arg Ser Phe Val Thr His Ala Val His Asp
        290                 295                 300

His Arg Met Thr Leu Ser Glu Asp Glu Arg Lys Ile Leu Ser Asn Lys
305                 310                 315                 320

Asn Ile Ser Ala Ile Ile Gln Gly Ile Gly Lys Asp Lys Glu Pro Leu
                325                 330                 335

Val Ser Phe Leu Glu Pro Lys Asn Lys Asn Phe Gln His Pro Leu Val
            340                 345                 350

Ser Thr Ala Asn Leu Ile Gly Pro Gly His Ser Phe Tyr Gly Lys Phe
        355                 360                 365

Ser Gly Ile Arg Met Glu Gly Glu Ala Leu Pro Ala Gly Ser Ala
    370                 375                 380

Ala Gly Pro Glu Gln Pro Gln Ala Gly Leu Leu Thr Pro Ser Thr Leu
385                 390                 395                 400

Leu Asn Leu Gly Gly Leu Thr Ser Ser Val Leu Lys Thr Pro Ile Thr
                405                 410                 415

Ser Val Pro Leu Gly Ala Leu Ala Ser Ser Pro Thr Lys Ser Ser Glu
            420                 425                 430

Gly Lys Asp Ser Gly Ala Ala Glu Gly Glu Lys Gln Glu Val Gly Asp
        435                 440                 445

Gly Asp Cys Phe Ser Glu Lys Val Glu Pro Ala Glu Glu Ala Glu
    450                 455                 460

Glu Glu Glu Glu Glu Glu Glu Ala Glu Glu Glu Glu Glu Glu Glu
465                 470                 475                 480

Glu Glu Glu Glu Glu Glu Asp Glu Gly Cys Lys Gly Leu Phe Pro
                485                 490                 495

Ser Glu Leu Asp Glu Glu Leu Glu Asp Arg Pro His Glu Glu Pro Gly
    500                 505                 510

Ala Ala Ala Gly Ser Ser Ser Lys Lys Asp Leu Ala Leu Ser Asn Gln
        515                 520                 525

Ser Ile Ser Asn Ser Pro Leu Met Pro Asn Val Leu Gln Thr Leu Ser
    530                 535                 540

Arg Gly Thr Ala Ser Thr Ser Ser Asn Ser Ala Ser Ser Phe Val Val
545                 550                 555                 560

Phe Asp Gly Ala Asn Arg Arg Asn Arg Leu Ser Phe Asn Ser Glu Gly
                565                 570                 575

Val Arg Thr Asn Val Ala Glu Gly Gly Arg Arg Leu Asp Phe Ala Asp
            580                 585                 590

Glu Ser Ala Asn Lys Asp Asn Ala Thr Ala Pro Glu Pro Asn Glu Ser
        595                 600                 605

Thr Glu Gly Asp Asp Gly Gly Phe Val Pro His His Gln His Ala Gly
    610                 615                 620

Ser Leu Cys Glu Leu Gly Val Gly Glu Cys Pro Ser Gly Ser Gly Val
625                 630                 635                 640

Glu Cys Pro Lys Cys Asp Thr Val Leu Gly Ser Ser Arg Ser Leu Gly
                645                 650                 655

Gly His Met Thr Met Met His Ser Arg Asn Ser Cys Lys Thr Leu Lys
            660                 665                 670

Cys Pro Lys Cys Asn Trp His Tyr Lys Tyr Gln Gln Thr Leu Glu Ala
        675                 680                 685
```

```
His Met Lys Glu Lys His Pro Glu Pro Gly Gly Ser Cys Val Tyr Cys
    690             695                 700

Lys Ser Gly Gln Pro His Pro Arg Leu Ala Arg Gly Glu Ser Tyr Thr
705             710                 715                 720

Cys Gly Tyr Lys Pro Phe Arg Cys Glu Val Cys Asn Tyr Ser Thr Thr
                725                 730                 735

Thr Lys Gly Asn Leu Ser Ile His Met Gln Ser Asp Lys His Leu Asn
        740                 745                 750

Asn Met Gln Asn Leu Gln Asn Gly Gly Gly Glu Gln Val Phe Ile His
        755                 760                 765

Thr Ala Gly Ala Ala Ala Ala Ala Ala Ala Ala Ala Ala Ala Ala Ala
    770                 775                 780

Asn Ile Ser Ser Ser Cys Gly Ala Pro Ser Pro Thr Lys Pro Lys Thr
785                 790                 795                 800

Lys Pro Thr Trp Arg Cys Glu Val Cys Asp Tyr Glu Thr Asn Val Ala
                805                 810                 815

Arg Asn Leu Arg Ile His Met Thr Ser Glu Lys His Met His Asn Met
                820                 825                 830

Met Leu Leu Gln Gln Asn Met Thr Gln Ile Gln His Asn His His Arg
        835                 840                 845

Val Leu Gly Ser Leu Pro Ser Pro Ala Glu Ala Glu Leu Tyr Gln Tyr
    850                 855                 860

Tyr Leu Ala Gln Asn Met Asn Leu Pro Asn Leu Lys Met Asp Ser Ala
865                 870                 875                 880

Ala Ser Asp Ala Gln Phe Met Met Ser Gly Phe Gln Leu Asp Pro Ala
                885                 890                 895

Gly Pro Met Ala Ala Met Thr Pro Ala Leu Val Gly Gly Glu Ile Pro
            900                 905                 910

Leu Asp Met Arg Leu Gly Gly Gly Gln Leu Val Ser Glu Leu Met
            915                 920                 925

Asn Leu Gly Glu Ser Phe Ile Gln Thr Asn Asp Pro Ser Leu Lys Leu
930                 935                 940

Phe Gln Cys Ala Val Cys Asn Lys Phe Thr Thr Asp Asn Leu Asp Met
945                 950                 955                 960

Leu Gly Leu His Met Asn Val Glu Arg Ser Leu Ser Glu Asp Glu Trp
                965                 970                 975

Lys Ala Val Met Gly Asp Ser Tyr Gln Cys Lys Leu Cys Arg Tyr Asn
                980                 985                 990

Thr Gln Leu Lys Ala Asn Phe Gln Leu His Cys Lys Thr Asp Lys His
        995                 1000                1005

Val Gln Lys Tyr Gln Leu Val Ala His Ile Lys Glu Gly Gly Lys
    1010                1015                1020

Ala Asn Glu Trp Arg Leu Lys Cys Val Ala Ile Gly Asn Pro Val
    1025                1030                1035

His Leu Lys Cys Asn Ala Cys Asp Tyr Tyr Thr Asn Ser Leu Glu
    1040                1045                1050

Lys Leu Arg Leu His Thr Val Asn Ser Arg His Glu Ala Ser Leu
    1055                1060                1065

Lys Leu Tyr Lys His Leu Gln Gln His Glu Ser Gly Val Glu Gly
    1070                1075                1080

Glu Ser Cys Tyr Tyr His Cys Val Leu Cys Asn Tyr Ser Thr Lys
    1085                1090                1095

Ala Lys Leu Asn Leu Ile Gln His Val Arg Ser Met Lys His Gln
```

-continued

```
            1100                1105                1110
Arg Ser Glu Ser Leu Arg Lys Leu Gln Arg Leu Gln Lys Gly Leu
    1115                1120                1125
Pro Glu Glu Asp Glu Asp Leu Gly Gln Ile Phe Thr Ile Arg Arg
    1130                1135                1140
Cys Pro Ser Thr Asp Pro Glu Glu Ala Ile Glu Asp Val Glu Gly
    1145                1150                1155
Pro Ser Glu Thr Ala Ala Asp Pro Glu Glu Leu Ala Lys Asp Gln
    1160                1165                1170
Glu Gly Gly Ala Ser Ser Gln Ala Glu Lys Glu Leu Thr Asp
    1175                1180                1185
Ser Pro Ala Thr Ser Lys Arg Ile Ser Phe Pro Gly Ser Ser Glu
    1190                1195                1200
Ser Pro Leu Ser Ser Lys Arg Pro Lys Thr Ala Glu Glu Ile Lys
    1205                1210                1215
Pro Glu Gln Met Tyr Gln Cys Pro Tyr Cys Lys Tyr Ser Asn Ala
    1220                1225                1230
Asp Val Asn Arg Leu Arg Val His Ala Met Thr Gln His Ser Val
    1235                1240                1245
Gln Pro Met Leu Arg Cys Pro Leu Cys Gln Asp Met Leu Asn Asn
    1250                1255                1260
Lys Ile His Leu Gln Leu His Leu Thr His Leu His Ser Val Ala
    1265                1270                1275
Pro Asp Cys Val Glu Lys Leu Ile Met Thr Val Thr Thr Pro Glu
    1280                1285                1290
Met Val Met Pro Ser Ser Met Phe Leu Pro Ala Ala Val Pro Asp
    1295                1300                1305
Arg Asp Gly Asn Ser Asn Leu Glu Glu Ala Gly Lys Gln Pro Glu
    1310                1315                1320
Thr Ser Glu Asp Leu Gly Lys Asn Ile Leu Pro Ser Ala Ser Thr
    1325                1330                1335
Glu Gln Ser Gly Asp Leu Lys Pro Ser Pro Ala Asp Pro Gly Ser
    1340                1345                1350
Val Arg Glu Asp Ser Gly Phe Ile Cys Trp Lys Lys Gly Cys Asn
    1355                1360                1365
Gln Val Phe Lys Thr Ser Ala Ala Leu Gln Thr His Phe Asn Glu
    1370                1375                1380
Val His Ala Lys Arg Pro Gln Leu Pro Val Ser Asp Arg His Val
    1385                1390                1395
Tyr Lys Tyr Arg Cys Asn Gln Cys Ser Leu Ala Phe Lys Thr Ile
    1400                1405                1410
Glu Lys Leu Gln Leu His Ser Gln Tyr His Val Ile Arg Ala Ala
    1415                1420                1425
Thr Met Cys Cys Leu Cys Gln Arg Ser Phe Arg Thr Phe Gln Ala
    1430                1435                1440
Leu Lys Lys His Leu Glu Thr Ser His Leu Glu Leu Ser Glu Ala
    1445                1450                1455
Asp Ile Gln Gln Leu Tyr Gly Gly Leu Leu Ala Asn Gly Asp Leu
    1460                1465                1470
Leu Ala Met Gly Asp Pro Thr Leu Ala Glu Asp His Thr Ile Ile
    1475                1480                1485
Val Glu Glu Asp Lys Glu Glu Ser Asp Leu Glu Asp Lys Gln
    1490                1495                1500
```

-continued

```
Ser Pro Thr Gly Ser Asp Ser Gly Ser Val Gln Glu Asp Ser Gly
    1505                1510                1515
Ser Glu Pro Lys Arg Ala Leu Pro Phe Arg Lys Gly Pro Asn Phe
    1520                1525                1530
Thr Met Glu Lys Phe Leu Asp Pro Ser Arg Pro Tyr Lys Cys Thr
    1535                1540                1545
Val Cys Lys Glu Ser Phe Thr Gln Lys Asn Ile Leu Leu Val His
    1550                1555                1560
Tyr Asn Ser Val Ser His Leu His Lys Leu Lys Arg Ala Leu Gln
    1565                1570                1575
Glu Ser Ala Thr Gly Gln Pro Glu Pro Thr Ser Ser Pro Asp Asn
    1580                1585                1590
Lys Pro Phe Lys Cys Asn Thr Cys Asn Val Ala Tyr Ser Gln Ser
    1595                1600                1605
Ser Thr Leu Glu Ile His Met Arg Ser Val Leu His Gln Thr Lys
    1610                1615                1620
Ala Arg Ala Ala Lys Leu Glu Ala Ala Ser Gly Ser Ser Asn Gly
    1625                1630                1635
Thr Gly Asn Ser Ser Ser Ile Ser Leu Ser Ser Ser Thr Pro Ser
    1640                1645                1650
Pro Val Ser Thr Ser Gly Ser Asn Thr Phe Thr Thr Ser Asn Pro
    1655                1660                1665
Ser Ser Ala Gly Ile Ala Pro Ser Ser Asn Leu Leu Ser Gln Val
    1670                1675                1680
Pro Thr Glu Ser Val Gly Met Pro Pro Leu Gly Asn Pro Ile Gly
    1685                1690                1695
Ala Asn Ile Ala Ser Pro Ser Glu Pro Lys Glu Ala Asn Arg Lys
    1700                1705                1710
Lys Leu Ala Asp Met Ile Ala Ser Arg Gln Gln Gln Gln Gln Gln
    1715                1720                1725
Gln Gln Gln Gln Gln Gln Gln Gln Gln Gln Gln Gln Ala Gln
    1730                1735                1740
Thr Leu Ala Gln Ala Gln Ala Gln Val Gln Ala His Leu Gln Gln
    1745                1750                1755
Glu Leu Gln Gln Gln Ala Ala Leu Ile Gln Ser Gln Leu Phe Asn
    1760                1765                1770
Pro Thr Leu Leu Pro His Phe Pro Met Thr Thr Glu Thr Leu Leu
    1775                1780                1785
Gln Leu Gln Gln Gln Gln His Leu Leu Phe Pro Phe Tyr Ile Pro
    1790                1795                1800
Ser Ala Glu Phe Gln Leu Asn Pro Glu Val Ser Leu Pro Val Thr
    1805                1810                1815
Ser Gly Ala Leu Thr Leu Thr Gly Thr Gly Pro Gly Leu Leu Glu
    1820                1825                1830
Asp Leu Lys Ala Gln Val Gln Val Pro Gln Gln Ser His Gln Gln
    1835                1840                1845
Ile Leu Pro Gln Gln Gln Gln Asn Gln Leu Ser Ile Ala Gln Ser
    1850                1855                1860
His Ser Ala Leu Leu Gln Pro Ser Gln His Pro Glu Lys Lys Asn
    1865                1870                1875
Lys Leu Val Ile Lys Glu Lys Glu Lys Glu Ser Gln Arg Glu Arg
    1880                1885                1890
```

-continued

```
Asp Ser Ala Glu Gly Gly Glu Gly Asn Thr Gly Pro Lys Glu Thr
    1895                1900                1905

Leu Pro Asp Ala Leu Lys Ala Lys Glu Lys Lys Glu Leu Ala Pro
    1910                1915                1920

Gly Gly Gly Ser Glu Pro Ser Met Leu Pro Pro Arg Ile Ala Ser
    1925                1930                1935

Asp Ala Arg Gly Asn Ala Thr Lys Ala Leu Leu Glu Asn Phe Gly
    1940                1945                1950

Phe Glu Leu Val Ile Gln Tyr Asn Glu Asn Lys Gln Lys Val Gln
    1955                1960                1965

Lys Lys Asn Gly Lys Thr Asp Gln Gly Glu Asn Leu Glu Lys Leu
    1970                1975                1980

Glu Cys Asp Ser Cys Gly Lys Leu Phe Ser Asn Ile Leu Ile Leu
    1985                1990                1995

Lys Ser His Gln Glu His Val His Gln Asn Tyr Phe Pro Phe Lys
    2000                2005                2010

Gln Leu Glu Arg Phe Ala Lys Gln Tyr Arg Asp His Tyr Asp Lys
    2015                2020                2025

Leu Tyr Pro Leu Arg Pro Gln Thr Pro Glu Pro Pro Pro Pro Pro
    2030                2035                2040

Pro Pro Pro Pro Pro Pro Leu Pro Ala Ala Pro Pro Gln Pro
    2045                2050                2055

Ala Ser Thr Pro Ala Ile Pro Ala Ser Ala Pro Ile Thr Ser
    2060                2065                2070

Pro Thr Ile Ala Pro Ala Gln Pro Ser Val Pro Leu Thr Gln Leu
    2075                2080                2085

Ser Met Pro Met Glu Leu Pro Ile Phe Ser Pro Leu Met Met Gln
    2090                2095                2100

Thr Met Pro Leu Gln Thr Leu Pro Ala Gln Leu Pro Pro Gln Leu
    2105                2110                2115

Gly Pro Val Glu Pro Leu Pro Ala Asp Leu Ala Gln Leu Tyr Gln
    2120                2125                2130

His Gln Leu Asn Pro Thr Leu Leu Gln Gln Gln Asn Lys Arg Pro
    2135                2140                2145

Arg Thr Arg Ile Thr Asp Asp Gln Leu Arg Val Leu Arg Gln Tyr
    2150                2155                2160

Phe Asp Ile Asn Asn Ser Pro Ser Glu Glu Gln Ile Lys Glu Met
    2165                2170                2175

Ala Asp Lys Ser Gly Leu Pro Gln Lys Val Ile Lys His Trp Phe
    2180                2185                2190

Arg Asn Thr Leu Phe Lys Glu Arg Gln Arg Asn Lys Asp Ser Pro
    2195                2200                2205

Tyr Asn Phe Ser Asn Pro Pro Ile Thr Ser Leu Glu Glu Leu Lys
    2210                2215                2220

Ile Asp Ser Arg Pro Pro Ser Pro Glu Pro Pro Lys Gln Glu Tyr
    2225                2230                2235

Trp Gly Ser Lys Arg Ser Ser Arg Thr Arg Phe Thr Asp Tyr Gln
    2240                2245                2250

Leu Arg Val Leu Gln Asp Phe Phe Asp Ala Asn Ala Tyr Pro Lys
    2255                2260                2265

Asp Asp Glu Phe Glu Gln Leu Ser Asn Leu Leu Asn Leu Pro Thr
    2270                2275                2280

Arg Val Ile Val Val Trp Phe Gln Asn Ala Arg Gln Lys Ala Arg
```

-continued

```
            2285                2290                2295
Lys Asn Tyr Glu Asn Gln Gly Glu Gly Lys Asp Gly Glu Arg Arg
    2300                2305                2310
Glu Leu Thr Asn Asp Arg Tyr Ile Arg Thr Ser Asn Leu Asn Tyr
    2315                2320                2325
Gln Cys Lys Lys Cys Ser Leu Val Phe Gln Arg Ile Phe Asp Leu
    2330                2335                2340
Ile Lys His Gln Lys Lys Leu Cys Tyr Lys Asp Glu Asp Glu Glu
    2345                2350                2355
Gly Gln Asp Asp Ser Gln Asn Glu Asp Ser Met Asp Ala Met Glu
    2360                2365                2370
Ile Leu Thr Pro Thr Ser Ser Ser Cys Ser Thr Pro Met Pro Ser
    2375                2380                2385
Gln Ala Tyr Ser Ala Pro Ala Pro Ser Ala Asn Asn Thr Ala Ser
    2390                2395                2400
Ser Ala Phe Leu Gln Leu Thr Ala Glu Ala Glu Glu Leu Ala Thr
    2405                2410                2415
Phe Asn Ser Lys Thr Glu Ala Gly Asp Glu Lys Pro Lys Leu Ala
    2420                2425                2430
Glu Ala Pro Ser Ala Gln Pro Asn Gln Thr Gln Glu Lys Gln Gly
    2435                2440                2445
Gln Pro Lys Pro Glu Leu Gln Gln Gln Glu Pro Glu Gln Lys
    2450                2455                2460
Thr Asn Thr Pro Gln Gln Lys Leu Pro Gln Leu Val Ser Leu Pro
    2465                2470                2475
Ser Leu Pro Gln Pro Pro Gln Ala Pro Pro Gln Cys Pro
    2480                2485                2490
Leu Pro Gln Ser Ser Pro Ser Pro Ser Gln Leu Ser His Leu Pro
    2495                2500                2505
Leu Lys Pro Leu His Thr Ser Thr Pro Gln Leu Ala Asn Leu
    2510                2515                2520
Pro Pro Gln Leu Ile Pro Tyr Gln Cys Asp Gln Cys Lys Leu Ala
    2525                2530                2535
Phe Pro Ser Phe Glu His Trp Gln Glu His Gln Leu His Phe
    2540                2545                2550
Leu Ser Ala Gln Asn Gln Phe Ile His Pro Gln Phe Leu Asp Arg
    2555                2560                2565
Ser Leu Asp Met Pro Phe Met Leu Phe Asp Pro Ser Asn Pro Leu
    2570                2575                2580
Leu Ala Ser Gln Leu Leu Ser Gly Ala Ile Pro Gln Ile Pro Ala
    2585                2590                2595
Ser Ser Ala Thr Ser Pro Thr Pro Thr Ser Thr Met Asn Thr
    2600                2605                2610
Leu Lys Arg Lys Leu Glu Glu Lys Ala Ser Ala Ser Pro Gly Glu
    2615                2620                2625
Asn Asp Ser Gly Thr Gly Gly Glu Glu Pro Gln Arg Asp Lys Arg
    2630                2635                2640
Leu Arg Thr Thr Ile Thr Pro Glu Gln Leu Glu Ile Leu Tyr Gln
    2645                2650                2655
Lys Tyr Leu Leu Asp Ser Asn Pro Thr Arg Lys Met Leu Asp His
    2660                2665                2670
Ile Ala His Glu Val Gly Leu Lys Lys Arg Val Val Gln Val Trp
    2675                2680                2685
```

```
Phe Gln Asn Thr Arg Ala Arg Glu Arg Lys Gly Gln Phe Arg Ala
2690                2695                2700

Val Gly Pro Ala Gln Ala His Arg Arg Cys Pro Phe Cys Arg Ala
2705                2710                2715

Leu Phe Lys Ala Lys Thr Ala Leu Glu Ala His Ile Arg Ser Arg
2720                2725                2730

His Trp His Glu Ala Lys Arg Ala Gly Tyr Asn Leu Thr Leu Ser
2735                2740                2745

Ala Met Leu Leu Asp Cys Asp Gly Gly Leu Gln Met Lys Gly Asp
2750                2755                2760

Ile Phe Asp Gly Thr Ser Phe Ser His Leu Pro Pro Ser Ser Ser
2765                2770                2775

Asp Gly Gln Gly Val Pro Leu Ser Pro Val Ser Lys Thr Met Glu
2780                2785                2790

Leu Ser Pro Arg Thr Leu Leu Ser Pro Ser Ser Ile Lys Val Glu
2795                2800                2805

Gly Ile Glu Asp Phe Glu Ser Pro Ser Met Ser Ser Val Asn Leu
2810                2815                2820

Asn Phe Asp Gln Thr Lys Leu Asp Asn Asp Asp Cys Ser Ser Val
2825                2830                2835

Asn Thr Ala Ile Thr Asp Thr Thr Thr Gly Asp Glu Gly Asn Ala
2840                2845                2850

Asp Asn Asp Ser Ala Thr Gly Ile Ala Thr Glu Thr Lys Ser Ser
2855                2860                2865

Ser Ala Pro Asn Glu Gly Leu Thr Lys Ala Ala Met Met Ala Met
2870                2875                2880

Ser Glu Tyr Glu Asp Arg Leu Ser Ser Gly Leu Val Ser Pro Ala
2885                2890                2895

Pro Ser Phe Tyr Ser Lys Glu Tyr Asp Asn Glu Gly Thr Val Asp
2900                2905                2910

Tyr Ser Glu Thr Ser Ser Leu Ala Asp Pro Cys Ser Pro Ser Pro
2915                2920                2925

Gly Ala Ser Gly Ser Ala Gly Lys Ser Gly Asp Ser Gly Asp Arg
2930                2935                2940

Pro Gly Gln Lys Arg Phe Arg Thr Gln Met Thr Asn Leu Gln Leu
2945                2950                2955

Lys Val Leu Lys Ser Cys Phe Asn Asp Tyr Arg Thr Pro Thr Met
2960                2965                2970

Leu Glu Cys Glu Val Leu Gly Asn Asp Ile Gly Leu Pro Lys Arg
2975                2980                2985

Val Val Gln Val Trp Phe Gln Asn Ala Arg Ala Lys Glu Lys Lys
2990                2995                3000

Ser Lys Leu Ser Met Ala Lys His Phe Gly Ile Asn Gln Thr Ser
3005                3010                3015

Tyr Glu Gly Pro Lys Thr Glu Cys Thr Leu Cys Gly Ile Lys Tyr
3020                3025                3030

Ser Ala Arg Leu Ser Val Arg Asp His Ile Phe Ser Gln Gln His
3035                3040                3045

Ile Ser Lys Val Lys Asp Thr Ile Gly Ser Gln Leu Asp Lys Glu
3050                3055                3060

Lys Glu Tyr Phe Asp Pro Ala Thr Val Arg Gln Leu Met Ala Gln
3065                3070                3075
```

-continued

```
Gln Glu Leu Asp Arg Ile Lys Lys Ala Asn Glu Val Leu Gly Leu
    3080                3085                3090

Ala Ala Gln Gln Gln Gly Met Phe Asp Asn Thr Pro Leu Gln Ala
    3095                3100                3105

Leu Asn Leu Pro Thr Ala Tyr Pro Ala Leu Gln Gly Ile Pro Pro
    3110                3115                3120

Val Leu Leu Pro Gly Leu Asn Ser Pro Ser Leu Pro Gly Phe Thr
    3125                3130                3135

Pro Ser Asn Thr Ala Leu Thr Ser Pro Lys Pro Asn Leu Met Gly
    3140                3145                3150

Leu Pro Ser Thr Thr Val Pro Ser Pro Gly Leu Pro Thr Ser Gly
    3155                3160                3165

Leu Pro Asn Lys Pro Ser Ser Ala Ser Leu Ser Ser Pro Thr Pro
    3170                3175                3180

Ala Gln Ala Thr Met Ala Met Gly Pro Gln Gln Pro Pro Gln Gln
    3185                3190                3195

Gln Gln Gln Gln Gln Gln Pro Gln Val Gln Gln Pro Pro Pro Pro
    3200                3205                3210

Pro Ala Ala Gln Pro Pro Thr Pro Gln Leu Pro Leu Gln Gln
    3215                3220                3225

Gln Gln Gln Arg Lys Asp Lys Asp Ser Glu Lys Val Lys Glu Lys
    3230                3235                3240

Glu Lys Ala His Lys Gly Lys Gly Glu Pro Leu Pro Val Pro Lys
    3245                3250                3255

Lys Glu Lys Gly Glu Ala Pro Thr Ala Thr Ala Ala Thr Ile Ser
    3260                3265                3270

Ala Pro Leu Pro Thr Met Glu Tyr Ala Val Asp Pro Ala Gln Leu
    3275                3280                3285

Gln Ala Leu Gln Ala Ala Leu Thr Ser Asp Pro Thr Ala Leu Leu
    3290                3295                3300

Thr Ser Gln Phe Leu Pro Tyr Phe Val Pro Gly Phe Ser Pro Tyr
    3305                3310                3315

Tyr Ala Pro Gln Ile Pro Gly Ala Leu Gln Ser Gly Tyr Leu Gln
    3320                3325                3330

Pro Met Tyr Gly Met Glu Gly Leu Phe Pro Tyr Ser Pro Ala Leu
    3335                3340                3345

Ser Gln Ala Leu Met Gly Leu Ser Pro Gly Ser Leu Leu Gln Gln
    3350                3355                3360

Tyr Gln Gln Tyr Gln Gln Ser Leu Gln Glu Ala Ile Gln Gln Gln
    3365                3370                3375

Gln Gln Arg Gln Leu Gln Gln Gln Gln Gln Gln Lys Val Gln Gln
    3380                3385                3390

Gln Gln Pro Lys Ala Ser Gln Thr Pro Val Pro Pro Gly Ala Pro
    3395                3400                3405

Ser Pro Asp Lys Asp Pro Ala Lys Glu Ser Pro Lys Pro Glu Glu
    3410                3415                3420

Gln Lys Asn Thr Pro Arg Glu Val Ser Pro Leu Leu Pro Lys Leu
    3425                3430                3435

Pro Glu Glu Pro Glu Ala Glu Ser Lys Ser Ala Asp Ser Leu Tyr
    3440                3445                3450

Asp Pro Phe Ile Val Pro Lys Val Gln Tyr Lys Leu Val Cys Arg
    3455                3460                3465

Lys Cys Gln Ala Gly Phe Ser Asp Glu Glu Ala Ala Arg Ser His
```

-continued

| | 3470 | | | | 3475 | | | | 3480 | | |
|---|---|---|---|---|---|---|---|---|---|---|---|
| Leu | Lys | Ser | Leu | Cys | Phe | Phe | Gly | Gln | Ser | Val | Val | Asn | Leu | Gln |
| | | 3485 | | | | 3490 | | | | 3495 | |

Glu Met Val Leu His Val Pro Thr Gly Gly Gly Gly Gly Ser
  3500              3505              3510

Gly Gly Gly Gly Gly Gly Gly Gly Gly Gly Gly Gly Gly Ser
  3515              3520              3525

Tyr His Cys Leu Ala Cys Glu Ser Ala Leu Cys Gly Glu Ala
  3530              3535              3540

Leu Ser Gln His Leu Glu Ser Ala Leu His Lys His Arg Thr Ile
  3545              3550              3555

Thr Arg Ala Ala Arg Asn Ala Lys Glu His Pro Ser Leu Leu Pro
  3560              3565              3570

His Ser Ala Cys Phe Pro Asp Pro Ser Thr Ala Ser Thr Ser Gln
  3575              3580              3585

Ser Ala Ala His Ser Asn Asp Ser Pro Pro Pro Ser Ala Ala
  3590              3595              3600

Ala Pro Ser Ser Ala Ser Pro His Ala Ser Arg Lys Ser Trp Pro
  3605              3610              3615

Gln Val Val Ser Arg Ala Ser Ala Ala Lys Pro Pro Ser Phe Pro
  3620              3625              3630

Pro Leu Ser Ser Ser Ser Thr Val Thr Ser Ser Ser Cys Ser Thr
  3635              3640              3645

Ser Gly Val Gln Pro Ser Met Pro Thr Asp Asp Tyr Ser Glu Glu
  3650              3655              3660

Ser Asp Thr Asp Leu Ser Gln Lys Ser Asp Gly Pro Ala Ser Pro
  3665              3670              3675

Val Glu Gly Pro Lys Asp Pro Ser Cys Pro Lys Asp Ser Gly Leu
  3680              3685              3690

Thr Ser Val Gly Thr Asp Thr Phe Arg Leu Glx
  3695              3700

<210> SEQ ID NO 3
<211> LENGTH: 11116
<212> TYPE: DNA
<213> ORGANISM: Homo sapiens

<400> SEQUENCE: 3

```
atggaaggct gtgactcgcc cgtcgtctcg gggaaggaca atgggtgcgg tatccctcag      60
caccagcaat ggactgaact caacagcacc cacctccctg acaaacccag tagcatggaa     120
cagtccacag gcgagagcca cgggcccttg acagcctga gggcccccttt caatgagcgc     180
ctcgcggaga gcaccgcgtc ggccgggccc ccgccgagc cgccagcaa ggaggtcacc       240
tgcaacgaat gttcggcctc ctttgccagc tccagacct acatggagca ccactgcccc     300
agcgcgcgcc ccccgccacc cctgagagag gagagcgcta gcgacaccgg tgaggagggg     360
gacgaggaga gtgacgtgga gaacctggcc ggggagatcg tctaccagcc ggacggctcc     420
gcatacattg tggagagcct gagccagctg acccaggggcg ggggcgcctg tgggagtggc     480
agtggcagtg gcctctcccc ctcgcttttc ctgaactctc tccctggcgc gggggggcaag    540
caaggggacc cttcgtgtgc tgcacccgtg tacccgcaga tcatcaacac tttccacata     600
gcctcatcct tcgggaaatg gtttgagggc cagaccagg cttttcccgaa tacctcagcc     660
ctggcggggc tcagccccgt cctgcacagc ttccgcgtgt tgacgtgcg acacaaaagc      720
```

```
aacaaggatt acctgaacag cgacggttct gccaaaagct cctgcgtatc caaagatgtt    780
cccaacaatg tggacctgtc caaattcgat ggctttgtgc tctatggcaa gaggaagccc    840
atcctgatgt gtttcttgtg caaactctcc tttgggtacg tccgttcgtt tgtgacccac    900
gcggtgcatg accatcgaat gaccctgagc gaagacgagc ggaaaattct tagcaataag    960
aacatctccg ctatcatcca agggatcggc aaagacaagg aacccttgt aagttttctg   1020 gaaccaaaaa acaaaaactt tcaacaccct ttagtttcca cagctaacct cataggcccc   1080
ggacacagtt tttatggtaa atttagtggc attcgaatgg aaggggagga agctctccca   1140
gcgggctccg ccgctggccc cgagcagccc caggctggtc tcttgacccc cagcaccctg   1200
ttgaaccttg gcgggctcac cagctcggta ctgaagaccc ccattacctc agtcccctg    1260 ggggctctgg cttccagtcc taccaaatcc tcagagggca aggactctgg ggcggcagaa   1320
ggagagaagc aggaagtggg cgacgggat tgcttctctg agaaggtaga gccagccgaa    1380
gaggaggcgg aggaggaaga ggaggaggaa gaggcggagg aggaggagga agaagaggag   1440
gaggaagaag aggaggagga agacgagggt tgcaaaggac tctttccaag cgagttggat   1500
gaggaactgg aggacaggcc ccatgaggag cctggggccg cagcaggtag tagcagcaaa   1560
aaggaccttg ctctctcaaa ccaaagcatt tctaactccc ccttaatgcc taacgtgctc   1620
cagaccctgt cgaggggcac agcttctact agttctaatt ctgcttcttc ctttgttgtc   1680
tttgatggtg cgaacaggag gaatcgttta agctttaaca gtgagggcgt caggaccaat   1740
gtggcagagg gcggcaggag gctggacttc gctgacgaaa gtgccaataa agacaatgcc   1800
acagcaccag aaccaaatga agtacagag ggtgacgatg ggggcttcgt tccccatcac    1860
cagcacgctg gctccctctg cgagcttggg gttggggagt gcccctcggg gagtggcgtg   1920
gagtgcccca aatgcgacac ggtcctgggc tcctcccgct cgctgggcgg ccacatgacc   1980
atgatgcatt ctcgtaactc gtgtaagaca ctcaagtgcc ccaagtgcaa ctggcactat   2040
aagtaccagc agaccctgga ggcacacatg aaggagaagc acccggagcc ggggggctcc   2100
tgtgtctact gcaaaagcgg gcagccccac ccccggctgg cacgaggcga gagctacacg   2160
tgtggttaca gccttttccg ctgcgaggtg tgtaactact ccacaactac caaaggcaac   2220
ctcagtattc atatgcagtc tgacaagcat ctcaacaaca tgcagaacct acagaatgga   2280
gggggggagc aggtcttcat ccacactgcc ggggcggcgg cggcggcggc ggctgcggcg   2340
gcggcggcag ccaatatcag tagctcctgc ggggccccct cgcccaccaa accaaaaacc   2400
aaacccacct ggcggtgcga ggtgtgtgat tatgagacca acgtggccag gaacctccgc   2460
attcacatga ccagtgagaa gcacatgcat aacatgatgt tactgcaaca gaacatgacc   2520
cagatccaac acaaccacca ccgggtcctc ggcagcctgc cctcacccgc cgaggccgag   2580
ctctaccaat actacctggc ccagaacatg aacctgccca acctgaagat ggacagtgct   2640
gcctcggacg cccagttcat gatgagcgga ttccagctgg atcccgccgg gcccatggcc   2700
gccatgacgc ctgctctagt gggcggtgag atcccctag acatgcggct cggggcggg    2760 cagctggtgt cagaggagct gatgaacctg ggcgagagct tcatccagac caacgacccg   2820
tcgctgaagc tcttccagtg cgccgtctgc aacaagttca cgacggacaa cctggacatg   2880
ctgggcctgc acatgaacgt ggagcgcagc ctgtcggagg acgagtggaa ggcggtgatg   2940
ggggactcat accagtgcaa gctctgccgc tacaacaccc agctcaaggc caacttccag   3000
ctgcactgca agacagacaa gcacgtgcag aagtaccagc tggtggccca catcaaggag   3060
ggcggcaagg ccaacgagtg gaggctcaag tgtgtggcca tcggcaaccc cgtgcacctc   3120
```

```
aagtgcaacg cctgtgacta ctacaccaac agcctggaga agctgcggct gcacacggtc   3180
aactccaggc acgaggccag cctgaagttg tacaagcacc tgcagcagca tgagagtggt   3240
gtagaaggtg agagctgcta ctaccactgc gttctgtgca actactccac caaggccaag   3300
ctcaacctca tccagcatgt gcgctccatg aagcaccagc gaagcgagag cctgcgaaag   3360
ctgcagcggc tgcagaaggg ccttccagag gaggacgagg acctgggca gatcttcacc    3420 atccgcaggt gcccctccac ggacccagaa gaagccattg aagatgttga aggacccagt   3480
gaaacagctg ctgatccaga ggagcttgct aaggaccaag agggcggagc atcgtccagc   3540
caagcagaga aggagctgac agattctcct gcaacctcca aacgcatctc cttcccaggt   3600
agctcagagt ctcccctctc ttcgaagcga ccaaaaacag ctgaggagat caaaccggag   3660
cagatgtacc agtgtcccta ctgcaagtac agtaatgccg atgtcaaccg gctccgggtg   3720
catgccatga cgcagcactc ggtgcaaccc atgcttcgct gccccctgtg ccaggacatg   3780
ctcaacaaca agatccacct ccagctgcac ctcacccacc tccacagcgt ggcacctgac   3840
tgcgtggaga agctcattat gacggtgacc accctgaga tggtgatgcc aagcagcatg    3900
ttcctcccag cagctgttcc agatcgagat gggaattcca atttggaaga ggcaggaaag   3960
cagcctgaaa cctcagagga tctgggaaag aacatcttgc catccgcaag cacagagcaa   4020
agcggagatt tgaaaccatc ccctgctgac ccaggctctg tgagagaaga ctcaggcttc   4080
atctgctgga agaaggggtg caaccaggtt tcaaaacttc tgctgccct tcagacgcat   4140 tttaatgaag tgcatgccaa gaggcctcag ctgccggtgt cagatcgcca tgtgtacaag   4200
taccgctgta atcagtgtag cctggccttc aagaccattg aaaagttgca gctccattct   4260
cagtaccatg tgatcagagc tgccaccatg tgctgtcttt gtcagcgcag tttccgaact   4320
ttccaggctc tgaagaagca ccttgagaca agccacctgg agctgagtga ggctgacatc   4380
caacagcttt atggtggcct gctggccaat ggggacctcc tggcaatggg agaccccact   4440
ctggctgagg accataccat aattgttgag gaagacaagg aggaagagag tgacttggaa   4500
gataaacaga gcccaacggg cagtgactct gggtcagtac aagaagactc gggctcagag   4560
ccaaagagag ctctgccttt cagaaaaggt cccaatttta ctatggaaaa gttcctagac   4620
ccttctcgcc cttacaagtg taccgtctgc aaggaatctt tcactcaaaa gaatatcctg   4680
ctagtacact acaattctgt ctcccacctg cataagttaa agagagccct tcaagaatca   4740
gcaaccggtc agccagaacc caccagcagc ccagacaaca aacctttaa gtgtaacact    4800 tgtaatgtgg cctacagcca gagttccact ctggagatcc atatgaggtc tgtgttacat   4860
caaaccaagg cccgggcagc caagctggag gctgcaagtg gcagcagcaa tgggactggg   4920
aacagcagca gtatttcctt gagctcctcc acgccaagtc ctgtgagcac cagtggcagt   4980 aacacccttta ccacctccaa tccaagcagt gctggcattg ctccaagctc taacttacta   5040
agccaagtgc ccactgagag tgtagggatg ccacccctgg ggaatcctat tggtgccaac   5100
attgcttccc cttcagagcc caaagaggcc aatcggaaga aactggcaga tatgattgca   5160
tccaggcagc agcaacaaca gcagcagcaa cagcaacaac aacaacaaca acaacaacaa   5220
caagcacaaa cgctggccca ggcccaggct caagttcaag ctcacctgca gcaggagctg   5280
cagcaacagg ctgccctgat ccagtctcag ctgtttaacc ccaccctcct tcctcacttc   5340
cccatgacaa ctgagaccct gctgcaacta cagcagcagc agcacctcct cttcccttc    5400 tacatcccca gtgctgagtt ccagcttaac cccgaggtga gcttgccagt gaccagtggg   5460
```

```
gcactgacac tgactgggac aggcccaggc ctgctggaag atctgaaggc tcaggttcag   5520
gtcccacagc agagccatca gcagatcttg ccgcagcagc agcagaacca actctctata   5580
gcccagagtc actctgccct ccttcagcca agccagcacc ccgaaaagaa gaacaaattg   5640
gtcatcaaag aaaaggaaaa agaaagccag agagagaggg acagcgccga ggggggagag   5700
ggcaacaccg gtccgaagga aacactgcca gatgccttga aggccaaaga gaagaaagag   5760
ttggcaccag ggggtggttc tgagccttcc atgctccctc cacgcattgc ttcagatgcc   5820
agagggaacg ccaccaaggc cctgctggag aactttggct ttgagttggt catccagtat   5880
aatgagaaca agcagaaggt gcagaaaaag aatgggaaga ctgaccaggg agagaacctg   5940
gaaaagctcg agtgtgactc ctgcggcaag ttgttttcca acatcttgat tttaaagagt   6000
catcaagagc acgttcatca gaattacttt cctttcaaac agctcgagag gtttgccaaa   6060
cagtacagag accactacga taaactgtac ccactgaggc cccagacccc agagccacca   6120
ccacctcccc ctccaccccc tccaccccca cttccggcag cgccgcctca gccggcgtcc   6180
acaccagcca tccccgcatc agccccaccc atcacctcac ctacaattgc accggcccag   6240
ccatcagtgc cgctcaccca gctctccatg ccgatggagc tgcccatctt ctcgccgctg   6300
atgatgcaga cgatgccgct gcagaccttg ccggctcagc tacccccgca gctgggacct   6360
gtggagcctc tgcctgcgga cctggcccaa ctctaccagc atcagctcaa tccaaccctg   6420
ctccagcagc agaacaagag gcctcgcacc aggatcacag atgatcagct ccgagtcttg   6480
cggcaatatt ttgacattaa caactccccc agtgaagagc aaataaaaga gatggcagac   6540
aagtccgggt tgcccagaa agtgatcaag cactggttca ggaacactct cttcaaagag   6600
aggcagcgta acaaggactc cccttacaac ttcagtaatc ctcctatcac cagcctggag   6660
gagctcaaga ttgactcccg gccccttcg ccggaacctc caaagcagga gtactgggga   6720
agcaagaggt cttcaagaac aaggtttacg gactaccagc tgagggtctt acaggacttc   6780
ttcgatgcca atgcttaccc aaaggatgat gaatttgagc aactctctaa tttactgaac   6840
cttccaaccc gagtgatagt ggtgtggttt cagaatgccc gacagaaggc caggaagaat   6900
tatgagaatc agggagaggg caaagatgga gagcggcgtg agcttacaaa tgatagatac   6960
attcgaacaa gcaacttgaa ctaccagtgc aaaaaatgta gcctggtgtt tcagcgcatc   7020
tttgatctca tcaagcacca aagaagctg tgttacaagg atgaggatga ggaggggcag   7080
gacgacagcc aaaatgagga ttccatggat gccatggaaa tcctgacgcc taccagctca   7140
tcctgcagta ccccgatgcc ctcacaggct acagcgcccc cagcaccatc agccaataat   7200
acagcttcct ccgctttctt gcagcttaca gcggaggctg aggaactggc caccttcaat   7260
tcaaaaacag aggcaggcga tgagaaacca aagctggcgg aagctcccag tgcacagcca   7320
aaccaaaccc aagaaaagca aggacaacca aagccagagc tgcagcagca agagcagccc   7380
gagcagaaga ccaacactcc ccagcagaag ctccccccagc tggtgtccct gccttcgttg   7440
ccacagcctc ctccacaagc gccccctcca cagtgcccct accccagtc gagcccagt   7500 ccttcccagc tctcccacct gccctcaag cccctccaca catcaactcc tcaacagctc   7560
gcaaacctac ctcctcagct aatcccctac cagtgtgacc agtgtaagtt ggcatttccg   7620
tcatttgagc actggcagga gcatcagcag ctccacttcc tgagcgcgca gaaccagttc   7680 atccacccc agttttggga caggtccctg gatatgcctt tcatgctctt tgatcccagt   7740
aacccactcc tggccagcca gctgctctct ggggccatac ctcagattcc agcaagctca   7800
gccacttctc cttcaactcc aacctccaca atgaacactc tcaagaggaa gctggaggaa   7860
```

-continued

```
aaggccagtg caagccctgg cgaaaacgac agtgggacag gaggagaaga gcctcagaga   7920
gacaagcgtt tgagaacaac catcacaccg gaacaactag aaattctcta ccagaagtat   7980
ctactggatt ccaatccgac tcgaaagatg ttggatcaca ttgcacacga ggtgggcttg   8040
aagaaacgtg tggtacaagt ctggtttcag aacacccgag ctcgggaaag gaaaggacag   8100
ttccgggctg taggcccagc gcaggccacc aggagatgcc cttttttgcag agcgctcttc   8160
aaagccaaga ctgctctcga ggctcatatc cggtcccgtc actggcatga agccaagaga   8220
gctggctaca acctaactct gtctgcgatg ctcttagact gtgatggggg actccagatg   8280
aaaggagata ttttttgacgg aactagcttt tcccacctac ccccaagcag tagtgatggt   8340
cagggtgtcc ccctctcacc tgtgagtaaa accatggaat tgtcacccag aactcttcta   8400
agcccttcct ccattaaggt ggaagggatt gaagactttg aaagcccctc catgtcctca   8460
gttaatctaa actttgacca aactaagctg gacaacgatg actgttcctc tgtcaacaca   8520
gcaatcacag ataccacaac tggagacgag ggcaacgcag ataacgacag tgcaacggga   8580
atagcaactg aaaccaaatc ctcttctgca cccaacgaag ggttgaccaa agcggccatg   8640
atggcaatgt ctgagtatga agatcggttg tcatctggtc tggtcagccc ggccccgagc   8700
ttttatagca aggaatatga caatgaaggt acagtggact acagtgaaac ctcaagcctt   8760
gcagatccct gctccccgag tcctggtgcg agtggatctg caggcaaatc tggtgacagc   8820
ggagatcggc ctgggcagaa acgttttcgc actcaaatga ccaatctgca gctgaaggtc   8880
ctcaagtcat gctttaatga ctacaggaca cccactatgc tagaatgtga ggtcctgggc   8940
aatgacattg gactgccaaa gagagtcgtt caggtctggt tccagaatgc ccgggcaaaa   9000
gaaaagaagt ccaagttaag catggccaag cattttggta taaaccaaac gagttatgag   9060
ggacccaaaa cagagtgcac tttgtgtggc atcaagtaca gcgctcggct gtctgtacgt   9120
gaccatatct tttcccaaca gcatatctcc aaagttaaag acaccattgg aagccagctg   9180
gacaaggaga aagaatactt tgacccagcc accgtacgtc agttgatggc tcaacaagag   9240
ttggaccgga ttaaaaaggc caacgaggtc cttggactgg cagctcagca gcaagggatg   9300
tttgacaaca cccctcttca ggcccttaac cttcctacag catatccagc gctccagggc   9360
attcctcctg tgttgctccc gggcctcaac agccctcct tgccaggctt tactccatcc   9420
aacacagctt taacgtctcc taagccgaac ttgatgggtc tgcccagcac aactgttcct   9480
tcccctggcc tccccacttc tggattacca aataaaccgt cctcagcgtc gctgagctcc   9540
ccaaccccag cacaagccac gatggcgatg ggccctcagc aacccccca gcagcagcag   9600
cagcagcagc aaccacaggt gcagcagcct ccccgccgc cagcagccca gccgccaccc   9660
acaccacagc tcccactgca acagcagcag caacgcaagg acaaagacag tgagaaagta   9720
aaggagaagg aaaaggcaca caagggaaa ggggaacccc tgcctgtccc caagaaggag   9780
aaaggagagg ccccacggc aactgcagcc acgatctcag cccgctgcc caccatggag   9840
tatgcggtag accctgcaca gctgcaggcc ctgcaggccg cgttgacttc ggaccccaca   9900
gcattgctca caagccagtt ccttccttac tttgtaccag gcttttctcc ttattatgct   9960
ccccagatcc ctggcgccct gcagagcggg tacctgcagc ctatgtatgg catggaaggc  10020
ctgttcccct acagccctgc actgtcgcag gccctgatgg ggctgtcccc aggctccta  10080
ctgcagcagt accagcaata ccagcagagt ctgcaggagg caattcagca gcagcagcag  10140
cggcaactac agcagcagca gcagcaaaaa gtgcagcagc agcagcccaa agcaagccaa  10200
```

-continued

```
acccccagtcc cccccggggc tccttcccca gacaaagacc ctgccaaaga atcccccaaa    10260
ccagaagaac agaaaaacac ccccccgtgag gtgtcccccc tcctgccgaa actccctgaa    10320
gagccagaag cagaaagcaa aagtgcggac tccctctacg acccccttcat tgttccaaag    10380 gtgcagtaca agttggtctg ccgcaagtgc caggcgggct tcagcgacga ggaggcagcg    10440
aggagccacc tgaagtccct ctgcttcttc ggccagtctg tggtgaacct gcaagagatg    10500
gtgcttcacg tccccaccgg cggcggcggc ggtggcagtg gcggcggcgg cggcggtggc    10560
ggcggcggcg gcggcggcgg ctcgtaccac tgcctggcgt gcgagagcgc gctctgtggg    10620
gaggaagctc tgagtcaaca tctcgagtcg gccttgcaca aacacagaac aatcacgaga    10680
gcagcaagaa acgccaaaga gcaccctagt ttattacctc actctgcctg cttccccgat    10740
cctagcaccg catctaccctc gcagtctgcc gctcactcaa acgacagccc ccctcccccg    10800
tcggccgccg ccccctcctc cgcttccccc cacgcctcca ggaagtcttg gccgcaagtg    10860
gtctcccggg cttcggcagc gaagcccct tctttttcctc ctctctcctc atcttcaacg    10920
gttacctcaa gttcatgcag cacctcaggg gttcagccct cgatgccaac agacgactat    10980
tcggaggagt ctgacacgga tctcagccaa aagtccgacg gaccggcgag cccggtggag    11040
ggtcccaaag accccagctg ccccaaggac agtggtctga ccagtgtagg aacggacacc    11100
ttcagattgt aagctt                                                     11116
```

<210> SEQ ID NO 4
<211> LENGTH: 2790
<212> TYPE: PRT
<213> ORGANISM: Homo sapiens

<400> SEQUENCE: 4

```
Met Arg Leu Gly Gly Gly Gln Leu Val Ser Glu Glu Leu Met Asn Leu
1               5                   10                  15

Gly Glu Ser Phe Ile Gln Thr Asn Asp Pro Ser Leu Lys Leu Phe Gln
            20                  25                  30

Cys Ala Val Cys Asn Lys Phe Thr Thr Asp Asn Leu Asp Met Leu Gly
        35                  40                  45

Leu His Met Asn Val Glu Arg Ser Leu Ser Glu Asp Glu Trp Lys Ala
    50                  55                  60

Val Met Gly Asp Ser Tyr Gln Cys Lys Leu Cys Arg Tyr Asn Thr Gln
65                  70                  75                  80

Leu Lys Ala Asn Phe Gln Leu His Cys Lys Thr Asp Lys His Val Gln
                85                  90                  95

Lys Tyr Gln Leu Val Ala His Ile Lys Glu Gly Gly Lys Ala Asn Glu
            100                 105                 110

Trp Arg Leu Lys Cys Val Ala Ile Gly Asn Pro Val His Leu Lys Cys
        115                 120                 125

Asn Ala Cys Asp Tyr Tyr Thr Asn Ser Leu Glu Lys Leu Arg Leu His
    130                 135                 140

Thr Val Asn Ser Arg His Glu Ala Ser Leu Lys Leu Tyr Lys His Leu
145                 150                 155                 160

Gln Gln His Glu Ser Gly Val Glu Gly Glu Ser Cys Tyr Tyr His Cys
                165                 170                 175

Val Leu Cys Asn Tyr Ser Thr Lys Ala Lys Leu Asn Leu Ile Gln His
            180                 185                 190

Val Arg Ser Met Lys His Gln Arg Ser Glu Ser Leu Arg Lys Leu Gln
        195                 200                 205
```

```
Arg Leu Gln Lys Gly Leu Pro Glu Glu Asp Glu Asp Leu Gly Gln Ile
    210                 215                 220

Phe Thr Ile Arg Arg Cys Pro Ser Thr Asp Pro Glu Glu Ala Ile Glu
225                 230                 235                 240

Asp Val Glu Gly Pro Ser Glu Thr Ala Ala Asp Pro Glu Glu Leu Ala
                245                 250                 255

Lys Asp Gln Glu Gly Gly Ala Ser Ser Ser Gln Ala Glu Lys Glu Leu
            260                 265                 270

Thr Asp Ser Pro Ala Thr Ser Lys Arg Ile Ser Phe Pro Gly Ser Ser
        275                 280                 285

Glu Ser Pro Leu Ser Ser Lys Arg Pro Lys Thr Ala Glu Glu Ile Lys
    290                 295                 300

Pro Glu Gln Met Tyr Gln Cys Pro Tyr Cys Lys Tyr Ser Asn Ala Asp
305                 310                 315                 320

Val Asn Arg Leu Arg Val His Ala Met Thr Gln His Ser Val Gln Pro
                325                 330                 335

Met Leu Arg Cys Pro Leu Cys Gln Asp Met Leu Asn Asn Lys Ile His
            340                 345                 350

Leu Gln Leu His Leu Thr His Leu His Ser Val Ala Pro Asp Cys Val
        355                 360                 365

Glu Lys Leu Ile Met Thr Val Thr Thr Pro Glu Met Val Met Pro Ser
    370                 375                 380

Ser Met Phe Leu Pro Ala Ala Val Pro Asp Arg Asp Gly Asn Ser Asn
385                 390                 395                 400

Leu Glu Glu Ala Gly Lys Gln Pro Glu Thr Ser Glu Asp Leu Gly Lys
                405                 410                 415

Asn Ile Leu Pro Ser Ala Ser Thr Glu Gln Ser Gly Asp Leu Lys Pro
            420                 425                 430

Ser Pro Ala Asp Pro Gly Ser Val Arg Glu Asp Ser Gly Phe Ile Cys
        435                 440                 445

Trp Lys Lys Gly Cys Asn Gln Val Phe Lys Thr Ser Ala Ala Leu Gln
    450                 455                 460

Thr His Phe Asn Glu Val His Ala Lys Arg Pro Gln Leu Pro Val Ser
465                 470                 475                 480

Asp Arg His Val Tyr Lys Tyr Arg Cys Asn Gln Cys Ser Leu Ala Phe
                485                 490                 495

Lys Thr Ile Glu Lys Leu Gln Leu His Ser Gln Tyr His Val Ile Arg
            500                 505                 510

Ala Ala Thr Met Cys Cys Leu Cys Gln Arg Ser Phe Arg Thr Phe Gln
        515                 520                 525

Ala Leu Lys Lys His Leu Glu Thr Ser His Leu Glu Leu Ser Glu Ala
    530                 535                 540

Asp Ile Gln Gln Leu Tyr Gly Gly Leu Leu Ala Asn Gly Asp Leu Leu
545                 550                 555                 560

Ala Met Gly Asp Pro Thr Leu Ala Glu Asp His Thr Ile Ile Val Glu
                565                 570                 575

Glu Asp Lys Glu Glu Ser Asp Leu Glu Asp Lys Gln Ser Pro Thr
            580                 585                 590

Gly Ser Asp Ser Gly Ser Val Gln Glu Asp Ser Gly Ser Glu Pro Lys
        595                 600                 605

Arg Ala Leu Pro Phe Arg Lys Gly Pro Asn Phe Thr Met Glu Lys Phe
    610                 615                 620

Leu Asp Pro Ser Arg Pro Tyr Lys Cys Thr Val Cys Lys Glu Ser Phe
```

-continued

```
              625                 630                 635                 640
Thr Gln Lys Asn Ile Leu Leu Val His Tyr Asn Ser Val Ser His Leu
                    645                 650                 655

His Lys Leu Lys Arg Ala Leu Gln Glu Ser Ala Thr Gly Gln Pro Glu
                    660                 665                 670

Pro Thr Ser Ser Pro Asp Asn Lys Pro Phe Lys Cys Asn Thr Cys Asn
                    675                 680                 685

Val Ala Tyr Ser Gln Ser Ser Thr Leu Glu Ile His Met Arg Ser Val
            690                 695                 700

Leu His Gln Thr Lys Ala Arg Ala Ala Lys Leu Glu Ala Ala Ser Gly
705                 710                 715                 720

Ser Ser Asn Gly Thr Gly Asn Ser Ser Ile Ser Leu Ser Ser Ser
                    725                 730                 735

Thr Pro Ser Pro Val Ser Thr Ser Gly Ser Asn Thr Phe Thr Thr Ser
                    740                 745                 750

Asn Pro Ser Ser Ala Gly Ile Ala Pro Ser Ser Asn Leu Leu Ser Gln
                    755                 760                 765

Val Pro Thr Glu Ser Val Gly Met Pro Pro Leu Gly Asn Pro Ile Gly
            770                 775                 780

Ala Asn Ile Ala Ser Pro Ser Glu Pro Lys Glu Ala Asn Arg Lys Lys
785                 790                 795                 800

Leu Ala Asp Met Ile Ala Ser Arg Gln Gln Gln Gln Gln Gln Gln Gln
                    805                 810                 815

Gln Gln Gln Gln Gln Gln Gln Gln Gln Ala Gln Thr Leu Ala
                820                 825                 830

Gln Ala Gln Ala Gln Val Gln Ala His Leu Gln Gln Glu Leu Gln Gln
            835                 840                 845

Gln Ala Ala Leu Ile Gln Ser Gln Leu Phe Asn Pro Thr Leu Leu Pro
        850                 855                 860

His Phe Pro Met Thr Thr Glu Thr Leu Leu Gln Leu Gln Gln Gln Gln
865                 870                 875                 880

His Leu Leu Phe Pro Phe Tyr Ile Pro Ser Ala Glu Phe Gln Leu Asn
                    885                 890                 895

Pro Glu Val Ser Leu Pro Val Thr Ser Gly Ala Leu Thr Leu Thr Gly
            900                 905                 910

Thr Gly Pro Gly Leu Leu Glu Asp Leu Lys Ala Gln Val Gln Val Pro
        915                 920                 925

Gln Gln Ser His Gln Ile Leu Pro Gln Gln Gln Asn Gln Leu
        930                 935                 940

Ser Ile Ala Gln Ser His Ser Ala Leu Leu Gln Pro Ser Gln His Pro
945                 950                 955                 960

Glu Lys Lys Asn Lys Leu Val Ile Lys Glu Lys Glu Lys Ser Gln
                    965                 970                 975

Arg Glu Arg Asp Ser Ala Glu Gly Gly Gly Asn Thr Gly Pro Lys
            980                 985                 990

Glu Thr Leu Pro Asp Ala Leu Lys  Ala Lys Glu Lys Lys  Glu Leu Ala
            995                 1000                1005

Pro Gly  Gly Gly Ser Glu Pro  Ser Met Leu Pro Pro  Arg Ile Ala
        1010                1015                1020

Ser Asp  Ala Arg Gly Asn Ala  Thr Lys Ala Leu Leu  Glu Asn Phe
        1025                1030                1035

Gly Phe  Glu Leu Val Ile Gln  Tyr Asn Glu Asn Lys  Gln Lys Val
        1040                1045                1050
```

-continued

```
Gln Lys Lys Asn Gly Lys Thr Asp Gln Gly Glu Asn Leu Glu Lys
    1055                1060                1065

Leu Glu Cys Asp Ser Cys Gly Lys Leu Phe Ser Asn Ile Leu Ile
    1070                1075                1080

Leu Lys Ser His Gln Glu His Val His Gln Asn Tyr Phe Pro Phe
    1085                1090                1095

Lys Gln Leu Glu Arg Phe Ala Lys Gln Tyr Arg Asp His Tyr Asp
    1100                1105                1110

Lys Leu Tyr Pro Leu Arg Pro Gln Thr Pro Glu Pro Pro Pro Pro
    1115                1120                1125

Pro Pro Pro Pro Pro Pro Pro Leu Pro Ala Ala Pro Pro Gln
    1130                1135                1140

Pro Ala Ser Thr Pro Ala Ile Pro Ala Ser Ala Pro Pro Ile Thr
    1145                1150                1155

Ser Pro Thr Ile Ala Pro Ala Gln Pro Ser Val Pro Leu Thr Gln
    1160                1165                1170

Leu Ser Met Pro Met Glu Leu Pro Ile Phe Ser Pro Leu Met Met
    1175                1180                1185

Gln Thr Met Pro Leu Gln Thr Leu Pro Ala Gln Leu Pro Pro Gln
    1190                1195                1200

Leu Gly Pro Val Glu Pro Leu Pro Ala Asp Leu Ala Gln Leu Tyr
    1205                1210                1215

Gln His Gln Leu Asn Pro Thr Leu Leu Gln Gln Gln Asn Lys Arg
    1220                1225                1230

Pro Arg Thr Arg Ile Thr Asp Asp Gln Leu Arg Val Leu Arg Gln
    1235                1240                1245

Tyr Phe Asp Ile Asn Asn Ser Pro Ser Glu Glu Gln Ile Lys Glu
    1250                1255                1260

Met Ala Asp Lys Ser Gly Leu Pro Gln Lys Val Ile Lys His Trp
    1265                1270                1275

Phe Arg Asn Thr Leu Phe Lys Glu Arg Gln Arg Asn Lys Asp Ser
    1280                1285                1290

Pro Tyr Asn Phe Ser Asn Pro Pro Ile Thr Ser Leu Glu Glu Leu
    1295                1300                1305

Lys Ile Asp Ser Arg Pro Pro Ser Pro Glu Pro Pro Lys Gln Glu
    1310                1315                1320

Tyr Trp Gly Ser Lys Arg Ser Arg Thr Arg Phe Thr Asp Tyr
    1325                1330                1335

Gln Leu Arg Val Leu Gln Asp Phe Phe Asp Ala Asn Ala Tyr Pro
    1340                1345                1350

Lys Asp Asp Glu Phe Glu Gln Leu Ser Asn Leu Leu Asn Leu Pro
    1355                1360                1365

Thr Arg Val Ile Val Val Trp Phe Gln Asn Ala Arg Gln Lys Ala
    1370                1375                1380

Arg Lys Asn Tyr Glu Asn Gln Gly Glu Gly Lys Asp Gly Glu Arg
    1385                1390                1395

Arg Glu Leu Thr Asn Asp Arg Tyr Ile Arg Thr Ser Asn Leu Asn
    1400                1405                1410

Tyr Gln Cys Lys Lys Cys Ser Leu Val Phe Gln Arg Ile Phe Asp
    1415                1420                1425

Leu Ile Lys His Gln Lys Lys Leu Cys Tyr Lys Asp Glu Asp Glu
    1430                1435                1440
```

-continued

```
Glu Gly Gln Asp Asp Ser Gln Asn Glu Asp Ser Met Asp Ala Met
    1445              1450              1455

Glu Ile Leu Thr Pro Thr Ser Ser Ser Cys Ser Thr Pro Met Pro
    1460              1465              1470

Ser Gln Ala Tyr Ser Ala Pro Ala Pro Ser Ala Asn Asn Thr Ala
    1475              1480              1485

Ser Ser Ala Phe Leu Gln Leu Thr Ala Glu Ala Glu Glu Leu Ala
    1490              1495              1500

Thr Phe Asn Ser Lys Thr Glu Ala Gly Asp Glu Lys Pro Lys Leu
    1505              1510              1515

Ala Glu Ala Pro Ser Ala Gln Pro Asn Gln Thr Gln Glu Lys Gln
    1520              1525              1530

Gly Gln Pro Lys Pro Glu Leu Gln Gln Gln Glu Gln Pro Glu Gln
    1535              1540              1545

Lys Thr Asn Thr Pro Gln Gln Lys Leu Pro Gln Leu Val Ser Leu
    1550              1555              1560

Pro Ser Leu Pro Gln Pro Pro Gln Ala Pro Pro Pro Gln Cys
    1565              1570              1575

Pro Leu Pro Gln Ser Ser Pro Ser Pro Ser Gln Leu Ser His Leu
    1580              1585              1590

Pro Leu Lys Pro Leu His Thr Ser Thr Pro Gln Leu Ala Asn
    1595              1600              1605

Leu Pro Pro Gln Leu Ile Pro Tyr Gln Cys Asp Gln Cys Lys Leu
    1610              1615              1620

Ala Phe Pro Ser Phe Glu His Trp Gln Glu His Gln Gln Leu His
    1625              1630              1635

Phe Leu Ser Ala Gln Asn Gln Phe Ile His Pro Gln Phe Leu Asp
    1640              1645              1650

Arg Ser Leu Asp Met Pro Phe Met Leu Phe Asp Pro Ser Asn Pro
    1655              1660              1665

Leu Leu Ala Ser Gln Leu Leu Ser Gly Ala Ile Pro Gln Ile Pro
    1670              1675              1680

Ala Ser Ser Ala Thr Ser Pro Ser Thr Pro Thr Ser Thr Met Asn
    1685              1690              1695

Thr Leu Lys Arg Lys Leu Glu Glu Lys Ala Ser Ala Ser Pro Gly
    1700              1705              1710

Glu Asn Asp Ser Gly Thr Gly Gly Glu Glu Pro Gln Arg Asp Lys
    1715              1720              1725

Arg Leu Arg Thr Thr Ile Thr Pro Glu Gln Leu Glu Ile Leu Tyr
    1730              1735              1740

Gln Lys Tyr Leu Leu Asp Ser Asn Pro Thr Arg Lys Met Leu Asp
    1745              1750              1755

His Ile Ala His Glu Val Gly Leu Lys Lys Arg Val Val Gln Val
    1760              1765              1770

Trp Phe Gln Asn Thr Arg Ala Arg Glu Arg Lys Gly Gln Phe Arg
    1775              1780              1785

Ala Val Gly Pro Ala Gln Ala His Arg Arg Cys Pro Phe Cys Arg
    1790              1795              1800

Ala Leu Phe Lys Ala Lys Thr Ala Leu Glu Ala His Ile Arg Ser
    1805              1810              1815

Arg His Trp His Glu Ala Lys Arg Ala Gly Tyr Asn Leu Thr Leu
    1820              1825              1830

Ser Ala Met Leu Leu Asp Cys Asp Gly Gly Leu Gln Met Lys Gly
```

-continued

```
           1835                1840                1845

Asp  Ile  Phe  Asp  Gly  Thr  Ser  Phe  Ser  His  Leu  Pro  Pro  Ser  Ser
           1850                1855                1860

Ser  Asp  Gly  Gln  Gly  Val  Pro  Leu  Ser  Pro  Val  Ser  Lys  Thr  Met
           1865                1870                1875

Glu  Leu  Ser  Pro  Arg  Thr  Leu  Leu  Ser  Pro  Ser  Ser  Ile  Lys  Val
           1880                1885                1890

Glu  Gly  Ile  Glu  Asp  Phe  Glu  Ser  Pro  Ser  Met  Ser  Ser  Val  Asn
           1895                1900                1905

Leu  Asn  Phe  Asp  Gln  Thr  Lys  Leu  Asp  Asn  Asp  Asp  Cys  Ser  Ser
           1910                1915                1920

Val  Asn  Thr  Ala  Ile  Thr  Asp  Thr  Thr  Thr  Gly  Asp  Glu  Gly  Asn
           1925                1930                1935

Ala  Asp  Asn  Asp  Ser  Ala  Thr  Gly  Ile  Ala  Thr  Glu  Thr  Lys  Ser
           1940                1945                1950

Ser  Ser  Ala  Pro  Asn  Glu  Gly  Leu  Thr  Lys  Ala  Ala  Met  Met  Ala
           1955                1960                1965

Met  Ser  Glu  Tyr  Glu  Asp  Arg  Leu  Ser  Ser  Gly  Leu  Val  Ser  Pro
           1970                1975                1980

Ala  Pro  Ser  Phe  Tyr  Ser  Lys  Glu  Tyr  Asp  Asn  Glu  Gly  Thr  Val
           1985                1990                1995

Asp  Tyr  Ser  Glu  Thr  Ser  Ser  Leu  Ala  Asp  Pro  Cys  Ser  Pro  Ser
           2000                2005                2010

Pro  Gly  Ala  Ser  Gly  Ser  Ala  Gly  Lys  Ser  Gly  Asp  Ser  Gly  Asp
           2015                2020                2025

Arg  Pro  Gly  Gln  Lys  Arg  Phe  Arg  Thr  Gln  Met  Thr  Asn  Leu  Gln
           2030                2035                2040

Leu  Lys  Val  Leu  Lys  Ser  Cys  Phe  Asn  Asp  Tyr  Arg  Thr  Pro  Thr
           2045                2050                2055

Met  Leu  Glu  Cys  Glu  Val  Leu  Gly  Asn  Asp  Ile  Gly  Leu  Pro  Lys
           2060                2065                2070

Arg  Val  Val  Gln  Val  Trp  Phe  Gln  Asn  Ala  Arg  Ala  Lys  Glu  Lys
           2075                2080                2085

Lys  Ser  Lys  Leu  Ser  Met  Ala  Lys  His  Phe  Gly  Ile  Asn  Gln  Thr
           2090                2095                2100

Ser  Tyr  Glu  Gly  Pro  Lys  Thr  Glu  Cys  Thr  Leu  Cys  Gly  Ile  Lys
           2105                2110                2115

Tyr  Ser  Ala  Arg  Leu  Ser  Val  Arg  Asp  His  Ile  Phe  Ser  Gln  Gln
           2120                2125                2130

His  Ile  Ser  Lys  Val  Lys  Asp  Thr  Ile  Gly  Ser  Gln  Leu  Asp  Lys
           2135                2140                2145

Glu  Lys  Glu  Tyr  Phe  Asp  Pro  Ala  Thr  Val  Arg  Gln  Leu  Met  Ala
           2150                2155                2160

Gln  Gln  Glu  Leu  Asp  Arg  Ile  Lys  Lys  Ala  Asn  Glu  Val  Leu  Gly
           2165                2170                2175

Leu  Ala  Ala  Gln  Gln  Gln  Gly  Met  Phe  Asp  Asn  Thr  Pro  Leu  Gln
           2180                2185                2190

Ala  Leu  Asn  Leu  Pro  Thr  Ala  Tyr  Pro  Ala  Leu  Gln  Gly  Ile  Pro
           2195                2200                2205

Pro  Val  Leu  Leu  Pro  Gly  Leu  Asn  Ser  Pro  Ser  Leu  Pro  Gly  Phe
           2210                2215                2220

Thr  Pro  Ser  Asn  Thr  Ala  Leu  Thr  Ser  Pro  Lys  Pro  Asn  Leu  Met
           2225                2230                2235
```

-continued

```
Gly Leu Pro Ser Thr Thr Val Pro Ser Pro Gly Leu Pro Thr Ser
2240                2245                2250

Gly Leu Pro Asn Lys Pro Ser Ser Ala Ser Leu Ser Ser Pro Thr
2255                2260                2265

Pro Ala Gln Ala Thr Met Ala Met Gly Pro Gln Gln Pro Pro Gln
2270                2275                2280

Gln Gln Gln Gln Gln Gln Gln Pro Gln Val Gln Gln Pro Pro Pro
2285                2290                2295

Pro Pro Ala Ala Gln Pro Pro Pro Thr Pro Gln Leu Pro Leu Gln
2300                2305                2310

Gln Gln Gln Gln Arg Lys Asp Lys Asp Ser Glu Lys Val Lys Glu
2315                2320                2325

Lys Glu Lys Ala His Lys Gly Lys Gly Glu Pro Leu Pro Val Pro
2330                2335                2340

Lys Lys Glu Lys Gly Glu Ala Pro Thr Ala Thr Ala Ala Thr Ile
2345                2350                2355

Ser Ala Pro Leu Pro Thr Met Glu Tyr Ala Val Asp Pro Ala Gln
2360                2365                2370

Leu Gln Ala Leu Gln Ala Ala Leu Thr Ser Asp Pro Thr Ala Leu
2375                2380                2385

Leu Thr Ser Gln Phe Leu Pro Tyr Phe Val Pro Gly Phe Ser Pro
2390                2395                2400

Tyr Tyr Ala Pro Gln Ile Pro Gly Ala Leu Gln Ser Gly Tyr Leu
2405                2410                2415

Gln Pro Met Tyr Gly Met Glu Gly Leu Phe Pro Tyr Ser Pro Ala
2420                2425                2430

Leu Ser Gln Ala Leu Met Gly Leu Ser Pro Gly Ser Leu Leu Gln
2435                2440                2445

Gln Tyr Gln Gln Tyr Gln Gln Ser Leu Gln Glu Ala Ile Gln Gln
2450                2455                2460

Gln Gln Gln Arg Gln Leu Gln Gln Gln Gln Gln Lys Val Gln
2465                2470                2475

Gln Gln Gln Pro Lys Ala Ser Gln Thr Pro Val Pro Pro Gly Ala
2480                2485                2490

Pro Ser Pro Asp Lys Asp Pro Ala Lys Glu Ser Pro Lys Pro Glu
2495                2500                2505

Glu Gln Lys Asn Thr Pro Arg Glu Val Ser Pro Leu Leu Pro Lys
2510                2515                2520

Leu Pro Glu Glu Pro Glu Ala Glu Ser Lys Ser Ala Asp Ser Leu
2525                2530                2535

Tyr Asp Pro Phe Ile Val Pro Lys Val Gln Tyr Lys Leu Val Cys
2540                2545                2550

Arg Lys Cys Gln Ala Gly Phe Ser Asp Glu Glu Ala Ala Arg Ser
2555                2560                2565

His Leu Lys Ser Leu Cys Phe Phe Gly Gln Ser Val Val Asn Leu
2570                2575                2580

Gln Glu Met Val Leu His Val Pro Thr Gly Gly Gly Gly Gly Gly
2585                2590                2595

Ser Gly Gly Gly Gly Gly Gly Gly Gly Gly Gly Gly Gly Gly Gly
2600                2605                2610

Ser Tyr His Cys Leu Ala Cys Glu Ser Ala Leu Cys Gly Glu Glu
2615                2620                2625
```

-continued

| | | | | | | | | | | | |
|---|---|---|---|---|---|---|---|---|---|---|---|
|Ala|Leu|Ser|Gln|His|Leu|Glu|Ser|Ala|Leu|His|Lys|His|Arg|Thr|
| |2630| | | |2635| | | |2640| | | | | |

Ile Thr Arg Ala Ala Arg Asn Ala Lys Glu His Pro Ser Leu Leu
    2645            2650            2655

Pro His Ser Ala Cys Phe Pro Asp Pro Ser Thr Ala Ser Thr Ser
    2660            2665            2670

Gln Ser Ala Ala His Ser Asn Asp Ser Pro Pro Pro Ser Ala
    2675            2680            2685

Ala Ala Pro Ser Ser Ala Ser Pro His Ala Ser Arg Lys Ser Trp
    2690            2695            2700

Pro Gln Val Val Ser Arg Ala Ser Ala Ala Lys Pro Pro Ser Phe
    2705            2710            2715

Pro Pro Leu Ser Ser Ser Ser Thr Val Thr Ser Ser Cys Ser
    2720            2725            2730

Thr Ser Gly Val Gln Pro Ser Met Pro Thr Asp Tyr Ser Glu
    2735            2740            2745

Glu Ser Asp Thr Asp Leu Ser Gln Lys Ser Asp Gly Pro Ala Ser
    2750            2755            2760

Pro Val Glu Gly Pro Lys Asp Pro Ser Cys Pro Lys Asp Ser Gly
    2765            2770            2775

Leu Thr Ser Val Gly Thr Asp Thr Phe Arg Leu Glx
    2780            2785            2790

<210> SEQ ID NO 5
<211> LENGTH: 8370
<212> TYPE: DNA
<213> ORGANISM: Homo sapiens

<400> SEQUENCE: 5

```
atgcggctcg gggcgggca gctggtgtca gaggagctga tgaacctggg cgagagcttc        60
atccagacca cgacccgtc gctgaagctc ttccagtgcg ccgtctgcaa caagttcacg       120
acggacaacc tggacatgct gggcctgcac atgaacgtgg agcgcagcct gtcggaggac       180
gagtggaagg cggtgatggg ggactcatac cagtgcaagc tctgccgcta caacacccag       240
ctcaaggcca acttccagct gcactgcaag acagacaagc acgtgcagaa gtaccagctg       300
gtggcccaca tcaaggaggg cggcaaggcc aacgagtgga ggctcaagtg tgtggccatc       360
ggcaaccccg tgcacctcaa gtgcaacgcc tgtgactact acaccaacag cctggagaag       420
ctgcggctgc acacggtcaa ctccaggcac gaggccagcc tgaagttgta caagcacctg       480
cagcagcatg agagtggtgt agaaggtgag agctgctact accactgcgt tctgtgcaac       540
tactccacca aggccaagct caacctcatc cagcatgtgc gctccatgaa gcaccagcga       600
agcgagagcc tgcgaaagct gcagcggctg cagaagggcc ttccagagga ggacgaggac       660
ctggggcaga tcttcaccat ccgcaggtgc ccctccacgg acccagaaga agccattgaa       720
gatgttgaag acccagtgaa acagctgctg atccagaggg agcttgctaa ggaccaagag       780
ggcggagcat cgtccagcca agcagagaag gagctgacag attctcctgc aacctccaaa       840
cgcatctcct tcccaggtag ctcagagtct cccctctctt cgaagcgacc aaaaacagct       900
gaggagatca aaccggagca gatgtaccag tgtccctact gcaagtacag taatgccgat       960
gtcaaccggc tccgggtgca tgccatgacg cagcactcgg tgcaacccat gcttcgctgc      1020
cccctgtgcc aggacatgct caacaacaag atccacctcc agctgcacct caccacctc      1080
cacagcgtgg cacctgactg cgtggagaag ctcattatga cggtgaccac ccctgagatg      1140
```

```
gtgatgccaa gcagcatgtt cctcccagca gctgttccag atcgagatgg gaattccaat    1200
ttggaagagg caggaaagca gcctgaaacc tcagaggatc tgggaaagaa catcttgcca    1260
tccgcaagca cagagcaaag cggagatttg aaaccatccc ctgctgaccc aggctctgtg    1320
agagaagact caggcttcat ctgctggaag aagggggtgca accaggtttt caaaacttct    1380 gctgccttc agacgcattt taatgaagtg catgccaaga ggcctcagct gccggtgtca    1440
gatcgccatg tgtacaagta ccgctgtaat cagtgtagcc tggccttcaa gaccattgaa    1500
aagttgcagc tccattctca gtaccatgtg atcagagctg ccaccatgtg ctgtctttgt    1560
cagcgcagtt tccgaacttt ccaggctctg aagaagcacc ttgagacaag ccacctggag    1620
ctgagtgagg ctgacatcca acagctttat ggtggcctgc tggccaatgg ggacctcctg    1680
gcaatgggag accccactct ggctgaggac ataccataa ttgttgagga agacaaggag    1740
gaagagagtg acttggaaga taaacagagc ccaacgggca gtgactctgg gtcagtacaa    1800
gaagactcgg gctcagagcc aaagagagct ctgcctttca gaaaaggtcc caatttact    1860 atggaaaagt tcctagaccc ttctcgccct tacaagtgta ccgtctgcaa ggaatctttc    1920
actcaaaaga atatcctgct agtacactac aattctgtct cccacctgca taagttaaag    1980
agagcccttc aagaatcagc aaccggtcag ccagaaccca ccagcagccc agacaacaaa    2040
ccttttaagt gtaacacttg taatgtggcc tacagccaga gttccactct ggagatccat    2100
atgaggtctg tgttacatca aaccaaggcc cgggcagcca agctggaggc tgcaagtggc    2160
agcagcaatg ggactgggaa cagcagcagt atttccttga gctcctccac gccaagtcct    2220
gtgagcacca gtggcagtaa caccttacc acctccaatc aagcagtgc tggcattgct    2280 ccaagctcta acttactaag ccaagtgccc actgagagtg tagggatgcc accctgggg    2340 aatcctattg gtgccaacat tgcttcccct tcagagccca agaggccaa tcggaagaaa    2400 ctggcagata tgattgcatc caggcagcag caacaacagc agcagcaaca gcaacaacaa    2460
caacaacaac aacaacaaca agcacaaacg ctggcccagg cccaggctca agttcaagct    2520
cacctgcagc aggagctgca gcaacaggct gccctgatcc agtctcagct gtttaaccc    2580 accctccttc ctcacttccc catgacaact gagaccctgc tgcaactaca gcagcagcag    2640
cacctcctct ccctttcta catccccagt gctgagttcc agcttaaccc cgaggtgagc    2700
ttgccagtga ccagtggggc actgacactg actgggacag gccaggcct gctggaagat    2760 ctgaaggctc aggttcaggt cccacagcag agccatcagc agatcttgcc gcagcagcag    2820
cagaaccaac tctctatagc ccagagtcac tctgccctcc ttcagccaag ccagcacccc    2880
gaaaagaaga acaaattggt catcaaagaa aggaaaaag aaagccagag agagagggac    2940
agcgccgagg ggggagaggg caacaccggt ccgaaggaaa cactgccaga tgccttgaag    3000
gccaaagaga agaaagagtt ggcaccaggg ggtggttctg agccttccat gctccctcca    3060
cgcattgctt cagatgccag agggaacgcc accaaggccc tgctggagaa ctttggcttt    3120
gagttggtca tccagtataa tgagaacaag cagaaggtgc agaaaaagaa tgggaagact    3180
gaccagggag agaacctgga aaagctcgag tgtgactcct gcggcaagtt gttttccaac    3240
atcttgattt taaagagtca tcaagagcac gttcatcaga attactttcc tttcaaacag    3300
ctcgagaggt ttgccaaaca gtacagagac cactacgata aactgtaccc actgaggccc    3360
cagaccccag agccaccacc acctccccct ccaccccctc caccccccact tccggcagcg    3420 ccgcctcagc cggcgtccac accagccatc cccgcatcag ccccacccat cacctcacct    3480
acaattgcac cggcccagcc atcagtgccg ctcacccagc tctccatgcc gatggagctg    3540
```

```
cccatcttct cgccgctgat gatgcagacg atgccgctgc agaccttgcc ggctcagcta    3600
cccccgcagc tgggacctgt ggagcctctg cctgcggacc tgcccaact ctaccagcat    3660 cagctcaatc caaccctgct ccagcagcag aacaagaggc ctcgcaccag gatcacagat    3720
gatcagctcc gagtcttgcg gcaatatttt gacattaaca actcccccag tgaagagcaa    3780
ataaaagaga tggcagacaa gtccggggttg ccccagaaag tgatcaagca ctggttcagg    3840
aacactctct tcaaagagag gcagcgtaac aaggactccc cttacaactt cagtaatcct    3900
cctatcacca gcctggagga gctcaagatt gactcccggc cccttcgcc ggaacctcca    3960 aagcaggagt actggggaag caagaggtct tcaagaacaa ggtttacgga ctaccagctg    4020
agggtcttac aggacttctt cgatgccaat gcttacccaa aggatgatga atttgagcaa    4080
ctctctaatt tactgaacct tccaacccga gtgatagtgg tgtggtttca gaatgcccga    4140
cagaaggcca ggaagaatta tgagaatcag ggagagggca agatggaga gcggcgtgag    4200 cttacaaatg atagatacat tcgaacaagc aacttgaact accagtgcaa aaaatgtagc    4260
ctggtgtttc agcgcatctt tgatctcatc aagcaccaga agaagctgtg ttacaaggat    4320
gaggatgagg aggggcagga cgacagccaa aatgaggatt ccatggatgc catggaaatc    4380
ctgacgccta ccagctcatc ctgcagtacc ccgatgccct cacaggctta cagcgcccca    4440
gcaccatcag ccaataatac agcttcctcc gctttcttgc agcttacagc ggaggctgag    4500
gaactggcca ccttcaattc aaaaacagag gcaggcgatg agaaaccaaa gctggcggaa    4560
gctcccagtg cacagccaaa ccaaacccaa gaaaagcaag acaaccaaa gccagagctg    4620 cagcagcaag agcagcccga gcagaagacc aacactcccc agcagaagct ccccagctg    4680 gtgtccctgc cttcgttgcc acagcctcct ccacaagcgc cccctccaca gtgccccttca    4740 ccccagtcga gccccagtcc ttcccagctc tcccacctgc ccctcaagcc cctccacaca    4800
tcaactcctc aacagctcgc aaacctacct cctcagctaa tccctacca gtgtgaccag    4860 tgtaagttgg catttccgtc atttgagcac tggcaggagc atcagcagct ccacttcctg    4920
agcgcgcaga accagttcat ccaccccag ttttttggaca ggtccctgga tatgcctttc    4980
atgctctttg atcccagtaa cccactcctg gccagccagc tgctctctgg ggccatacct    5040
cagattccag caagctcagc cacttctcct tcaactccaa cctccacaat gaacactctc    5100
aagaggaagc tggaggaaaa ggccagtgca agccctggcg aaaacgacag tgggacagga    5160
ggagaagagc ctcagagaga caagcgtttg agaacaacca tcacccggga caactagaa    5220 attctctacc agaagtatct actggattcc aatccgactc gaaagatgtt ggatcacatt    5280
gcacacgagg tgggcttgaa gaacgtgtg gtacaagtct ggtttcagaa cacccgagct    5340 cgggaagga aaggacagtt ccgggctgta ggcccagcgc aggcccacag gagatgccct    5400
ttttgcagag cgctcttcaa agccaagact gctcttgagg ctcatatccg gtcccgtcac    5460
tggcatgaag ccaagagagc tggctacaac ctaactctgt ctgcgatgct cttagactgt    5520
gatgggggac tccagatgaa aggagatatt tttgacggaa ctagcttttc ccacctaccc    5580
ccaagcagta gtgatggtca gggtgtcccc ctctcacctg tgagtaaaac catggaattg    5640
tcacccagaa ctcttctaag cccttcctcc attaaggtgg aagggattga agactttgaa    5700
agcccctcca tgtcctcagt taatctaaac tttgaccaaa ctaagctgga caacgatgac    5760
tgttcctctg tcaacacagc aatcacagat accacaactg gagacgaggg caacgcagat    5820
aacgacagtg caacgggaat agcaactgaa accaaatcct cttctgcacc caacgaaggg    5880
```

```
ttgaccaaag cggccatgat ggcaatgtct gagtatgaag atcggttgtc atctggtctg   5940
gtcagcccgg ccccgagctt ttatagcaag gaatatgaca atgaaggtac agtggactac   6000
agtgaaacct caagccttgc agatccctgc tccccgagtc ctggtgcgag tggatctgca   6060
ggcaaatctg gtgacagcgg agatcggcct gggcagaaac gttttcgcac tcaaatgacc   6120
aatctgcagc tgaaggtcct caagtcatgc tttaatgact acaggacacc cactatgcta   6180
gaatgtgagg tcctgggcaa tgacattgga ctgccaaaga gagtcgttca ggtctggttc   6240
cagaatgccc gggcaaaaga aaagaagtcc aagttaagca tggccaagca ttttggtata   6300
aaccaaacga gttatgaggg acccaaaaca gagtgcactt tgtgtggcat caagtacagc   6360
gctcggctgt ctgtacgtga ccatatcttt tcccaacagc atatctccaa agttaaagac   6420
accattggaa gccagctgga caaggagaaa gaatactttg acccagccac cgtacgtcag   6480
ttgatggctc aacaagagtt ggaccggatt aaaaaggcca acgaggtcct tggactggca   6540
gctcagcagc aagggatgtt tgacaacacc cctcttcagg cccttaacct tcctacagca   6600
tatccagcgc tccagggcat tcctcctgtg ttgctcccgg gcctcaacag cccctccttg   6660
ccaggcttta ctccatccaa cacagcttta acgtctccta agccgaactt gatgggtctg   6720
cccagcacaa ctgttccttc cctggcctc cccacttctg gattaccaaa taaaccgtcc   6780
tcagcgtcgc tgagctcccc aaccccagca caagccacga tggcgatggg ccctcagcaa   6840
cccccccagc agcagcagca gcagcagcaa ccacaggtgc agcagcctcc ccgccgcca   6900 gcagcccagc cgccacccac accacagctc ccactgcaac agcagcagca acgcaaggac   6960
aaagacagtg agaaagtaaa ggagaaggaa aaggcacaca aagggaaagg ggaaccctg   7020 cctgtcccca agaaggagaa aggagaggcc cccacggcaa ctgcagccac gatctcagcc   7080
ccgctgccca ccatggagta tgcggtagac cctgcacagc tgcaggccct gcaggccgcg   7140
ttgacttcgg accccacagc attgctcaca agccagttcc ttccttactt tgtaccaggc   7200
ttttctcctt attatgctcc ccagatccct ggcgccctgc agagcgggta cctgcagcct   7260
atgtatggca tggaaggcct gttccctac agccctgcac tgtcgcaggc cctgatgggg   7320
ctgtccccag gctccctact gcagcagtac cagcaatacc agcagagtct gcaggaggca   7380
attcagcagc agcagcagcg gcaactacag cagcagcagc agcaaaaagt gcagcagcag   7440
cagcccaaag caagccaaac cccagtcccc ccgggggctc cttccccaga caaagaccct   7500
gccaaagaat cccccaaacc agaagaacag aaaaacaccc ccgtgaggt gtccccctc   7560 ctgccgaaac tccctgaaga gccagaagca gaaagcaaaa gtgcggactc cctctacgac   7620
cccttcattg ttccaaaggt gcagtacaag ttggtctgcc gcaagtgcca ggcgggcttc   7680
agcgacgagg aggcagcgag gagccacctg aagtccctct gcttcttcgg ccagtctgtg   7740
gtgaacctgc aagagatggt gcttcacgtc cccaccggcg gcggcggcgg tggcagtggc   7800
ggcggcggcg gcgtggcgg cggcggcggc ggcggcggct cgtaccactg cctggcgtgc   7860
gagagcgcgc tctgtgggga ggaagctctg agtcaacatc tcgagtcggc cttgcacaaa   7920
cacagaacaa tcacgagagc agcaagaaac gccaaagagc accctagttt attacctcac   7980
tctgcctgct tccccgatcc tagcaccgca tctacctcgc agtctgccgc tcactcaaac   8040
gacagccccc ctcccccgtc ggccgccgcc cctcctccg cttcccccca cgcctccagg   8100
aagtcttggc cgcaagtggt ctcccgggct tcggcagcga agccccctc ttttcctcct   8160 ctctcctcat cttcaacggt tacctcaagt tcatgcagca cctcagggt tcagccctcg   8220 atgccaacag acgactattc ggaggagtct gacacggatc tcagccaaaa gtccgacgga   8280
```

```
ccggcgagcc cggtggaggg tcccaaagac cccagctgcc ccaaggacag tggtctgacc      8340
agtgtaggaa cggacacctt cagattgtaa                                      8370
```

<210> SEQ ID NO 6
<211> LENGTH: 12
<212> TYPE: PRT
<213> ORGANISM: Homo sapiens

<400> SEQUENCE: 6

Cys Asp Ser Pro Val Ser Gly Lys Asp Asn Gly
1               5                   10

<210> SEQ ID NO 7
<211> LENGTH: 18
<212> TYPE: PRT
<213> ORGANISM: Homo sapiens

<400> SEQUENCE: 7

Cys Lys Ser Ser Glu Gly Lys Asp Ser Gly Ala Ala Glu Gly Glu Lys
1               5                   10                  15

Gln Glu

<210> SEQ ID NO 8
<211> LENGTH: 18
<212> TYPE: PRT
<213> ORGANISM: Homo sapiens

<400> SEQUENCE: 8

Cys Pro Ser Glu Leu Asp Glu Glu Leu Glu Asp Arg Pro His Glu Glu
1               5                   10                  15

Pro Gly

<210> SEQ ID NO 9
<211> LENGTH: 14
<212> TYPE: PRT
<213> ORGANISM: Homo sapiens

<400> SEQUENCE: 9

Cys Ile Val Glu Ser Leu Ser Gln Leu Thr Gln Gly Gly Gly
1               5                   10

<210> SEQ ID NO 10
<211> LENGTH: 145
<212> TYPE: PRT
<213> ORGANISM: Homo sapiens

<400> SEQUENCE: 10

Pro Gly Ala Pro Ser Pro Asp Lys Asp Pro Ala Lys Glu Ser Pro Lys
1               5                   10                  15

Pro Glu Glu Gln Lys Asn Thr Pro Arg Glu Val Ser Pro Leu Leu Pro
                20                  25                  30

Lys Leu Pro Glu Glu Pro Glu Ala Glu Ser Lys Ser Ala Asp Ser Leu
            35                  40                  45

Tyr Asp Pro Phe Ile Val Pro Lys Val Gln Tyr Lys Leu Val Cys Arg
        50                  55                  60

Lys Cys Gln Ala Gly Phe Ser Asp Glu Glu Ala Arg Ser His Leu
65                  70                  75                  80

Lys Ser Leu Cys Phe Phe Gly Gln Ser Val Val Asn Leu Gln Glu Met
                85                  90                  95

```
Val Leu His Val Pro Thr Gly Gly Gly Gly Gly Ser Gly Gly Gly
            100                 105                 110
Gly Gly Gly Gly Gly Gly Gly Gly Gly Ser Tyr His Cys Leu
        115                 120                 125
Ala Cys Glu Ser Ala Leu Cys Gly Glu Glu Ala Leu Ser Gln His Leu
    130                 135                 140
Glu
145

<210> SEQ ID NO 11
<211> LENGTH: 906
<212> TYPE: PRT
<213> ORGANISM: Homo sapiens

<400> SEQUENCE: 11

Met Glu Gly Cys Asp Ser Pro Val Val Ser Gly Lys Asp Asn Gly Cys
1               5                   10                  15
Gly Ile Pro Gln His Gln Gln Trp Thr Glu Leu Asn Ser Thr His Leu
            20                  25                  30
Pro Asp Lys Pro Ser Ser Met Glu Gln Ser Thr Gly Glu Ser His Gly
        35                  40                  45
Pro Leu Asp Ser Leu Arg Ala Pro Phe Asn Glu Arg Leu Ala Glu Ser
    50                  55                  60
Thr Ala Ser Ala Gly Pro Pro Ala Glu Pro Ala Ser Lys Glu Val Thr
65                  70                  75                  80
Cys Asn Glu Cys Ser Ala Ser Phe Ala Ser Leu Gln Thr Tyr Met Glu
                85                  90                  95
His His Cys Pro Ser Ala Arg Pro Pro Pro Leu Arg Glu Glu Ser
            100                 105                 110
Ala Ser Asp Thr Gly Glu Glu Gly Asp Glu Glu Ser Asp Val Glu Asn
        115                 120                 125
Leu Ala Gly Glu Ile Val Tyr Gln Pro Asp Gly Ser Ala Tyr Ile Val
    130                 135                 140
Glu Ser Leu Ser Gln Leu Thr Gln Gly Gly Ala Cys Gly Ser Gly
145                 150                 155                 160
Ser Gly Ser Gly Pro Leu Pro Ser Leu Phe Leu Asn Ser Leu Pro Gly
                165                 170                 175
Ala Gly Gly Lys Gln Gly Asp Pro Ser Cys Ala Ala Pro Val Tyr Pro
            180                 185                 190
Gln Ile Ile Asn Thr Phe His Ile Ala Ser Ser Phe Gly Lys Trp Phe
        195                 200                 205
Glu Gly Pro Asp Gln Ala Phe Pro Asn Thr Ser Ala Leu Ala Gly Leu
    210                 215                 220
Ser Pro Val Leu His Ser Phe Arg Val Phe Asp Val Arg His Lys Ser
225                 230                 235                 240
Asn Lys Asp Tyr Leu Asn Ser Asp Gly Ser Ala Lys Ser Ser Cys Val
                245                 250                 255
Ser Lys Asp Val Pro Asn Asn Val Asp Leu Ser Lys Phe Asp Gly Phe
            260                 265                 270
Val Leu Tyr Gly Lys Arg Lys Pro Ile Leu Met Cys Phe Leu Cys Lys
        275                 280                 285
Leu Ser Phe Gly Tyr Val Arg Ser Phe Val Thr His Ala Val His Asp
    290                 295                 300
His Arg Met Thr Leu Ser Glu Asp Glu Arg Lys Ile Leu Ser Asn Lys
305                 310                 315                 320
```

-continued

```
Asn Ile Ser Ala Ile Ile Gln Gly Ile Gly Lys Asp Lys Glu Pro Leu
                325                 330                 335

Val Ser Phe Leu Glu Pro Lys Asn Lys Asn Phe Gln His Pro Leu Val
            340                 345                 350

Ser Thr Ala Asn Leu Ile Gly Pro Gly His Ser Phe Tyr Gly Lys Phe
        355                 360                 365

Ser Gly Ile Arg Met Glu Gly Glu Ala Leu Pro Ala Gly Ser Ala
    370                 375                 380

Ala Gly Pro Glu Gln Pro Gln Ala Gly Leu Leu Thr Pro Ser Thr Leu
385                 390                 395                 400

Leu Asn Leu Gly Gly Leu Thr Ser Ser Val Leu Lys Thr Pro Ile Thr
                405                 410                 415

Ser Val Pro Leu Gly Ala Leu Ala Ser Ser Pro Thr Lys Ser Ser Glu
            420                 425                 430

Gly Lys Asp Ser Gly Ala Ala Glu Gly Glu Lys Gln Glu Val Gly Asp
        435                 440                 445

Gly Asp Cys Phe Ser Glu Lys Val Glu Pro Ala Glu Glu Ala Glu
    450                 455                 460

Glu Glu Glu Glu Glu Glu Ala Glu Glu Glu Glu Glu Glu Glu Glu
465                 470                 475                 480

Glu Glu Glu Glu Glu Glu Glu Asp Glu Gly Cys Lys Gly Leu Phe Pro
                485                 490                 495

Ser Glu Leu Asp Glu Glu Leu Glu Asp Arg Pro His Glu Glu Pro Gly
            500                 505                 510

Ala Ala Ala Gly Ser Ser Ser Lys Lys Asp Leu Ala Leu Ser Asn Gln
        515                 520                 525

Ser Ile Ser Asn Ser Pro Leu Met Pro Asn Val Leu Gln Thr Leu Ser
    530                 535                 540

Arg Gly Thr Ala Ser Thr Ser Ser Asn Ser Ala Ser Ser Phe Val Val
545                 550                 555                 560

Phe Asp Gly Ala Asn Arg Arg Asn Arg Leu Ser Phe Asn Ser Glu Gly
                565                 570                 575

Val Arg Thr Asn Val Ala Glu Gly Gly Arg Arg Leu Asp Phe Ala Asp
            580                 585                 590

Glu Ser Ala Asn Lys Asp Asn Ala Thr Ala Pro Glu Pro Asn Glu Ser
        595                 600                 605

Thr Glu Gly Asp Asp Gly Gly Phe Val Pro His His Gln His Ala Gly
    610                 615                 620

Ser Leu Cys Glu Leu Gly Val Gly Glu Cys Pro Ser Gly Ser Gly Val
625                 630                 635                 640

Glu Cys Pro Lys Cys Asp Thr Val Leu Gly Ser Ser Arg Ser Leu Gly
                645                 650                 655

Gly His Met Thr Met Met His Ser Arg Asn Ser Cys Lys Thr Leu Lys
            660                 665                 670

Cys Pro Lys Cys Asn Trp His Tyr Lys Tyr Gln Gln Thr Leu Glu Ala
        675                 680                 685

His Met Lys Glu Lys His Pro Glu Pro Gly Gly Ser Cys Val Tyr Cys
    690                 695                 700

Lys Ser Gly Gln Pro His Pro Arg Leu Ala Arg Gly Glu Ser Tyr Thr
705                 710                 715                 720

Cys Gly Tyr Lys Pro Phe Arg Cys Glu Val Cys Asn Tyr Ser Thr Thr
                725                 730                 735
```

```
Thr Lys Gly Asn Leu Ser Ile His Met Gln Ser Asp Lys His Leu Asn
            740                 745                 750
Asn Met Gln Asn Leu Gln Asn Gly Gly Glu Gln Val Phe Ile His
        755                 760                 765
Thr Ala Gly Ala Ala Ala Ala Ala Ala Ala Ala Ala Ala Ala
        770                 775                 780
Asn Ile Ser Ser Cys Gly Ala Pro Ser Pro Thr Lys Pro Lys Thr
785                 790                 795                 800
Lys Pro Thr Trp Arg Cys Glu Val Cys Asp Tyr Glu Thr Asn Val Ala
            805                 810                 815
Arg Asn Leu Arg Ile His Met Thr Ser Glu Lys His Met His Asn Met
            820                 825                 830
Met Leu Leu Gln Gln Asn Met Thr Gln Ile Gln His Asn His Arg
        835                 840                 845
Val Leu Gly Ser Leu Pro Ser Pro Ala Glu Ala Glu Leu Tyr Gln Tyr
        850                 855                 860
Tyr Leu Ala Gln Asn Met Asn Leu Pro Asn Leu Lys Met Asp Ser Ala
865                 870                 875                 880
Ala Ser Asp Ala Gln Phe Met Met Ser Gly Phe Gln Leu Asp Pro Ala
            885                 890                 895
Gly Pro Met Ala Ala Met Thr Pro Ala Leu
            900                 905

<210> SEQ ID NO 12
<211> LENGTH: 2719
<212> TYPE: DNA
<213> ORGANISM: Homo sapiens

<400> SEQUENCE: 12
atggaaggct gtgactcgcc cgtcgtctcg gggaaggaca atgggtgcgg tatccctcag      60
caccagcaat ggactgaact caacagcacc cacctccctg acaaacccag tagcatggaa     120
cagtccacag gcgagagcca cgggcccttg acagcctga gggccccctt caatgagcgc     180
ctcgcggaga gcaccgcgtc ggccgggccc ccgccgagc cgccagcaa ggaggtcacc     240
tgcaacgaat gttcggcctc ctttgccagc ctccagacct acatggagca ccactgcccc     300
agcgcgcgcc ccccgccacc cctgagagag gagagcgcta cgacaccgg tgaggagggg     360
gacgaggaga gtgacgtgga gaacctggcc ggggagatcg tctaccagcc ggacggctcc     420
gcatacattg tggagagcct gagccagctg acccagggcg gggcgcctg tgggagtggc     480
agtggcagtg ggcctctccc ctcgcttttc ctgaactctc tccctggcgc ggggggcaag     540
caagggacc cttcgtgtgc tgcacccgtg tacccgcaga tcatcaacac tttccacata     600
gcctcatcct tcgggaaatg gtttgagggc ccagaccagg ctttcccgaa tacctcagcc     660
ctggcggggc tcagccccgt cctgcacagc ttccgcgtgt ttgacgtgcg acacaaaagc     720
aacaaggatt acctgaacag cgacggttct gccaaaagct cctgcgtatc caagatgtt     780
cccaacaatg tggacctgtc caattcgat ggctttgtgc tctatggcaa gaggaagccc     840
atcctgatgt gtttcttgtg caaactctcc tttgggtacg tccgttcgtt tgtgacccac     900
gcggtgcatg accatcgaat gaccctgagc gaagacgagc ggaaaattct tagcaataag     960
aacatctccg ctatcatcca agggatcggc aaagacaagg aaccccttgt aagttttctg    1020
gaaccaaaaa acaaaaactt tcaacaccct ttagtttcca cagctaacct cataggcccc    1080
ggacacagtt tttatggtaa atttagtggc attcgaatgg aaggggagga agctctccca    1140
```

-continued

```
gcgggctccg ccgctggccc cgagcagccc caggctggtc tcttgacccc cagcaccctg   1200
ttgaaccttg gcgggctcac cagctcggta ctgaagaccc ccattacctc agtcccsctg   1260
ggggctctgg cttccagtcc taccaaatcc tcagagggca aggactctgg ggcggcagaa   1320
ggagagaagc aggaagtggg cgacggggat tgcttctctg agaaggtaga gccagccgaa   1380
gaggaggcgg aggaggaaga ggaggaggaa gaggcggagg aggaggagga agaagaggag   1440
gaggaagaag aggaggagga gacgagggt tgcaaaggac tctttccaag cgagttggat   1500
gaggaactgg aggacaggcc ccatgaggag cctggggccg cagcaggtag tagcagcaaa   1560
aaggaccttg ctctctcaaa ccaaagcatt tctaactccc ccttaatgcc taacgtgctc   1620
cagaccctgt cgaggggcac agcttctact agttctaatt ctgcttcttc ctttgttgtc   1680
tttgatggtg cgaacaggag gaatcgttta agctttaaca gtgagggcgt caggaccaat   1740
gtggcagagg gcggcaggag gctggacttc gctgacgaaa gtgccaataa agacaatgcc   1800
acagcaccag aaccaaatga agtacagag ggtgacgatg ggggcttcgt tccccatcac   1860
cagcacgctg gctccctctg cgagcttggg gttggggagt gccctcgggg agtggcgtg   1920 gagtgcccca aatgcgacac ggtcctgggc tcctcccgct cgctgggcgg ccacatgacc   1980
atgatgcatt ctcgtaactc gtgtaagaca ctcaagtgcc ccaagtgcaa ctggcactat   2040
aagtaccagc agaccctgga ggcacacatg aaggagaagc accggagcc ggggggctcc   2100 tgtgtctact gcaaaagcgg gcagccccac ccccggctgg cacgaggcga gagctacacg   2160
tgtggttaca gccttttccg ctgcgaggtg tgtaactact ccacaactac caaaggcaac   2220
ctcagtattc atatgcagtc tgacaagcat ctcaacaaca tgcagaacct acagaatgga   2280
gggggggagc aggtcttcat ccacactgcc ggggcggcgg cggcggcggc ggctgcggcg   2340
gcggcggcag ccaatatcag tagctcctgc ggggcccct cgcccaccaa accaaaaacc   2400
aaacccacct ggcggtgcga ggtgtgtgat tatgagacca acgtggccag gaacctccgc   2460
attcacatga ccagtgagaa gcacatgcat aacatgatgt tactgcaaca gaacatgacc   2520
cagatccaac acaaccacca ccgggtcctc ggcagcctgc cctcacccgc cgaggccgag   2580
ctctaccaat actacctggc ccagaacatg aacctgccca acctgaagat ggacagtgct   2640
gcctcggacg cccagttcat gatgagcgga ttccagctgg atcccgccgg gcccatggcc   2700
gccatgacgc ctgctctag                                             2719
```

<210> SEQ ID NO 13
<211> LENGTH: 1819
<212> TYPE: PRT
<213> ORGANISM: Homo sapiens

<400> SEQUENCE: 13

```
Thr Ser Glu Asp Leu Gly Lys Asn Ile Leu Pro Ser Ala Ser Thr Glu
1               5                   10                  15

Gln Ser Gly Asp Leu Lys Pro Ser Pro Ala Asp Pro Gly Ser Val Arg
            20                  25                  30

Glu Asp Ser Gly Phe Ile Cys Trp Lys Lys Gly Cys Asn Gln Val Phe
        35                  40                  45

Lys Thr Ser Ala Ala Leu Gln Thr His Phe Asn Glu Val His Ala Lys
    50                  55                  60

Arg Pro Gln Leu Pro Val Ser Asp Arg His Val Tyr Lys Tyr Arg Cys
65                  70                  75                  80

Asn Gln Cys Ser Leu Ala Phe Lys Thr Ile Glu Lys Leu Gln Leu His
                85                  90                  95
```

```
Ser Gln Tyr His Val Ile Arg Ala Ala Thr Met Cys Cys Leu Cys Gln
            100                 105                 110

Arg Ser Phe Arg Thr Phe Gln Ala Leu Lys Lys His Leu Glu Thr Ser
        115                 120                 125

His Leu Glu Leu Ser Glu Ala Asp Ile Gln Gln Leu Tyr Gly Gly Leu
    130                 135                 140

Leu Ala Asn Gly Asp Leu Leu Ala Met Gly Asp Pro Thr Leu Ala Glu
145                 150                 155                 160

Asp His Thr Ile Ile Val Glu Glu Asp Lys Glu Glu Glu Ser Asp Leu
                165                 170                 175

Glu Asp Lys Gln Ser Pro Thr Gly Ser Asp Ser Gly Ser Val Gln Glu
            180                 185                 190

Asp Ser Gly Ser Glu Pro Lys Arg Ala Leu Pro Phe Arg Lys Gly Pro
        195                 200                 205

Asn Phe Thr Met Glu Lys Phe Leu Asp Pro Ser Arg Pro Tyr Lys Cys
    210                 215                 220

Thr Val Cys Lys Glu Ser Phe Thr Gln Lys Asn Ile Leu Leu Val His
225                 230                 235                 240

Tyr Asn Ser Val Ser His Leu His Lys Leu Lys Arg Ala Leu Gln Glu
                245                 250                 255

Ser Ala Thr Gly Gln Pro Glu Pro Thr Ser Ser Pro Asp Asn Lys Pro
            260                 265                 270

Phe Lys Cys Asn Thr Cys Asn Val Ala Tyr Ser Gln Ser Ser Thr Leu
        275                 280                 285

Glu Ile His Met Arg Ser Val Leu His Gln Thr Lys Ala Arg Ala Ala
    290                 295                 300

Lys Leu Glu Ala Ala Ser Gly Ser Ser Asn Gly Thr Gly Asn Ser Ser
305                 310                 315                 320

Ser Ile Ser Leu Ser Ser Ser Thr Pro Ser Pro Val Ser Thr Ser Gly
                325                 330                 335

Ser Asn Thr Phe Thr Thr Ser Asn Pro Ser Ser Ala Gly Ile Ala Pro
            340                 345                 350

Ser Ser Asn Leu Leu Ser Gln Val Pro Thr Glu Ser Val Gly Met Pro
        355                 360                 365

Pro Leu Gly Asn Pro Ile Gly Ala Asn Ile Ala Ser Pro Ser Glu Pro
    370                 375                 380

Lys Glu Ala Asn Arg Lys Lys Leu Ala Asp Met Ile Ala Ser Arg Gln
385                 390                 395                 400

Gln Gln Gln Gln Gln Gln Gln Gln Gln Gln Gln Gln Gln Gln Gln Gln
                405                 410                 415

Gln Gln Ala Gln Thr Leu Ala Gln Ala Gln Ala Gln Val Gln Ala His
            420                 425                 430

Leu Gln Gln Glu Leu Gln Gln Ala Ala Leu Ile Gln Ser Gln Leu
        435                 440                 445

Phe Asn Pro Thr Leu Leu Pro His Phe Pro Met Thr Thr Glu Thr Leu
    450                 455                 460

Leu Gln Leu Gln Gln Gln His Leu Leu Phe Pro Phe Tyr Ile Pro
465                 470                 475                 480

Ser Ala Glu Phe Gln Leu Asn Pro Glu Val Ser Leu Pro Val Thr Ser
                485                 490                 495

Gly Ala Leu Thr Leu Thr Gly Thr Gly Pro Gly Leu Leu Glu Asp Leu
            500                 505                 510
```

-continued

```
Lys Ala Gln Val Gln Val Pro Gln Gln Ser His Gln Gln Ile Leu Pro
            515                 520                 525
Gln Gln Gln Gln Asn Gln Leu Ser Ile Ala Gln Ser His Ser Ala Leu
        530                 535                 540
Leu Gln Pro Ser Gln His Pro Glu Lys Lys Asn Lys Leu Val Ile Lys
545                 550                 555                 560
Glu Lys Glu Lys Glu Ser Gln Arg Glu Arg Asp Ser Ala Glu Gly Gly
                565                 570                 575
Glu Gly Asn Thr Gly Pro Lys Glu Thr Leu Pro Asp Ala Leu Lys Ala
            580                 585                 590
Lys Glu Lys Lys Glu Leu Ala Pro Gly Gly Gly Ser Glu Pro Ser Met
        595                 600                 605
Leu Pro Pro Arg Ile Ala Ser Asp Ala Arg Gly Asn Ala Thr Lys Ala
610                 615                 620
Leu Leu Glu Asn Phe Gly Phe Glu Leu Val Ile Gln Tyr Asn Glu Asn
625                 630                 635                 640
Lys Gln Lys Val Gln Lys Asn Gly Lys Thr Asp Gln Gly Glu Asn
                645                 650                 655
Leu Glu Lys Leu Glu Cys Asp Ser Cys Gly Lys Leu Phe Ser Asn Ile
            660                 665                 670
Leu Ile Leu Lys Ser His Gln Glu His Val His Gln Asn Tyr Phe Pro
        675                 680                 685
Phe Lys Gln Leu Glu Arg Phe Ala Lys Gln Tyr Arg Asp His Tyr Asp
            690                 695                 700
Lys Leu Tyr Pro Leu Arg Pro Gln Thr Pro Glu Pro Pro Pro Pro
705                 710                 715                 720
Pro Pro Pro Pro Pro Pro Leu Pro Ala Ala Pro Pro Gln Pro Ala
                725                 730                 735
Ser Thr Pro Ala Ile Pro Ala Ser Ala Pro Ile Thr Ser Pro Thr
            740                 745                 750
Ile Ala Pro Ala Gln Pro Ser Val Pro Leu Thr Gln Leu Ser Met Pro
        755                 760                 765
Met Glu Leu Pro Ile Phe Ser Pro Leu Met Met Gln Thr Met Pro Leu
770                 775                 780
Gln Thr Leu Pro Ala Gln Leu Pro Pro Gln Leu Gly Pro Val Glu Pro
785                 790                 795                 800
Leu Pro Ala Asp Leu Ala Gln Leu Tyr Gln His Gln Leu Asn Pro Thr
            805                 810                 815
Leu Leu Gln Gln Gln Asn Lys Arg Pro Arg Thr Arg Ile Thr Asp Asp
        820                 825                 830
Gln Leu Arg Val Leu Arg Gln Tyr Phe Asp Ile Asn Asn Ser Pro Ser
            835                 840                 845
Glu Glu Gln Ile Lys Glu Met Ala Asp Lys Ser Gly Leu Pro Gln Lys
        850                 855                 860
Val Ile Lys His Trp Phe Arg Asn Thr Leu Phe Lys Glu Arg Gln Arg
865                 870                 875                 880
Asn Lys Asp Ser Pro Tyr Asn Phe Ser Asn Pro Ile Thr Ser Leu
                885                 890                 895
Glu Glu Leu Lys Ile Asp Ser Arg Pro Pro Ser Pro Glu Pro Pro Lys
            900                 905                 910
Gln Glu Tyr Trp Gly Ser Lys Arg Ser Arg Thr Arg Phe Thr Asp
        915                 920                 925
Tyr Gln Leu Arg Val Leu Gln Asp Phe Phe Asp Ala Asn Ala Tyr Pro
```

-continued

```
            930                 935                 940
Lys Asp Asp Glu Phe Glu Gln Leu Ser Asn Leu Leu Asn Leu Pro Thr
945                 950                 955                 960

Arg Val Ile Val Val Trp Phe Gln Asn Ala Arg Gln Lys Ala Arg Lys
                965                 970                 975

Asn Tyr Glu Asn Gln Gly Glu Gly Lys Asp Gly Glu Arg Arg Glu Leu
                980                 985                 990

Thr Asn Asp Arg Tyr Ile Arg Thr Ser Asn Leu Asn Tyr Gln Cys Lys
                995                1000                1005

Lys Cys Ser Leu Val Phe Gln Arg Ile Phe Asp Leu Ile Lys His
    1010                1015                1020

Gln Lys Lys Leu Cys Tyr Lys Asp Glu Asp Glu Gly Gln Asp
    1025                1030                1035

Asp Ser Gln Asn Glu Asp Ser Met Asp Ala Met Glu Ile Leu Thr
    1040                1045                1050

Pro Thr Ser Ser Ser Cys Ser Thr Pro Met Pro Ser Gln Ala Tyr
    1055                1060                1065

Ser Ala Pro Ala Pro Ser Ala Asn Asn Thr Ala Ser Ser Ala Phe
    1070                1075                1080

Leu Gln Leu Thr Ala Glu Ala Glu Glu Leu Ala Thr Phe Asn Ser
    1085                1090                1095

Lys Thr Glu Ala Gly Asp Glu Lys Pro Lys Leu Ala Glu Ala Pro
    1100                1105                1110

Ser Ala Gln Pro Asn Gln Thr Gln Glu Lys Gln Gly Gln Pro Lys
    1115                1120                1125

Pro Glu Leu Gln Gln Gln Gln Pro Glu Gln Lys Thr Asn Thr
    1130                1135                1140

Pro Gln Gln Lys Leu Pro Gln Leu Val Ser Leu Pro Ser Leu Pro
    1145                1150                1155

Gln Pro Pro Gln Ala Pro Pro Pro Gln Cys Pro Leu Pro Gln
    1160                1165                1170

Ser Ser Pro Ser Pro Ser Gln Leu Ser His Leu Pro Leu Lys Pro
    1175                1180                1185

Leu His Thr Ser Thr Pro Gln Leu Ala Asn Leu Pro Pro Gln
    1190                1195                1200

Leu Ile Pro Tyr Gln Cys Asp Gln Cys Lys Leu Ala Phe Pro Ser
    1205                1210                1215

Phe Glu His Trp Gln Glu His Gln Gln Leu His Phe Leu Ser Ala
    1220                1225                1230

Gln Asn Gln Phe Ile His Pro Gln Phe Leu Asp Arg Ser Leu Asp
    1235                1240                1245

Met Pro Phe Met Leu Phe Asp Pro Ser Asn Pro Leu Leu Ala Ser
    1250                1255                1260

Gln Leu Leu Ser Gly Ala Ile Pro Gln Ile Pro Ala Ser Ser Ala
    1265                1270                1275

Thr Ser Pro Ser Thr Pro Thr Ser Thr Met Asn Thr Leu Lys Arg
    1280                1285                1290

Lys Leu Glu Glu Lys Ala Ser Ala Ser Pro Gly Glu Asn Asp Ser
    1295                1300                1305

Gly Thr Gly Gly Glu Glu Pro Gln Arg Asp Lys Arg Leu Arg Thr
    1310                1315                1320

Thr Ile Thr Pro Glu Gln Leu Glu Ile Leu Tyr Gln Lys Tyr Leu
    1325                1330                1335
```

-continued

```
Leu Asp Ser Asn Pro Thr Arg Lys Met Leu Asp His Ile Ala His
    1340                1345                1350
Glu Val Gly Leu Lys Lys Arg Val Val Gln Val Trp Phe Gln Asn
    1355                1360                1365
Thr Arg Ala Arg Glu Arg Lys Gly Gln Phe Arg Ala Val Gly Pro
    1370                1375                1380
Ala Gln Ala His Arg Arg Cys Pro Phe Cys Arg Ala Leu Phe Lys
    1385                1390                1395
Ala Lys Thr Ala Leu Glu Ala His Ile Arg Ser Arg His Trp His
    1400                1405                1410
Glu Ala Lys Arg Ala Gly Tyr Asn Leu Thr Leu Ser Ala Met Leu
    1415                1420                1425
Leu Asp Cys Asp Gly Gly Leu Gln Met Lys Gly Asp Ile Phe Asp
    1430                1435                1440
Gly Thr Ser Phe Ser His Leu Pro Pro Ser Ser Asp Gly Gln
    1445                1450                1455
Gly Val Pro Leu Ser Pro Val Ser Lys Thr Met Glu Leu Ser Pro
    1460                1465                1470
Arg Thr Leu Leu Ser Pro Ser Ser Ile Lys Val Glu Gly Ile Glu
    1475                1480                1485
Asp Phe Glu Ser Pro Ser Met Ser Ser Val Asn Leu Asn Phe Asp
    1490                1495                1500
Gln Thr Lys Leu Asp Asn Asp Asp Cys Ser Ser Val Asn Thr Ala
    1505                1510                1515
Ile Thr Asp Thr Thr Thr Gly Asp Glu Gly Asn Ala Asp Asn Asp
    1520                1525                1530
Ser Ala Thr Gly Ile Ala Thr Glu Thr Lys Ser Ser Ser Ala Pro
    1535                1540                1545
Asn Glu Gly Leu Thr Lys Ala Ala Met Met Ala Met Ser Glu Tyr
    1550                1555                1560
Glu Asp Arg Leu Ser Ser Gly Leu Val Ser Pro Ala Pro Ser Phe
    1565                1570                1575
Tyr Ser Lys Glu Tyr Asp Asn Glu Gly Thr Val Asp Tyr Ser Glu
    1580                1585                1590
Thr Ser Ser Leu Ala Asp Pro Cys Ser Pro Ser Pro Gly Ala Ser
    1595                1600                1605
Gly Ser Ala Gly Lys Ser Gly Asp Ser Gly Asp Arg Pro Gly Gln
    1610                1615                1620
Lys Arg Phe Arg Thr Gln Met Thr Asn Leu Gln Leu Lys Val Leu
    1625                1630                1635
Lys Ser Cys Phe Asn Asp Tyr Arg Thr Pro Thr Met Leu Glu Cys
    1640                1645                1650
Glu Val Leu Gly Asn Asp Ile Gly Leu Pro Lys Arg Val Val Gln
    1655                1660                1665
Val Trp Phe Gln Asn Ala Arg Ala Lys Glu Lys Ser Lys Leu
    1670                1675                1680
Ser Met Ala Lys His Phe Gly Ile Asn Gln Thr Ser Tyr Glu Gly
    1685                1690                1695
Pro Lys Thr Glu Cys Thr Leu Cys Gly Ile Lys Tyr Ser Ala Arg
    1700                1705                1710
Leu Ser Val Arg Asp His Ile Phe Ser Gln Gln His Ile Ser Lys
    1715                1720                1725
```

```
Val Lys Asp Thr Ile Gly Ser     Gln Leu Asp Lys Glu     Lys Glu Tyr
    1730                1735                1740

Phe Asp Pro Ala Thr Val Arg     Gln Leu Met Ala Gln     Gln Glu Leu
    1745                1750                1755

Asp Arg Ile Lys Lys Ala Asn     Glu Val Leu Gly Leu     Ala Ala Gln
    1760                1765                1770

Gln Gln Gly Met Phe Asp Asn     Thr Pro Leu Gln Ala     Leu Asn Leu
    1775                1780                1785

Pro Thr Ala Tyr Pro Ala Leu     Gln Gly Ile Pro Pro     Val Leu Leu
    1790                1795                1800

Pro Gly Leu Asn Ser Pro Ser     Leu Pro Gly Phe Thr     Pro Ser Asn
    1805                1810                1815

Thr

<210> SEQ ID NO 14
<211> LENGTH: 5458
<212> TYPE: DNA
<213> ORGANISM: Homo sapiens

<400> SEQUENCE: 14
acctcagagg atctgggaaa gaacatcttg ccatccgcaa gcacagagca aagcggagat      60
ttgaaaccat cccctgctga cccaggctct gtgagagaag actcaggctt catctgctgg     120 aagaagggt  gcaaccaggt tttcaaaact tctgctgccc ttcagacgca ttttaatgaa     180
gtgcatgcca agaggcctca gctgccggtg tcagatcgcc atgtgtacaa gtaccgctgt     240
aatcagtgta gcctggcctt caagaccatt gaaaagttgc agctccattc tcagtaccat     300
gtgatcagag ctgccaccat gtgctgtctt tgtcagcgca gtttccgaac tttccaggct     360
ctgaagaagc accttgagac aagccacctg gagctgagtg aggctgacat ccaacagctt     420
tatggtggcc tgctggccaa tggggacctc ctggcaatgg agacccccac tctggctgag     480
gaccatacca taattgttga ggaagacaag gaggaagaga gtgacttgga agataaacag     540
agcccaacgg gcagtgactc tgggtcagta caagaagact cgggctcaga gccaaagaga     600
gctctgcctt tcagaaaagg tcccaatttt actatggaaa agttcctaga cccttctcgc     660
ccttacaagt gtaccgtctg caaggaatct ttcactcaaa agaatatcct gctagtacac     720
tacaattctg tctcccacct gcataagtta aagagagccc ttcaagaatc agcaaccggt     780
cagccagaac ccaccagcag cccagacaac aaacctttta gtgtaacac  ttgtaatgtg     840 gcctacagcc agagttccac tctggagatc catatgaggt ctgtgttaca tcaaaccaag     900
gcccgggcag ccaagctgga ggctgcaagt ggcagcagca tgggactgg  aacagcagc     960 agtatttcct tgagctcctc cacgccaagt cctgtgagca ccagtggcag taacaccttt    1020
accacctcca atccaagcag tgctggcatt gctccaagct ctaacttact aagccaagtg    1080
cccactgaga gtgtagggat gccaccccctg gggaatccta ttggtgccaa cattgcttcc    1140
ccttcagagc ccaaagaggc caatcggaag aaactggcag atatgattgc atccaggcag    1200
cagcaacaac agcagcagca acagcaacaa caacaacaac acaagcacaa                1260
acgctggccc aggcccaggc tcaagttcaa gctcacctgc agcaggagct gcagcaacag    1320
gctgccctga tccagtctca gctgtttaac cccaccctcc ttcctcactt ccccatgaca    1380
actgagaccc tgctgcaact acagcagcag cagcacctcc tcttcccttt ctacatcccc    1440
agtgctgagt tccagcttaa ccccgaggtg agcttgccag tgaccagtgg ggcactgaca    1500
ctgactggga caggcccagg cctgctggaa gatctgaagg ctcaggttca ggtcccacag    1560
```

```
cagagccatc agcagatctt gccgcagcag cagcagaacc aactctctat agcccagagt   1620
cactctgccc tccttcagcc aagccagcac cccgaaaaga agaacaaatt ggtcatcaaa   1680
gaaaaggaaa aagaaagcca gagagagagg gacagcgccg agggggggaga gggcaacacc   1740
ggtccgaagg aaacactgcc agatgccttg aaggccaaag agaagaaaga gttggcacca   1800
gggggtggtt ctgagccttc catgctccct ccacgcattg cttcagatgc cagagggaac   1860
gccaccaagg ccctgctgga aactttggc tttgagttgg tcatccagta taatgagaac   1920
aagcagaagg tgcagaaaaa gaatgggaag actgaccagg gagagaacct ggaaaagctc   1980
gagtgtgact cctgcggcaa gttgttttcc aacatcttga ttttaaagag tcatcaagag   2040
cacgttcatc agaattactt tcctttcaaa cagctcgaga ggtttgccaa acagtacaga   2100
gaccactacg ataaactgta cccactgagg ccccagaccc cagagccacc accacctccc   2160
cctccacccc ctccacccc acttccggca gcgccgcctc agccggcgtc cacaccagcc   2220
atccccgcat cagccccacc catcacctca cctacaattg caccggccca gccatcagtg   2280
ccgctcaccc agctctccat gccgatggag ctgcccatct tctcgccgct gatgatgcag   2340
acgatgccgc tgcagacctt gccggctcag ctaccccgc agctgggacc tgtggagcct   2400
ctgcctgcgg acctgcccca actctaccag catcagctca atccaaccct gctccagcag   2460
cagaacaaga ggcctcgcac caggatcaca gatgatcagc tccgagtctt gcggcaatat   2520
tttgacatta caactcccc cagtgaagag caaataaaag agatggcaga caagtccggg   2580
ttgccccaga aagtgatcaa gcactggttc aggaacactc tcttcaaaga gaggcagcgt   2640
aacaaggact cccttacaa cttcagtaat cctcctatca ccagcctgga ggagctcaag   2700
attgactccc ggccccttc gccggaacct ccaaagcagg agtactgggg aagcaagagg   2760
tcttcaagaa caaggtttac ggactaccag ctgagggtct acaggactt cttcgatgcc   2820
aatgcttacc caaggatga tgaatttgag caactctcta atttactgaa ccttccaacc   2880
cgagtgatag tggtgtggtt tcagaatgcc cgacagaagg ccaggaagaa ttatgagaat   2940
cagggagagg gcaaagatgg agagcggcgt gagcttacaa atgatagata cattcgaaca   3000
agcaacttga actaccagtg caaaaaatgt agcctggtgt ttcagcgcat ctttgatctc   3060
atcaagcacc agaagaagct gtgttacaag gatgaggatg aggagggca ggacgacagc   3120
caaaatgagg attccatgga tgccatggaa atcctgacgc ctaccagctc atcctgcagt   3180
accccgatgc cctcacaggc ttacagcgcc ccagcaccat cagccaataa tacagcttcc   3240
tccgctttct tgcagcttac agcggaggct gaggaactgg ccaccttcaa ttcaaaaaca   3300
gaggcaggcg atgagaaacc aaagctggcg gaagctccca gtgcacagcc aaaccaaaacc   3360
caagaaaagc aaggacaacc aaagccagag ctgcagcagc aagagcagcc cgagcagaag   3420
accaacactc cccagcagaa gctccccag ctggtgtccc tgccttcgtt gccacagcct   3480
cctccacaag cgccccctcc acagtgcccc ttacccccagt cgagcccccag tccttcccag   3540
ctctcccacc tgcccctcaa gcccctccac acatcaactc ctcaacagct cgcaaaccta   3600
cctcctcagc taatcccta ccagtgtgac cagtgtaagt tggcatttcc gtcatttgag   3660
cactggcagg agcatcagca gctccacttc ctgagcgcgc agaaccagtt catccacccc   3720
cagttttggg acaggtccct ggatatgcct ttcatgctct ttgatcccag taacccactc   3780
ctggccagcc agctgctctc tggggccata cctcagattc cagcaagctc agccacttct   3840
ccttcaactc caacctccac aatgaacact ctcaagagga agctggagga aaaggccagt   3900
```

```
gcaagccctg gcgaaaacga cagtgggaca ggaggagaag agcctcagag agacaagcgt    3960
ttgagaacaa ccatcacacc ggaacaacta gaaattctct accagaagta tctactggat    4020
tccaatccga ctcgaaagat gttggatcac attgcacacg aggtgggctt gaagaaacgt    4080
gtggtacaag tctggtttca gaacacccga gctcgggaaa ggaaaggaca gttccgggct    4140
gtaggcccag cgcaggccca caggagatgc ccttttttgca gagcgctctt caaagccaag    4200
actgctctcg aggctcatat ccggtcccgt cactggcatg aagccaagag agctggctac    4260
aacctaactc tgtctgcgat gctcttagac tgtgatgggg gactccagat gaaggagat    4320
atttttgacg gaactagctt ttcccaccta cccccaagca gtagtgatgg tcagggtgtc    4380
cccctctcac ctgtgagtaa aaccatggaa ttgtcaccca gaactcttct aagcccttcc    4440
tccattaagg tggaagggat tgaagacttt gaaagcccct ccatgtcctc agttaatcta    4500
aactttgacc aaactaagct ggacaacgat gactgttcct ctgtcaacac agcaatcaca    4560
gataccacaa ctggagacga gggcaacgca gataacgaca gtgcaacggg aatagcaact    4620
gaaaccaaat cctcttctgc acccaacgaa gggttgacca agcggccat gatggcaatg    4680
tctgagtatg aagatcggtt gtcatctggt ctggtcagcc cggcccccgag ctttttatagc    4740
aaggaatatg acaatgaagg tacagtggac tacagtgaaa cctcaagcct tgcagatccc    4800
tgctccccga gtcctggtgc gagtggatct gcaggcaaat ctggtgacag cggagatcgg    4860
cctgggcaga aacgttttcg cactcaaatg accaatctgc agctgaaggt cctcaagtca    4920
tgctttaatg actacaggac acccactatg ctagaatgtg aggtcctggg caatgacatt    4980
ggactgccaa agagagtcgt tcaggtctgg ttccagaatg cccgggcaaa agaaaagaag    5040
tccaagttaa gcatggccaa gcattttggt ataaaccaaa cgagttatga gggacccaaa    5100
acagagtgca ctttgtgtgg catcaagtac agcgctcggc tgtctgtacg tgaccatatc    5160
ttttcccaac agcatatctc caaagttaaa gacaccattg gaagccagct ggacaaggag    5220
aaagaatact ttgacccagc caccgtacgt cagttgatgg ctcaacaaga gttggaccgg    5280
attaaaaagg ccaacgaggt ccttggactg gcagctcagc agcaagggat gtttgacaac    5340
acccctcttc aggcccttaa ccttcctaca gcatatccag cgctccaggg cattcctcct    5400
gtgttgctcc cgggcctcaa cagcccctcc ttgccaggct ttactccatc caacacag     5458
```

<210> SEQ ID NO 15
<211> LENGTH: 562
<212> TYPE: PRT
<213> ORGANISM: Homo sapiens

<400> SEQUENCE: 15

```
Leu Thr Ser Pro Lys Pro Asn Leu Met Gly Leu Pro Ser Thr Thr Val
1               5                   10                  15

Pro Ser Pro Gly Leu Pro Thr Ser Gly Leu Pro Asn Lys Pro Ser Ser
            20                  25                  30

Ala Ser Leu Ser Ser Pro Thr Pro Ala Gln Ala Thr Met Ala Met Gly
        35                  40                  45

Pro Gln Gln Pro Pro Gln Gln Gln Gln Gln Gln Gln Pro Gln Val
    50                  55                  60

Gln Gln Pro Pro Pro Pro Ala Ala Gln Pro Pro Thr Pro Gln
65                  70                  75                  80

Leu Pro Leu Gln Gln Gln Gln Arg Lys Asp Lys Asp Ser Glu Lys
                85                  90                  95

Val Lys Glu Lys Glu Lys Ala His Lys Gly Lys Gly Glu Pro Leu Pro
```

-continued

```
              100                 105                 110
Val Pro Lys Lys Glu Lys Gly Glu Ala Pro Thr Ala Thr Ala Ala Thr
            115                 120                 125

Ile Ser Ala Pro Leu Pro Thr Met Glu Tyr Ala Val Asp Pro Ala Gln
    130                 135                 140

Leu Gln Ala Leu Gln Ala Ala Leu Thr Ser Asp Pro Thr Ala Leu Leu
145                 150                 155                 160

Thr Ser Gln Phe Leu Pro Tyr Phe Val Pro Gly Phe Ser Pro Tyr Tyr
                165                 170                 175

Ala Pro Gln Ile Pro Gly Ala Leu Gln Ser Gly Tyr Leu Gln Pro Met
            180                 185                 190

Tyr Gly Met Glu Gly Leu Phe Pro Tyr Ser Pro Ala Leu Ser Gln Ala
                195                 200                 205

Leu Met Gly Leu Ser Pro Gly Ser Leu Leu Gln Gln Tyr Gln Gln Tyr
    210                 215                 220

Gln Gln Ser Leu Gln Glu Ala Ile Gln Gln Gln Gln Arg Gln Leu
225                 230                 235                 240

Gln Gln Gln Gln Gln Gln Lys Val Gln Gln Gln Pro Lys Ala Ser
                245                 250                 255

Gln Thr Pro Val Pro Pro Gly Ala Pro Ser Pro Asp Lys Asp Pro Ala
            260                 265                 270

Lys Glu Ser Pro Lys Pro Glu Gln Lys Asn Thr Pro Arg Glu Val
    275                 280                 285

Ser Pro Leu Leu Pro Lys Leu Pro Glu Glu Pro Glu Ala Glu Ser Lys
    290                 295                 300

Ser Ala Asp Ser Leu Tyr Asp Pro Phe Ile Val Pro Lys Val Gln Tyr
305                 310                 315                 320

Lys Leu Val Cys Arg Lys Cys Gln Ala Gly Phe Ser Asp Glu Glu Ala
                325                 330                 335

Ala Arg Ser His Leu Lys Ser Leu Cys Phe Phe Gly Gln Ser Val Val
            340                 345                 350

Asn Leu Gln Glu Met Val Leu His Val Pro Thr Gly Gly Gly Gly Gly
    355                 360                 365

Gly Ser Gly Gly Gly Gly Gly Gly Gly Gly Gly Gly Gly Gly Gly Gly
    370                 375                 380

Ser Tyr His Cys Leu Ala Cys Glu Ser Ala Leu Cys Gly Glu Glu Ala
385                 390                 395                 400

Leu Ser Gln His Leu Glu Ser Ala Leu His Lys His Arg Thr Ile Thr
                405                 410                 415

Arg Ala Ala Arg Asn Ala Lys Glu His Pro Ser Leu Leu Pro His Ser
            420                 425                 430

Ala Cys Phe Pro Asp Pro Ser Thr Ala Ser Thr Ser Gln Ser Ala Ala
    435                 440                 445

His Ser Asn Asp Ser Pro Pro Pro Ser Ala Ala Ala Pro Ser Ser
    450                 455                 460

Ala Ser Pro His Ala Ser Arg Lys Ser Trp Pro Gln Val Val Ser Arg
465                 470                 475                 480

Ala Ser Ala Ala Lys Pro Pro Ser Phe Pro Pro Leu Ser Ser Ser Ser
                485                 490                 495

Thr Val Thr Ser Ser Ser Cys Ser Thr Ser Gly Val Gln Pro Ser Met
            500                 505                 510

Pro Thr Asp Asp Tyr Ser Glu Glu Ser Asp Thr Asp Leu Ser Gln Lys
    515                 520                 525
```

Ser Asp Gly Pro Ala Ser Pro Val Glu Gly Pro Lys Asp Pro Ser Cys
    530                 535                 540

Pro Lys Asp Ser Gly Leu Thr Ser Val Gly Thr Asp Thr Phe Arg Leu
545                 550                 555                 560

Glx Ala

<210> SEQ ID NO 16
<211> LENGTH: 1689
<212> TYPE: DNA
<213> ORGANISM: Homo sapiens

<400> SEQUENCE: 16

| | | | | |
|---|---|---|---|---|
| ctttaacgtc | tcctaagccg | aacttgatgg | gtctgcccag | cacaactgtt | ccttcccctg | 60 |
| gcctccccac | ttctggatta | ccaaataaac | cgtcctcagc | gtcgctgagc | tccccaaccc | 120 |
| cagcacaagc | cacgatggcg | atgggccctc | agcaaccccc | ccagcagcag | cagcagcagc | 180 |
| agcaaccaca | ggtgcagcag | cctcccccgc | cgccagcagc | ccagccgcca | cccacaccac | 240 |
| agctcccact | gcaacagcag | cagcaacgca | aggacaaaga | cagtgagaaa | gtaaaggaga | 300 |
| aggaaaaggc | acacaaaggg | aaggggaac | ccctgcctgt | ccccaagaag | gagaaaggag | 360 |
| aggcccccac | ggcaactgca | gccacgatct | cagccccgct | gcccaccatg | gagtatgcgg | 420 |
| tagaccctgc | acagctgcag | gccctgcagg | ccgcgttgac | ttcggacccc | acagcattgc | 480 |
| tcacaagcca | gttccttcct | tactttgtac | caggcttttc | tccttattat | gctccccaga | 540 |
| tccctggcgc | cctgcagagc | gggtacctgc | agcctatgta | tggcatggaa | ggcctgttcc | 600 |
| cctacagccc | tgcactgtcg | caggccctga | tggggctgtc | cccaggctcc | ctactgcagc | 660 |
| agtaccagca | ataccagcag | agtctgcagg | aggcaattca | gcagcagcag | cagcggcaac | 720 |
| tacagcagca | gcagcagcaa | aaagtgcagc | agcagcagcc | caaagcaagc | caaacccag | 780 |
| tccccccgg | ggctccttcc | ccagacaaag | accctgccaa | gaatccccc | aaaccagaag | 840 |
| aacagaaaaa | caccccccgt | gaggtgtccc | ccctcctgcc | gaaactccct | gaagagccag | 900 |
| aagcagaaag | caaaagtgcg | gactccctct | acgaccctt | cattgttcca | aggtgcagt | 960 |
| acaagttggt | ctgccgcaag | tgccaggcgg | gcttcagcga | cgaggaggca | gcgaggagcc | 1020 |
| acctgaagtc | cctctgcttc | ttcggccagt | ctgtggtgaa | cctgcaagag | atggtgcttc | 1080 |
| acgtccccac | cggcggcggc | ggcggtggca | gtggcggcgg | cggcggcggt | ggcggcggcg | 1140 |
| gcggcggcgg | cggctcgtac | cactgcctgg | cgtgcgagag | cgcgctctgt | ggggaggaag | 1200 |
| ctctgagtca | acatctcgag | tcggccttgc | acaaacacag | aacaatcacg | agagcagcaa | 1260 |
| gaaacgccaa | agagcaccct | agtttattac | ctcactctgc | ctgcttcccc | gatcctagca | 1320 |
| ccgcatctac | ctcgcagtct | gccgctcact | caaacgacag | ccccctccc | ccgtcggccg | 1380 |
| ccgcccctc | ctccgcttcc | ccccacgcct | ccaggaagtc | ttggccgcaa | gtggtctccc | 1440 |
| gggcttcggc | agcgaagccc | ccttctttc | ctcctctctc | ctcatcttca | acggttacct | 1500 |
| caagttcatg | cagcacctca | ggggttcagc | cctcgatgcc | aacagacgac | tattcggagg | 1560 |
| agtctgacac | ggatctcagc | caaaagtccg | acggaccggc | gagcccggtg | gagggtccca | 1620 |
| aagaccccag | ctgccccaag | gacagtggtc | tgaccagtgt | aggaacggac | accttcagat | 1680 |
| tgtaagctt | | | | | 1689 |

<210> SEQ ID NO 17
<211> LENGTH: 12
<212> TYPE: PRT

<213> ORGANISM: Homo sapiens

<400> SEQUENCE: 17

Lys Arg Lys Pro Ile Leu Met Cys Phe Leu Cys Lys
1               5                   10

<210> SEQ ID NO 18
<211> LENGTH: 19
<212> TYPE: PRT
<213> ORGANISM: Homo sapiens

<400> SEQUENCE: 18

Lys Arg Val Val Gln Val Trp Phe Gln Asn Ala Arg Ala Lys Glu Lys
1               5                   10                  15

Lys Ser Lys

<210> SEQ ID NO 19
<211> LENGTH: 4
<212> TYPE: PRT
<213> ORGANISM: Homo sapiens

<400> SEQUENCE: 19

Leu Leu Leu Leu
1

<210> SEQ ID NO 20
<211> LENGTH: 8
<212> TYPE: PRT
<213> ORGANISM: Homo sapiens

<400> SEQUENCE: 20

Leu Gln Leu His Leu Thr His Leu
1               5

<210> SEQ ID NO 21
<211> LENGTH: 10
<212> TYPE: PRT
<213> ORGANISM: Homo sapiens

<400> SEQUENCE: 21

Leu Pro Gln Leu Val Ser Leu Pro Ser Leu
1               5                   10

<210> SEQ ID NO 22
<211> LENGTH: 9
<212> TYPE: PRT
<213> ORGANISM: Homo sapiens

<400> SEQUENCE: 22

Leu Ser His Leu Pro Leu Lys Pro Leu
1               5

<210> SEQ ID NO 23
<211> LENGTH: 12
<212> TYPE: PRT
<213> ORGANISM: Mus musculus

<400> SEQUENCE: 23

Cys Asp Ser Pro Val Val Ser Gly Lys Asp Asn Gly
1               5                   10

<210> SEQ ID NO 24
<211> LENGTH: 18
<212> TYPE: PRT

```
<213> ORGANISM: Mus musculus

<400> SEQUENCE: 24

Cys Lys Ser Ser Glu Gly Lys Asp Ser Gly Ala Ala Glu Gly Asp Lys
1               5                   10                  15

Gln Glu

<210> SEQ ID NO 25
<211> LENGTH: 18
<212> TYPE: PRT
<213> ORGANISM: Mus musculus

<400> SEQUENCE: 25

Cys Pro Asn Asp Leu Glu Glu Glu Leu Glu Asp Ser Pro Ser Glu Glu
1               5                   10                  15

Ser Gly

<210> SEQ ID NO 26
<211> LENGTH: 14
<212> TYPE: PRT
<213> ORGANISM: Mus musculus

<400> SEQUENCE: 26

Cys Ile Val Glu Ser Leu Ser Gln Leu Thr Gln Ser Gly Ala
1               5                   10

<210> SEQ ID NO 27
<211> LENGTH: 41
<212> TYPE: PRT
<213> ORGANISM: Homo sapiens

<400> SEQUENCE: 27

Leu Gln Thr Leu Pro Ala Gln Leu Pro Pro Gln Leu Gly Pro Val Glu
1               5                   10                  15

Pro Leu Pro Ala Asp Leu Ala Gln Leu Tyr Gln His Gln Leu Asn Pro
            20                  25                  30

Thr Leu Leu Gln Gln Gln Asn Lys Arg
        35                  40
```